(12) United States Patent
Boettcher et al.

(10) Patent No.: US 11,236,159 B2
(45) Date of Patent: Feb. 1, 2022

(54) METHODS OF TREATING FGF21-ASSOCIATED DISORDERS

(71) Applicant: Novartis AG, Basel (CH)

(72) Inventors: Brian Boettcher, Winchester, MA (US); Shari Lynn Caplan, Lunenburg, MA (US); Regis Cebe, Saint-Louis (FR); Guochun Li, San Diego, CA (US); John A. Taraszka, Arlington, MA (US); Fangmin Xu, Belmont, MA (US); David Langdon Yowe, Belmont, MA (US)

(73) Assignee: Novartis AG, Basel (CH)

( * ) Notice: Subject to any disclaimer, the term of this patent is extended or adjusted under 35 U.S.C. 154(b) by 400 days.

(21) Appl. No.: 15/749,775

(22) PCT Filed: Aug. 2, 2016

(86) PCT No.: PCT/IB2016/054660
§ 371 (c)(1),
(2) Date: Feb. 1, 2018

(87) PCT Pub. No.: WO2017/021893
PCT Pub. Date: Feb. 9, 2017

(65) Prior Publication Data
US 2020/0087392 A1    Mar. 19, 2020

Related U.S. Application Data

(60) Provisional application No. 62/200,445, filed on Aug. 3, 2015.

(51) Int. Cl.
*C07K 16/28* (2006.01)
*A61P 3/00* (2006.01)
*A61K 39/00* (2006.01)

(52) U.S. Cl.
CPC ............ *C07K 16/28* (2013.01); *A61P 3/00* (2018.01); *A61K 39/001107* (2018.08); *C07K 2317/24* (2013.01); *C07K 2317/34* (2013.01); *C07K 2317/55* (2013.01); *C07K 2317/92* (2013.01); *C07K 2317/94* (2013.01); *C07K 2318/00* (2013.01)

(58) Field of Classification Search
None
See application file for complete search history.

(56) References Cited

U.S. PATENT DOCUMENTS

| | | |
|---|---|---|
| 8,372,952 B2 | 2/2013 | Smith et al. |
| 8,697,369 B2 | 4/2014 | Suzuki et al. |
| 8,722,622 B2 | 5/2014 | Das et al. |
| 9,006,400 B2 | 4/2015 | Boettcher et al. |
| 9,085,626 B2 | 6/2015 | Sonoda et al. |
| 9,284,378 B2 | 3/2016 | Hu et al. |
| 2010/0184665 A1 | 7/2010 | Suzuki et al. |
| 2011/0135657 A1 | 6/2011 | Hu et al. |
| 2011/0150901 A1 | 6/2011 | Smith et al. |
| 2012/0282279 A1 | 11/2012 | Das et al. |
| 2012/0294861 A1 | 11/2012 | Sonoda et al. |
| 2012/0328616 A1 | 12/2012 | Li et al. |
| 2013/0129725 A1 | 5/2013 | Fachini et al. |
| 2013/0197191 A1 | 8/2013 | Smith et al. |
| 2014/0142023 A1 | 5/2014 | Sommerfeld et al. |
| 2014/0189893 A1 | 7/2014 | Li et al. |
| 2014/0206023 A1 | 7/2014 | Gao et al. |
| 2015/0210764 A1 | 7/2015 | Mondal et al. |
| 2015/0218276 A1 | 8/2015 | Chen et al. |
| 2015/0376283 A1 | 12/2015 | Sonoda et al. |

FOREIGN PATENT DOCUMENTS

| | | |
|---|---|---|
| EA | 21425 B1 | 6/2015 |
| RU | 2492234 C2 | 9/2013 |
| WO | 38123625 A1 | 10/2008 |
| WO | 11068893 A1 | 6/2011 |
| WO | 11071783 A1 | 6/2011 |
| WO | 11130417 A2 | 10/2011 |
| WO | 12059873 A2 | 5/2012 |
| WO | 12154263 A1 | 11/2012 |
| WO | 12158704 A1 | 11/2012 |
| WO | 12170438 A2 | 12/2012 |
| WO | 2012177481 A2 | 12/2012 |
| WO | 13010780 A1 | 1/2013 |
| WO | 2013184958 A1 | 12/2013 |
| WO | 14149699 A1 | 9/2014 |
| WO | 15100366 A1 | 7/2015 |
| WO | 15112886 A2 | 7/2015 |
| WO | 15148708 A1 | 10/2015 |

OTHER PUBLICATIONS

Stein et al., "Serum fibroblast growth factor 21 levels in gestationsl diabetes mellitus in relation to insulin resistance and dyslipidemia", Metabolism Clinical and experimental 59:33-31, (2010).

Tucci et al., "Evidencefor Association of Polycystic Ovary Syndrome in Caucasian Women with a Marker at the Insulin Receptor Gene Locus", Journal of Clinical Endocrinology & Metabolism, 86(1):446-449, (2001).

Siegel et al., "A C/T single nucleotide polymorphism at the tyrosine kinase domain of the insulin receptor gene is associated with polycystic ovary syndrome", Fertility and Sterility, 78(6):1240-1243, (2002).

Gorar et al., "Serum fibroblast growth factor 21 levels in polycystic ovary syndrome", Gynecological Endocrinoloay, 26(11):819-826, (2010).

Foltz et al., "Treating Diabetes and Obesity with the FGF21-Mimetic Antibody Activating the B-Klotho/FGFR1c Receptor Complex", Science Translational Medicine, vol. 4, No. 162(162ra153) (2012).

M. Singer et al., Geny i genomy, Moscow, Mir, 1998, vol. 1, pp. 63-64.

(Continued)

*Primary Examiner* — Marianne P Allen
(74) *Attorney, Agent, or Firm* — Clark & Elbing LLP

(57) ABSTRACT

The present invention relates to monoclonal antibodies and antigen-binding fragments thereof that bind to human β-klotho, and pharmaceutical compositions and methods of treatment comprising the same.

8 Claims, 10 Drawing Sheets
Specification includes a Sequence Listing.

(56) References Cited

OTHER PUBLICATIONS

Roitt I et al., Immunologia, Moscow, "Mir", 2000, pp. 110-111.
Pakula A.A. et al., Genetic analysis of protein stability and function. Annu. Rev. Genet, 1989, vol. 23, pp. 289-310 (see pp. 305-306).
Lu et al., "Acquired antagonistic activity of a bispecific diabody directed against two different epitopes on vascular endothelial growth factor receptor 2," J Immunol Methods. 230(1-2):159-171 (1999).
Official Action for Russian Patent Application No. 2018106642/10(010195), dated Feb. 25, 2021 (6 pages).
Communication pursuant to Article 94(3) EPC for European Patent Application No. 16754564.9 dated Nov. 29, 2021 (5 pages).
Caldas et al., "Humanization of the anti-CD18 antibody 6.7: an unexpected effect of a framework residue in binding to antigen," Mol Immunol. 39(15):941-52 (2003).
Casadevall et al., "Immunoglobulin isotype influences affinity and specificity," Proc Natl Acad Sci USA. 109(31):12272-3 (2012).
Du et al., "Molecular basis of recognition of human osteopontin by 23C3, a potential therapeutic antibody for treatment of rheumatoid arthritis," J Mol Biol. 382(4):835-42 (2008).
Kunik et al., "Structural consensus among antibodies defines the antigen binding site," PLoS Comput Biol. 8(2):e1002388 (2012) (12 pages).

METHODS OF TREATING FGF21-ASSOCIATED DISORDERS

RELATED APPLICATIONS

This application is a U.S. National Phase filing of International Application Serial No. PCT/IB2016/054660 filed 2 Aug. 2016 and claims priority to U.S. Provisional Application Serial No. 62/200,445 filed 3 Aug. 2015 all of which are incorporated in their entireties herein.

SEQUENCE LISTING

The instant application contains a Sequence Listing which has been submitted electronically in ASCII format and is hereby incorporated by reference in its entirety. Said ASCII copy, created on Jul. 28, 2016, is named PAT056954_SL.txt and is 124,487 bytes in size.

FIELD

The present invention relates to fibroblast growth factor 21 (FGF21) mimetic antibodies. Also disclosed are methods for treating FGF21-associated disorders, such as obesity, type 1 and type 2 diabetes mellitus, pancreatitis, dyslipidemia, nonalcoholic steatohepatitis (NASH), insulin resistance, hyperinsulinemia, glucose intolerance, hyperglycemia, metabolic syndrome, and other metabolic disorders, and in reducing the mortality and morbidity of critically ill patients.

BACKGROUND

The fibroblast growth factor (FGF) family is characterized by 22 genetically distinct, homologous ligands, which are grouped into seven subfamilies. According to the published literature, the FGF family now consists of at least twenty-three members, FGF-1 to FGF-23 (Reuss et al. (2003) Cell Tissue Res. 313:139-157).

Fibroblast growth factor 21 (FGF21) was isolated from mouse embryos and is closest to FGF19 and FGF23. This FGF subfamily regulates diverse physiological processes uncommon to classical FGFs, namely energy and bile acid homeostasis, glucose and lipid metabolism, and phosphate as well as vitamin D homeostasis. Moreover, unlike classical FGFs, this subfamily acts in an endocrine fashion (Moore, D. D. (2007) Science 316, 1436-8). FGF21 has been reported to be preferentially expressed in the liver (Nishimura et al. (2000) Biochimica et Biophysica Acta, 1492:203-206; patent publication WO01/36640; and patent publication WO01/18172) and described as a treatment for ischemic vascular disease, wound healing, and diseases associated with loss of pulmonary, bronchia or alveolar cell function and numerous other disorders.

FGF21 has been identified as a potent metabolic regulator. Systemic administration of FGF21 to rodents and rhesus monkeys with diet-induced or genetic obesity and diabetes exerts strong anti-hyperglycemic and triglyceride-lowering effects, and reduction of body weight (Coskun, T, et al. (2008) Endocrinology 149:6018-6027; Kharitonenkov, A. et al. (2005) Journal of Clinical Investigation 115:1627-1635; Kharitonenkov, A., et al. (2007) Endocrinology 148:774-781; Xu, J, et al. (2009) Diabetes 58:250-259). FGF21 is a 209 amino acid polypeptide containing a 28 amino acid leader sequence. Human FGF21 has about 79% amino acid identity to mouse FGF21 and about 80% amino acid identity to rat FGF21.

In mammals, FGFs mediate their action via a set of four FGF receptors FGFR1-4 that in turn are expressed in multiple spliced variants. Each FGF receptor contains an intracellular tyrosine kinase domain that is activated upon ligand binding, leading to downstream signaling pathways involving MAPKs (Erk1/2), RAF1, AKT1 and STATs. (Kharitonenkov, A. et al. (2008) BioDrugs 22:37-44). Several reports suggested that the "c"-reporter splice variants of FGFR1-3 exhibit specific affinity to β-klotho and could act as endogenous receptors for FGF21 (Kurosu et al., 2007 J. Biol. Chem. 282:26687-26695); Ogawa et al., 2007 Proc. Natl. Acad. Sci. USA 104:7432-7437; Kharitonenkov et al., 2008 J. Cell Physiol. 215, 1-7). In 3T3-L1 cells and white adipose tissue, FGFR1 is by far the most abundant receptor, and it is therefore most likely that FGF21's main functional receptors in this tissue are the β-klotho-FGFR1c complexes.

Although FGF21 activates FGF receptors and downstream signaling molecules, including FRS2a and ERK, direct interaction of FGFRs and FGF21 has not been detected. Furthermore, various non-adipocyte cells do not respond to FGF21, even though they express multiple FGFR isoforms. All of these data suggest that a cofactor must mediate FGF21 signaling through FGFRs. Studies have identified beta-klotho (β-klotho), which is highly expressed in liver, adipocytes and in pancreas, as a determinant of the cellular response to FGF21 (Kurosu, H. et al. (2007) J Biol Chem 282, 26687-95). The β-klotho-FGFR complex, but not FGFR alone, binds to FGF21 in vitro (Kharitonenkov, A., et al. (2008) J Cell Physiol 215, 1-7). FGF21 binds to β-klotho in complex with FGFR1c, 2c, or 3c; but not to β-klotho in complex with FGFR4 (Owen et al., 2015 Trends in Endocrinology 26: 22-29). A similar mechanism has been identified in the FGF23-klotho-FGFR system (Urakawa, I. et al. (2006) Nature 444, 770-4).

The bioactivity of FGF21 was first identified in a mouse 3T3-L1 adipocyte glucose uptake assay (Kharitonenkov, A. et al. (2005) J Clin Invest 115, 1627-35). Subsequently, FGF21 was shown to induce insulin-independent glucose uptake and GLUT1 expression. FGF21 has also been shown to ameliorate hyperglycemia in a range of diabetic rodent models. In addition, transgenic mice over-expressing FGF21 were found to be resistant to diet-induced metabolic abnormalities, including decreased body weight and fat mass, and enhancements in insulin sensitivity (Badman, M. K. et al. (2007) Cell Metab 5, 426-37). Administration of FGF21 to diabetic non-human primates (NHP) caused a decline in fasting plasma glucose, triglycerides, insulin and glucagon levels, and led to significant improvements in lipoprotein profiles including a nearly 80% increase in HDL cholesterol (Kharitonenkov, A. et al. (2007) Endocrinology 148, 774-81). Importantly, hypoglycemia was not observed at any point during this NHP study. Other studies identified FGF21 as an important endocrine hormone that helps to control adaptation to the fasting state. This provides a previously missing link, downstream of PPARα, by which the liver communicates with the rest of the body in regulating the biology of energy homeostasis. The combined observations that FGF21 regulates adipose (lipolysis), liver (fatty acid oxidation and ketogenesis), and brain (torpor) establish it as a major endocrine regulator of the response to fasting (Kharitonenkov, A. & Shanafelt, A. B. (2008) BioDrugs 22, 37-44).

The problem with using FGF21 directly as a biotherapeutic is that its half-life is very short. In mice, the half-life of human FGF21 is 0.5 to 1 hours, and in cynomolgus monkeys, the half-life is 2 to 3 hours. Furthermore, when wild type FGF21 is used in pharmaceutical formulations or preparations, its stability is adversely affected by preservatives e.g., m-cresol.

SUMMARY

The present invention relates to FGF21 mimetic antibodies, i.e., monoclonal antibodies that bind to beta-klotho (β-klotho) and activate the human Fibroblast Growth Factor 21 (hereinafter, sometimes referred to as "FGF21") receptor complex and FGF21-mediated signaling (e.g., FGF21-receptor-dependent signaling), antigen-binding fragments thereof, and pharmaceutical compositions and methods of treatment comprising the same.

Antigen-binding fragments (of the FGF21 mimetic, β-klotho-binding antibodies) of the invention can be molecules with FGF21-like activity and selectivity but with added therapeutically desirable characteristics such as protein stability, low immunogenicity, ease of production and a desirable in vivo half-life.

The monoclonal FGF21 mimetic antibodies of the invention, antigen-binding fragments thereof, and pharmaceutical compositions comprising the same are useful for the treatment of FGF21-associated disorders, such as obesity, type 2 diabetes mellitus, type 1 diabetes mellitus, pancreatitis, dyslipidemia, nonalcoholic steatohepatitis (NASH), insulin resistance, hyperinsulinemia, glucose intolerance, hyperglycemia, metabolic syndrome, hypertension, cardiovascular disease, atherosclerosis, peripheral arterial disease, stroke, heart failure, coronary heart disease, kidney disease, diabetic complications, neuropathy, gastroparesis and other metabolic disorders, and in reducing the mortality and morbidity of critically ill patients.

The isolated FGF21 mimetic antibodies, or antigen-binding fragments, described herein bind β-klotho, with an equilibrium dissociation constant ($K_D$) of less than or equal to 100 pM. For example, the isolated antibodies or antigen-binding fragments described herein may bind to human β-klotho with a $K_D$ of less than or equal to 100 pM, less than or equal to 50 pM, less than or equal to 45 pM, less than or equal to 40 pM, less than or equal to 35 pM, less than or equal to 25 pM, or less than or equal to 15 pM. More specifically, the isolated antibodies or antigen-binding fragments described herein may also bind human β-klotho with a $K_D$ of less than or equal to 10 pM, as measured by solution equilibrium titration assay (SET); and may also activate the cynomolgus monkey FGFR1c_β-klotho receptor complex with an EC50 of less than or equal to 50 nM, as measured by pERK cell assays.

The present invention relates to an isolated antibody, or antigen-binding fragments thereof, that binds to human and cynomolgus monkey β-klotho. The invention also relates to an isolated antibody, or antigen-binding fragments thereof, that binds β-klotho and activates the FGF21 receptor complex and FGF21-mediated signaling (e.g., FGF21-receptor-dependent signaling). In particular aspects, an isolated antibody or antigen-binding fragment thereof described herein does not activate human FGFR2c_β-klotho, FGFR3c_β-klotho, or FGFR4_β-klotho receptor complexes.

The present invention also relates to an isolated antibody, or antigen-binding fragments thereof, that binds β-klotho and further competes for binding with an antibody as described in Table 1. The present invention also further relates to an isolated antibody, or antigen-binding fragments thereof, that binds the same epitope as an antibody as described in Table 1.

As described here, "competition" between antibodies and/or antigen-binding fragments thereof signifies that both antibodies (or binding fragments thereof) bind to the same β-klotho epitope (e.g., as determined by a competitive binding assay, by any of the methods well known to those of skill in the art). An antibody or antigen-binding fragment thereof also "competes" with a β-klotho antibody or antigen-binding fragment of the invention (e.g., NOV001 or NOV002) if said competing antibody or antigen-binding fragment thereof binds the same β-klotho epitope, or an overlapping β-klotho epitope, as an antibody or antigen-binding fragment of the invention. As used herein, a competing antibody or antigen-binding fragment thereof can also include one which (i) sterically blocks an antibody or antigen-binding fragment of the invention from binding its target (e.g., if said competing antibody binds to a nearby, non-overlapping β-klotho and/or β-klotho epitope and physically prevents an antibody or antigen-binding fragment of the invention from binding its target); and/or (ii) binds to a different, non-overlapping β-klotho epitope and induces a conformational change to the β-klotho protein such that said protein can no longer be bound by a β-klotho antibody or antigen-binding fragment of the invention in a way that would occur absent said conformational change.

The binding affinity of isolated antibodies and antigen-binding fragments described herein can be determined by solution equilibrium titration (SET). Methods for SET are known in the art and are described in further detail below. Alternatively, binding affinity of the isolated antibodies, or fragments, described herein can be determined by Biacore assay. Methods for Biacore kinetic assays are know in the art and are described in further detail below.

The isolated FGF21 mimetic antibodies, or antigen-binding fragments thereof, may be used to increase the activation of the FGF21 receptor complex, and thereby, the FGF21 signaling pathway.

The isolated FGF21 mimetic antibodies, or antigen-binding fragments thereof, as described herein can be monoclonal antibodies, human or humanized antibodies, chimeric antibodies, single chain antibodies, Fab fragments, Fv fragments, F(ab')2 fragments, or scFv fragments, and/or IgG isotypes.

The isolated FGF21 mimetic antibodies, or antigen-binding fragments thereof, as described herein can also include a framework in which an amino acid has been substituted into the antibody framework from the respective human VH or VL germline sequences.

Another aspect of the invention includes an isolated antibody or antigen-binding fragments thereof having the full heavy and light chain sequences of Fabs described in Table 1. More specifically, the isolated antibody or antigen-binding fragments thereof can have the heavy and light chain sequences of Fab NOV001, NOV002, NOV003, NOV004.

A further aspect of the invention includes an isolated antibody or antigen-binding fragments thereof having the heavy and light chain variable domain sequences of Fabs described in Table 1. More specifically, the isolated antibody or antigen-binding fragment thereof can have the heavy and light chain variable domain sequence of Fab NOV001, NOV002, NOV003, NOV004.

The invention also relates to an isolated antibody or antigen-binding fragments thereof that includes a heavy chain CDR1 selected from the group consisting of SEQ ID NOs: 3, 23, 43, and 63; a heavy chain CDR2 selected from the group consisting of SEQ ID NOs: 4, 24, 44, and 64; and a heavy chain CDR3 selected from the group consisting of SEQ ID NOs: 5, 25, 45, and 65, wherein the isolated antibody or antigen-binding fragments thereof binds to human β-klotho. In another aspect, such isolated antibody or antigen-binding fragments thereof further includes a light chain CDR1 selected from the group consisting of SEQ ID NOs: 13, 33, 53, and 73; a light chain CDR2 selected from the group consisting of SEQ ID NOs: 14, 34, 54, and 74; and a light chain CDR3 selected from the group consisting of SEQ ID NOs: 15, 35, 55, and 75.

The invention also relates to an isolated antibody or antigen-binding fragments thereof that includes a light chain CDR1 selected from the group consisting of SEQ ID NOs: 13, 33, 53, and 73; a light chain CDR2 selected from the group consisting of SEQ ID NOs: 14, 34, 54, and 74; and a light chain CDR3 selected from the group consisting of SEQ ID NOs: 15, 35, 55, and 75, wherein the isolated antibody or antigen-binding fragments thereof binds to human β-klotho.

The invention also relates to an isolated antibody or antigen-binding fragments thereof that binds β-klotho having HCDR1, HCDR2, and HCDR3 and LCDR1, LCDR2, and LCDR3, as defined by Kabat, wherein HCDR1, HCDR2, and HCDR3 comprises SEQ ID NOs: 3, 4, and 5, and LCDR1, LCDR2, LCDR3 comprises SEQ ID NOs: 13, 14, and 15; or HCDR1, HCDR2, and HCDR3 comprises SEQ ID NOs: 23, 24, and 25, and LCDR1, LCDR2, LCDR3 comprises SEQ ID NOs: 33, 34, and 35; or HCDR1, HCDR2, and HCDR3 comprises SEQ ID NOs: 43, 44, and 45, and LCDR1, LCDR2, LCDR3 comprises SEQ ID NOs: 53, 54, and 55; or HCDR1, HCDR2, and HCDR3 comprises SEQ ID NOs: 63, 64, and 65, and LCDR1, LCDR2, LCDR3 comprises SEQ ID NOs: 73, 74, and 75.

The invention also relates to an isolated antibody or antigen-binding fragments thereof that binds β-klotho having HCDR1, HCDR2, and HCDR3 and LCDR1, LCDR2, and LCDR3, as defined by Chothia, wherein HCDR1, HCDR2, and HCDR3 comprises SEQ ID NOs: 6, 7, and 8, and LCDR1, LCDR2, LCDR3 comprises SEQ ID NOs: 16, 17, and 18; or HCDR1, HCDR2, and HCDR3 comprises SEQ ID NOs: 26, 27, and 28, and LCDR1, LCDR2, LCDR3 comprises SEQ ID NOs: 36, 37, and 38; or HCDR1, HCDR2, and HCDR3 comprises SEQ ID NOs: 46, 47, and 48, and LCDR1, LCDR2, LCDR3 comprises SEQ ID NOs: 56, 57, and 58; or HCDR1, HCDR2, and HCDR3 comprises SEQ ID NOs: 66, 67, and 68, and LCDR1, LCDR2, LCDR3 comprises SEQ ID NOs: 76, 77, and 78.

In one aspect of the invention the isolated antibody or antigen-binding fragments thereof includes a heavy chain variable domain sequence selected from the group consisting of SEQ ID NOs: 9, 29, 49, and 69. The isolated antibody or antigen-binding fragment further can comprise a light chain variable domain sequence wherein the heavy chain variable domain and light chain variable domain combine to form and antigen-binding site for β-klotho. In particular the light chain variable domain sequence can be selected from SEQ ID NOs: 19, 39, 59, and 79 wherein said isolated antibody or antigen-binding fragments thereof binds beta-klotho.

The invention also relates to an isolated antibody or antigen-binding fragments thereof that includes a light chain variable domain sequence selected from the group consisting of SEQ ID NOs: 19, 39, 59, and 79, wherein said isolated antibody or antigen-binding fragments thereof binds to human β-klotho. The isolated antibody or antigen-binding fragment may further comprise a heavy chain variable domain sequence wherein the light chain variable domain and heavy chain variable domain combine to form and antigen-binding site for β-klotho.

In particular, the isolated antibody or antigen-binding fragments thereof that binds β-klotho, may have heavy and light chain variable domains comprising the sequences of SEQ ID NOs: 9 and 19; 29 and 39; 49 and 59; or 69 and 79, respectively.

The invention further relates to an isolated antibody or antigen-binding fragments thereof, that includes a heavy chain variable domain having at least 90% sequence identity to a sequence selected from the group consisting of SEQ ID NOs: 9, 29, 49, and 69, wherein said antibody binds to β-klotho. In one aspect, the isolated antibody or antigen-binding fragments thereof also includes a light chain variable domain having at least 90% sequence identity to a sequence selected from the group consisting of SEQ ID NOs: 19, 39, 59, and 79. In a further aspect of the invention, the isolated antibody or antigen-binding fragment has an HCDR1, HCDR2, HCDR3, LCDR1, LCDR2 and LCDR3 as defined by Kabat and as described in Table 1.

The invention also relates to an isolated antibody or antigen-binding fragments thereof, having a light chain variable domain having at least 90% sequence identity to a sequence selected from the group consisting of SEQ ID NOs: 19, 39, 59, and 79, wherein said antibody binds β-klotho.

In another aspect of the invention, the isolated antibody, or antigen-binding fragments thereof, that binds to β-klotho may have a heavy chain comprising the sequence of SEQ ID NOs: 11, 31, 51, or 71. The isolated antibody can also includes a light chain that can combine with the heavy chain to form an antigen-binding site to human β-klotho. In particular, the light chain may have a sequence comprising SEQ ID NOs: 21, 41, 61, or 81. In particular, the isolated antibody or antigen-binding fragments thereof that binds β-klotho, may have a heavy chain and a light chain comprising the sequences of SEQ ID NOs: 11 and 21; 31 and 41; 51 and 61; or 71 and 81, respectively.

The invention still further relates to an isolated antibody or antigen-binding fragments thereof that includes a heavy chain having at least 90% sequence identity to a sequence selected from the group consisting of SEQ ID NOs: 9, 29, 49, or 69, wherein said antibody binds to β-klotho. In one aspect, the isolated antibody or antigen-binding fragments thereof also includes a light chain having at least 90% sequence identity to a sequence selected from the group consisting of SEQ ID NOs: 21, 41, 61, or 81.

The invention still further relates to an isolated antibody or antigen-binding fragments thereof that includes a light chain having at least 90% sequence identity to a sequence selected from the group consisting of SEQ ID NOs: 21, 41, 61, or 81, wherein said antibody binds β-klotho.

The invention also relates to compositions comprising the isolated antibody, or antigen-binding fragments thereof, described herein. As well as, antibody compositions in combination with a pharmaceutically acceptable carrier. Specifically, the invention further includes pharmaceutical compositions comprising an antibody or antigen-binding fragments thereof of Table 1, such as, for example antibody NOV001, NOV002, NOV003, NOV004. The invention also relates to pharmaceutical compositions comprising a combination of two or more of the isolated antibodies or antigen-binding fragments thereof of Table 1.

The invention also relates to an isolated nucleic acid sequence encoding the variable heavy chain having a sequence selected from SEQ ID NOs: 9, 29, 49, and 69. In particular the nucleic acid has a sequence at least 90% sequence identity to a sequence selected from the group consisting of SEQ ID NOs: 10, 30, 50, and 70. In a further aspect of the invention the sequence is SEQ ID NOs: 10, 30, 50, and 70.

The invention also relates to an isolated nucleic acid sequence encoding the variable light chain having a sequence selected from SEQ ID NOs: 20, 40, 60, and 80. In particular the nucleic acid has a sequence at least 90% sequence identity to a sequence selected from the group consisting of SEQ ID NOs: 20, 40, 60, and 80. In a further aspect of the invention the sequence is SEQ ID NOs: 20, 40, 60, and 80.

The invention also relates to an isolated nucleic acid comprising a sequence encoding a polypeptide that includes a light chain variable domain having at least 90% sequence identity to a sequence selected from the group consisting of SEQ ID NOs: 20, 40, 60, and 80.

The invention also relates to a vector that includes one or more of the nucleic acid molecules described herein.

The invention also relates to an isolated host cell that includes a recombinant DNA sequence encoding a heavy chain of the antibody described above, and a second recombinant DNA sequence encoding a light chain of the antibody described above, wherein said DNA sequences are operably linked to a promoter and are capable of being expressed in the host cell. It is contemplated that the antibody can be a human monoclonal antibody. It is also contemplated that the host cell is a non-human mammalian cell.

The invention also relates to activating a Fibroblast Growth Factor 21 (FGF21) receptor, and, thereby, FGF21-mediated signaling (e.g., FGF21-receptor-dependent signaling), wherein the method includes the step of contacting a cell with an effective amount of a composition comprising the isolated antibody or antigen-binding fragments thereof described herein.

It is contemplated that the cell is a human cell. It is further contemplated that the cell is in a subject. In one embodiment, it is contemplated that the cell is an adipocyte. In other embodiments, the cell may be one or more of hepatocytes, pancreas cells, endothelial cells, muscle, or renal cells. It is still further contemplated that the subject is human.

The invention also relates to a method of treating, improving, or preventing a FGF21-associated disorder in a subject, wherein the method includes the step of administering to the subject an effective amount of a composition comprising the antibody or antigen-binding fragments thereof described herein. In one aspect, the FGF21-associated disorder is obesity. In one aspect, the FGF21-associated disorder is type 2 diabetes. It is contemplated that the subject is human.

Any of the foregoing isolated antibodies or antigen-binding fragments thereof may be a monoclonal antibody or antigen-binding fragments thereof.

Non-limiting embodiments of the disclosure are described in the following aspects:

1. An isolated antibody or antigen-binding fragment thereof that binds to an epitope within the extracellular domain of β-klotho.

2. An isolated antibody or antigen-binding fragment thereof that binds to an epitope of β-klotho, wherein the epitope comprises one or more of the SEQ ID NOs shown in Table 2.

3. An isolated FGF21 mimetic antibody or antigen-binding fragment thereof that binds to β-klotho, wherein said antibody or fragment increases the activity of β-klotho and FGFR1c.

4. An isolated antibody or antigen-binding fragment thereof that binds to a human β-klotho protein with a $K_D$ of less than or equal to 10 pM, as measured by solution equilibrium titration assay (SET).

5. An isolated antibody or antigen-binding fragment thereof that binds to an epitope of β-klotho, wherein said epitope comprises one or more amino acids of residues 246-265, 536-550, 834-857 and 959-986 of the β-klotho sequence (SEQ ID NO:262).

6. An isolated antibody or antigen-binding fragment thereof that binds to one or more epitopes of β-klotho, wherein said epitopes comprises one or more of amino acids of residues 646-670, 696-700, and 646-689 of the β-klotho sequence (SEQ ID NO:262).

7. An isolated antibody or antigen-binding fragment thereof that activates the cynomolgus monkey FGFR1c_β-klotho receptor complex with an EC50 of less than or equal to 50 nM, as measured by pERK cell assays.

8. The isolated antibody or antigen-binding fragment of aspect 1, wherein said antibody or fragment comprises at least one complementarity determining region having at least 95% identity to at least one of the CDRs recited in Table 1.

9. The isolated antibody or antigen-binding fragment of aspect 1, wherein said antibody or fragment comprises at least one complementarity determining region having at least 98% identity to at least one of the CDRs recited in Table 1.

10. The isolated antibody or antigen-binding fragment of aspect 1, wherein said antibody or fragment comprises at least one complementarity determining region having at least 99% identity to at least one of the CDRs recited in Table 1.

11. The isolated antibody or antigen-binding fragment of any of the preceding aspects, wherein said antibody or fragment comprises a heavy chain CDR1, heavy chain CDR2, and heavy chain CDR3 from Table 1, and/or a light chain CDR1, light chain CDR2, and light chain CDR3 from Table 1.

12. The isolated antibody or antigen-binding fragment of any of aspects 1-7, wherein said antibody or fragment comprises a CDR1, CDR2, and CDR3 from Table 1, and wherein the variant has at least one to four amino acid changes in one of CDR1, CDR2, or CDR3.

13. The isolated antibody or antigen-binding fragment of any of aspects 1-7, wherein the antibody or fragment comprises a heavy chain CDR3 selected from the group consisting of SEQ ID NO: 5, 25, 45, and 65.

14. The isolated antibody or antigen-binding fragment of any of aspects 1-7, wherein the antibody or fragment comprises a VH selected from the group consisting of SEQ ID NO: 9, 29, 49, 69 or an amino acid sequence with 90% identity thereof; and a VL selected from the group consisting of SEQ ID NO: 19, 39, 59, and 79 or an amino acid sequence with 90% identity thereof.

15. The isolated antibody or antigen-binding fragment of any of aspects 1-7, wherein the antibody or fragment comprises a VH selected from the group consisting of SEQ ID NO: 9, 29, 49, and 29 or an amino acid sequence with 95% identity thereof; and a VL selected from the group consisting of SEQ ID NO: 19, 39, 59, and 79 or an amino acid sequence with 95% identity thereof.

16. The isolated antibody or antigen-binding fragment of any of aspects 1-7, wherein the antibody or fragment comprises a VH selected from the group consisting of SEQ ID NO: 9, 29, 49, and 69 or an amino acid sequence with 97% identity thereof; and a VL selected from the group consisting of SEQ ID NO: 19, 39, 59, and 79 or an amino acid sequence with 97% identity thereof.

17. The isolated antibody or antigen-binding fragment of any of aspects 1-7, wherein the antibody or fragment comprises a variable heavy chain sequence selected from the group consisting of SEQ ID NO: 9, 29, 49, and 69.

18. The isolated antibody or antigen-binding fragment of any of aspects 1-7, wherein the antibody or fragment comprises a variable light chain sequence selected from the group consisting of SEQ ID NO: 19, 39, 59, and 79.

19. The isolated antibody or antigen-binding fragment of any of aspects 1-7, wherein the antibody or fragment comprises a variable heavy chain selected from the group consisting of SEQ ID NO: 9, 29, 49, and 69; and variable light chain sequence selected from the group consisting of SEQ ID NO: 19, 39, 59, and 79.

20. The isolated antibody or antigen-binding fragment of any of aspects 1-7, wherein the antibody or fragment is selected from the group consisting of an antibody or fragment comprising a variable heavy chain of SEQ ID NO: 9 and a variable light chain sequence of SEQ ID NO: 19, an antibody or fragment comprising a variable heavy chain of SEQ ID NO: 29 and a variable light chain sequence of SEQ ID NO: 39; an antibody or fragment comprising a variable heavy chain of SEQ ID NO: 49 and a variable light chain sequence of SEQ ID NO: 59; and an antibody or fragment comprising a variable heavy chain of SEQ ID NO: 69 and a variable light chain sequence of SEQ ID NO: 79.

21. The isolated antibody or antigen-binding fragment of any of aspects 1-7, wherein the antibody or fragment comprises a heavy chain CDR1 selected from the group consisting of SEQ ID NO: 3, 23, 43, and 63; a heavy chain CDR2 selected from the group consisting of SEQ ID NO: 4, 24, 44, and 64; a heavy chain CDR3 selected from the group consisting of 5, 25, 45, and 65; a light chain CDR1 selected from the group consisting of SEQ ID NO: 13, 33, 53, and 73; a light chain CDR2 selected from the group consisting of SEQ ID NO: 14, 34, 54, and 74; and a light chain CDR3 selected from the group consisting of SEQ ID NO: 15, 35, 55, and 75.

22. The isolated antibody or antigen-binding fragment of any of aspects 1-7, wherein the antibody or fragment comprises a heavy chain CDR1 selected from the group consisting of SEQ ID NO: 6, 26, 46, and 66; a heavy chain CDR2 selected from the group consisting of SEQ ID NO: 7, 27, 47, and 67; a heavy chain CDR3 selected from the group consisting of 8, 28, 48, and 68; a light chain CDR1 selected from the group consisting of SEQ ID NO: 16, 36, 56, and 76; a light chain CDR2 selected from the group consisting of SEQ ID NO: 17, 37, 57, and 77; and a light chain CDR3 selected from the group consisting of SEQ ID NO: 18, 38, 58, and 78.

23. The isolated antibody or antigen-binding fragment of any of aspects 1-7, wherein the antibody or fragment comprises a heavy chain CDR1 of SEQ ID NO: 3; a heavy chain CDR2 of SEQ ID NO: 4; a heavy chain CDR3 of SEQ ID NO: 5; a light chain CDR1 of SEQ ID NO: 13; a light chain CDR2 of SEQ ID NO: 14; and a light chain CDR3 of SEQ ID NO: 15.

24. The isolated antibody or antigen-binding fragment of any of aspects 1-7, wherein the antibody or fragment comprises a heavy chain CDR1 of SEQ ID NO: 23; a heavy chain CDR2 of SEQ ID NO: 24; a heavy chain CDR3 of SEQ ID NO: 25; a light chain CDR1 of SEQ ID NO: 33; a light chain CDR2 of SEQ ID NO: 34; and a light chain CDR3 of SEQ ID NO: 35.

25. The isolated antibody or antigen-binding fragment of any of aspects 1-7, wherein the antibody or fragment comprises a heavy chain CDR1 of SEQ ID NO: 43; a heavy chain CDR2 of SEQ ID NO: 44; a heavy chain CDR3 of SEQ ID NO: 45; a light chain CDR1 of SEQ ID NO: 53; a light chain CDR2 of SEQ ID NO: 54; and a light chain CDR3 of SEQ ID NO: 55.

26. The isolated antibody or antigen-binding fragment of any of aspects 1-7, wherein the antibody or fragment comprises a heavy chain CDR1 of SEQ ID NO: 63; a heavy chain CDR2 of SEQ ID NO: 64; a heavy chain CDR3 of SEQ ID NO: 65; a light chain CDR1 of SEQ ID NO: 73; a light chain CDR2 of SEQ ID NO: 74; and a light chain CDR3 of SEQ ID NO: 75.

27. The isolated antibody or antigen-binding fragment of any of aspects 1-7, wherein the antibody or fragment comprises a heavy chain CDR1 of SEQ ID NO: 6; a heavy chain CDR2 of SEQ ID NO: 7; a heavy chain CDR3 of SEQ ID NO: 8; a light chain CDR1 of SEQ ID NO: 16; a light chain CDR2 of SEQ ID NO: 17; and a light chain CDR3 of SEQ ID NO: 18.

28. The isolated antibody or antigen-binding fragment of any of aspects 1-7, wherein the antibody or fragment comprises a heavy chain CDR1 of SEQ ID NO: 26; a heavy chain CDR2 of SEQ ID NO: 27; a heavy chain CDR3 of SEQ ID NO: 28; a light chain CDR1 of SEQ ID NO: 36; a light chain CDR2 of SEQ ID NO: 37; and a light chain CDR3 of SEQ ID NO: 38.

29. The isolated antibody or antigen-binding fragment of any of aspects 1-7, wherein the antibody or fragment comprises a heavy chain CDR1 of SEQ ID NO: 46; a heavy chain CDR2 of SEQ ID NO: 47; a heavy chain CDR3 of SEQ ID NO: 48; a light chain CDR1 of SEQ ID NO: 56; a light chain CDR2 of SEQ ID NO: 57; and a light chain CDR3 of SEQ ID NO: 58.

30. The isolated antibody or antigen-binding fragment of any of aspects 1-7, wherein the antibody or fragment comprises a heavy chain CDR1 of SEQ ID NO: 66; a heavy chain CDR2 of SEQ ID NO: 67; a heavy chain CDR3 of SEQ ID NO: 68; a light chain CDR1 of SEQ ID NO: 76; a light chain CDR2 of SEQ ID NO: 77; and a light chain CDR3 of SEQ ID NO: 78.

31. An isolated antibody or antigen-binding fragment thereof, wherein the antibody or fragment binds to the same epitope as an isolated antibody or fragment according to any of aspects 12-30.

32. An isolated antibody or antigen-binding fragment thereof, wherein the antibody or fragment competes for binding to β-klotho with an isolated antibody or fragment according to any of aspects 12-30.

33. The isolated antibody or antigen-binding fragment of any of aspects 1-7, wherein the antibody or fragment is selected from the group consisting of NOV001, NOV002, NOV003, and NOV004.

34. A pharmaceutical composition comprising an antibody or antigen-binding fragment thereof of one of the above aspects and a pharmaceutically acceptable carrier.

35. A method of treating a metabolic disorder comprising administering to a subject afflicted with a metabolic disorder an effective amount of a pharmaceutical composition comprising an antibody or antigen-binding fragment according to any of aspects 1-30.

36. The method of aspect 35, wherein the subject is afflicted with one or more of obesity, type 1 and type 2 diabetes mellitus, pancreatitis, dyslipidemia, nonalcoholic steatohepatitis (NASH), insulin resistance, hyperinsulinemia, glucose intolerance, hyperglycemia, and metabolic syndrome.

37. The method of aspect 35, wherein the subject is afflicted with one or more of obesity, diabetes, and dyslipidemia.

38. A method of treating a cardiovascular disorder comprising administering to a subject afflicted with a cardiovascular disorder an effective amount of a pharmaceutical composition comprising an antibody or fragment according to any previous aspect.

39. The method of aspect 38, wherein the subject is afflicted with one or more of atherosclerosis, peripheral arterial disease, stroke, heart failure, and coronary heart disease.

40. An antibody or antigen-binding fragment thereof according to any of aspects 1-30, for use as a medicament.

41. A nucleic acid coding for one or more of the antibodies according to any previous aspect.

42. A nucleic acid comprising a sequence with at least 90% identity to the sequences set forth in Table 1.

43. A nucleic acid comprising a sequence with at least 95% identity to the sequences set forth in Table 1.

44. A vector comprising the nucleic acid according to aspect 41.

45. A host cell comprising the vector of aspect 44.

46. A pharmaceutical composition comprising an antibody or antigen-binding fragment according to any of aspects 1-30 for use in treating a metabolic disorder.

Definitions

Unless defined otherwise, all technical and scientific terms used herein have the same meaning as commonly understood by those of ordinary skill in the art to which this invention pertains.

As used herein, the term "FGF21" refers to a member of the fibroblast growth factor (FGF) protein family. An amino acid sequence of FGF21 (GenBank Accession No. NP_061986.1) is set forth as SEQ ID NO:1, the corresponding polynucleotide sequence of which is set forth as SEQ ID NO:2 (NCBI reference sequence number NM_019113.2).

As used herein, the term "FGF21 receptor" refers to a receptor for FGF21 (Kharitonenkov, A, et al. (2008) Journal of Cellular Physiology 215:1-7; Kurosu, H, et al. (2007) JBC 282:26687-26695; Ogawa, Y, et al. (2007) PNAS 104:7432-7437).

The term "FGF21 polypeptide" refers to a naturally-occurring polypeptide expressed in humans. For purposes of this disclosure, the term "FGF21 polypeptide" can be used interchangeably to refer to any full-length FGF21 polypeptide, e.g., SEQ ID NO:1, which consists of 209 amino acid residues and which is encoded by the nucleotide sequence of SEQ ID NO:2; any mature form of the polypeptide, which consists of 181 amino acid residues, and in which the 28 amino acid residues at the amino-terminal end of the full-length FGF21 polypeptide (i.e., which constitute the signal peptide) have been removed, and variants thereof.

The term "antibody" as used herein means a whole antibody and any antigen-binding fragment (i.e., "antigen-binding portion") or single chain thereof. A whole antibody is a glycoprotein comprising at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "antigen-binding portion" or "antigen-binding fragment" of an antibody, as used herein, refers to one or more fragments of an intact antibody that retain the ability to specifically bind to a given antigen (e.g., β-klotho). Antigen-binding functions of an antibody can be performed by fragments of an intact antibody. Examples of binding fragments encompassed within the term antigen-binding portion or antigen-binding fragment of an antibody include a Fab fragment, a monovalent fragment consisting of the VL, VH, CL and CH1 domains; a F(ab)$_2$ fragment, a bivalent fragment comprising two Fab fragments linked by a disulfide bridge at the hinge region; an Fd fragment consisting of the VH and CH1 domains; an Fv fragment consisting of the VL and VH domains of a single arm of an antibody; a single domain antibody (dAb) fragment (Ward et al., 1989 Nature 341:544-546), which consists of a VH domain or a VL domain; and an isolated complementarity determining region (CDR).

Furthermore, although the two domains of the Fv fragment, VL and VH, are coded for by separate genes, they can be joined, using recombinant methods, by an artificial peptide linker that enables them to be made as a single protein chain in which the VL and VH regions pair to form monovalent molecules (known as single chain Fv (scFv); see, e.g., Bird et al., 1988 Science 242:423-426; and Huston et al., 1988 Proc. Natl. Acad. Sci. 85:5879-5883). Such single chain antibodies include one or more antigen-binding portions or fragments of an antibody. These antibody fragments are obtained using conventional techniques known to those of skill in the art, and the fragments are screened for utility in the same manner as are intact antibodies.

Antigen-binding fragments can also be incorporated into single domain antibodies, maxibodies, minibodies, intrabodies, diabodies, triabodies, tetrabodies, v-NAR and bis-scFv (see, e.g., Hollinger and Hudson, 2005, Nature Biotechnology, 23, 9, 1126-1136). Antigen-binding portions of antibodies can be grafted into scaffolds based on polypeptides such as Fibronectin type III (Fn3) (see U.S. Pat. No. 6,703,199, which describes fibronectin polypeptide monobodies).

Antigen-binding fragments can be incorporated into single chain molecules comprising a pair of tandem Fv segments (VH-CH1-VH-CH1) which, together with complementary light chain polypeptides, form a pair of antigen-binding regions (Zapata et al. (1995) Protein Eng. 8(10):1057-1062; and U.S. Pat. No. 5,641,870).

As used herein, the term "affinity" refers to the strength of interaction between antibody and antigen at single antigenic sites. Within each antigenic site, the variable region of the antibody "arm" interacts through weak non-covalent forces with antigen at numerous sites; the more interactions, the stronger the affinity. As used herein, the term "high affinity" for an antibody or antigen-binding fragments thereof (e.g., a Fab fragment) generally refers to an antibody, or antigen-binding fragment, having a KD of $10^{-9}$M or less.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine Amino acid analogs refer to compounds that have the same basic chemical structure as a naturally occurring amino acid, i.e., an alpha carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid Amino acid mimetics refers to chemical compounds that have a structure that is different from the general chemical structure of an amino acid, but that functions in a manner similar to a naturally occurring amino acid.

The term "binding specificity" as used herein refers to the ability of an individual antibody combining site to react with only one antigenic determinant.

The phrase "specifically (or selectively) binds" to an antibody (e.g., a β-klotho-binding antibody) refers to a binding reaction that is determinative of the presence of a cognate antigen (e.g., a human β-klotho or cynomolgus β-klotho) in a heterogeneous population of proteins and other biologics. The phrases "an antibody recognizing an antigen" and "an antibody specific for an antigen" are used interchangeably herein with the term "an antibody which binds specifically to an antigen".

The term "FGF21 mediated" or similar refers to the fact that the FGF21 receptor and/or the antibodies of the invention mediate the cellular response and the FGF21 signaling pathway upon binding to β-klotho, thereby triggering a variety of physiological effects, including but not limited to a reduction in one or more of the following: plasma triglycerides, plasma insulin, plasma glucose, food intake, and body weight.

An "FGF21-associated disorder," "FGF21-associated condition," "disease or condition associated with FGF21," or similar terms as used herein, refer to any number of conditions or diseases for which the prevention, diagnosis, and/or treatment by activation of the FGF21 signaling pathway (e.g., by activation of FGF21 receptor signaling), is sought. These can include conditions, diseases, or disorders characterized by aberrant FGF21 signaling (e.g., aberrant activation of FGF21-mediated signaling and/or FGF21 receptor signaling). These conditions include but are not limited to metabolic, endocrine, and cardiovascular disorders, such as obesity, type 1 and type 2 diabetes mellitus, pancreatitis, dyslipidemia, nonalcoholic fatty liver disease (NAFLD), nonalcoholic steatohepatitis (NASH), insulin resistance, hyperinsulinemia, glucose intolerance, hyperglycemia, metabolic syndrome, acute myocardial infarction, hypertension, cardiovascular disease, atherosclerosis, peripheral arterial disease, stroke, heart failure, coronary heart disease, kidney disease, diabetic complications, neuropathy, gastroparesis, disorders associated with severe inactivating mutations in the insulin receptor, and other metabolic disorders, and in reducing the mortality and morbidity of critically ill patients.

"Type 2 diabetes mellitus" is a condition characterized by excess glucose production in spite of the availability of insulin, and circulating glucose levels remain excessively high as a result of inadequate glucose clearance.

"Type 1 diabetes mellitus" is a condition characterized by high blood glucose levels caused by total lack of insulin. This occurs when the body's immune system attacks the insulin-producing beta cells in the pancreas and destroys them. The pancreas then produces little or no insulin.

"Pancreatitis" is inflammation of the pancreas.

"Dyslipidemia" is a disorder of lipoprotein metabolism, including lipoprotein overproduction or deficiency. Dyslipidemias may be manifested by elevation of the total cholesterol, low-density lipoprotein (LDL) cholesterol and triglyceride concentrations, and a decrease in high-density lipoprotein (HDL) cholesterol concentration in the blood.

"Nonalcoholic steatohepatitis (NASH)" is a liver disease, not associated with alcohol consumption, characterized by fatty change of hepatocytes, accompanied by intralobular inflammation and fibrosis.

"Glucose intolerance," or Impaired Glucose Tolerance (IGT) is a pre-diabetic state of dysglycemia that is associated with increased risk of cardiovascular pathology. The pre-diabetic condition prevents a subject from moving glucose into cells efficiently and utilizing it as an efficient fuel source, leading to elevated glucose levels in blood and some degree of insulin resistance.

"Hyperglycemia" is defined as an excess of sugar (glucose) in the blood.

"Hypoglycemia", also called low blood sugar, occurs when your blood glucose level drops too low to provide enough energy for your body's activities.

"Hyperinsulinemia" is defined as a higher-than-normal level of insulin in the blood.

"Insulin resistance" is defined as a state in which a normal amount of insulin produces a subnormal biologic response.

"Obesity," in terms of the human subject, can be defined as that body weight over 20 percent above the ideal body weight for a given population (R. H. Williams, Textbook of Endocrinology, 1974, p. 904-916). It can also be defined as a Body Mass Index (BMI, defined as a person's weight in kilograms divided by the square of his height in meters (kg/m2)) as greater than or equal to 30.

"Metabolic syndrome" can be defined as a cluster of at least three of the following signs: abdominal fat—in most men, a 40-inch waist or greater; high blood sugar—at least 110 milligrams per deciliter (mg/dl) after fasting; high triglycerides—at least 150 mg/dL in the bloodstream; low HDL—less than 40 mg/dl; and, blood pressure of 130/85 mmHg or higher.

"Hypertension" or high blood pressure that is a transitory or sustained elevation of systemic arterial blood pressure to a level likely to induce cardiovascular damage or other adverse consequences. Hypertension has been arbitrarily defined as a systolic blood pressure above 140 mmHg or a diastolic blood pressure above 90 mmHg.

"Cardiovascular diseases" are diseases related to the heart or blood vessels.

"Peripheral arterial disease" occurs when plaque builds up in the arteries that carry blood to the head, organs and limbs. Over time, plaque can harden and narrow the arteries which limits the flow of oxygen-rich blood to organs and other parts of the the body.

"Atherosclerosis" is a vascular disease characterized by irregularly distributed lipid deposits in the intima of large and medium-sized arteries, causing narrowing of arterial lumens and proceeding eventually to fibrosis and calcification. Lesions are usually focal and progress slowly and intermittently. Limitation of blood flow accounts for most clinical manifestations, which vary with the distribution and severity of lesions.

"Stroke" is any acute clinical event, related to impairment of cerebral circulation, that lasts longer than 24 hours. A stroke involves irreversible brain damage, the type and severity of symptoms depending on the location and extent of brain tissue whose circulation has been compromised.

"Heart failure", also called congestive heart failure, is a condition in which the heart can no longer pump enough blood to the rest of the body.

"Coronary heart disease", also called coronary artery disease, is a narrowing of the small blood vessels that supply blood and oxygen to the heart.

"Kidney disease" or nephropathy is any disease of the kidney. Diabetic nephropathy is a major cause of morbidity and mortality in people with type 1 or type 2 diabetes mellitus.

"Diabetic complications" are problems, caused by high blood glucose levels, with other body functions such as kidneys, nerves (neuropathies), feet (foot ulcers and poor circulation) and eyes (e.g. retinopathies). Diabetes also increases the risk for heart disease and bone and joint disorders. Other long-term complications of diabetes include skin problems, digestive problems, sexual dysfunction and problems with teeth and gums.

"Neuroapathies" are any diseases involving the cranial nerves or the peripheral or autonomic nervous system.

"Gastroparesis" is weakness of gastric peristalsis, which results in delayed emptying of the bowels.

The critically ill patients encompassed by the present invention generally experience an unstable hypermetabolic state. This unstable metabolic state is due to changes in substrate metabolism, which may lead to relative deficiencies in some nutrients. Generally there is an increased oxidation of both fat and muscle.

Moreover, critically ill patients are preferably patients that experience systemic inflammatory response syndrome or respiratory distress. A reduction in morbidity means reducing the likelihood that a critically ill patient will develop additional illnesses, conditions, or symptoms or reducing the severity of additional illnesses, conditions, or symptoms. For example reducing morbidity may correspond to a decrease in the incidence of bacteremia or sepsis or complications associated with multiple organ failure.

The term "conservatively modified variant" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

For polypeptide sequences, "conservatively modified variants" include individual substitutions, deletions or additions to a polypeptide sequence which result in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. The following eight groups contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)). In some embodiments, the term "conservative sequence modifications" are used to refer to amino acid modifications that do not significantly affect or alter the binding characteristics of the antibody containing the amino acid sequence.

The term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents.

The term "human antibody", as used herein, is intended to include antibodies having variable regions in which both the framework and CDR regions are derived from sequences of human origin. Furthermore, if the antibody contains a constant region, the constant region also is derived from such human sequences, e.g., human germline sequences, or mutated versions of human germline sequences. The human antibodies of the invention may include amino acid residues not encoded by human sequences (e.g., mutations introduced by random or site-specific mutagenesis in vitro or by somatic mutation in vivo).

The term "human monoclonal antibody" refers to antibodies displaying a single binding specificity which have variable regions in which both the framework and CDR regions are derived from human sequences. In one embodiment, the human monoclonal antibodies are produced by a hybridoma which includes a B cell obtained from a transgenic nonhuman animal, e.g., a transgenic mouse, having a genome comprising a human heavy chain transgene and a light chain transgene fused to an immortalized cell.

A "humanized" antibody is an antibody that retains the reactivity of a non-human antibody while being less immunogenic in humans. This can be achieved, for instance, by retaining the non-human CDR regions and replacing the remaining parts of the antibody with their human counterparts (i.e., the constant region as well as the framework portions of the variable region). See, e.g., Morrison et al., Proc. Natl. Acad. Sci. USA, 81:6851-6855, 1984; Morrison and Oi, Adv. Immunol., 44:65-92, 1988; Verhoeyen et al., Science, 239:1534-1536, 1988; Padlan, Molec. Immun., 28:489-498, 1991; and Padlan, Molec. Immun., 31:169-217, 1994. Other examples of human engineering technology include, but are not limited to Xoma technology disclosed in U.S. Pat. No. 5,766,886.

The terms "identical" or percent "identity," in the context of two or more nucleic acids or polypeptide sequences, refer to two or more sequences or subsequences that are the same.

Two sequences are "substantially identical" if two sequences have a specified percentage of amino acid residues or nucleotides that are the same (i.e., 60% identity, optionally 65%, 70%, 75%, 80%, 85%, 90%, 95%, or 99% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 50 nucleotides (or 10 amino acids) in length, or more preferably over a region that is 100 to 500 or 1000 or more nucleotides (or 20, 50, 200 or more amino acids) in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (1970) Adv. Appl. Math. 2:482c, by the homology alignment algorithm of Needleman and Wunsch, J. Mol. Biol. 48:443, 1970, by the search for similarity method of Pearson and Lipman, Proc. Nat'l. Acad. Sci. USA 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Brent et al., Current Protocols in Molecular Biology, John Wiley & Sons, Inc. (Ringbou ed., 2003)).

Two examples of algorithms that are suitable for determining percent sequence identity and sequence similarity are the BLAST and BLAST 2.0 algorithms, which are described in Altschul et al., Nuc. Acids Res. 25:3389-3402, 1977; and Altschul et al., J. Mol. Biol. 215:403-410, 1990, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0).

For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff, Proc. Natl. Acad. Sci. USA 89:10915, 1989) alignments (B) of 50, expectation (E) of 10, M=5, N=−4, and a comparison of both strands.

The BLAST algorithm also performs a statistical analysis of the similarity between two sequences (see, e.g., Karlin and Altschul, Proc. Natl. Acad. Sci. USA 90:5873-5787, 1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The percent identity between two amino acid sequences can also be determined using the algorithm of E. Meyers and W. Miller (Comput. Appl. Biosci., 4:11-17, 1988) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. Mol. Biol. 48:444-453, 1970) algorithm which has been incorporated into the GAP program in the GCG software package (available on the world wide web at gcg.com), using either a Blossom 62 matrix or a PAM250 matrix, and a gap weight of 16, 14, 12, 10, 8, 6, or 4 and a length weight of 1, 2, 3, 4, 5, or 6.

Other than percentage of sequence identity noted above, another indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The term "isolated antibody" refers to an antibody that is substantially free of other antibodies having different antigenic specificities (e.g., an isolated antibody that specifically binds β-klotho is substantially free of antibodies that specifically bind antigens other than β-klotho). An isolated antibody that specifically binds β-klotho may, however, have cross-reactivity to other antigens. Moreover, an isolated antibody may be substantially free of other cellular material and/or chemicals.

The term "isotype" refers to the antibody class (e.g., IgM, IgE, IgG such as IgG1 or IgG4) that is provided by the heavy chain constant region genes. Isotype also includes modified versions of one of these classes, where modifications have been made to alter the Fc function, for example, to enhance or reduce effector functions or binding to Fc receptors.

The term "$k_{assoc}$" or "$k_a$", as used herein, is intended to refer to the association rate of a particular antibody-antigen interaction, whereas the term "$k_{dis}$" or "$k_d$," as used herein, is intended to refer to the dissociation rate of a particular antibody-antigen interaction. The term "$K_D$", as used herein, is intended to refer to the dissociation constant, which is obtained from the ratio of $k_d$ to $k_a$ (i.e. $k_d/k_a$) and is expressed as a molar concentration (M). $K_D$ values for antibodies can be determined using methods well established in the art. Methods for determining the $K_D$ of an antibody include measuring surface plasmon resonance using a biosensor system such as a Biacore® system, or measuring affinity in solution by solution equilibrium titration (SET).

The terms "monoclonal antibody" or "monoclonal antibody composition" as used herein refer to a preparation of antibody molecules of single molecular composition. A monoclonal antibody composition displays a single binding specificity and affinity for a particular epitope.

The term "nucleic acid" is used herein interchangeably with the term "polynucleotide" and refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, as detailed below, degenerate codon substitutions may be achieved by generating sequences in which the third position of one or more selected (or all) codons is substituted with mixed-base and/or deoxyinosine residues (Batzer et al., Nucleic Acid Res. 19:5081, 1991; Ohtsuka et al., J. Biol. Chem. 260:2605-2608, 1985; and Rossolini et al., Mol. Cell. Probes 8:91-98, 1994).

The term "operably linked" refers to a functional relationship between two or more polynucleotide (e.g., DNA) segments. Typically, the term refers to the functional relationship of a transcriptional regulatory sequence to a transcribed sequence. For example, a promoter or enhancer sequence is operably linked to a coding sequence if it stimulates or modulates the transcription of the coding sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

As used herein, the term, "optimized" means that a nucleotide sequence has been altered to encode an amino acid sequence using codons that are preferred in the production cell or organism, generally a eukaryotic cell, for example, a cell of *Pichia*, a Chinese Hamster Ovary cell (CHO) or a human cell. The optimized nucleotide sequence is engineered to retain completely or as much as possible the amino acid sequence originally encoded by the starting nucleotide sequence, which is also known as the "parental" sequence. The optimized sequences herein have been engineered to have codons that are preferred in mammalian cells. However, optimized expression of these sequences in other eukaryotic cells or prokaryotic cells is also envisioned herein. The amino acid sequences encoded by optimized nucleotide sequences are also referred to as optimized.

The terms "polypeptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. Unless otherwise indicated, a particular polypeptide sequence also implicitly encompasses conservatively modified variants thereof.

The term "recombinant human antibody", as used herein, includes all human antibodies that are prepared, expressed, created or isolated by recombinant means, such as antibodies isolated from an animal (e.g., a mouse) that is transgenic or transchromosomal for human immunoglobulin genes or a hybridoma prepared therefrom, antibodies isolated from a host cell transformed to express the human antibody, e.g., from a transfectoma, antibodies isolated from a recombinant, combinatorial human antibody library, and antibodies prepared, expressed, created or isolated by any other means that involve splicing of all or a portion of a human immunoglobulin gene, sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

The term "recombinant host cell" (or simply "host cell") refers to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

The term "subject" includes human and non-human animals Non-human animals include all vertebrates (e.g.: mammals and non-mammals) such as, non-human primates (e.g.: cynomolgus monkey), sheep, dog, cow, chickens, amphibians, and reptiles. Except when noted, the terms "patient" or "subject" are used herein interchangeably. As used herein, the terms "cyno" or "cynomolgus" refer to the cynomolgus monkey (*Macaca fascicularis*).

As used herein, the term "treating" or "treatment" of any disease or disorder (e.g., FGF21 associated disorder) refers in one embodiment, to ameliorating the disease or disorder (i.e., slowing or arresting or reducing the development of the disease or at least one of the clinical symptoms thereof). In another embodiment "treating" or "treatment" refers to alleviating or ameliorating at least one physical parameter including those which may not be discernible by the patient. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to preventing or delaying the onset or development or progression of the disease or disorder.

"Prevention" as it relates to indications described herein, including, e.g., FGF21 associated disorder, means any action that prevents or slows a worsening in e.g., FGF21 associated disease parameters, as described below, in a patient at risk for said worsening.

The term "vector" is intended to refer to a polynucleotide molecule capable of transporting another polynucleotide to which it has been linked. One type of vector is a "plasmid", which refers to a circular double stranded DNA loop into which additional DNA segments may be ligated. Another type of vector is a viral vector, such as an adeno-associated viral vector (AAV, or AAV2), wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors").

In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

"Modulation of FGF21 activity," as used herein, refers to an increase or decrease in FGF21 activity that can be a result of, for example, interaction of an agent with an FGF21 polynucleotide or polypeptide, activation of the FGF21 signaling pathway and/or activation of FGF21-mediated signaling (e.g., FGF21-receptor-dependent signaling), and the like. For example, modulation of a biological activity refers to an increase or a decrease in a biological activity. FGF21 activity can be assessed by means including, without limitation, assaying blood glucose, insulin, triglyceride, or cholesterol levels in a subject; by assessing polypeptide levels of beta-klotho and/or FGF receptors (e.g., FGFR-1c); or by assessing activation of FGF21-mediated signaling (e.g., of FGF21-receptor-dependent signaling).

Comparisons of FGF21 activity can also be accomplished by, e.g., measuring levels of an FGF21 downstream biomarker, and measuring increases in FGF21 signaling. Activity can also be assessed by measuring: cell signaling; kinase activity; glucose uptake into adipocytes; blood insulin, triglyceride, or cholesterol level fluctuations; liver lipid or liver triglyceride level changes; interactions between FGF21 and/or beta-klotho and an FGF21 receptor; or phosphorylation of an FGF21 receptor. In some embodiments phosphorylation of an FGF21 receptor can be tyrosine phosphorylation. In some embodiments modulation of FGF21 activity can cause modulation of an FGF21-related phenotype.

An "FGF21 downstream biomarker," as used herein, is a gene or gene product, or measurable indicia of a gene or gene product. In some embodiments, a gene or activity that is a downstream marker of FGF21 exhibits an altered level of expression, or in a vascular tissue. In some embodiments, an activity of the downstream marker is altered in the presence of an FGF21 modulator. In some embodiments, the downstream markers exhibit altered levels of expression when FGF21 is perturbed with an FGF21 modulator of the present invention. FGF21 downstream markers include, without limitation, glucose or 2-deoxy-glucose uptake, pERK and other phosphorylated or acetylated proteins or NAD levels.

As used herein, the term "up-regulates" refers to an increase, activation or stimulation of an activity or quantity. For example, in the context of the present invention, FGF21 modulators may increase the activity of beta-klotho and/or an FGF21 receptor. In one embodiment, FGFR-1c may be upregulated in response to an FGF21 modulator. Upregulation can also refer to an FGF21-related activity, such as e.g., the ability to lower blood glucose, insulin, triglyceride, or cholesterol levels; to reduce liver lipid or triglyceride levels; to reduce body weight; to improve glucose tolerance, energy expenditure, or insulin sensitivity; or to cause phosphorylation of an FGF21 receptor; or to increase an FGF21 downstream marker. The FGF21 receptor can be β-klotho and FGFR-1c. Up-regulation may be at least 25%, at least 50%, at least 75%, at least 100%, at least 150%, at least 200%, at least 250%, at least 400%, or at least 500% as compared to a control.

As used herein, the term "modulator" refers to a composition that modulates one or more physiological or biochemical events associated with an FGF21-associated disorder, such as type 1 or type 2 diabetes mellitus or a metabolic condition like obesity. Said events include but are not limited to the ability to lower blood glucose, insulin, triglyceride, or cholesterol levels; to reduce liver lipid or liver triglyceride levels; to reduce body weight; and to improve glucose tolerance, energy expenditure, or insulin sensitivity.

DETAILED DESCRIPTION

Figure 1A:
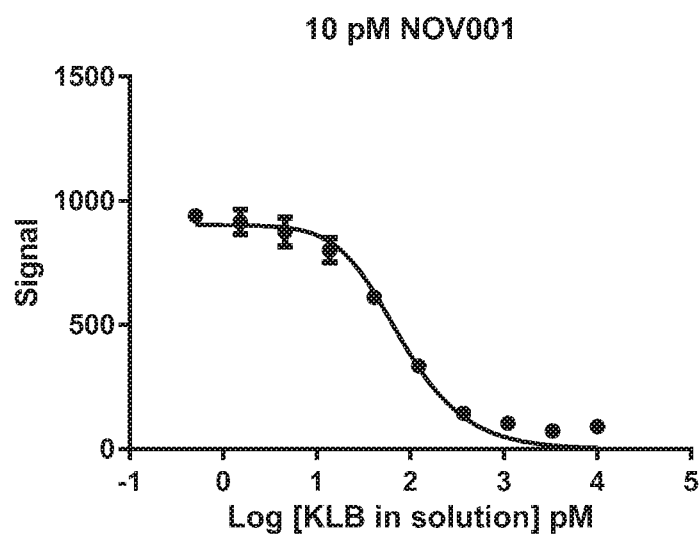
FIGS. 1A-C: Solution equilibrium titration binding assay of FGF21 mimetic antibodies A) NOV001, B) NOV002, and C) NOV004 to human β-klotho.

The present invention is based, in part, on the discovery of antibody molecules that specifically bind to β-klotho and lead to activation of FGF receptors, e.g., FGFR1c, and the activation of FGF21-mediated signaling (e.g., FGF21-receptor-dependent signaling). The invention relates to both full IgG format antibodies as well as antigen-binding fragments thereof, such as Fab fragments (e.g., antibodies NOV001, NOV002, NOV003, and NOV004).

Accordingly, the present invention provides antibodies that specifically bind to β-klotho (e.g., human and cynomolgus monkey β-klotho), pharmaceutical compositions, production methods, and methods of use of such antibodies and compositions.

FGF21 Proteins

The present disclosure provides FGF21 mimetic mAbs (i.e., monoclonal antibodies that bind to beta-klotho (β-klotho)) that can induce FGF21-mediated signaling (e.g., FGF21-receptor-mediated signaling), as defined herein. In vivo, the mature form of FGF21 is the active form of the molecule. The FGF21 wild-type sequence has NCBI reference sequence number NP_061986.1, and can be found in such issued patents as, e.g., U.S. Pat. No. 6,716,626 B1, assigned to Chiron Corporation (SEQ ID NO:1).

```
Met Asp Ser Asp Glu Thr Gly Phe Glu His Ser Gly
 1               5                  10

Leu Trp Val Ser Val Leu Ala Gly Leu Leu Leu Gly
            15                  20

Ala Cys Gln Ala His Pro Ile Pro Asp Ser Ser Pro
25                  30                  35

Leu Leu Gln Phe Gly Gly Gln Val Arg Gln Arg Tyr
                40                  45

Leu Tyr Thr Asp Asp Ala Gln Gln Thr Glu Ala His
    50                  55                  60

Leu Glu Ile Arg Glu Asp Gly Thr Val Gly Gly Ala
                65                  70

Ala Asp Gln Ser Pro Glu Ser Leu Leu Gln Leu Lys
                75                  80

Ala Leu Lys Pro Gly Val Ile Gln Ile Leu Gly Val
85                  90                  95

Lys Thr Ser Arg Phe Leu Cys Gln Arg Pro Asp Gly
                100                 105

Ala Leu Tyr Gly Ser Leu His Phe Asp Pro Glu Ala
        110                 115                 120

Cys Ser Phe Arg Glu Leu Leu Leu Glu Asp Gly Tyr
                    125                 130

Asn Val Tyr Gln Ser Glu Ala His Gly Leu Pro Leu
                    135                 140

His Leu Pro Gly Asn Lys Ser Pro His Arg Asp Pro
145                 150                 155

Ala Pro Arg Gly Pro Ala Arg Phe Leu Pro Leu Pro
                    160                 165

Gly Leu Pro Pro Ala Leu Pro Glu Pro Pro Gly Ile
                    170                 175                 180

Leu Ala Pro Gln Pro Pro Asp Val Gly Ser Ser Asp
                    185                 190

Pro Leu Ser Met Val Gly Pro Ser Gln Gly Arg Ser
                    195                 200

Pro Ser Tyr Ala Ser
205             209
```

The corresponding mRNA sequence coding for the full-length FGF21 polypeptide (NCBI reference sequence number NM_019113.2) is shown below (SEQ ID NO:2)

```
  1  ctgtcagctg aggatccagc cgaaagagga gccaggcact caggccacct gagtctactc
 61  acctggacaa ctggaatctg gcaccaattc taaaccactc agcttctccg agctcacacc
121  ccggagatca cctgaggacc cgagccattg atggactcgg acgagaccgg gttcgagcac
181  tcaggactgt gggtttctgt gctggctggt cttctgctgg gagcctgcca ggcacacccc
241  atccctgact ccagtcctct cctgcaattc gggggccaag tccggcagcg gtacctctac
301  acagatgatg cccagcagac agaagcccac ctggagatca gggaggatgg gacggtgggg
361  ggcgctgctg accagagccc cgaaagtctc ctgcagctga aagccttgaa gccgggagtt
421  attcaaatct tgggagtcaa gacatccagg ttcctgtgcc agcggccaga tggggccctg
481  tatggatcgc tccactttga ccctgaggcc tgcagcttcc gggagctgct tcttgaggac
541  ggatacaatg tttaccagtc cgaagcccac ggcctcccgc tgcacctgcc agggaacaag
601  tccccacacc gggaccctgc acccgagga ccagctcgct tcctgccact accaggcctg
661  cccccgcac tcccggagcc acccggaatc ctggccccc agcccccga tgtgggctcc
```

```
721  tcggaccctc tgagcatggt gggaccttcc cagggccgaa gccccagcta cgcttcctga 781  agccagaggc tgtttactat gacatctcct ctttatttat taggttattt atcttattta 841  ttttttatt tttcttactt gagataataa agagttccag aggagaaaaa aaaaaaaaaa 901  aaaaaaaa aaaaaaaaaa aaaaaaaaaa aaaaaaaaaa
```

The mature FGF21 sequence lacks a leader sequence and may also include other modifications of a polypeptide such as proteolytic processing of the amino terminus (with or without a leader sequence) and/or the carboxyl terminus, cleavage of a smaller polypeptide from a larger precursor, N-linked and/or O-linked glycosylation, and other post-translational modifications understood by those with skill in the art. A representative example of a mature FGF21 sequence has the following sequence (SEQ ID NO:83, which represents amino acid positions 29-209 of full length FGF21 protein sequence (NCBI reference sequence number NP_061986.1)):

```
His Pro Ile Pro Asp Ser Ser Pro Leu Leu Gln
                 5                      10

Phe Gly Gly Gln Val Arg Gln Arg Tyr Leu Tyr
            15                  20

Thr Asp Asp Ala Gln Gln Thr Glu Ala His Leu
            25                  30

Glu Ile Arg Glu Asp Gly Thr Val Gly Gly Ala
        35                  40

Ala Asp Gln Ser Pro Glu Ser Leu Leu Gln Leu
45                  50                  55

Lys Ala Leu Lys Pro Gly Val Ile Gln Ile Leu
                60                  65

Gly Val Lys Thr Ser Arg Phe Leu Cys Gln Arg
            70                  75

Pro Asp Gly Ala Leu Tyr Gly Ser Leu His Phe
        80                  85

Asp Pro Glu Ala Cys Ser Phe Arg Glu Leu Leu
        90                  95

Leu Glu Asp Gly Tyr Asn Val Tyr Gln Ser Glu
100                 105                 110

Ala His Gly Leu Pro Leu His Leu Pro Gly Asn
                115                 120

Lys Ser Pro His Arg Asp Pro Ala Pro Arg Gly
                125                 130

Pro Ala Arg Phe Leu Pro Leu Pro Gly Leu Pro
            135                 140

Pro Ala Leu Pro Glu Pro Pro Gly Ile Leu Ala
            145                 150

Pro Gln Pro Pro Asp Val Gly Ser Ser Asp Pro
155                 160                 165

Leu Ser Met Val Gly Pro Ser Gln Gly Arg Ser
                170                 175

Pro Ser Tyr Ala Ser
                180
```

The corresponding cDNA sequence coding for the mature FGF21 polypeptide (SEQ ID NO:83) is shown below (SEQ ID NO:84):

```
  1  cacccccatcc ctgactccag tcctctcctg caattcgggg gccaagtccg gcagcggtac 61  ctctacacag atgatgccca gcagacagaa gcccacctgg agatcaggga ggatgggacg 121  gtgggggggcg ctgctgacca gagccccgaa agtctcctgc agctgaaagc cttgaagccg 181  ggagttattc aaatcttggg agtcaagaca tccaggttcc tgtgccagcg gccagatggg 240  gccctgtatg gatcgctcca ctttgaccct gaggcctgca gcttccggga gctgcttctt 301  gaggacggat acaatgttta ccagtccgaa gcccacggcc tccogctgca cctgccaggg 360  aacaagtccc cacaccggga ccctgcaccc cgaggaccag ctcgcttcct gccactacca 421  ggcctgcccc ccgcactccc ggagccaccc ggaatcctgg cccccagcc ccccgatgtg 481  ggctcctcgg accctctgag catggtggga ccttcccagg gccgaagccc cagctacgct 541  tcctga
```

FGF21 Mimetic Antibodies & Antigen-Binding Fragments

The present invention provides antibodies that specifically bind to β-klotho. In some embodiments, the present invention provides antibodies that specifically bind to human and cynomolgus monkey β-klotho. Antibodies of the invention include, but are not limited to, the human monoclonal antibodies and Fabs, isolated as described in the Examples.

The β-klotho wild-type sequence has NCBI reference sequence number NP_783864.1, and can be found in such literature as Xu, et al. (2007) J Biol Chem. 282(40):29069-72 and Lin, et al. (2007) J Biol Chem. 282(37):27277-84. The full-length cDNA encoding human β-klotho has Gen-Bank Accession number NM_175737). The protein sequence is as follows (SEQ ID NO:262).

```
   1  mkpgcaagsp gnewiffstd eittryrntm sngglqrsvi lsalillrav tgfsgdgrai
  61  wsknpnftpv nesqlflydt fpknffwgig tgalqvegsw kkdgkgpsiw dhfihthlkn
 121  vsstngssds yiflekdlsa ldfigvsfyq fsiswprlfp dgivtvanak glqyystlld
 181  alvlrniepi vtlyhwdlpl alqekyggwk ndtiidifnd yatycfqmfg drvkywitih
 241  npylvawhgy gtgmhapgek gnlaavytvg hnlikahskv whnynthfrp hqkgwlsitl
 301  gshwiepnrs entmdifkcq qsmvsvlgwf anpihgdgdy pegmrkklfs vlpifseaek
 361  hemrgtadff afsfgpnnfk pintmakmgq nvslnlreal nwikleynnp riliaengwf
 421  tdsrvktedt taiymmknfl sqvlqairld eirvfgytaw slldgfewqd aytirrglfy
 481  vdfnskqker kpkssahyyk qiirengfsl kestpdvqgq fpcdfswgvt esvlkpesva
 541  sspqfsdphl yvwnatgnrl lhrvegvrlk trpaqctdfv nikkqlemla rmkvthyrfa
 601  ldwasvlptg nlsavnrqal ryyrcvvseg lklgisamvt lyypthahlg lpepllhadg
 661  wlnpstaeaf qayaglcfqe lgdlvklwit inepnrlsdi ynrsgndtyg aahnllvaha
 721  lawrlydrqf rpsqrgaysl slhadwaepa npyadshwra aerflqfeia wfaeplfktg
 781  dypaamreyi askhrrglss salprlteae rrllkgtvdf calnhfttrf vmheqlagsr
 841  ydsdrdiqfl qditrlsspt rlavipwgvr kllrwvrrny gdmdiyitas giddqaledd
 901  rlrkyylgky lqevlkayli dkvrikgyya fklaeekskp rfgfftsdfk akssiqfynk
 961  vissrgfpfe nsssrcsqtq entectvclf lvqkkplifl gccffstivl llsiaifqrq
1021  krrkfwkakn lqhiplkkgk rvvs
```

The present invention provides antibodies that specifically bind a β-klotho protein (e.g., human and cynomolgus monkey β-klotho), wherein the antibodies comprise a VH domain having an amino acid sequence of SEQ ID NOs: 9, 29, 49, or 69. The present invention also provides antibodies that specifically bind to a β-klotho protein, wherein the antibodies comprise a VH CDR having an amino acid sequence of any one of the VH CDRs listed in Table 1, infra. In particular, the invention provides antibodies that specifically bind to a β-klotho protein (e.g., human and cynomolgus monkey β-klotho), wherein the antibodies comprise (or alternatively, consist of) one, two, three, or more VH CDRs having an amino acid sequence of any of the VH CDRs listed in Table 1, infra.

The present invention provides antibodies that specifically bind to a β-klotho protein, said antibodies comprising a VL domain having an amino acid sequence of SEQ ID NOs: 19, 39, 59, or 79. The present invention also provides antibodies that specifically bind to a β-klotho protein (e.g., human and cynomolgus monkey β-klotho), said antibodies comprising a VL CDR having an amino acid sequence of any one of the VL CDRs listed in Table 1, infra. In particular, the invention provides antibodies that specifically bind to a β-klotho protein (e.g., human and cynomolgus monkey β-klotho), said antibodies comprising (or alternatively, consisting of) one, two, three or more VL CDRs having an amino acid sequence of any of the VL CDRs listed in Table 1, infra.

Other antibodies of the invention include amino acids that have been mutated, yet have at least 60, 70, 80, 85, 90 or 95 percent identity in the CDR regions with the CDR regions depicted in the sequences described in Table 1. In some embodiments, it includes mutant amino acid sequences wherein no more than 1, 2, 3, 4 or 5 amino acids have been mutated in the CDR regions when compared with the CDR regions depicted in the sequence described in Table 1.

The present invention also provides nucleic acid sequences that encode VH, VL, the full length heavy chain, and the full length light chain of the antibodies that specifically bind to a β-klotho protein (e.g., human and cynomolgus monkey β-klotho). Such nucleic acid sequences can be optimized for expression in mammalian cells (for example, Table 1 shows the optimized nucleic acid sequences for the heavy chain and light chain of antibodies of the invention).

TABLE 1

Examples of FGF21 Mimetic Antibodies and Fabs

| Sequence Description | Sequence Identifier (SEQ ID NO:) | Amino acid or polynucleotide sequence |
|---|---|---|
| NOV001 (IgG1 LALA version of NOV003) | | |
| HCDR1 (Kabat) | 3 | DYYIN |
| HCDR2 (Kabat) | 4 | RIHPGSGNTYYNEKFQG |

TABLE 1-continued

Examples of FGF21 Mimetic Antibodies and Fabs

| Sequence Description | Sequence Identifier (SEQ ID NO:) | Amino acid or polynucleotide sequence |
|---|---|---|
| HCDR3 (Kabat) | 5 | LLLRSYGMDD |
| HCDR1 (Chothia) | 6 | GYTFTDY |
| HCDR2 (Chothia) | 7 | HPGSGN |
| HCDR3 (Chothia) | 8 | LLLRSYGMDD |
| HCDR1 (Combined) | 263 | GYTFTDYYIN |
| HCDR2 (Combined) | 4 | RIHPGSGNTYYNEKFQG |
| HCDR3 (Combined) | 5 | LLLRSYGMDD |
| HCDR1 (IMGT) | 264 | GYTFTDYY |
| HCDR2 (IMGT) | 265 | IHPGSGNT |
| HCDR3 (IMGT) | 266 | AILLLRSYGMDD |
| VH | 9 | QVQLVQSGAEVKKPGSSVKVSCKASGYTFTDYYINWVRQA PGQGLEWMGRIHPGSGNTYYNEKFQGRVTLTADKSTSTAY MELSSLRSEDTAVYYCAILLLRSYGMDDWGQGTTVTVSS |
| DNA VH | 10 | CAGGTGCAGCTGGTGCAGTCTGGCGCCGAAGTGAAGAAAC CCGGCAGCAGCGTGAAGGTGTCCTGCAAGGCCAGCGGCTA CACCTTTACCGACTACTACATCAACTGGGTGCGCCAGGCC CCTGGACAGGGCCTGGAATGGATGGGCAGAATCCACCCCG GCTCCGGCAACACCTACTACAACGAGAAGTTCCAGGGCAG AGTGACCCTGACCGCCGACAAGAGCACCAGCACCGCCTAC ATGGAACTGAGCAGCCTGCGGAGCGAGGACACCGCCGTGT ACTACTGTGCCATCCTGCTGCTGCGGAGCTACGGCATGGA TGATTGGGGCCAGGGCACCACCGTGACCGTCAGCTCA |
| Heavy Chain | 11 | QVQLVQSGAEVKKPGSSVKVSCKASGYTFTDYYINWVRQA PGQGLEWMGRIHPGSGNTYYNEKFQGRVTLTADKSTSTAY MELSSLRSEDTAVYYCAILLLRSYGMDDWGQGTTVTVSSA STKGPSVFPLAPSSKSTSGGTAALGCLVKDYFPEPVTVSW NSGALTSGVHTFPAVLQSSGLYSLSSVVTVPSSSLGTQTY ICNVNHKPSNTKVDKRVEPKSCDKTHTCPPCPAPEAAGGP SVFLFPPKPKDTLMISRTPEVTCVVVDVSHEDPEVKFNWY VDGVEVHNAKTKPREEQYNSTYRVVSVLTVLHQDWLNGKE YKCKVSNKALPAPIEKTISKAKGQPREPQVYTLPPSREEM TKNQVSLTCLVKGFYPSDIAVEWESNGQPENNYKTTPPVL DSDGSFFLYSKLTVDKSRWQQGNVFSCSVMHEALHNHYTQ KSLSLSPGK |
| DNA Heavy Chain | 12 | CAGGTGCAGCTGGTGCAGTCTGGCGCCGAAGTGAAGAAAC CCGGCAGCAGCGTGAAGGTGTCCTGCAAGGCCAGCGGCTA CACCTTTACCGACTACTACATCAACTGGGTGCGCCAGGCC CCTGGACAGGGCCTGGAATGGATGGGCAGAATCCACCCCG GCTCCGGCAACACCTACTACAACGAGAAGTTCCAGGGCAG AGTGACCCTGACCGCCGACAAGAGCACCAGCACCGCCTAC ATGGAACTGAGCAGCCTGCGGAGCGAGGACACCGCCGTGT ACTACTGTGCCATCCTGCTGCTGCGGAGCTACGGCATGGA TGATTGGGGCCAGGGCACCACCGTGACCGTCAGCTCAGCT AGCACCAAGGGCCCCAGCGTGTTCCCCCTGGCCCCCAGCA GCAAGAGCACCAGCGGCGGCACAGCCGCCCTGGGCTGCCT GGTGAAGGACTACTTCCCCGAGCCCGTGACCGTGTCCTGG AACAGCGGAGCCCTGACCTCCGGCGTGCACACCTTCCCCG CCGTGCTGCAGAGCAGCGGCCTGTACAGCCTGTCCAGCGT GGTGACAGTGCCCAGCAGCAGCCTGGGCACCCAGACCTAC ATCTGCAACGTGAACCACAAGCCCAGCAACACCAAGGTGG ACAAGAGAGTGGAGCCCAAGAGCTGCGACAAGACCCACAC CTGCCCCCCCTGCCCAGCCCCAGAGGCAGCGGGCGGACCC TCCGTGTTCCTGTTCCCCCCCAAGCCCAAGGACACCCTGA TGATCAGCAGGACCCCCGAGGTGACCTGCGTGGTGGTGGA CGTGAGCCACGAGGACCCCGAGGTGAAGTTCAACTGGTAC GTGGACGGCGTGGAGGTGCACAACGCCAAGACCAAGCCCA GAGAGGAGCAGTACAACAGCACCTACAGGGTGGTGTCCGT GCTGACCGTGCTGCACCAGGACTGGCTGAACGGCAAGGAA TACAAGTGCAAGGTCTCCAACAAGGCCCTGCCAGCCCCCA TCGAAAAGACCATCAGCAAGGCCAAGGGCCAGCCACGGGA |

TABLE 1-continued

Examples of FGF21 Mimetic Antibodies and Fabs

| Sequence Description | Sequence Identifier (SEQ ID NO:) | Amino acid or polynucleotide sequence |
|---|---|---|
| | | GCCCCAGGTGTACACCCTGCCCCCCTCCCGGGAGGAGATG<br>ACCAAGAACCAGGTGTCCCTGACCTGTCTGGTGAAGGGCT<br>TCTACCCCAGCGACATCGCCGTGGAGTGGGAGAGCAACGG<br>CCAGCCCGAGAACAACTACAAGACCACCCCCCCAGTGCTG<br>GACAGCGACGGCAGCTTCTTCCTGTACAGCAAGCTGACCG<br>TGGACAAGTCCAGGTGGCAGCAGGGCAACGTGTTCAGCTG<br>CAGCGTGATGCACGAGGCCCTGCACAACCACTACACCCAG<br>AAGAGCCTGAGCCTGTCCCCCGGCAAG |
| LCDR1 (Kabat) | 13 | KSSQSIVHSSGNTYLE |
| LCDR2 (Kabat) | 14 | KVSNRFS |
| LCDR3 (Kabat) | 15 | FQGSHIPYT |
| LCDR1 (Chothia) | 16 | SQSIVHSSGNTY |
| LCDR2 (Chothia) | 17 | KVS |
| LCDR3 (Chothia) | 18 | GSHIPY |
| LCDR1 (Combined) | 13 | KSSQSIVHSSGNTYLE |
| LCDR2 (Combined) | 14 | KVSNRFS |
| LCDR3 (Combined) | 15 | FQGSHIPYT |
| LCDR1 (IMGT) | 267 | QSIVHSSGNTY |
| LCDR2 (IMGT) | 17 | KVS |
| LCDR3 (IMGT) | 15 | FQGSHIPYT |
| VL | 19 | DVVMTQTPLSLSVTPGQPASISCKSSQSIVHSSGNTYLEW<br>YLQKPGQSPQLLIYKVSNRFSGVPDRFSGSGSGTDFTLKI<br>SRVEAEDVGVYYCFQGSHIPYTFGQGTKLEIK |
| DNA VL | 20 | GACGTGGTGATGACCCAGACCCCCCTGAGCCTGAGCGTGA<br>CACCTGGACAGCCTGCCAGCATCTCCTGCAAGAGCAGCCA<br>GAGCATCGTGCACAGCAGCGGCAACACCTACCTGGAATGG<br>TATCTGCAGAAGCCCGGCCAGAGCCCCAGCTGCTGATCT<br>ACAAGGTGTCCAACCGGTTCAGCGGCGTGCCCGACAGATT<br>TTCTGGCAGCGGCTCCGGCACCGACTTCACCCTGAAGATC<br>TCCCGGGTGGAAGCCGAGGACGTGGGCGTGTACTACTGTT<br>TTCAAGGCTCCCACATCCCCTACACCTTCGGCCAGGGCAC<br>CAAGCTGGAAATCAAG |
| Light Chain | 21 | DVVMTQTPLSLSVTPGQPASISCKSSQSIVHSSGNTYLEW<br>YLQKPGQSPQLLIYKVSNRFSGVPDRFSGSGSGTDFTLKI<br>SRVEAEDVGVYYCFQGSHIPYTFGQGTKLEIKRTVAAPSV<br>FIFPPSDEQLKSGTASVVCLLNNFYPREAKVQWKVDNALQ<br>SGNSQESVTEQDSKDSTYSLSSTLTLSKADYEKHKVYACE<br>VTHQGLSSPVTKSFNRGEC |
| DNA Light Chain | 22 | GACGTGGTGATGACCCAGACCCCCCTGAGCCTGAGCGTGA<br>CACCTGGACAGCCTGCCAGCATCTCCTGCAAGAGCAGCCA<br>GAGCATCGTGCACAGCAGCGGCAACACCTACCTGGAATGG<br>TATCTGCAGAAGCCCGGCCAGAGCCCCAGCTGCTGATCT<br>ACAAGGTGTCCAACCGGTTCAGCGGCGTGCCCGACAGATT<br>TTCTGGCAGCGGCTCCGGCACCGACTTCACCCTGAAGATC<br>TCCCGGGTGGAAGCCGAGGACGTGGGCGTGTACTACTGTT<br>TTCAAGGCTCCCACATCCCCTACACCTTCGGCCAGGGCAC<br>CAAGCTGGAAATCAAGCGTACGGTGGCCGCTCCCAGCGTG<br>TTCATCTTCCCCCCCAGCGACGAGCAGCTGAAGAGCGGCA<br>CCGCCAGCGTGGTGTGCCTGCTGAACAACTTCTACCCCCG<br>GGAGGCCAAGGTGCAGTGGAAGGTGGACAACGCCCTGCAG<br>AGCGGCAACAGCCAGGAGAGCGTCACCGAGCAGGACAGCA<br>AGGACTCCACCTACAGCCTGAGCAGCACCCTGACCCTGAG<br>CAAGGCCGACTACGAGAAGCATAAGGTGTACGCCTGCGAG<br>GTGACCCACCAGGGCCTGTCCAGCCCCGTGACCAAGAGCT<br>TCAACAGGGGCGAGTGC |

TABLE 1-continued

Examples of FGF21 Mimetic Antibodies and Fabs

| Sequence Description | Sequence Identifier (SEQ ID NO:) | Amino acid or polynucleotide sequence |
|---|---|---|
| NOV002 (IgG1 LALA version of NOV004) | | |
| HCDR1 (Kabat) | 23 | SGYTWH |
| HCDR2 (Kabat) | 24 | YIHYSVYTNYNPSVKG |
| HCDR3 (Kabat) | 25 | RTTSLERYFDV |
| HCDR1 (Chothia) | 26 | GYSITSGY |
| HCDR2 (Chothia) | 27 | HYSVY |
| HCDR3 (Chothia) | 28 | RTTSLERYFDV |
| HCDR1 (Combined) | 268 | GYSITSGYTWH |
| HCDR2 (Combined) | 24 | YIHYSVYTNYNPSVKG |
| HCDR3 (Combined) | 25 | RTTSLERYFDV |
| HCDR1 (IMGT) | 269 | GYSITSGYT |
| HCDR2 (IMGT) | 270 | IHYSVYT |
| HCDR3 (IMGT) | 271 | ARRTTSLERYFDV |
| VH | 29 | EVQLVESGGGLVKPGGSLRLSCAVSGYSITSGYTWHWVRQ APGKGLEWLSYIHYSVYTNYNPSVKGRFTISRDTAKNSFY LQMNSLRAEDTAVYYCARRTTSLERYFDVWGQGTLVTVSS |
| DNA VH | 30 | GAGGTGCAGCTGGTGGAATCTGGCGGCGGACTCGTGAAGC CTGGCGGCTCTCTGAGACTGAGCTGTGCCGTGTCCGGCTA CAGCATCACCAGCGGCTACACCTGGCATTGGGTGCGCCAG GCCCCTGGCAAAGGACTGGAATGGCTGTCCTACATCCACT ACAGCGTGTACACCAACTACAACCCCAGCGTGAAGGGCCG GTTCACCATCAGCAGAGACACCGCCAAGAACAGCTTCTAC CTGCAAATGAACAGCCTGCGGGCCGAGGACACCGCCGTGT ACTACTGTGCCAGACGGACCACCAGCCTGGAACGGTACTT CGACGTGTGGGGCCAGGGCACACTCGTGACCGTCAGCTCA |
| Heavy Chain | 31 | EVQLVESGGGLVKPGGSLRLSCAVSGYSITSGYTWHWVRQ APGKGLEWLSYIHYSVYTNYNPSVKGRFTISRDTAKNSFY LQMNSLRAEDTAVYYCARRTTSLERYFDVWGQGTLVTVSS ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKRVEPKSCDKTHTCPPCPAPEAAGG PSVFLFPPKPKDTLMISRTPEVTCVVVDVSHEDPEVKFNW YVDGVEVHNAKTKPREEQYNSTYRVVSVLTVLHQDWLNGK EYKCKVSNKALPAPIEKTISKAKGQPREPQVYTLPPSREE MTKNQVSLTCLVKGFYPSDIAVEWESNGQPENNYKTTPPV LDSDGSFFLYSKLTVDKSRWQQGNVFSCSVMHEALHNHYT QKSLSLSPGK |
| DNA Heavy Chain | 32 | GAGGTGCAGCTGGTGGAATCTGGCGGCGGACTCGTGAAGC CTGGCGGCTCTCTGAGACTGAGCTGTGCCGTGTCCGGCTA CAGCATCACCAGCGGCTACACCTGGCATTGGGTGCGCCAG GCCCCTGGCAAAGGACTGGAATGGCTGTCCTACATCCACT ACAGCGTGTACACCAACTACAACCCCAGCGTGAAGGGCCG GTTCACCATCAGCAGAGACACCGCCAAGAACAGCTTCTAC CTGCAAATGAACAGCCTGCGGGCCGAGGACACCGCCGTGT ACTACTGTGCCAGACGGACCACCAGCCTGGAACGGTACTT CGACGTGTGGGGCCAGGGCACACTCGTGACCGTCAGCTCA GCTAGCACCAAGGGCCCCAGCGTGTTCCCCCTGGCCCCCA GCAGCAAGAGCACCAGCGGCGGCACAGCCGCCCTGGGCTG CCTGGTGAAGGACTACTTCCCCGAGCCCGTGACCGTGTCC TGGAACAGCGGAGCCCTGACCTCCGGCGTGCACACCTTCC CCGCCGTGCTGCAGAGCAGCGGCCTGTACAGCCTGTCCAG CGTGGTGACAGTGCCCAGCAGCAGCCTGGGCACCCAGACC TACATCTGCAACGTGAACCACAAGCCCAGCAACACCAAGG TGGACAAGAGAGTGGAGCCCAAGAGCTGCGACAAGACCCA CACCTGCCCCCCCTGCCCAGCCCCAGAGGCAGCGGGCGGA |

TABLE 1-continued

Examples of FGF21 Mimetic Antibodies and Fabs

| Sequence Description | Sequence Identifier (SEQ ID NO:) | Amino acid or polynucleotide sequence |
|---|---|---|
| | | CCCTCCGTGTTCCTGTTCCCCCCCAAGCCCAAGGACACCC TGATGATCAGCAGGACCCCCGAGGTGACCTGCGTGGTGGT GGACGTGAGCCACGAGGACCCAGAGGTGAAGTTCAACTGG TACGTGGACGGCGTGGAGGTGCACAACGCCAAGACCAAGC CCAGAGAGGAGCAGTACAACAGCACCTACAGGGTGGTGTC CGTGCTGACCGTGCTGCACCAGGACTGGCTGAACGGCAAG GAATACAAGTGCAAGGTCTCCAACAAGGCCCTGCCAGCCC CCATCGAAAAGACCATCAGCAAGGCCAAGGGCCAGCCACG GGAGCCCCAGGTGTACACCCTGCCCCCCTCCCGGGAGGAG ATGACCAAGAACCAGGTGTCCCTGACCTGTCTGGTGAAGG GCTTCTACCCCAGCGACATCGCCGTGGAGTGGGAGAGCAA CGGCCAGCCCGAGAACAACTACAAGACCACCCCCCCAGTG CTGGACAGCGACGGCAGCTTCTTCCTGTACAGCAAGCTGA CCGTGGACAAGTCCAGGTGGCAGCAGGGCAACGTGTTCAG CTGCAGCGTGATGCACGAGGCCCTGCACAACCACTACACC CAGAAGAGCCTGAGCCTGTCCCCCGGCAAG |
| LCDR1 (Kabat) | 33 | QASQDISNYLN |
| LCDR2 (Kabat) | 34 | YTSRLQS |
| LCDR3 (Kabat) | 35 | QQGNTLPYT |
| LCDR1 (Chothia) | 36 | SQDISNY |
| LCDR2 (Chothia) | 37 | YTS |
| LCDR3 (Chothia) | 38 | GNTLPY |
| LCDR1 (Combined) | 33 | QASQDISNYLN |
| LCDR2 (Combined) | 34 | YTSRLQS |
| LCDR3 (Combined) | 35 | QQGNTLPYT |
| LCDR1 (IMGT) | 272 | QDISNY |
| LCDR2 (IMGT) | 273 | YTS |
| LCDR3 (IMGT) | 35 | QQGNTLPYT |
| VL | 39 | DIQMTQSPSSLSASVGDRVTITCQASQDISNYLNWYQQKP GKAPKLLIYYTSRLQSGVPSRFTGSGSGADYTFTISSLQP EDIATYFCQQGNTLPYTFGQGTKLEIK |
| DNA VL | 40 | GACATCCAGATGACCCAGAGCCCCAGCAGCCTGTCTGCCA GCGTGGGCGACAGAGTGACCATCACCTGTCAGGCCAGCCA GGACATCAGCAACTACCTGAACTGGTATCAGCAGAAGCCC GGCAAGGCCCCCAAGCTGCTGATCTACTACACCAGCAGAC TGCAGAGCGGCGTGCCCAGCAGATTTACCGGCTCTGGAAG CGGAGCCGACTACACCTTCACCATCAGCTCCCTGCAGCCC GAGGATATCGCTACCTACTTCTGTCAGCAAGGCAACACCC TGCCTTACACCTTCGGCCAGGGCACCAAGCTGGAAATCAA G |
| Light Chain | 41 | DIQMTQSPSSLSASVGDRVTITCQASQDISNYLNWYQQKP GKAPKLLIYYTSRLQSGVPSRFTGSGSGADYTFTISSLQP EDIATYFCQQGNTLPYTFGQGTKLEIKRTVAAPSVFIFPP SDEQLKSGTASVVCLLNNFYPREAKVQWKVDNALQSGNSQ ESVTEQDSKDSTYSLSSTLTLSKADYEKHKVYACEVTHQG LSSPVTKSFNRGEC |
| DNA Light Chain | 42 | GACATCCAGATGACCCAGAGCCCCAGCAGCCTGTCTGCCA GCGTGGGCGACAGAGTGACCATCACCTGTCAGGCCAGCCA GGACATCAGCAACTACCTGAACTGGTATCAGCAGAAGCCC GGCAAGGCCCCCAAGCTGCTGATCTACTACACCAGCAGAC TGCAGAGCGGCGTGCCCAGCAGATTTACCGGCTCTGGAAG CGGAGCCGACTACACCTTCACCATCAGCTCCCTGCAGCCC GAGGATATCGCTACCTACTTCTGTCAGCAAGGCAACACCC TGCCTTACACCTTCGGCCAGGGCACCAAGCTGGAAATCAA GCGTACGGTGGCCGCTCCCAGCGTGTTCATCTTCCCCCCC AGCGACGAGCAGCTGAAGAGCGGCACCGCCAGCGTGGTGT GCCTGCTGAACAACTTCTACCCCGGGAGGCCAAGGTGCA GTGGAAGGTGGACAACGCCCTGCAGAGCGGCAACAGCCAG |

TABLE 1-continued

Examples of FGF21 Mimetic Antibodies and Fabs

| Sequence Description | Sequence Identifier (SEQ ID NO:) | Amino acid or polynucleotide sequence |
|---|---|---|
| | | GAGAGCGTCACCGAGCAGGACAGCAAGGACTCCACCTACA GCCTGAGCAGCACCCTGACCCTGAGCAAGGCCGACTACGA GAAGCATAAGGTGTACGCCTGCGAGGTGACCCACCAGGGC CTGTCCAGCCCCGTGACCAAGAGCTTCAACAGGGGCGAGT GC |
| NOV003 (IgG1 DAPA version of NOV001) | | |
| HCDR1 (Kabat) | 43 | DYYIN |
| HCDR2 (Kabat) | 44 | RIHPGSGNTYYNEKFQG |
| HCDR3 (Kabat) | 45 | LLLRSYGMDD |
| HCDR1 (Chothia) | 46 | GYTFTDY |
| HCDR2 (Chothia) | 47 | HPGSGN |
| HCDR3 (Chothia) | 48 | LLLRSYGMDD |
| HCDR1 (Combined) | 263 | GYTFTDYYIN |
| HCDR2 (Combined) | 44 | RIHPGSGNTYYNEKFQG |
| HCDR3 (Combined) | 45 | LLLRSYGMDD |
| HCDR1 (IMGT) | 264 | GYTFTDYY |
| HCDR2 (IMGT) | 265 | IHPGSGNT |
| HCDR3 (IMGT) | 266 | AILLLRSYGMDD |
| VH | 49 | QVQLVQSGAEVKKPGSSVKVSCKASGYTFTDYYINWVRQA PGQGLEWMGRIHPGSGNTYYNEKFQGRVTLTADKSTSTAY MELSSLRSEDTAVYYCAILLLRSYGMDDWGQGTTVTVSS |
| DNA VH | 50 | CAAGTCCAACTCGTCCAGTCCGGAGCCGAAGTGAAAAAGC CGGGCTCATCAGTGAAGGTGTCCTGCAAGGCGTCGGGCTA CACCTTCACCGACTACTACATCAACTGGGTGCGCCAGGCC CCGGGACAGGGTCTGGAATGGATGGGGAGGATTCACCCCG GATCGGGAAACACCTACTACAACGAGAAGTTCCAGGGCAG AGTGACCCTGACTGCCGACAAGTCCACGTCCACTGCCTAC ATGGAACTGTCGTCCCTGCGGTCCGAGGATACCGCCGTGT ACTATTGTGCGATCCTGCTGTTGCGGAGCTACGGGATGGA TGACTGGGGACAGGGTACCACTGTGACTGTGTCCAGC |
| Heavy Chain | 51 | QVQLVQSGAEVKKPGSSVKVSCKASGYTFTDYYINWVRQA PGQGLEWMGRIHPGSGNTYYNEKFQGRVTLTADKSTSTAY MELSSLRSEDTAVYYCAILLLRSYGMDDWGQGTTVTVSSA STKGPSVFPLAPSSKSTSGGTAALGCLVKDYFPEPVTVSW NSGALTSGVHTFPAVLQSSGLYSLSSVVTVPSSSLGTQTY ICNVNHKPSNTKVDKRVEPKSCDKTHTCPPCPAPELLGGP SVFLFPPKPKDTLMISRTPEVTCVVVAVSHEDPEVKFNWY VDGVEVHNAKTKPREEQYNSTYRVVSVLTVLHQDWLNGKE YKCKVSNKALAAPIEKTISKAKGQPREPQVYTLPPSREEM TKNQVSLTCLVKGFYPSDIAVEWESNGQPENNYKTTPPVL DSDGSFFLYSKLTVDKSRWQQGNVFSCSVMHEALHNHYTQ KSLSLSPGK |
| DNA Heavy Chain | 52 | CAAGTCCAACTCGTCCAGTCCGGAGCCGAAGTGAAAAAGC CGGGCTCATCAGTGAAGGTGTCCTGCAAGGCGTCGGGCTA CACCTTCACCGACTACTACATCAACTGGGTGCGCCAGGCC CCGGGACAGGGTCTGGAATGGATGGGGAGGATTCACCCCG GATCGGGAAACACCTACTACAACGAGAAGTTCCAGGGCAG AGTGACCCTGACTGCCGACAAGTCCACGTCCACTGCCTAC ATGGAACTGTCGTCCCTGCGGTCCGAGGATACCGCCGTGT ACTATTGTGCGATCCTGCTGTTGCGGAGCTACGGGATGGA TGACTGGGGACAGGGTACCACTGTGACTGTGTCCAGCGCT AGCACCAAGGGCCCCTCCGTGTTCCCTCTGGCCCCTTCCA GCAAGTCTACCTCCGGCGGCACAGCTGCTCTGGGCTGCCT GGTCAAGGACTACTTCCCTGAGCCTGTGACAGTGTCCTGG |

TABLE 1-continued

Examples of FGF21 Mimetic Antibodies and Fabs

| Sequence Description | Sequence Identifier (SEQ ID NO:) | Amino acid or polynucleotide sequence |
|---|---|---|
| | | AACTCTGGCGCCCTGACCTCTGGCGTGCACACCTTCCCTG CCGTGCTGCAGTCCTCCGGCCTGTACTCCCTGTCCTCCGT GGTCACAGTGCCTTCAAGCAGCCTGGGCACCCAGACCTAT ATCTGCAACGTGAACCACAAGCCTTCCAACACCAAGGTGG ACAAGCGGGTGGAGCCTAAGTCCTGCGACAAGACCCACAC CTGTCCTCCCTGCCCTGCTCCTGAACTGCTGGGCGGCCCT TCTGTGTTCCTGTTCCCTCCAAAGCCCAAGGACACCCTGA TGATCTCCCGGACCCCTGAAGTGACCTGCGTGGTGGTGGC CGTGTCCCACGAGGATCCTGAAGTGAAGTTCAATTGGTAC GTGGACGGCGTGGAGGTGCACAACGCCAAGACCAAGCCTC GGGAGGAACAGTACAACTCCACCTACCGGGTGGTGTCCGT GCTGACCGTGCTGCACCAGGACTGGCTGAACGGCAAAGAG TACAAGTGCAAAGTCTCCAACAAGGCCCTGGCCGCCCCTA TCGAAAAGACAATCTCCAAGGCCAAGGGCCAGCCTAGGGA ACCCCAGGTGTACACCCTGCCACCCAGCCGGGAGGAAATG ACCAAGAACCAGGTGTCCCTGACCTGTCTGGTCAAGGGCT TCTACCCTTCCGATATCGCCGTGGAGTGGGAGTCTAACGG CCAGCCTGAGAACAACTACAAGACCACCCCTCCTGTGCTG GACTCCGACGGCTCCTTCTTCCTGTACTCCAAACTGACCG TGGACAAGTCCCGGTGGCAGCAGGGCAACGTGTTCTCCTG CTCCGTGATGCACGAGGCCCTGCACAACCACTACACCCAG AAGTCCCTGTCCCTGTCTCCCGGCAAG |
| LCDR1 (Kabat) | 53 | KSSQSIVHSSGNTYLE |
| LCDR2 (Kabat) | 54 | KVSNRFS |
| LCDR3 (Kabat) | 55 | FQGSHIPYT |
| LCDR1 (Chothia) | 56 | SQSIVHSSGNTY |
| LCDR2 (Chothia) | 57 | KVS |
| LCDR3 (Chothia) | 58 | GSHIPY |
| LCDR1 (Combined) | 53 | KSSQSIVHSSGNTYLE |
| LCDR2 (Combined) | 54 | KVSNRFS |
| LCDR3 (Combined) | 55 | FQGSHIPYT |
| LCDR1 (IMGT) | 267 | QSIVHSSGNTY |
| LCDR2 (IMGT) | 57 | KVS |
| LCDR3 (IMGT) | 55 | FQGSHIPYT |
| VL | 59 | DVVMTQTPLSLSVTPGQPASISCKSSQSIVHSSGNTYLEW YLQKPGQSPQLLIYKVSNRFSGVPDRFSGSGSGTDFTLKI SRVEAEDVGVYYCFQGSHIPYTFGQGTKLEIK |
| DNA VL | 60 | GATGTCGTGATGACCCAGACTCCGCTGTCCCTGTCCGTGA CCCCTGGACAGCCCGCGTCTATCTCGTGCAAGAGCTCCCA GTCCATTGTGCATTCAAGCGGGAACACCTATCTGGAGTGG TACCTCCAGAAGCCTGGCCAGAGCCCACAGCTGCTGATCT ACAAAGTGTCGAACAGATTCTCCGGTGTCCCGGACCGGTT CTCCGGCTCGGGAAGCGGCACTGACTTTACACTGAAGATC TCACGGGTGGAAGCCGAGGACGTGGGAGTGTACTACTGTT TCCAAGGGTCCCACATTCCCTACACCTTCGGCCAAGGAAC TAAGCTGGAAATCAAG |
| Light Chain | 61 | DVVMTQTPLSLSVTPGQPASISCKSSQSIVHSSGNTYLEW YLQKPGQSPQLLIYKVSNRFSGVPDRFSGSGSGTDFTLKI SRVEAEDVGVYYCFQGSHIPYTFGQGTKLEIKRTVAAPSV FIFPPSDEQLKSGTASVVCLLNNFYPREAKVQWKVDNALQ SGNSQESVTEQDSKDSTYSLSSTLTLSKADYEKHKVYACE VTHQGLSSPVTKSFNRGEC |
| DNA Light Chain | 62 | GATGTCGTGATGACCCAGACTCCGCTGTCCCTGTCCGTGA CCCCTGGACAGCCCGCGTCTATCTCGTGCAAGAGCTCCCA GTCCATTGTGCATTCAAGCGGGAACACCTATCTGGAGTGG TACCTCCAGAAGCCTGGCCAGAGCCCACAGCTGCTGATCT ACAAAGTGTCGAACAGATTCTCCGGTGTCCCGGACCGGTT CTCCGGCTCGGGAAGCGGCACTGACTTTACACTGAAGATC |

TABLE 1-continued

Examples of FGF21 Mimetic Antibodies and Fabs

| Sequence Description | Sequence Identifier (SEQ ID NO:) | Amino acid or polynucleotide sequence |
|---|---|---|
| | | TCACGGGTGGAAGCCGAGGACGTGGGAGTGTACTACTGTT<br>TCCAAGGGTCCCACATTCCCTACACCTTCGGCCAAGGAAC<br>TAAGCTGGAAATCAAGCGTACGGTGGCCGCTCCCAGCGTG<br>TTCATCTTCCCCCCCAGCGACGAGCAGCTGAAGAGCGGCA<br>CCGCCAGCGTGGTGTGCCTGCTGAACAACTTCTACCCCCG<br>GGAGGCCAAGGTGCAGTGGAAGGTGGACAACGCCCTGCAG<br>AGCGGCAACAGCCAGGAGAGCGTCACCGAGCAGGACAGCA<br>AGGACTCCACCTACAGCCTGAGCAGCACCCTGACCCTGAG<br>CAAGGCCGACTACGAGAAGCATAAGGTGTACGCCTGCGAG<br>GTGACCCACCAGGGCCTGTCCAGCCCCGTGACCAAGAGCT<br>TCAACAGGGGCGAGTGC |
| NOV004<br>(IgG1 DAPA<br>version of<br>NOV002) | | |
| HCDR1 (Kabat) | 63 | SGYTWH |
| HCDR2 (Kabat) | 64 | YIHYSVYTNYNPSVKG |
| HCDR3 (Kabat) | 65 | RTTSLERYFDV |
| HCDR1 (Chothia) | 66 | GYSITSGY |
| HCDR2 (Chothia) | 67 | HYSVY |
| HCDR3 (Chothia) | 68 | RTTSLERYFDV |
| HCDR1 (Combined) | 268 | GYSITSGYTWH |
| HCDR2 (Combined) | 64 | YIHYSVYTNYNPSVKG |
| HCDR3 (Combined) | 25 | RTTSLERYFDV |
| HCDR1 (IMGT) | 269 | GYSITSGYT |
| HCDR2 (IMGT) | 270 | IHYSVYT |
| HCDR3 (IMGT) | 271 | ARRTTSLERYFDV |
| VH | 69 | EVQLVESGGGLVKPGGSLRLSCAVSGYSITSGYTWHWVRQ<br>APGKGLEWLSYIHYSVYTNYNPSVKGRFTISRDTAKNSFY<br>LQMNSLRAEDTAVYYCARRTTSLERYFDVWGQGTLVTVSS |
| DNA VH | 70 | GAAGTCCAACTCGTCGAATCCGGCGGCGGACTGGTCAAGC<br>CGGGAGGATCGCTGAGACTGTCGTGCGCAGTGTCAGGGTA<br>CAGCATCACCTCCGGTTACACCTGGCACTGGGTCAGACAG<br>GCGCCGGGAAAAGGCCTGGAATGGCTGTCCTACATTCATT<br>ACTCCGTGTACACTAACTACAACCCCTCAGTGAAGGGGCG<br>GTTCACCATCTCCCGGGACACTGCCAAGAATAGCTTCTAT<br>CTGCAAATGAACTCCCTGCGGGCCGAGGATACCGCCGTGT<br>ACTACTGCGCGAGGCGCACCACGTCCCTGGAGCGCTACTT<br>TGACGTGTGGGGCCAGGGTACCCTCGTGACTGTGTCCTCG |
| Heavy Chain | 71 | EVQLVESGGGLVKPGGSLRLSCAVSGYSITSGYTWHWVRQ<br>APGKGLEWLSYIHYSVYTNYNPSVKGRFTISRDTAKNSFY<br>LQMNSLRAEDTAVYYCARRTTSLERYFDVWGQGTLVTVSS<br>ASTKGPSVFPLAPSSKSTSGGTAALGCLVKDYFPEPVTVS<br>WNSGALTSGVHTFPAVLQSSGLYSLSSVVTVPSSSLGTQT<br>YICNVNHKPSNTKVDKRVEPKSCDKTHTCPPCPAPELLGG<br>PSVFLFPPKPKDTLMISRTPEVTCVVVAVSHEDPEVKFNW<br>YVDGVEVHNAKTKPREEQYNSTYRVVSVLTVLHQDWLNGK<br>EYKCKVSNKALAAPIEKTISKAKGQPREPQVYTLPPSREE<br>MTKNQVSLTCLVKGFYPSDIAVEWESNGQPENNYKTTPPV<br>LDSDGSFFLYSKLTVDKSRWQQGNVFSCSVMHEALHNHYT<br>QKSLSLSPGK |
| DNA Heavy Chain | 72 | GAAGTCCAACTCGTCGAATCCGGCGGCGGACTGGTCAAGC<br>CGGGAGGATCGCTGAGACTGTCGTGCGCAGTGTCAGGGTA<br>CAGCATCACCTCCGGTTACACCTGGCACTGGGTCAGACAG<br>GCGCCGGGAAAAGGCCTGGAATGGCTGTCCTACATTCATT<br>ACTCCGTGTACACTAACTACAACCCCTCAGTGAAGGGGCG<br>GTTCACCATCTCCCGGGACACTGCCAAGAATAGCTTCTAT |

TABLE 1-continued

Examples of FGF21 Mimetic Antibodies and Fabs

| Sequence Description | Sequence Identifier (SEQ ID NO:) | Amino acid or polynucleotide sequence |
|---|---|---|
| | | CTGCAAATGAACTCCCTGCGGGCCGAGGATACCGCCGTGT
ACTACTGCGCGAGGCGCACCACGTCCCTGGAGCGCTACTT
TGACGTGTGGGGCCAGGGTACCCTCGTGACTGTGTCCTCG
GCTAGCACCAAGGGCCCCTCCGTGTTCCCTCTGGCCCCTT
CCAGCAAGTCTACCTCCGGCGGCACAGCTGCTCTGGGCTG
CCTGGTCAAGGACTACTTCCCTGAGCCTGTGACAGTGTCC
TGGAACTCTGGCGCCCTGACCTCTGGCGTGCACACCTTCC
CTGCCGTGCTGCAGTCCTCCGGCCTGTACTCCCTGTCCTC
CGTGGTCACAGTGCCTTCAAGCAGCCTGGGCACCCAGACC
TATATCTGCAACGTGAACCACAAGCCTTCCAACACCAAGG
TGGACAAGCGGGTGGAGCCTAAGTCCTGCGACAAGACCCA
CACCTGTCCTCCCTGCCCTGCTCCTGAACTGCTGGGCGGC
CCTTCTGTGTTCCTGTTCCCTCCAAAGCCCAAGGACACCC
TGATGATCTCCCGGACCCCTGAAGTGACCTGCGTGGTGGT
GGCCGTGTCCCACGAGGATCCTGAAGTGAAGTTCAATTGG
TACGTGGACGGCGTGGAGGTGCACAACGCCAAGACCAAGC
CTCGGGAGGAACAGTACAACTCCACCTACCGGGTGGTGTC
CGTGCTGACCGTGCTGCACCAGGACTGGCTGAACGGCAAA
GAGTACAAGTGCAAAGTCTCCAACAAGGCCCTGGCCGCCC
CTATCGAAAAGACAATCTCCAAGGCCAAGGGCCAGCCTAG
GGAACCCCAGGTGTACACCCTGCCACCCAGCCGGGAGGAA
ATGACCAAGAACCAGGTGTCCCTGACCTGTCTGGTCAAGG
GCTTCTACCCTTCCGATATCGCCGTGGAGTGGGAGTCTAA
CGGCCAGCCTGAGAACAACTACAAGACCACCCCTCCTGTG
CTGGACTCCGACGGCTCCTTCTTCCTGTACTCCAAACTGA
CCGTGGACAAGTCCCGGTGGCAGCAGGGCAACGTGTTCTC
CTGCTCCGTGATGCACGAGGCCCTGCACAACCACTACACC
CAGAAGTCCCTGTCCCTGTCTCCCGGCAAG |
| LCDR1 (Kabat) | 73 | QASQDISNYLN |
| LCDR2 (Kabat) | 74 | YTSRLQS |
| LCDR3 (Kabat) | 75 | QQGNTLPYT |
| LCDR1 (Chothia) | 76 | SQDISNY |
| LCDR2 (Chothia) | 77 | YTS |
| LCDR3 (Chothia) | 78 | GNTLPY |
| LCDR1 (Combined) | 73 | QASQDISNYLN |
| LCDR2 (Combined) | 74 | YTSRLQS |
| LCDR3 (Combined) | 75 | QQGNTLPYT |
| LCDR1 (IMGT) | 272 | QDISNY |
| LCDR2 (IMGT) | 273 | YTS |
| LCDR3 (IMGT) | 75 | QQGNTLPYT |
| VL | 79 | DIQMTQSPSSLSASVGDRVTITCQASQDISNYLNWYQQKP
GKAPKLLIYYTSRLQSGVPSRFTGSGSGADYTFTISSLQP
EDIATYFCQQGNTLPYTFGQGTKLEIK |
| DNA VL | 80 | GATATTCAGATGACTCAGAGCCCCTCCTCGCTCTCCGCCT
CCGTGGGGGATCGCGTGACAATCACCTGTCAAGCGTCCCA
GGACATCTCAAACTACCTGAACTGGTATCAGCAGAAGCCA
GGGAAGGCCCCGAAGCTGCTGATCTACTACACTTCGCGGC
TGCAGTCCGGCGTGCCGTCACGGTTCACTGGCTCGGGCTC
CGGAGCAGACTACACCTTCACCATTAGCAGCCTGCAGCCC
GAGGACATCGCTACCTACTTTTGCCAACAAGGAAACACCC
TGCCTTACACCTTCGGACAGGGTACTAAGCTGGAAATCAA
A |
| Light Chain | 81 | DIQMTQSPSSLSASVGDRVTITCQASQDISNYLNWYQQKP
GKAPKLLIYYTSRLQSGVPSRFTGSGSGADYTFTISSLQP
EDIATYFCQQGNTLPYTFGQGTKLEIKRTVAAPSVFIFPP
SDEQLKSGTASVVCLLNNFYPREAKVQWKVDNALQSGNSQ
ESVTEQDSKDSTYSLSSTLTLSKADYEKHKVYACEVTHQG
LSSPVTKSFNRGEC |

TABLE 1-continued

Examples of FGF21 Mimetic Antibodies and Fabs

| Sequence Description | Sequence Identifier (SEQ ID NO:) | Amino acid or polynucleotide sequence |
|---|---|---|
| DNA Light Chain | 82 | GATATTCAGATGACTCAGAGCCCCTCCTCGCTCTCCGCCT<br>CCGTGGGGATCGCGTGACAATCACCTGTCAAGCGTCCCA<br>GGACATCTCAAACTACCTGAACTGGTATCAGCAGAAGCCA<br>GGGAAGGCCCCGAAGCTGCTGATCTACTACACTTCGCGGC<br>TGCAGTCCGGCGTGCCGTCACGGTTCACTGGCTCGGGCTC<br>CGGAGCAGACTACACCTTCACCATTAGCAGCCTGCAGCCC<br>GAGGACATCGCTACCTACTTTTGCCAACAAGGAAACACCC<br>TGCCTTACACCTTCGGACAGGGTACTAAGCTGGAAATCAA<br>ACGTACGGTGGCCGCTCCCAGCGTGTTCATCTTCCCCCCC<br>AGCGACGAGCAGCTGAAGAGCGGCACCGCCAGCGTGGTGT<br>GCCTGCTGAACAACTTCTACCCCCGGGAGGCCAAGGTGCA<br>GTGGAAGGTGGACAACGCCCTGCAGAGCGGCAACAGCCAG<br>GAGAGCGTCACCGAGCAGGACAGCAAGGACTCCACCTACA<br>GCCTGAGCAGCACCCTGACCCTGAGCAAGGCCGACTACGA<br>GAAGCATAAGGTGTACGCCTGCGAGGTGACCCACCAGGGC<br>CTGTCCAGCCCCGTGACCAAGAGCTTCAACAGGGGCGAGT<br>GC |

Other antibodies of the invention include those where the amino acids or nucleic acids encoding the amino acids have been mutated, yet have at least 60, 65, 70, 75, 80, 85, 90, or 95 percent identity to the sequences described in Table 1. Some embodiments include mutant amino acid sequences wherein no more than 1, 2, 3, 4 or 5 amino acids have been mutated in the variable regions when compared with the variable regions depicted in the sequence described in Table 1, while retaining substantially the same antigen-binding activity.

Other antibodies of the invention include those where the amino acids or nucleic acids encoding the amino acids have been mutated, yet have at least 60, 65, 70, 75, 80, 85, 90, or 95 percent identity to the sequences described in Table 1. Some embodiments include mutant amino acid sequences wherein no more than 1, 2, 3, 4 or 5 amino acids have been mutated in the variable regions when compared with the variable regions depicted in the sequence described in Table 1, while retaining substantially the same antigen-binding activity.

Since each of these antibodies can bind to β-klotho, the VH, VL, full length light chain, and full length heavy chain sequences (amino acid sequences and the nucleotide sequences encoding the amino acid sequences) can be "mixed and matched" to create other β-klotho-binding antibodies of the invention. Such "mixed and matched"-β-klotho binding antibodies can be tested using the binding assays known in the art (e.g., ELISAs, and other assays described in the Example section). When these chains are mixed and matched, a VH sequence from a particular VH/VL pairing should be replaced with a structurally similar VH sequence. Likewise a full length heavy chain sequence from a particular full length heavy chain/full length light chain pairing should be replaced with a structurally similar full length heavy chain sequence. Likewise, a VL sequence from a particular VH/VL pairing should be replaced with a structurally similar VL sequence. Likewise a full length light chain sequence from a particular full length heavy chain/full length light chain pairing should be replaced with a structurally similar full length light chain sequence.

Accordingly, in one aspect, the invention provides an isolated antibody or antigen-binding region thereof having: a heavy chain variable domain comprising an amino acid sequence selected from the group consisting of SEQ ID NOs: 9, 29, 49, and 69, and a light chain variable domain comprising an amino acid sequence selected from the group consisting of SEQ ID NOs: 19, 39, 59, and 79, wherein the antibody specifically binds to β-klotho (e.g., human and cynomolgus monkey β-klotho).

More specifically, in certain aspects, the invention provides an isolated antibody or antigen-binding region thereof having a heavy chain variable domain and a light chain variable domain comprising amino acid sequences selected from SEQ ID NOs: 9 and 19; 29 and 39; 49 and 59; or 69 and 79, respectively.

In another aspect, the invention provides (i) an isolated antibody having: a full length heavy chain comprising an amino acid sequence that has been optimized for expression in a mammalian cell selected from the group consisting of SEQ ID NOs: 9, 29, 49, or 69, and a full length light chain comprising an amino acid sequence that has been optimized for expression in a mammalian cell selected from the group consisting of SEQ ID NOs: 21, 41, 61, or 81; or (ii) a functional protein comprising an antigen-binding portion thereof. More specifically, in certain aspects, the invention provides an isolated antibody or antigen-binding region thereof having a heavy chain and a light chain comprising amino acid sequences selected from SEQ ID NOs: 9 and 19; 29 and 39; 49 and 59; or 69 and 79, respectively.

The terms "complementarity determining region," and "CDR," as used herein refer to the sequences of amino acids within antibody variable regions which confer antigen specificity and binding affinity. In general, there are three CDRs in each heavy chain variable region (HCDR1, HCDR2, HCDR3) and three CDRs in each light chain variable region (LCDR1, LCDR2, LCDR3).

The precise amino acid sequence boundaries of a given CDR can be readily determined using any of a number of well-known schemes, including those described by Kabat et al. (1991), "Sequences of Proteins of Immunological Interest," 5th Ed. Public Health Service, National Institutes of Health, Bethesda, Md. ("Kabat" numbering scheme), Al-Lazikani et al., (1997) JMB 273, 927-948 ("Chothia" numbering scheme), and ImMunoGenTics (IMGT) numbering (Lefranc, M.-P., The Immunologist, 7, 132-136 (1999); Lefranc, M.-P. et al., Dev. Comp. Immunol., 27, 55-77 (2003) ("IMGT" numbering scheme). For example, for classic formats, under Kabat, the CDR amino acid residues in the heavy chain variable domain (VH) are numbered 31-35 (HCDR1), 50-65 (HCDR2), and 95-102 (HCDR3); and the CDR amino acid residues in the light chain variable domain (VL) are numbered 24-34 (LCDR1), 50-56 (LCDR2), and 89-97 (LCDR3). Under Chothia the CDR amino acids in the VH are numbered 26-32 (HCDR1), 52-56 (HCDR2), and 95-102 (HCDR3); and the amino acid residues in VL are numbered 26-32 (LCDR1), 50-52 (LCDR2), and 91-96 (LCDR3). By combining the CDR definitions of both Kabat and Chothia, the CDRs consist of amino acid residues 26-35 (HCDR1), 50-65 (HCDR2), and 95-102 (HCDR3) in human VH and amino acid residues 24-34 (LCDR1), 50-56 (LCDR2), and 89-97 (LCDR3) in human VL. Under IMGT the CDR amino acid residues in the VH are numbered approximately 26-35 (CDR1), 51-57 (CDR2) and 93-102 (CDR3), and the CDR amino acid residues in the VL are numbered approximately 27-32 (CDR1), 50-52 (CDR2), and 89-97 (CDR3) (numbering according to "Kabat"). Under IMGT, the CDR regions of an antibody can be determined using the program IMGT/DomainGap Align.

For example, under Kabat, the CDR amino acid residues of antibody NOV001 in the heavy chain variable domain (VH) are numbered 31-35 (HCDR1), 50-65 (HCDR2), and 99-108 (HCDR3); and the CDR amino acid residues in the light chain variable domain (VL) are numbered 24-39 (LCDR1), 55-61 (LCDR2), and 94-102 (LCDR3). Under Chothia the CDR amino acids in the VH are numbered 26-32 (HCDR1), 52-57 (HCDR2), and 99-108 (HCDR3); and the amino acid residues in VL are numbered 26-39 (LCDR1), 55-57 (LCDR2), and 96-101 (LCDR3). By combining the CDR definitions of both Kabat and Chothia, the CDRs consist of amino acid residues 26-35 (HCDR1), 50-65 (HCDR2), and 99-108 (HCDR3) in human VH and amino acid residues 24-39 (LCDR1), 55-61 (LCDR2), and 94-102 (LCDR3) in human VL.

In another aspect, the present invention provides β-klotho binding antibodies that comprise the heavy chain and light chain CDR1s, CDR2s, and CDR3s as described in Table 1, or combinations thereof. The amino acid sequences of the VH CDR1s of the antibodies are shown in SEQ ID NOs: 3, 23, 43, and 63. The amino acid sequences of the VH CDR2s of the antibodies and are shown in SEQ ID NOs: 4, 24, 44, and 64. The amino acid sequences of the VH CDR3s of the antibodies are shown in SEQ ID NOs: 5, 25, 45, and 65. The amino acid sequences of the VL CDR1s of the antibodies are shown in SEQ ID NOs: 13, 33, 53, and 73. The amino acid sequences of the VL CDR2s of the antibodies are shown in SEQ ID NOs: 14, 34, 54, and 74. The amino acid sequences of the VL CDR3s of the antibodies are shown in SEQ ID NOs: 15, 35, 55, and 75. These CDR regions are delineated using the Kabat system.

Alternatively, as defined using the Chothia system (Al-Lazikani et al., (1997) JMB 273, 927-948), the amino acid sequences of the VH CDR1s of the antibodies are shown in SEQ ID NOs: 6, 26, 46, and 66. The amino acid sequences of the VH CDR2s of the antibodies and are shown in SEQ ID NOs: 7, 27, 47, and 67. The amino acid sequences of the VH CDR3s of the antibodies are shown in SEQ ID NOs: 8, 28, 48, and 68. The amino acid sequences of the VL CDR1s of the antibodies are shown in SEQ ID NOs: 16, 36, 56, and 76. The amino acid sequences of the VL CDR2s of the antibodies are shown in SEQ ID NOs: 17, 37, 57, and 77. The amino acid sequences of the VL CDR3s of the antibodies are shown in SEQ ID NOs: 18, 38, 58, and 78.

Alternatively, as defined using the Combined system, the amino acid sequences of the VH CDR1s of the antibodies are shown in SEQ ID NOs: 263 and 268. The amino acid sequences of the VH CDR2s of the antibodies and are shown in SEQ ID NOs: 4, 24, 44, and 64. The amino acid sequences of the VH CDR3s of the antibodies are shown in SEQ ID NOs: 5, 25, and 45. The amino acid sequences of the VL CDR1s of the antibodies are shown in SEQ ID NOs: 13, 33, 53, and 73. The amino acid sequences of the VL CDR2s of the antibodies are shown in SEQ ID NOs: 14, 34, 54, and 74. The amino acid sequences of the VL CDR3s of the antibodies are shown in SEQ ID NOs: 15, 35, 55, and 75.

Alternatively, as defined using the IMGT system, the amino acid sequences of the VH CDR1s of the antibodies are shown in SEQ ID NOs: 264 and 269. The amino acid sequences of the VH CDR2s of the antibodies and are shown in SEQ ID NOs: 265 and 270. The amino acid sequences of the VH CDR3s of the antibodies are shown in SEQ ID NOs: 266 and 271. The amino acid sequences of the VL CDR1s of the antibodies are shown in SEQ ID NOs: 267, and 272. The amino acid sequences of the VL CDR2s of the antibodies are shown in SEQ ID NOs: 17, 273, and 57. The amino acid sequences of the VL CDR3s of the antibodies are shown in SEQ ID NOs: 15, 35, 55, and 75.

Given that each of these antibodies can bind to β-klotho and that antigen-binding specificity is provided primarily by the CDR1, 2 and 3 regions, the VH CDR1, 2 and 3 sequences and VL CDR1, 2 and 3 sequences can be "mixed and matched" (i.e., CDRs from different antibodies can be mixed and matched, although each antibody preferably contains a VH CDR1, 2 and 3 and a VL CDR1, 2 and 3 to create other β-klotho binding molecules of the invention. Such "mixed and matched" β-klotho binding antibodies can be tested using the binding assays known in the art and those described in the Examples (e.g., ELISAs, SET, Biacore® binding assays). When VH CDR sequences are mixed and matched, the CDR1, CDR2 and/or CDR3 sequence from a particular VH sequence should be replaced with a structurally similar CDR sequence(s). Likewise, when VL CDR sequences are mixed and matched, the CDR1, CDR2 and/or CDR3 sequence from a particular VL sequence should be replaced with a structurally similar CDR sequence(s). It will be readily apparent to the ordinarily skilled artisan that novel VH and VL sequences can be created by substituting one or more VH and/or VL CDR region sequences with structurally similar sequences from the CDR sequences shown herein for monoclonal antibodies of the present invention. In addition to the foregoing, in one embodiment, the antigen-binding fragments of the antibodies described herein can comprise a VH CDR1, 2, and 3, or a VL CDR 1, 2, and 3, wherein the fragment binds to β-klotho as a single variable domain.

In certain embodiments of the invention, the antibodies or antigen-binding fragments thereof may have the heavy and light chain sequences of the Fabs described in Table 1. More specifically, the antibody or antigen-binding fragments thereof may have the heavy and light sequence of Fab NOV001, NOV002, NOV003, NOV004.

In certain embodiments of the invention, the antibody or antigen-binding fragment that specifically binds β-klotho comprises heavy chain variable region CDR1, CDR2, and CDR3 of Fab NOV001, NOV002, NOV003, or NOV004, and light chain variable region CDR1, CDR2, and CDR3 of Fab NOV001, NOV002, NOV003, or NOV004, for example, as set forth in Table 1.

In other embodiments of the invention the antibody or antigen-binding fragment in that specifically binds β-klotho comprises a heavy chain variable region CDR1, a heavy chain variable region CDR2, a heavy chain variable region CDR3, a light chain variable region CDR1, a light chain variable region CDR2, and a light chain variable region CDR3 as defined by Kabat and described in Table 1. In still other embodiments of the invention the antibody or antigen-binding fragment in that specifically binds β-klotho comprises a heavy chain variable region CDR1, a heavy chain variable region CDR2, a heavy chain variable region CDR3, a light chain variable region CDR1, a light chain variable region CDR2, and a light chain variable region CDR3 as defined by Chothia and described in Table 1. In still other embodiments of the invention the antibody or antigen-binding fragment in that specifically binds β-klotho comprises a heavy chain variable region CDR1, a heavy chain variable region CDR2, a heavy chain variable region CDR3, a light chain variable region CDR1, a light chain variable region CDR2, and a light chain variable region CDR3 as defined by Combined Kabat and Chothia and described in Table 1. In still other embodiments of the invention the antibody or antigen-binding fragment in that specifically binds β-klotho comprises a heavy chain variable region CDR1, a heavy chain variable region CDR2, a heavy chain variable region CDR3, a light chain variable region CDR1, a light chain variable region CDR2, and a light chain variable region CDR3 as defined by IMGT and described in Table 1.

In a specific embodiment, the invention includes an antibody that specifically binds to β-klotho comprising a heavy chain variable region CDR1 of SEQ ID NO: 3; a heavy chain variable region CDR2 of SEQ ID NO: 4; a heavy chain variable region CDR3 of SEQ ID NO: 5; a light chain variable region CDR1 of SEQ ID NO: 13; a light chain variable region CDR2 of SEQ ID NO: 14; and a light chain variable region CDR3 of SEQ ID NO: 15.

In a specific embodiment, the invention includes an antibody that specifically binds to β-klotho comprising a heavy chain variable region CDR1 of SEQ ID NO: 23; a heavy chain variable region CDR2 of SEQ ID NO: 24; a heavy chain variable region CDR3 of SEQ ID NO: 25; a light chain variable region CDR1 of SEQ ID NO: 33; a light chain variable region CDR2 of SEQ ID NO: 34; and a light chain variable region CDR3 of SEQ ID NO: 35.

In a specific embodiment, the invention includes an antibody that specifically binds to β-klotho comprising a heavy chain variable region CDR1 of SEQ ID NO: 43; a heavy chain variable region CDR2 of SEQ ID NO: 44; a heavy chain variable region CDR3 of SEQ ID NO: 45; a light chain variable region CDR1 of SEQ ID NO: 53; a light chain variable region CDR2 of SEQ ID NO: 54; and a light chain variable region CDR3 of SEQ ID NO: 55.

In a specific embodiment, the invention includes an antibody that specifically binds to β-klotho comprising a heavy chain variable region CDR1 of SEQ ID NO: 63; a heavy chain variable region CDR2 of SEQ ID NO: 64; a heavy chain variable region CDR3 of SEQ ID NO: 65; a light chain variable region CDR1 of SEQ ID NO: 73; a light chain variable region CDR2 of SEQ ID NO: 74; and a light chain variable region CDR3 of SEQ ID NO: 75.

In a specific embodiment, the invention includes an antibody that specifically binds to β-klotho comprising a heavy chain variable region CDR1 of SEQ ID NO: 6; a heavy chain variable region CDR2 of SEQ ID NO: 7; a heavy chain variable region CDR3 of SEQ ID NO: 8; a light chain variable region CDR1 of SEQ ID NO: 16; a light chain variable region CDR2 of SEQ ID NO: 17; and a light chain variable region CDR3 of SEQ ID NO: 18.

In a specific embodiment, the invention includes an antibody that specifically binds to β-klotho comprising a heavy chain variable region CDR1 of SEQ ID NO: 26; a heavy chain variable region CDR2 of SEQ ID NO: 27; a heavy chain variable region CDR3 of SEQ ID NO: 28; a light chain variable region CDR1 of SEQ ID NO: 36; a light chain variable region CDR2 of SEQ ID NO: 37; and a light chain variable region CDR3 of SEQ ID NO: 38.

In a specific embodiment, the invention includes an antibody that specifically binds to β-klotho comprising a heavy chain variable region CDR1 of SEQ ID NO: 46; a heavy chain variable region CDR2 of SEQ ID NO: 47; a heavy chain variable region CDR3 of SEQ ID NO: 48; a light chain variable region CDR1 of SEQ ID NO: 56; a light chain variable region CDR2 of SEQ ID NO: 57; and a light chain variable region CDR3 of SEQ ID NO: 58.

In a specific embodiment, the invention includes an antibody that specifically binds to β-klotho comprising a heavy chain variable region CDR1 of SEQ ID NO: 66; a heavy chain variable region CDR2 of SEQ ID NO: 67; a heavy chain variable region CDR3 of SEQ ID NO: 68; a light chain variable region CDR1 of SEQ ID NO: 76; a light chain variable region CDR2 of SEQ ID NO: 77; and a light chain variable region CDR3 of SEQ ID NO: 78.

In a specific embodiment, the invention includes an antibody that specifically binds to β-klotho comprising a heavy chain variable region CDR1 of SEQ ID NO: 263; a heavy chain variable region CDR2 of SEQ ID NO: 4; a heavy chain variable region CDR3 of SEQ ID NO: 5; a light chain variable region CDR1 of SEQ ID NO: 13; a light chain variable region CDR2 of SEQ ID NO: 14; and a light chain variable region CDR3 of SEQ ID NO: 15.

In a specific embodiment, the invention includes an antibody that specifically binds to β-klotho comprising a heavy chain variable region CDR1 of SEQ ID NO: 268; a heavy chain variable region CDR2 of SEQ ID NO: 24; a heavy chain variable region CDR3 of SEQ ID NO: 25; a light chain variable region CDR1 of SEQ ID NO: 33; a light chain variable region CDR2 of SEQ ID NO: 34; and a light chain variable region CDR3 of SEQ ID NO: 35.

In a specific embodiment, the invention includes an antibody that specifically binds to β-klotho comprising a heavy chain variable region CDR1 of SEQ ID NO: 263; a heavy chain variable region CDR2 of SEQ ID NO: 44; a heavy chain variable region CDR3 of SEQ ID NO: 45; a light chain variable region CDR1 of SEQ ID NO: 53; a light chain variable region CDR2 of SEQ ID NO: 54; and a light chain variable region CDR3 of SEQ ID NO: 55.

In a specific embodiment, the invention includes an antibody that specifically binds to β-klotho comprising a heavy chain variable region CDR1 of SEQ ID NO: 268; a heavy chain variable region CDR2 of SEQ ID NO: 64; a heavy chain variable region CDR3 of SEQ ID NO: 25; a light chain variable region CDR1 of SEQ ID NO: 73; a light chain variable region CDR2 of SEQ ID NO: 74; and a light chain variable region CDR3 of SEQ ID NO: 75.

In a specific embodiment, the invention includes an antibody that specifically binds to β-klotho comprising a heavy chain variable region CDR1 of SEQ ID NO: 264; a heavy chain variable region CDR2 of SEQ ID NO: 265; a heavy chain variable region CDR3 of SEQ ID NO: 266; a light chain variable region CDR1 of SEQ ID NO: 267; a light chain variable region CDR2 of SEQ ID NO: 17; and a light chain variable region CDR3 of SEQ ID NO: 15.

In a specific embodiment, the invention includes an antibody that specifically binds to β-klotho comprising a heavy chain variable region CDR1 of SEQ ID NO: 269; a heavy chain variable region CDR2 of SEQ ID NO: 270; a heavy chain variable region CDR3 of SEQ ID NO: 271; a light chain variable region CDR1 of SEQ ID NO: 272; a light chain variable region CDR2 of SEQ ID NO: 273; and a light chain variable region CDR3 of SEQ ID NO: 35.

In a specific embodiment, the invention includes an antibody that specifically binds to β-klotho comprising a heavy chain variable region CDR1 of SEQ ID NO: 264; a heavy chain variable region CDR2 of SEQ ID NO: 265; a heavy chain variable region CDR3 of SEQ ID NO: 266; a light chain variable region CDR1 of SEQ ID NO: 267; a light chain variable region CDR2 of SEQ ID NO: 57; and a light chain variable region CDR3 of SEQ ID NO: 55.

In a specific embodiment, the invention includes an antibody that specifically binds to β-klotho comprising a heavy chain variable region CDR1 of SEQ ID NO: 269; a heavy chain variable region CDR2 of SEQ ID NO: 270; a heavy chain variable region CDR3 of SEQ ID NO: 271; a light chain variable region CDR1 of SEQ ID NO: 272; a light chain variable region CDR2 of SEQ ID NO: 273; and a light chain variable region CDR3 of SEQ ID NO: 75.

In certain embodiments, the invention includes antibodies or antigen-binding fragments that specifically bind to β-klotho as described in Table 1. In a preferred embodiment, the antibody, or antigen-binding fragment, that binds β-klotho and activates the FGF21 receptor complex is Fab NOV001, NOV002, NOV003, NOV004.

As used herein, a human antibody comprises heavy or light chain variable regions or full length heavy or light chains that are "the product of" or "derived from" a particular germline sequence if the variable regions or full length chains of the antibody are obtained from a system that uses human germline immunoglobulin genes. Such systems include immunizing a transgenic mouse carrying human immunoglobulin genes with the antigen of interest or screening a human immunoglobulin gene library displayed on phage with the antigen of interest. A human antibody that is "the product of" or "derived from" a human germline immunoglobulin sequence can be identified as such by comparing the amino acid sequence of the human antibody to the amino acid sequences of human germline immunoglobulins and selecting the human germline immunoglobulin sequence that is closest in sequence (i.e., greatest % identity) to the sequence of the human antibody.

A human antibody that is "the product of" or "derived from" a particular human germline immunoglobulin sequence may contain amino acid differences as compared to the germline sequence, due to, for example, naturally occurring somatic mutations or intentional introduction of site-directed mutations. However, in the VH or VL framework regions, a selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 60%, 70%, 80%, 90%, or at least 95%, or even at least 96%, 97%, 98%, or 99% identical in amino acid sequence to the amino acid sequence encoded by the germline immunoglobulin gene.

Typically, a recombinant human antibody will display no more than 10 amino acid differences from the amino acid sequence encoded by the human germline immunoglobulin gene in the VH or VL framework regions. In certain cases, the human antibody may display no more than 5, or even no more than 4, 3, 2, or 1 amino acid difference from the amino acid sequence encoded by the germline immunoglobulin gene. Examples of human germline immunoglobulin genes include, but are not limited to the variable domain germline fragments described below, as well as DP47 and DPK9.

Homologous Antibodies

In yet another embodiment, the present invention provides an antibody, or an antigen-binding fragment thereof, comprising amino acid sequences that are homologous to the sequences described in Table 1, and the antibody binds to a β-klotho protein (e.g., human and cynomolgus monkey β-klotho), and retains the desired functional properties of those antibodies described in Table 1.

For example, the invention provides an isolated antibody, or a functional antigen-binding fragment thereof, comprising a heavy chain variable domain and a light chain variable domain, wherein the heavy chain variable domain comprises an amino acid sequence that is at least 80%, at least 90%, 95%, 96%, 97%, 98%, or at least 99% identical to an amino acid sequence selected from the group consisting of SEQ ID NOs: 9, 29, 49, or 69; the light chain variable domain comprises an amino acid sequence that is at least 80%, at least 90%, 95%, 96%, 97%, 98%, or at least 99% identical to an amino acid sequence selected from the group consisting of SEQ ID NOs: 19, 39, 59, or 79; and the antibody specifically binds to β-klotho (e.g., human and cynomolgus monkey β-klotho). In certain aspects of the invention the heavy and light chain sequences further comprise HCDR1, HCDR2, HCDR3, LCDR1, LCDR2, and LCDR3 sequences as defined by Kabat, for example SEQ ID NOs: 3, 4, 5, 13, 14, and 15, respectively. In certain other aspects of the invention the heavy and light chain sequences further comprise HCDR1, HCDR2, HCDR3, LCDR1, LCDR2, and LCDR3 sequences as defined by Chothia, for example SEQ ID NOs: 6, 7, 8, 16, 17, and 18, respectively. In certain other aspects of the invention the heavy and light chain sequences further comprise HCDR1, HCDR2, HCDR3, LCDR1, LCDR2, and LCDR3 sequences as defined by Combined, for example SEQ ID NOs: 263, 4, 5, 13, 14, and 15, respectively. In certain other aspects of the invention the heavy and light chain sequences further comprise HCDR1, HCDR2, HCDR3, LCDR1, LCDR2, and LCDR3 sequences as defined by IMGT, for example SEQ ID NOs: 264, 265, 266, 267, 17, and 15, respectively.

For example, the invention provides an isolated antibody, or a functional antigen-binding fragment thereof, comprising a heavy chain variable domain and a light chain variable domain, wherein the heavy chain variable domain comprises an amino acid sequence that is at least 80%, at least 90%, 95%, 96%, 97%, 98%, or at least 99% identical to an amino acid sequence of SEQ ID NOs: 9; the light chain variable domain comprises an amino acid sequence that is at least 80%, at least 90%, 95%, 96%, 97%, 98%, or at least 99% identical to an amino acid sequence of SEQ ID NOs: 19; and the antibody specifically binds to β-klotho (e.g., human and cynomolgus monkey β-klotho). In certain aspects of the invention the heavy and light chain sequences further comprise HCDR1, HCDR2, HCDR3, LCDR1, LCDR2, and LCDR3 sequences as defined by Kabat, for example SEQ ID NOs: 3, 4, 5, 13, 14, and 15, respectively. In certain other aspects of the invention the heavy and light chain sequences further comprise HCDR1, HCDR2, HCDR3, LCDR1, LCDR2, and LCDR3 sequences as defined by Chothia, for example SEQ ID NOs: 6, 7, 8, 16, 17, and 18, respectively. In certain other aspects of the invention the heavy and light chain sequences further comprise HCDR1, HCDR2, HCDR3, LCDR1, LCDR2, and LCDR3 sequences as defined by Combined, for example SEQ ID NOs: 263, 4, 5, 13, 14, and 15, respectively. In certain other aspects of the invention the heavy and light chain sequences further comprise HCDR1, HCDR2, HCDR3, LCDR1, LCDR2, and LCDR3 sequences as defined by IMGT, for example SEQ ID NOs: 264, 265, 266, 267, 17, and 15, respectively.

For example, the invention provides an isolated antibody, or a functional antigen-binding fragment thereof, comprising a heavy chain variable domain and a light chain variable domain, wherein the heavy chain variable domain comprises an amino acid sequence that is at least 80%, at least 90%, 95%, 96%, 97%, 98%, or at least 99% identical to an amino acid sequence of SEQ ID NOs: 29; the light chain variable domain comprises an amino acid sequence that is at least 80%, at least 90%, 95%, 96%, 97%, 98%, or at least 99% identical to an amino acid sequence of SEQ ID NO: 39; and the antibody specifically binds to β-klotho (e.g., human and cynomolgus monkey β-klotho). In certain aspects of the invention the heavy and light chain sequences further comprise HCDR1, HCDR2, HCDR3, LCDR1, LCDR2, and LCDR3 sequences as defined by Kabat, for example SEQ ID NOs: 23, 24, 25, 33, 34, and 35, respectively. In certain other aspects of the invention the heavy and light chain sequences further comprise HCDR1, HCDR2, HCDR3, LCDR1, LCDR2, and LCDR3 sequences as defined by Chothia, for example SEQ ID NOs: 26, 27, 28, 36, 37, and 38, respectively. In certain other aspects of the invention the heavy and light chain sequences further comprise HCDR1, HCDR2, HCDR3, LCDR1, LCDR2, and LCDR3 sequences as defined by Combined, for example SEQ ID NOs: 268, 24, 25, 33, 34, and 35, respectively. In certain other aspects of the invention the heavy and light chain sequences further comprise HCDR1, HCDR2, HCDR3, LCDR1, LCDR2, and LCDR3 sequences as defined by IMGT, for example SEQ ID NOs: 269, 270, 271, 272, 273, and 35, respectively.

For example, the invention provides an isolated antibody, or a functional antigen-binding fragment thereof, comprising a heavy chain variable domain and a light chain variable domain, wherein the heavy chain variable domain comprises an amino acid sequence that is at least 80%, at least 90%, 95%, 96%, 97%, 98%, or at least 99% identical to an amino acid sequence of SEQ ID NOs: 49; the light chain variable domain comprises an amino acid sequence that is at least 80%, at least 90%, 95%, 96%, 97%, 98%, or at least 99% identical to an amino acid sequence of SEQ ID NOs: 59; and the antibody specifically binds to β-klotho (e.g., human and cynomolgus monkey β-klotho). In certain aspects of the invention the heavy and light chain sequences further comprise HCDR1, HCDR2, HCDR3, LCDR1, LCDR2, and LCDR3 sequences as defined by Kabat, for example SEQ ID NOs: 43, 44, 45, 53, 54, and 55, respectively. In certain other aspects of the invention the heavy and light chain sequences further comprise HCDR1, HCDR2, HCDR3, LCDR1, LCDR2, and LCDR3 sequences as defined by Chothia, for example SEQ ID NOs: 46, 47, 48, 56, 57, and 58, respectively. In certain other aspects of the invention the heavy and light chain sequences further comprise HCDR1, HCDR2, HCDR3, LCDR1, LCDR2, and LCDR3 sequences as defined by Combined, for example SEQ ID NOs: 263, 44, 45, 53, 54, and 55, respectively. In certain other aspects of the invention the heavy and light chain sequences further comprise HCDR1, HCDR2, HCDR3, LCDR1, LCDR2, and LCDR3 sequences as defined by IMGT, for example SEQ ID NOs: 264, 265, 266, 267, 57, and 55, respectively.

For example, the invention provides an isolated antibody, or a functional antigen-binding fragment thereof, comprising a heavy chain variable domain and a light chain variable domain, wherein the heavy chain variable domain comprises an amino acid sequence that is at least 80%, at least 90%, 95%, 96%, 97%, 98%, or at least 99% identical to an amino acid sequence of SEQ ID NOs: 69; the light chain variable domain comprises an amino acid sequence that is at least 80%, at least 90%, 95%, 96%, 97%, 98%, or at least 99% identical to an amino acid sequence of SEQ ID NOs: 79; and the antibody specifically binds to β-klotho (e.g., human and cynomolgus monkey β-klotho). In certain aspects of the invention the heavy and light chain sequences further comprise HCDR1, HCDR2, HCDR3, LCDR1, LCDR2, and LCDR3 sequences as defined by Kabat, for example SEQ ID NOs: 63, 64, 65, 73, 74, and 75, respectively. In certain other aspects of the invention the heavy and light chain sequences further comprise HCDR1, HCDR2, HCDR3, LCDR1, LCDR2, and LCDR3 sequences as defined by Chothia, for example SEQ ID NOs: 66, 67, 68, 76, 77, and 78, respectively. In certain other aspects of the invention the heavy and light chain sequences further comprise HCDR1, HCDR2, HCDR3, LCDR1, LCDR2, and LCDR3 sequences as defined by Combined, for example SEQ ID NOs: 268, 64, 25, 73, 74, and 75, respectively. In certain other aspects of the invention the heavy and light chain sequences further comprise HCDR1, HCDR2, HCDR3, LCDR1, LCDR2, and LCDR3 sequences as defined by IMGT, for example SEQ ID NOs: 269, 270, 271, 272, 273, and 75, respectively.

In other embodiments, the VH and/or VL amino acid sequences may be 50%, 60%, 70%, 80%, 90%, 95%, 96%, 97%, 98% or 99% identical to the sequences set forth in Table 1. In other embodiments, the VH and/or VL amino acid sequences may be identical except for an amino acid substitution in no more than 1, 2, 3, 4 or 5 amino acid positions. An antibody having VH and VL regions having high (i.e., 80% or greater) identity to the VH and VL regions of those described in Table 1 can be obtained by mutagenesis (e.g., site-directed or PCR-mediated mutagenesis) of nucleic acid molecules encoding SEQ ID NOs: 10, 30, 50, or 70 and SEQ ID NOs: 20, 40, 60, or 80, respectively, followed by testing of the encoded altered antibody for retained function using the functional assays described herein.

In other embodiments, the full length heavy chain and/or full length light chain amino acid sequences may be 50% 60%, 70%, 80%, 90%, 95%, 96%, 97%, 98% or 99% identical to the sequences set forth in Table 1. An antibody having a full length heavy chain and full length light chain having high (i.e., 80% or greater) identity to the full length heavy chains of any of SEQ ID NOs: 9, 29, 49, or 69, and full length light chains of any of SEQ ID NOs: 19, 39, 59, or 79, can be obtained by mutagenesis (e.g., site-directed or PCR-mediated mutagenesis) of nucleic acid molecules encoding such polypeptides, followed by testing of the encoded altered antibody for retained function using the functional assays described herein. An antibody having a full length heavy chain and full length light chain having high (i.e., 80% or greater) identity to the full length heavy chains of any of SEQ ID NOs: 11, 31, 51, or 71, and full length light chains of any of SEQ ID NOs: 21, 41, 61, or 81, can be obtained by mutagenesis (e.g., site-directed or PCR-mediated mutagenesis) of nucleic acid molecules encoding such polypeptides, followed by testing of the encoded altered antibody for retained function using the functional assays described herein.

In other embodiments, the full length heavy chain and/or full length light chain nucleotide sequences may be 60%, 70%, 80%, 90%, 95%, 96%, 97%, 98% or 99% identical to the sequences set forth in Table 1.

In other embodiments, the variable regions of heavy chain and/or the variable regions of light chain nucleotide sequences may be 60%, 70%, 80%, 90%, 95%, 96%, 97%, 98% or 99% identical to the sequences set forth in Table 1.

In some embodiments, the heavy chain and/or the light chain CDRs may be 90%, 95%, 96%, 97%, 98% or 99% identical to the sequences set forth in Table 1.

As used herein, the percent identity between the two sequences is a function of the number of identical positions shared by the sequences (i.e., % identity equals number of identical positions/total number of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

Additionally or alternatively, the protein sequences of the present invention can further be used as a "query sequence" to perform a search against public databases to, for example, identify related sequences. For example, such searches can be performed using the BLAST program (version 2.0) of Altschul, et al., 1990 J. Mol. Biol. 215:403-10.

Antibodies with Conservative Modifications

In certain embodiments, an antibody of the invention has a heavy chain variable region comprising CDR1, CDR2, and CDR3 sequences and a light chain variable region comprising CDR1, CDR2, and CDR3 sequences, wherein one or more of these CDR sequences have specified amino acid sequences based on the antibodies described herein or conservative modifications thereof, and wherein the antibodies retain the desired functional properties of the β-klotho-binding antibodies of the invention.

Accordingly, the invention provides an isolated antibody, or a antigen-binding fragment thereof, consisting of a heavy chain variable region comprising CDR1, CDR2, and CDR3 sequences and a light chain variable region comprising CDR1, CDR2, and CDR3 sequences, wherein: the heavy chain variable region CDR1 amino acid sequences are selected from the group consisting of SEQ ID NOs: 3, 23, 43, and 63, and conservative modifications thereof; the heavy chain variable region CDR2 amino acid sequences are selected from the group consisting of SEQ ID NOs: 4, 24, 44, and 64, and conservative modifications thereof; the heavy chain variable region CDR3 amino acid sequences are selected from the group consisting of SEQ ID NOs: 5, 25, 45, and 65, and conservative modifications thereof; the light chain variable regions CDR1 amino acid sequences are selected from the group consisting of SEQ ID NOs: 13, 33, 53, and 73, and conservative modifications thereof; the light chain variable regions CDR2 amino acid sequences are selected from the group consisting of SEQ ID NOs: 14, 34, 54, and 74, and conservative modifications thereof; the light chain variable regions of CDR3 amino acid sequences are selected from the group consisting of SEQ ID NOs: 15, 35, 55, and 75, and conservative modifications thereof; and the antibody or antigen-binding fragments thereof specifically binds to β-klotho.

Accordingly, the invention provides an isolated antibody, or a antigen-binding fragment thereof, consisting of a heavy chain variable region comprising CDR1, CDR2, and CDR3 sequences and a light chain variable region comprising CDR1, CDR2, and CDR3 sequences, wherein: the heavy chain variable region CDR1 amino acid sequences are selected from the group consisting of SEQ ID NOs: 263 and 268, and conservative modifications thereof; the heavy chain variable region CDR2 amino acid sequences are selected from the group consisting of SEQ ID NOs: 4, 24, 44, and 64, and conservative modifications thereof; the heavy chain variable region CDR3 amino acid sequences are selected from the group consisting of SEQ ID NOs: 5, 25, and 45, and conservative modifications thereof; the light chain variable regions CDR1 amino acid sequences are selected from the group consisting of SEQ ID NOs: 13, 33, 53, and 73, and conservative modifications thereof; the light chain variable regions CDR2 amino acid sequences are selected from the group consisting of SEQ ID NOs: 14, 34, 54, and 74, and conservative modifications thereof; the light chain variable regions of CDR3 amino acid sequences are selected from the group consisting of SEQ ID NOs: 15, 35, 55, and 75, and conservative modifications thereof; and the antibody or antigen-binding fragments thereof specifically binds to β-klotho.

In other embodiments, the antibody of the invention is optimized for expression in a mammalian cell has a full length heavy chain sequence and a full length light chain sequence, wherein one or more of these sequences have specified amino acid sequences based on the antibodies described herein or conservative modifications thereof, and wherein the antibodies retain the desired functional properties of the β-klotho binding antibodies of the invention. Accordingly, the invention provides an isolated antibody optimized for expression in a mammalian cell consisting of a full length heavy chain and a full length light chain wherein the full length heavy chain has amino acid sequences selected from the group of SEQ ID NOs: 11, 31, 51, or 71, and conservative modifications thereof; and the full length light chain has amino acid sequences selected from the group of SEQ ID NOs: 21, 41, 61, or 81, and conservative modifications thereof; and the antibody specifically binds to β-klotho (e.g., human and cynomolgus monkey β-klotho).

Antibodies that Bind to the Same Epitope

The present invention provides antibodies that bind to the same epitope as the β-klotho binding antibodies described in Table 1 (e.g., NOV001, NOV002, NOV003, or NOV004). In a particular aspect, such antibodies and antigen-binding fragments are capable of increasing the activity of β-klotho and FGFR1c. Additional antibodies can therefore be identified based on their ability to compete (e.g., to competitively inhibit the binding of, in a statistically significant manner) with other antibodies of the invention in β-klotho binding assays (such as those described in the Examples). The ability of a test antibody to inhibit the binding of antibodies of the present invention to a β-klotho protein demonstrates that the test antibody can compete with that antibody for binding to β-klotho; such an antibody may, according to non-limiting theory, bind to the same or a related (e.g., a structurally similar or spatially proximal) epitope on the β-klotho protein as the antibody with which it competes. In a certain embodiment, the antibody that binds to the same epitope on β-klotho as the antibodies of the present invention is a human monoclonal antibody. Such human monoclonal antibodies can be prepared and isolated as described herein. As used herein, an antibody "competes" for binding when the competing antibody inhibits β-klotho binding of an antibody or antigen-binding fragment of the invention by more than 50% (for example, 80%, 85%, 90%, 95%, 98% or 99%) in the presence of an equimolar concentration of competing antibody. In a certain embodiment, the antibody that binds to the same epitope on β-klotho as the antibodies of the present invention is a humanized monoclonal antibody. Such humanized monoclonal antibodies can be prepared and isolated as described herein.

In a particular aspect, the present invention provides antibodies that bind to the same epitope as β-klotho binding antibody NOV001. In a particular aspect, the present invention provides antibodies that bind to the same epitope as β-klotho binding antibody NOV002. In a particular aspect, the present invention provides antibodies that bind to the same epitope as β-klotho binding antibody NOV003. In a particular aspect, the present invention provides antibodies that bind to the same epitope as β-klotho binding antibody NOV004.

In a particular aspect, the present invention provides antibodies that bind to the same epitope as a β-klotho binding antibody which comprises a heavy chain variable region (VH) comprising the amino acid sequence of SEQ ID NO: 9 and a light chain variable region (VL) comprising the amino acid sequence of SEQ ID NO: 19.

In a particular aspect, the present invention provides antibodies that bind to the same epitope as a β-klotho binding antibody which comprises a heavy chain variable region (VH) comprising the amino acid sequence of SEQ ID NO: 29 and a light chain variable region (VL) comprising the amino acid sequence of SEQ ID NO: 39.

In a particular aspect, the present invention provides antibodies that bind to the same epitope as a β-klotho binding antibody which comprises a heavy chain variable region (VH) comprising the amino acid sequence of SEQ ID NO: 49 and a light chain variable region (VL) comprising the amino acid sequence of SEQ ID NO: 59.

In a particular aspect, the present invention provides antibodies that bind to the same epitope as a β-klotho binding antibody which comprises a heavy chain variable region (VH) comprising the amino acid sequence of SEQ ID NO: 69 and a light chain variable region (VL) comprising the amino acid sequence of SEQ ID NO: 79.

In specific aspects, provided herein are isolated antibodies or an antigen-binding fragment thereof that bind to an epitope of β-klotho, wherein the epitope comprises one or more of the SEQ ID NOs shown in Table 2. In a particular aspect, such antibodies and antigen-binding fragments are capable of increasing the activity of β-klotho and FGFR1c.

In a particular aspect, provided herein is an isolated antibody or antigen-binding fragment thereof that binds to an epitope of β-klotho, wherein said epitope comprises one or more amino acids of residues 246-265 of the β-klotho sequence (SEQ ID NO:262). In a particular aspect, provided herein is an isolated antibody or antigen-binding fragment thereof that binds to an epitope of β-klotho, wherein said epitope comprises one or more amino acids of residues 536-550 of the β-klotho sequence (SEQ ID NO:262). In a particular aspect, provided herein is an isolated antibody or antigen-binding fragment thereof that binds to an epitope of β-klotho, wherein said epitope comprises one or more amino acids of residues 834-857 of the β-klotho sequence (SEQ ID NO:262). In a particular aspect, provided herein is an isolated antibody or antigen-binding fragment thereof that binds to an epitope of β-klotho, wherein said epitope comprises one or more amino acids of residues 959-986 of the β-klotho sequence (SEQ ID NO:262).

In a particular aspect, provided herein is an isolated antibody or antigen-binding fragment thereof that binds to an epitope of β-klotho, wherein said epitope comprises one or more amino acids of residues 246-265, 536-550, 834-857 and 959-986 of the β-klotho sequence (SEQ ID NO:262). In specific aspects, provided herein is an isolated antibody or antigen-binding fragment thereof that binds to an epitope of β-klotho, wherein said epitope comprises two or more amino acids of residues 246-265, 536-550, 834-857 and 959-986 of the β-klotho sequence (SEQ ID NO:262). In specific aspects, provided herein is an isolated antibody or antigen-binding fragment thereof that binds to an epitope of β-klotho, wherein said epitope comprises three or more amino acids of residues 246-265, 536-550, 834-857 and 959-986 of the β-klotho sequence (SEQ ID NO:262). In specific aspects, provided herein is an isolated antibody or antigen-binding fragment thereof that binds to an epitope of β-klotho, wherein said epitope comprises amino acids of residues 246-265, 536-550, 834-857 and 959-986 of the β-klotho sequence (SEQ ID NO:262).

In a particular aspect, provided herein is an isolated antibody or antigen-binding fragment thereof that binds to one or more epitopes of β-klotho, wherein said epitopes comprises one or more of amino acids of residues 646-670 of the β-klotho sequence (SEQ ID NO:262). In a particular aspect, provided herein is an isolated antibody or antigen-binding fragment thereof that binds to one or more epitopes of β-klotho, wherein said epitopes comprises one or more of amino acids of residues 696-700 of the β-klotho sequence (SEQ ID NO:262). In a particular aspect, provided herein is an isolated antibody or antigen-binding fragment thereof that binds to one or more epitopes of β-klotho, wherein said epitopes comprises one or more of amino acids of residues 646-689 of the β-klotho sequence (SEQ ID NO:262).

In a particular aspect, provided herein is an isolated antibody or antigen-binding fragment thereof that binds to one or more epitopes of β-klotho, wherein said epitopes comprises one, or two, or three, or four, or five, or more of amino acids of residues 646-670, 696-700, and 646-689 of the β-klotho sequence (SEQ ID NO:262). In a certain aspect, provided herein is an isolated antibody or antigen-binding fragment thereof that binds to two or more epitopes of β-klotho, wherein said epitopes comprises one or more of amino acids of residues 646-670, 696-700, and 646-689 of the β-klotho sequence (SEQ ID NO:262). In a specific aspect, provided herein is an isolated antibody or antigen-binding fragment thereof that binds to three or more epitopes of β-klotho, wherein said epitopes comprises one or more of amino acids of residues 646-670, 696-700, and 646-689 of the β-klotho sequence (SEQ ID NO:262). In a specific aspect, provided herein is an isolated antibody or antigen-binding fragment thereof that binds to three or more epitopes of β-klotho, wherein said epitopes comprises amino acids of residues 646-670, 696-700, and 646-689 of the β-klotho sequence (SEQ ID NO:262).

In specific aspects, provided herein are isolated antibodies or an antigen-binding fragment thereof that bind to an epitope of β-klotho, wherein the epitope comprises one or more of the SEQ ID NOs shown in Table 2, wherein said antibodies and antigen-binding fragments are capable of increasing the activity of β-klotho and FGFR1c, and wherein said antibodies and antigen-binding fragments are capable of protecting, by hydrogen-deuterium exchange (HDx), one or more peptides of β-klotho as characterized by a change in deuterium incorporation in the range of −0.5 to −2.1, for example as set forth in Table 2.

In a particular aspect, provided herein is an isolated antibody or antigen-binding fragment thereof that protects, as determined by hydrogen-deuterium exchange (HDx), one, two, three, four, five, or more of the following peptides of β-klotho (SEQ ID NO: 262): 245-266, 246-265, 343-349, 344-349, 421-429, 488-498, 509-524, 536-550, 568-576, 646-669, 646-670, 696-700, 773-804, 834-857, and 959-986 aa.

In a specific aspect, provided herein is an isolated antibody or antigen-binding fragment thereof, which increases the activity of β-klotho and FGFR1c, wherein the antibody or antigen-binding fragment thereof protects, as determined by hydrogen-deuterium exchange (HDx), one, two, three, four, five, or more peptides from the following as set forth in Table 2: SEQ ID NOs: 109, 110, 111, 112, 113, 125, 126, 127, 128, 129, 141, 142, 143, 156, 157, 158, 159, 160, 161, 163, 164, 165, 167, 168, 169, 170, 171, 172, 184, 185, 186, 187, 188, 195, 196, 197, 198, 204, 212, 213, 214, 215, 216, 217, 224, 225, 226, 227, 228, 229, 230, 231, 232, 233, 256, 257, 258, 259, 260, and 261.

In certain aspects, provided herein is isolated antibody or antigen-binding fragment thereof, which increases the activity of β-klotho and FGFR1c, wherein the antibody or antigen-binding fragment thereof protects, as determined by hydrogen-deuterium exchange (HDx), six, seven, eight, nine, ten, or more peptides from the following as set forth in Table 2: SEQ ID NOs: 109, 110, 111, 112, 113, 125, 126, 127, 128, 129, 141, 142, 143, 156, 157, 158, 159, 160, 161, 163, 164, 165, 167, 168, 169, 170, 171, 172, 184, 185, 186, 187, 188, 195, 196, 197, 198, 204, 212, 213, 214, 215, 216, 217, 224, 225, 226, 227, 228, 229, 230, 231, 232, 233, 256, 257, 258, 259, 260, and 261.

In certain aspects, provided herein is isolated antibody or antigen-binding fragment thereof, which increases the activity of β-klotho and FGFR1c, wherein the antibody or antigen-binding fragment thereof does not contact residues 701 (Tyr) or 703 (Arg) of human β-klotho (SEQ ID NO: 262).

Engineered and Modified Antibodies

An antibody of the invention further can be prepared using an antibody having one or more of the VH and/or VL sequences shown herein as starting material to engineer a modified antibody, which modified antibody may have altered properties from the starting antibody. An antibody can be engineered by modifying one or more residues within one or both variable regions (i. e., VH and/or VL), for example within one or more CDR regions and/or within one or more framework regions. Additionally or alternatively, an antibody can be engineered by modifying residues within the constant region(s), for example to alter the effector function(s) of the antibody.

One type of variable region engineering that can be performed is CDR grafting. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al., 1998 Nature 332:323-327; Jones, P. et al., 1986 Nature 321:522-525; Queen, C. et al., 1989 Proc. Natl. Acad., U.S.A. 86:10029-10033; U.S. Pat. No. 5,225,539 to Winter, and U.S. Pat. Nos. 5,530,101; 5,585,089; 5,693,762 and 6,180,370 to Queen et al.)

Accordingly, another embodiment of the invention pertains to an isolated antibody, or an antigen-binding fragment thereof, comprising a heavy chain variable region comprising CDR1 sequences having an amino acid sequence selected from the HCDR1 sequences set forth in Table 1; CDR2 sequences having an amino acid sequence selected from the HCDR2 sequences set forth in Table 1; CDR3 sequences having an amino acid sequence selected from the HCDR3 sequences set forth in table 1; and a light chain variable region having CDR1 sequences having an amino acid sequence selected from the LCDR1 sequences set forth in Table 1; CDR2 sequences having an amino acid sequence selected from the LCDR2 sequences set forth in Table 1; and CDR3 sequences consisting of an amino acid sequence selected from the LCDR3 sequences set forth in Table 1. Thus, such antibodies contain the VH and VL CDR sequences of monoclonal antibodies, yet may contain different framework sequences from these antibodies.

Accordingly, another embodiment of the invention pertains to an isolated antibody, or an antigen-binding fragment thereof, comprising a heavy chain variable region comprising CDR1 sequences having an amino acid sequence selected from the group consisting of SEQ ID NOs: 3, 23, 43, and 63; CDR2 sequences having an amino acid sequence selected from the group consisting of SEQ ID NOs: 4, 24, 44, and 64; CDR3 sequences having an amino acid sequence selected from the group consisting of SEQ ID NOs: 5, 25, 45, and 65, respectively; and a light chain variable region having CDR1 sequences having an amino acid sequence selected from the group consisting of SEQ ID NOs: 13, 33, 53, and 73; CDR2 sequences having an amino acid sequence selected from the group consisting of SEQ ID NOs: 14, 34, 54, and 74; and CDR3 sequences consisting of an amino acid sequence selected from the group consisting of SEQ ID NOs: 15, 35, 55, and 75, respectively. Thus, such antibodies contain the VH and VL CDR sequences of monoclonal antibodies, yet may contain different framework sequences from these antibodies.

Such framework sequences can be obtained from public DNA databases or published references that include germline antibody gene sequences. For example, germline DNA sequences for human heavy and light chain variable region genes can be found in the "VBase" human germline sequence database (available on the world wide web at mrc-cpe.cam.ac.uk/vbase), as well as in Kabat, E. A., et al., 1991 Sequences of Proteins of Immunological Interest, Fifth Edition, U.S. Department of Health and Human Services, NIH Publication No. 91-3242; Tomlinson, I. M., et al., 1992 J. Mol. Biol. 227:776-798; and Cox, J. P. L. et al., 1994 Eur. J Immunol. 24:827-836; the contents of each of which are expressly incorporated herein by reference.

An example of framework sequences for use in the antibodies of the invention are those that are structurally similar to the framework sequences used by selected antibodies of the invention, e.g., consensus sequences and/or framework sequences used by monoclonal antibodies of the invention. The VH CDR1, 2 and 3 sequences, and the VL CDR1, 2 and 3 sequences, can be grafted onto framework regions that have the identical sequence as that found in the germline immunoglobulin gene from which the framework sequence derive, or the CDR sequences can be grafted onto framework regions that contain one or more mutations as compared to the germline sequences. For example, it has been found that in certain instances it is beneficial to mutate residues within the framework regions to maintain or enhance the antigen-binding ability of the antibody (see e.g., U.S. Pat. Nos. 5,530,101; 5,585,089; 5,693,762 and 6,180,370 to Queen et al). Frameworks that can be utilized as scaffolds on which to build the antibodies and antigen-binding fragments described herein include, but are not limited to VH1A, VH1B, VH3, Vk1, Vl2, and Vk2. Additional frameworks are known in the art and may be found, for example, in the vBase data base on the world wide web at vbase.mrc-cpe.cam.ac.uk/index.php?&MMN_position=1:1.

Accordingly, an embodiment of the invention relates to isolated β-klotho binding antibodies, or antigen-binding fragments thereof, comprising a heavy chain variable region comprising an amino acid sequence selected from the group consisting of SEQ ID NOs: 9, 29, 49, or 69, or an amino acid sequence having one, two, three, four or five amino acid substitutions, deletions or additions in the framework region of such sequences, and further comprising a light chain variable region having an amino acid sequence selected from the group consisting of SEQ ID NOs: 19, 39, 59, or 79, or an amino acid sequence having one, two, three, four or five amino acid substitutions, deletions or additions in the framework region of such sequences.

Accordingly, an embodiment of the invention relates to isolated β-klotho binding antibodies, or antigen-binding fragments thereof, comprising a heavy chain variable region comprising the amino acid sequence of SEQ ID NO: 9, or an amino acid sequence having one, two, three, four or five amino acid substitutions, deletions or additions in the framework region of such sequences, and further comprising a light chain variable region comprising the amino acid sequence of SEQ ID NO: 19, or an amino acid sequence having one, two, three, four or five amino acid substitutions, deletions or additions in the framework region of such sequences.

In a particular aspect, an embodiment of the invention relates to isolated β-klotho binding antibodies, or antigen-binding fragments thereof, comprising a heavy chain variable region comprising the amino acid sequence of SEQ ID NO: 29, or an amino acid sequence having one, two, three, four or five amino acid substitutions, deletions or additions in the framework region of such sequences, and further comprising a light chain variable region comprising the amino acid sequence of SEQ ID NO: 39, or an amino acid sequence having one, two, three, four or five amino acid substitutions, deletions or additions in the framework region of such sequences.

In a particular aspect, an embodiment of the invention relates to isolated β-klotho binding antibodies, or antigen-binding fragments thereof, comprising a heavy chain variable region comprising the amino acid sequence of SEQ ID NO: 49, or an amino acid sequence having one, two, three, four or five amino acid substitutions, deletions or additions in the framework region of such sequences, and further comprising a light chain variable region comprising the amino acid sequence of SEQ ID NO: 59, or an amino acid sequence having one, two, three, four or five amino acid substitutions, deletions or additions in the framework region of such sequences.

In a particular aspect, an embodiment of the invention relates to isolated β-klotho binding antibodies, or antigen-binding fragments thereof, comprising a heavy chain variable region comprising the amino acid sequence of SEQ ID NO: 69, or an amino acid sequence having one, two, three, four or five amino acid substitutions, deletions or additions in the framework region of such sequences, and further comprising a light chain variable region comprising the amino acid sequence of SEQ ID NO: 79, or an amino acid sequence having one, two, three, four or five amino acid substitutions, deletions or additions in the framework region of such sequences.

Another type of variable region modification is to mutate amino acid residues within the VH and/or VL CDR1, CDR2 and/or CDR3 regions to thereby improve one or more binding properties (e.g., affinity) of the antibody of interest, known as "affinity maturation." Site-directed mutagenesis or PCR-mediated mutagenesis can be performed to introduce the mutation(s) and the effect on antibody binding, or other functional property of interest, can be evaluated in in vitro or in vivo assays as described herein and provided in the Examples. Conservative modifications (as discussed above) can be introduced. The mutations may be amino acid substitutions, additions or deletions. Moreover, typically no more than one, two, three, four or five residues within a CDR region are altered.

Certain amino acid sequence motifs are known to undergo post-translational modification (PTM) such as glycosylation (i.e. N×S/T, x any but P), oxidation of free cysteines, deamidation (e.g. NG) or isomerization (e.g. DG). If present in the CDR regions, those motifs are ideally removed by site-directed mutagenesis in order to increase product homogeneity.

The process of affinity maturation is well described in the art. Among many display systems, phage display (Smith G P (1985) Science 228:1315-1317) and display on eukaryotic cells such as yeast (Boder E T and Wittrup K D (1997) Nature Biotechnology 15: 553-557) seem to be the most commonly applied systems to select for antibody-antigen interaction. Advantages of those display systems are that they are suitable for a wide range of antigens and that the selection stringency can be easily adjusted. In phage display, scFv or Fab fragments can be displayed and in yeast display full-length IgG in addition. Those commonly applied methods allow selection of a desired antibody variants from larger libraries with diversities of more than 10E7. Libraries with smaller diversity, e.g. 10E3, may be screen by micro-expression and ELISA.

Non-targeted or random antibody variant libraries can be generated for example by error-prone PCR (Cadwell R C and Joyce G F (1994) Mutagenic PCR. PCR Methods Appl. 3: S136-S140) and provide a very simple, but sometimes limited approach. Another strategy is the CDR directed diversification of an antibody candidate. One or more positions in one or more CDRs can be targeted specifically using for example degenerated oligos (Thompson J et al. (1996) J. Mol. Biol. 256: 77-88) trinucleotide mutagenesis (TRIM) (Kayushin A L et al. (1996) Nucleic Acids Res. 24: 3748-3755) or any other approach known to the art.

Accordingly, in another embodiment, the invention provides isolated β-klotho-binding antibodies, or antigen-binding fragments thereof, consisting of a heavy chain variable region having a VH CDR1 region consisting of an amino acid sequence selected from the group having SEQ ID NOs: 3, 23, 43, and 63 or an amino acid sequence having one, two, three, four or five amino acid substitutions, deletions or additions as compared to SEQ ID NOs: 3, 23, 43, and 63; a VH CDR2 region having an amino acid sequence selected from the group consisting of SEQ ID NOs: 4, 24, 44, and 64 or an amino acid sequence having one, two, three, four or five amino acid substitutions, deletions or additions as compared to SEQ ID NOs: 4, 24, 44, and 64; a VH CDR3 region having an amino acid sequence selected from the group consisting of SEQ ID NOs: 5, 25, 45, and 65, or an amino acid sequence having one, two, three, four or five amino acid substitutions, deletions or additions as compared to SEQ ID NOs: 5, 25, 45, and 65; a VL CDR1 region having an amino acid sequence selected from the group consisting of SEQ ID NOs: 13, 33, 53, and 73, or an amino acid sequence having one, two, three, four or five amino acid substitutions, deletions or additions as compared to SEQ ID NOs: 13, 33, 53, and 73; a VL CDR2 region having an amino acid sequence selected from the group consisting of SEQ ID NOs: 14, 34, 54, and 74, or an amino acid sequence having one, two, three, four or five amino acid substitutions, deletions or additions as compared to SEQ ID NOs: 14, 34, 54, and 74; and a VL CDR3 region having an amino acid sequence selected from the group consisting of SEQ ID NOs: 15, 35, 55, and 75, or an amino acid sequence having one, two, three, four or five amino acid substitutions, deletions or additions as compared to SEQ ID NOs: 15, 35, 55, and 75.

Accordingly, in another embodiment, the invention provides isolated β-klotho-binding antibodies, or antigen-binding fragments thereof, consisting of a heavy chain variable region having a VH CDR1 region consisting of an amino acid sequence selected from the group having SEQ ID NOs: 6, 26, 46, and 66 or an amino acid sequence having one, two, three, four or five amino acid substitutions, deletions or additions as compared to SEQ ID NOs: 6, 26, 46, and 66; a VH CDR2 region having an amino acid sequence selected from the group consisting of SEQ ID NOs: 7, 27, 47, and 67 or an amino acid sequence having one, two, three, four or five amino acid substitutions, deletions or additions as compared to SEQ ID NOs: 7, 27, 47, and 67; a VH CDR3 region having an amino acid sequence selected from the group consisting of SEQ ID NOs: 8, 28, 48, and 68, or an amino acid sequence having one, two, three, four or five amino acid substitutions, deletions or additions as compared to SEQ ID NOs: 8, 28, 48, and 68; a VL CDR1 region having an amino acid sequence selected from the group consisting of SEQ ID NOs: 13, 33, 53, and 73, or an amino acid sequence having one, two, three, four or five amino acid substitutions, deletions or additions as compared to SEQ ID NOs: 13, 33, 53, and 73; a VL CDR2 region having an amino acid sequence selected from the group consisting of SEQ ID NOs: 14, 34, 54, and 74, or an amino acid sequence having one, two, three, four or five amino acid substitutions, deletions or additions as compared to SEQ ID NOs: 14, 34, 54, and 74; and a VL CDR3 region having an amino acid sequence selected from the group consisting of SEQ ID NOs: 15, 35, 55, and 75, or an amino acid sequence having one, two, three, four or five amino acid substitutions, deletions or additions as compared to SEQ ID NOs: 15, 35, 55, and 75.

Grafting Antigen-Binding Domains into Alternative Frameworks or Scaffolds

A wide variety of antibody/immunoglobulin frameworks or scaffolds can be employed so long as the resulting polypeptide includes at least one binding region which specifically binds to β-klotho. Such frameworks or scaffolds include the 5 main idiotypes of human immunoglobulins, or fragments thereof, and include immunoglobulins of other animal species, preferably having humanized aspects. Single heavy-chain antibodies such as those identified in camelids are of particular interest in this regard. Novel frameworks, scaffolds and fragments continue to be discovered and developed by those skilled in the art.

In one aspect, the invention pertains to generating non-immunoglobulin based antibodies using non-immunoglobulin scaffolds onto which CDRs of the invention can be grafted. Known or future non-immunoglobulin frameworks and scaffolds may be employed, as long as they comprise a binding region specific for the target β-klotho protein. Known non-immunoglobulin frameworks or scaffolds include, but are not limited to, fibronectin (Compound Therapeutics, Inc., Waltham, Mass.), ankyrin (Molecular Partners AG, Zurich, Switzerland), domain antibodies (Domantis, Ltd., Cambridge, Mass., and Ablynx nv, Zwijnaarde, Belgium), lipocalin (Pieris Proteolab AG, Freising, Germany), small modular immuno-pharmaceuticals (Trubion Pharmaceuticals Inc., Seattle, Wash.), maxybodies (Avidia, Inc., Mountain View, Calif.), Protein A (Affibody AG, Sweden), and affilin (gamma-crystallin or ubiquitin) (Scil Proteins GmbH, Halle, Germany)

The fibronectin scaffolds are based on fibronectin type III domain (e.g., the tenth module of the fibronectin type III (10 Fn3 domain)). The fibronectin type III domain has 7 or 8 beta strands which are distributed between two beta sheets, which themselves pack against each other to form the core of the protein, and further containing loops (analogous to CDRs) which connect the beta strands to each other and are solvent exposed. There are at least three such loops at each edge of the beta sheet sandwich, where the edge is the boundary of the protein perpendicular to the direction of the beta strands (see U.S. Pat. No. 6,818,418). These fibronectin-based scaffolds are not an immunoglobulin, although the overall fold is closely related to that of the smallest functional antibody fragment, the variable region of the heavy chain, which comprises the entire antigen recognition unit in camel and llama IgG. Because of this structure, the non-immunoglobulin antibody mimics antigen-binding properties that are similar in nature and affinity to those of antibodies. These scaffolds can be used in a loop randomization and shuffling strategy in vitro that is similar to the process of affinity maturation of antibodies in vivo. These fibronectin-based molecules can be used as scaffolds where the loop regions of the molecule can be replaced with CDRs of the invention using standard cloning techniques.

The ankyrin technology is based on using proteins with ankyrin derived repeat modules as scaffolds for bearing variable regions which can be used for binding to different targets. The ankyrin repeat module is a 33 amino acid polypeptide consisting of two anti-parallel α-helices and a β-turn. Binding of the variable regions is mostly optimized by using ribosome display.

Avimers are derived from natural A-domain containing protein such as LRP-1. These domains are used by nature for protein-protein interactions and in human over 250 proteins are structurally based on A-domains. Avimers consist of a number of different "A-domain" monomers (2-10) linked via amino acid linkers. Avimers can be created that can bind to the target antigen using the methodology described in, for example, U.S. Patent Application Publication Nos. 20040175756; 20050053973; 20050048512; and 20060008844.

Affibody affinity ligands are small, simple proteins composed of a three-helix bundle based on the scaffold of one of the IgG-binding domains of Protein A. Protein A is a surface protein from the bacterium *Staphylococcus aureus*. This scaffold domain consists of 58 amino acids, 13 of which are randomized to generate affibody libraries with a large number of ligand variants (See e.g., U.S. Pat. No. 5,831,012). Affibody molecules mimic antibodies, they have a molecular weight of 6 kDa, compared to the molecular weight of antibodies, which is 150 kDa. In spite of its small size, the binding site of affibody molecules is similar to that of an antibody.

Anticalins are products developed by the company Pieris ProteoLab AG. They are derived from lipocalins, a widespread group of small and robust proteins that are usually involved in the physiological transport or storage of chemically sensitive or insoluble compounds. Several natural lipocalins occur in human tissues or body liquids. The protein architecture is reminiscent of immunoglobulins, with hypervariable loops on top of a rigid framework. However, in contrast with antibodies or their recombinant fragments, lipocalins are composed of a single polypeptide chain with 160 to 180 amino acid residues, being just marginally bigger than a single immunoglobulin domain. The set of four loops, which makes up the binding pocket, shows pronounced structural plasticity and tolerates a variety of side chains.

The binding site can thus be reshaped in a proprietary process in order to recognize prescribed target molecules of different shape with high affinity and specificity. One protein of lipocalin family, the bilin-binding protein (BBP) of Pieris Brassicae has been used to develop anticalins by mutagenizing the set of four loops. One example of a patent application describing anticalins is in PCT Publication No. WO 199916873.

Affilin molecules are small non-immunoglobulin proteins which are designed for specific affinities towards proteins and small molecules. New affilin molecules can be very quickly selected from two libraries, each of which is based on a different human derived scaffold protein. Affilin molecules do not show any structural homology to immunoglobulin proteins. Currently, two affilin scaffolds are employed, one of which is gamma crystalline, a human structural eye lens protein and the other is "ubiquitin" superfamily proteins. Both human scaffolds are very small, show high temperature stability and are almost resistant to pH changes and denaturing agents. This high stability is mainly due to the expanded beta sheet structure of the proteins. Examples of gamma crystalline derived proteins are described in WO200104144 and examples of "ubiquitin-like" proteins are described in WO2004106368.

Protein epitope mimetics (PEM) are medium-sized, cyclic, peptide-like molecules (MW 1-2 kDa) mimicking beta-hairpin secondary structures of proteins, the major secondary structure involved in protein-protein interactions.

The present invention provides fully human antibodies that specifically bind to a β-klotho protein. Compared to the chimeric or humanized antibodies, the human β-klotho-binding antibodies of the invention have further reduced antigenicity when administered to human subjects.

Camelid Antibodies

Antibody proteins obtained from members of the camel and dromedary (Camelus bactrianus and Calelus dromaderius) family including new world members such as llama species (Lama paccos, Lama glama and Lama vicugna) have been characterized with respect to size, structural complexity and antigenicity for human subjects. Certain IgG antibodies from this family of mammals as found in nature lack light chains, and are thus structurally distinct from the typical four chain quaternary structure having two heavy and two light chains, for antibodies from other animals. See PCT/EP93/02214 (WO 94/04678 published 3 Mar. 1994).

A region of the camelid antibody which is the small single variable domain identified as VHH can be obtained by genetic engineering to yield a small protein having high affinity for a target, resulting in a low molecular weight antibody-derived protein known as a "camelid nanobody". See U.S. Pat. No. 5,759,808 issued Jun. 2, 1998; see also Stijlemans, B. et al., 2004 J Biol Chem 279: 1256-1261; Dumoulin, M. et al., 2003 Nature 424: 783-788; Pleschberger, M. et al. 2003 Bioconjugate Chem 14: 440-448; Cortez-Retamozo, V. et al. 2002 Int J Cancer 89: 456-62; and Lauwereys, M. et al. 1998 EMBO J 17: 3512-3520. Engineered libraries of camelid antibodies and antibody fragments are commercially available, for example, from Ablynx, Ghent, Belgium. As with other antibodies of non-human origin, an amino acid sequence of a camelid antibody can be altered recombinantly to obtain a sequence that more closely resembles a human sequence, i.e., the nanobody can be "humanized". Thus the natural low antigenicity of camelid antibodies to humans can be further reduced.

The camelid nanobody has a molecular weight approximately one-tenth that of a human IgG molecule, and the protein has a physical diameter of only a few nanometers. One consequence of the small size is the ability of camelid nanobodies to bind to antigenic sites that are functionally invisible to larger antibody proteins, i.e., camelid nanobodies are useful as reagents detect antigens that are otherwise cryptic using classical immunological techniques, and as possible therapeutic agents. Thus yet another consequence of small size is that a camelid nanobody can inhibit as a result of binding to a specific site in a groove or narrow cleft of a target protein, and hence can serve in a capacity that more closely resembles the function of a classical low molecular weight drug than that of a classical antibody.

The low molecular weight and compact size further result in camelid nanobodies being extremely thermostable, stable to extreme pH and to proteolytic digestion, and poorly antigenic. Another consequence is that camelid nanobodies readily move from the circulatory system into tissues, and even cross the blood-brain barrier and can treat disorders that affect nervous tissue. Nanobodies can further facilitated drug transport across the blood brain barrier. See U.S. patent application 20040161738 published Aug. 19, 2004. These features combined with the low antigenicity to humans indicate great therapeutic potential. Further, these molecules can be fully expressed in prokaryotic cells such as E. coli and are expressed as fusion proteins with bacteriophage and are functional.

Accordingly, a feature of the present invention is a camelid antibody or nanobody having high affinity for β-klotho. In certain embodiments herein, the camelid antibody or nanobody is naturally produced in the camelid animal, i.e., is produced by the camelid following immunization with β-klotho or a peptide fragment thereof, using techniques described herein for other antibodies. Alternatively, the β-klotho-binding camelid nanobody is engineered, i.e., produced by selection for example from a library of phage displaying appropriately mutagenized camelid nanobody proteins using panning procedures with β-klotho as a target as described in the examples herein. Engineered nanobodies can further be customized by genetic engineering to have a half life in a recipient subject of from 45 minutes to two weeks. In a specific embodiment, the camelid antibody or nanobody is obtained by grafting the CDRs sequences of the heavy or light chain of the human antibodies of the invention into nanobody or single domain antibody framework sequences, as described for example in PCT/EP93/02214.

Bispecific Molecules and Multivalent Antibodies

In another aspect, the present invention features bispecific or multispecific molecules comprising a β-klotho-binding antibody, or a fragment thereof, of the invention. An antibody of the invention, or antigen-binding regions thereof, can be derivatized or linked to another functional molecule, e.g., another peptide or protein (e.g., another antibody or ligand for a receptor) to generate a bispecific molecule that binds to at least two different binding sites or target molecules. The antibody of the invention may in fact be derivatized or linked to more than one other functional molecule to generate multi-specific molecules that bind to more than two different binding sites and/or target molecules; such multi-specific molecules are also intended to be encompassed by the term "bispecific molecule" as used herein. To create a bispecific molecule of the invention, an antibody of the invention can be functionally linked (e.g., by chemical coupling, genetic fusion, noncovalent association or otherwise) to one or more other binding molecules, such as another antibody, antibody fragment, peptide or binding mimetic, such that a bispecific molecule results.

Accordingly, the present invention includes bispecific molecules comprising at least one first binding specificity for β-klotho and a second binding specificity for a second target epitope. For example, the second target epitope is another epitope of β-klotho different from the first target epitope.

Additionally, for the invention in which the bispecific molecule is multi-specific, the molecule can further include a third binding specificity, in addition to the first and second target epitope.

In one embodiment, the bispecific molecules of the invention comprise as a binding specificity at least one antibody, or an antibody fragment thereof, including, e.g., a Fab, Fab', F(ab')2, Fv, or a single chain Fv. The antibody may also be a light chain or heavy chain dimer, or any minimal fragment thereof such as a Fv or a single chain construct as described in Ladner et al. U.S. Pat. No. 4,946,778.

Diabodies are bivalent, bispecific molecules in which VH and VL domains are expressed on a single polypeptide chain, connected by a linker that is too short to allow for pairing between the two domains on the same chain. The VH and VL domains pair with complementary domains of another chain, thereby creating two antigen-binding sites (see e.g., Holliger et al., 1993 Proc. Natl. Acad. Sci. USA 90:6444-6448; Poljak et al., 1994 Structure 2:1121-1123). Diabodies can be produced by expressing two polypeptide chains with either the structure VHA-VLB and VHB-VLA (VH-VL configuration), or VLA-VHB and VLB-VHA (VL-VH configuration) within the same cell. Most of them can be expressed in soluble form in bacteria. Single chain diabodies (scDb) are produced by connecting the two diabody-forming polypeptide chains with linker of approximately 15 amino acid residues (see Holliger and Winter, 1997 Cancer Immunol. Immunother., 45(3-4):128-30; Wu et al., 1996 Immunotechnology, 2(1):21-36). scDb can be expressed in bacteria in soluble, active monomeric form (see Holliger and Winter, 1997 Cancer Immunol. Immunother., 45(34): 128-30; Wu et al., 1996 Immunotechnology, 2(1):21-36; Pluckthun and Pack, 1997 Immunotechnology, 3(2): 83-105; Ridgway et al., 1996 Protein Eng., 9(7):617-21). A diabody can be fused to Fc to generate a "di-diabody" (see Lu et al., 2004 J. Biol. Chem., 279(4):2856-65).

Other antibodies which can be employed in the bispecific molecules of the invention are murine, chimeric and humanized monoclonal antibodies.

Bispecific molecules can be prepared by conjugating the constituent binding specificities, using methods known in the art. For example, each binding specificity of the bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-S-acetyl-thioacetate (SATA), 5,5'-dithiobis(2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl) cyclohaxane-1-carboxylate (sulfo-SMCC) (see e.g., Karpovsky et al., 1984 J. Exp. Med. 160:1686; Liu, M A et al., 1985 Proc. Natl. Acad. Sci. USA 82:8648). Other methods include those described in Paulus, 1985 Behring Ins. Mitt. No. 78, 118-132; Brennan et al., 1985 Science 229:81-83), and Glennie et al., 1987 J. Immunol. 139: 2367-2375). Conjugating agents are SATA and sulfo-SMCC, both available from Pierce Chemical Co. (Rockford, Ill.).

When the binding specificities are antibodies, they can be conjugated by sulfhydryl bonding of the C-terminus hinge regions of the two heavy chains. In a particularly embodiment, the hinge region is modified to contain an odd number of sulfhydryl residues, for example one, prior to conjugation.

Alternatively, both binding specificities can be encoded in the same vector and expressed and assembled in the same host cell. This method is particularly useful where the bispecific molecule is a mAb x mAb, mAb x Fab, Fab x F(ab')2 or ligand x Fab fusion protein. A bispecific molecule of the invention can be a single chain molecule comprising one single chain antibody and a binding determinant, or a single chain bispecific molecule comprising two binding determinants. Bispecific molecules may comprise at least two single chain molecules. Methods for preparing bispecific molecules are described for example in U.S. Pat. Nos. 5,260,203; 5,455,030; 4,881,175; 5,132,405; 5,091,513; 5,476,786; 5,013,653; 5,258,498; and 5,482,858.

Binding of the bispecific molecules to their specific targets can be confirmed by, for example, enzyme-linked immunosorbent assay (ELISA), radioimmunoassay (REA), FACS analysis, bioassay (e.g., growth inhibition), or Western Blot assay. Each of these assays generally detects the presence of protein-antibody complexes of particular interest by employing a labeled reagent (e.g., an antibody) specific for the complex of interest.

In another aspect, the present invention provides multivalent compounds comprising at least two identical or different antigen-binding portions of the antibodies of the invention binding to β-klotho. The antigen-binding portions can be linked together via protein fusion or covalent or non covalent linkage. Alternatively, methods of linkage have been described for the bispecfic molecules. Tetravalent compounds can be obtained for example by cross-linking antibodies of the antibodies of the invention with an antibody that binds to the constant regions of the antibodies of the invention, for example the Fc or hinge region.

Trimerizing domain are described for example in Borean patent EP 1 012 280B1. Pentamerizing modules are described for example in PCT/EP97/05897.

Antibodies with Extended Half Life

The present invention provides for antibodies that specifically bind to beta-klotho protein which have an extended half-life in vivo.

Many factors may affect a protein's half life in vivo. For examples, kidney filtration, metabolism in the liver, degradation by proteolytic enzymes (proteases), and immunogenic responses (e.g., protein neutralization by antibodies and uptake by macrophages and dendritic cells). A variety of strategies can be used to extend the half life of the antibodies of the present invention. For example, by chemical linkage to polyethyleneglycol (PEG), reCODE PEG, antibody scaffold, polysialic acid (PSA), hydroxyethyl starch (HES), albumin-binding ligands, and carbohydrate shields; by genetic fusion to proteins binding to serum proteins, such as albumin, IgG, FcRn, and transferring; by coupling (genetically or chemically) to other binding moieties that bind to serum proteins, such as nanobodies, Fabs, DARPins, avimers, affibodies, and anticalins; by genetic fusion to rPEG, albumin, domain of albumin, albumin-binding proteins, and Fc; or by incorporation into nanocarriers, slow release formulations, or medical devices.

To prolong the serum circulation of antibodies in vivo, inert polymer molecules such as high molecular weight PEG can be attached to the antibodies or a fragment thereof with or without a multifunctional linker either through site-specific conjugation of the PEG to the N- or C-terminus of the antibodies or via epsilon-amino groups present on lysine residues. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. The pegylation can be carried out by an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antibody. Linear or branched polymer derivatization that results in minimal loss of biological activity will be used. The degree of conjugation can be closely monitored by SDS-PAGE and mass spectrometry to ensure proper conjugation of PEG molecules to the antibodies. Unreacted PEG can be separated from antibody-PEG conjugates by size-exclusion or by ion-exchange chromatography. PEG-derivatized antibodies can be tested for binding activity as well as for in vivo efficacy using methods well-known to those of skill in the art, for example, by immunoassays described herein. Methods for pegylating proteins are known in the art and can be applied to the antibodies of the invention. See for example, EP 0 154 316 by Nishimura et al. and EP 0 401 384 by Ishikawa et al.

Other modified pegylation technologies include reconstituting chemically orthogonal directed engineering technology (ReCODE PEG), which incorporates chemically specified side chains into biosynthetic proteins via a reconstituted system that includes tRNA synthetase and tRNA. This technology enables incorporation of more than 30 new amino acids into biosynthetic proteins in E. coli, yeast, and mammalian cells. The tRNA incorporates a nonnative amino acid any place an amber codon is positioned, converting the amber from a stop codon to one that signals incorporation of the chemically specified amino acid.

Recombinant pegylation technology (rPEG) can also be used for serum halflife extension. This technology involves genetically fusing a 300-600 amino acid unstructured protein tail to an existing pharmaceutical protein. Because the apparent molecular weight of such an unstructured protein chain is about 15-fold larger than its actual molecular weight, the serum halflife of the protein is greatly increased. In contrast to traditional PEGylation, which requires chemical conjugation and repurification, the manufacturing process is greatly simplified and the product is homogeneous.

Polysialytion is another technology, which uses the natural polymer polysialic acid (PSA) to prolong the active life and improve the stability of therapeutic peptides and proteins. PSA is a polymer of sialic acid (a sugar). When used for protein and therapeutic peptide drug delivery, polysialic acid provides a protective microenvironment on conjugation. This increases the active life of the therapeutic protein in the circulation and prevents it from being recognized by the immune system. The PSA polymer is naturally found in the human body. It was adopted by certain bacteria which evolved over millions of years to coat their walls with it. These naturally polysialylated bacteria were then able, by virtue of molecular mimicry, to foil the body's defense system. PSA, nature's ultimate stealth technology, can be easily produced from such bacteria in large quantities and with predetermined physical characteristics. Bacterial PSA is completely non-immunogenic, even when coupled to proteins, as it is chemically identical to PSA in the human body.

Another technology includes the use of hydroxyethyl starch ("HES") derivatives linked to antibodies. HES is a modified natural polymer derived from waxy maize starch and can be metabolized by the body's enzymes. HES solutions are usually administered to substitute deficient blood volume and to improve the rheological properties of the blood. Hesylation of an antibody enables the prolongation of the circulation half-life by increasing the stability of the molecule, as well as by reducing renal clearance, resulting in an increased biological activity. By varying different parameters, such as the molecular weight of HES, a wide range of HES antibody conjugates can be customized.

Antibodies having an increased half-life in vivo can also be generated introducing one or more amino acid modifications (i.e., substitutions, insertions or deletions) into an IgG constant domain, or FcRn binding fragment thereof (preferably a Fc or hinge Fc domain fragment). See, e.g., International Publication No. WO 98/23289; International Publication No. WO 97/34631; and U.S. Pat. No. 6,277,375.

Further, antibodies can be conjugated to albumin (e.g., human serum albumin; HSA) in order to make the antibody or antibody fragment more stable in vivo or have a longer half life in vivo. The techniques are well-known in the art, see, e.g., International Publication Nos. WO 93/15199, WO 93/15200, and WO 01/77137; and European Patent No. EP 413,622. In addition, in the context of a bispecific antibody as described above, the specificities of the antibody can be designed such that one binding domain of the antibody binds to FGF21 while a second binding domain of the antibody binds to serum albumin, preferably HSA.

The strategies for increasing half life is especially useful in nanobodies, fibronectin-based binders, and other antibodies or proteins for which increased in vivo half life is desired.

Antibody Conjugates

The present invention provides antibodies or fragments thereof that specifically bind to a β-klotho protein recombinantly fused or chemically conjugated (including both covalent and non-covalent conjugations) to a heterologous protein or polypeptide (or fragment thereof, preferably to a polypeptide of at least 10, at least 20, at least 30, at least 40, at least 50, at least 60, at least 70, at least 80, at least 90 or at least 100 amino acids) to generate fusion proteins. In particular, the invention provides fusion proteins comprising an antigen-binding fragment of an antibody described herein (e.g., a Fab fragment, Fd fragment, Fv fragment, F(ab)2 fragment, a VH domain, a VH CDR, a VL domain or a VL CDR) and a heterologous protein, polypeptide, or peptide. Methods for fusing or conjugating proteins, polypeptides, or peptides to an antibody or an antibody fragment are known in the art. See, e.g., U.S. Pat. Nos. 5,336,603, 5,622,929, 5,359,046, 5,349,053, 5,447,851, and 5,112,946; European Patent Nos. EP 307,434 and EP 367,166; International Publication Nos. WO 96/04388 and WO 91/06570; Ashkenazi et al., 1991, Proc. Natl. Acad. Sci. USA 88: 10535-10539; Zheng et al., 1995, J. Immunol. 154:5590-5600; and Vil et al., 1992, Proc. Natl. Acad. Sci. USA 89:11337-11341.

Additional fusion proteins may be generated through the techniques of gene-shuffling, motif-shuffling, exon-shuffling, and/or codon-shuffling (collectively referred to as "DNA shuffling"). DNA shuffling may be employed to alter the activities of antibodies of the invention or fragments thereof (e.g., antibodies or fragments thereof with higher affinities and lower dissociation rates). See, generally, U.S. Pat. Nos. 5,605,793, 5,811,238, 5,830,721, 5,834,252, and 5,837,458; Patten et al., 1997, Curr. Opinion Biotechnol. 8:724-33; Harayama, 1998, Trends Biotechnol. 16(2):76-82; Hansson, et al., 1999, J. Mol. Biol. 287:265-76; and Lorenzo and Blasco, 1998, Biotechniques 24(2):308-313 (each of these patents and publications are hereby incorporated by reference in its entirety). Antibodies or fragments thereof, or the encoded antibodies or fragments thereof, may be altered by being subjected to random mutagenesis by error-prone PCR, random nucleotide insertion or other methods prior to recombination. A polynucleotide encoding an antibody or fragment thereof that specifically binds to a β-klotho protein may be recombined with one or more components, motifs, sections, parts, domains, fragments, etc. of one or more heterologous molecules.

Moreover, the antibodies or fragments thereof can be fused to marker sequences, such as a peptide to facilitate purification. In preferred embodiments, the marker amino acid sequence is a hexa-histidine peptide (SEQ ID NO: 274), such as the tag provided in a pQE vector (QIAGEN, Inc., 9259 Eton Avenue, Chatsworth, Calif., 91311), among others, many of which are commercially available. As described in Gentz et al., 1989, Proc. Natl. Acad. Sci. USA 86:821-824, for instance, hexa-histidine (SEQ ID NO: 274) provides for convenient purification of the fusion protein. Other peptide tags useful for purification include, but are not limited to, the hemagglutinin ("HA") tag, which corresponds to an epitope derived from the influenza hemagglutinin protein (Wilson et al., 1984, Cell 37:767), and the "flag" tag.

In other embodiments, antibodies of the present invention or fragments thereof conjugated to a diagnostic or detectable agent. Such antibodies can be useful for monitoring or prognosing the onset, development, progression and/or severity of a disease or disorder as part of a clinical testing procedure, such as determining the efficacy of a particular therapy. Such diagnosis and detection can accomplished by coupling the antibody to detectable substances including, but not limited to, various enzymes, such as, but not limited to, horseradish peroxidase, alkaline phosphatase, beta-galactosidase, or acetylcholinesterase; prosthetic groups, such as, but not limited to, streptavidinlbiotin and avidin/biotin; fluorescent materials, such as, but not limited to, umbelliferone, fluorescein, fluorescein isothiocynate, rhodamine, dichlorotriazinylamine fluorescein, dansyl chloride or phycoerythrin; luminescent materials, such as, but not limited to, luminol; bioluminescent materials, such as but not limited to, luciferase, luciferin, and aequorin; radioactive materials, such as, but not limited to, iodine (131I, 125I, 123I, and 121I), carbon (14C), sulfur (35S), tritium (3H), indium (115In, 113In, 112In, and 111In,), technetium (99Tc), thallium (201Ti), gallium (68Ga, 67Ga), palladium (103Pd), molybdenum (99Mo), xenon (133Xe), fluorine (18F), 153Sm, 177Lu, 159Gd, 149Pm, 140La, 175Yb, 166Ho, 90Y, 47Sc, 186Re, 188Re, 142 Pr, 105Rh, 97Ru, 68Ge, 57Co, 65Zn, 85Sr, 32P, 153Gd, 169Yb, 51Cr, 54Mn, 75Se, 113Sn, and 117Tin; and positron emitting metals using various positron emission tomographies, and noradioactive paramagnetic metal ions.

The present invention further encompasses uses of antibodies or fragments thereof conjugated to a therapeutic moiety. An antibody or fragment thereof may be conjugated to a therapeutic moiety such as a cytotoxin, e.g., a cytostatic or cytocidal agent, a therapeutic agent or a radioactive metal ion, e.g., alpha-emitters. A cytotoxin or cytotoxic agent includes any agent that is detrimental to cells.

Further, an antibody or fragment thereof may be conjugated to a therapeutic moiety or drug moiety that modifies a given biological response. Therapeutic moieties or drug moieties are not to be construed as limited to classical chemical therapeutic agents. For example, the drug moiety may be a protein, peptide, or polypeptide possessing a desired biological activity. Such proteins may include, for example, a toxin such as abrin, ricin A, *pseudomonas* exotoxin, cholera toxin, or diphtheria toxin; a protein such as tumor necrosis factor, α-interferon, β-interferon, nerve growth factor, platelet derived growth factor, tissue plasminogen activator, an apoptotic agent, an anti-angiogenic agent; or, a biological response modifier such as, for example, a lymphokine.

Moreover, an antibody can be conjugated to therapeutic moieties such as a radioactive metal ion, such as alphemiters such as 213Bi or macrocyclic chelators useful for conjugating radiometal ions, including but not limited to, 131In, 131LU, 131Y, 131Ho, 131Sm, to polypeptides. In certain embodiments, the macrocyclic chelator is 1,4,7,10-tetraazacyclododecane-N,N',N",N"'-tetraacetic acid (DOTA) which can be attached to the antibody via a linker molecule. Such linker molecules are commonly known in the art and described in Denardo et al., 1998, Clin Cancer Res. 4(10):2483-90; Peterson et al., 1999, Bioconjug. Chem. 10(4):553-7; and Zimmerman et al., 1999, Nucl. Med. Biol. 26(8):943-50, each incorporated by reference in their entireties.

Techniques for conjugating therapeutic moieties to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies 84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., 1982, Immunol. Rev. 62:119-58.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Methods of Producing Antibodies of the Invention

Nucleic Acids Encoding the Antibodies

The invention provides substantially purified nucleic acid molecules which encode polypeptides comprising segments or domains of the β-klotho-binding antibody chains described above. Some of the nucleic acids of the invention comprise the nucleotide sequence encoding the heavy chain variable region shown in SEQ ID NO: 10, 30, 50, or 70, and/or the nucleotide sequence encoding the light chain variable region shown in SEQ ID NO: 20, 40, 60, or 80. In a specific embodiment, the nucleic acid molecules are those identified in Table 1. Some other nucleic acid molecules of the invention comprise nucleotide sequences that are substantially identical (e.g., at least 65, 80%, 95%, or 99%) to the nucleotide sequences of those identified in Table 1. When expressed from appropriate expression vectors, polypeptides encoded by these polynucleotides are capable of exhibiting FGF21 antigen-binding capacity.

Also provided in the invention are polynucleotides which encode at least one CDR region and usually all three CDR regions from the heavy or light chain of the β-klotho-binding antibody set forth above. Some other polynucleotides encode all or substantially all of the variable region sequence of the heavy chain and/or the light chain of the β-klotho-binding antibody set forth above. Because of the degeneracy of the code, a variety of nucleic acid sequences will encode each of the immunoglobulin amino acid sequences.

The nucleic acid molecules of the invention can encode both a variable region and a constant region of the antibody. Some of nucleic acid sequences of the invention comprise nucleotides encoding a heavy chain sequence that is substantially identical (e.g., at least 80%, 90%, or 99%) to the heavy chain sequence set forth in SEQ ID NO: 11, 31, 51, or 71. Some other nucleic acid sequences comprising nucleotide encoding a light chain sequence that is substantially identical (e.g., at least 80%, 90%, or 99%) to the light chain sequence set forth in SEQ ID NO: 21, 41, 61, or 81.

The polynucleotide sequences can be produced by de novo solid-phase DNA synthesis or by PCR mutagenesis of an existing sequence (e.g., sequences as described in the Examples below) encoding a β-klotho-binding antibody or its binding fragment. Direct chemical synthesis of nucleic acids can be accomplished by methods known in the art, such as the phosphotriester method of Narang et al., 1979, Meth. Enzymol. 68:90; the phosphodiester method of Brown et al., Meth. Enzymol. 68:109, 1979; the diethylphosphoramidite method of Beaucage et al., Tetra. Lett., 22:1859, 1981; and the solid support method of U.S. Pat. No. 4,458,066. Introducing mutations to a polynucleotide sequence by PCR can be performed as described in, e.g., PCR Technology: Principles and Applications for DNA Amplification, H. A. Erlich (Ed.), Freeman Press, NY, NY, 1992; PCR Protocols: A Guide to Methods and Applications, Innis et al. (Ed.), Academic Press, San Diego, Calif., 1990; Mattila et al., Nucleic Acids Res. 19:967, 1991; and Eckert et al., PCR Methods and Applications 1:17, 1991.

Also provided in the invention are expression vectors and host cells for producing the β-klotho-binding antibodies described above. Various expression vectors can be employed to express the polynucleotides encoding the β-klotho-binding antibody chains or binding fragments. Both viral-based and nonviral expression vectors can be used to produce the antibodies in a mammalian host cell. Nonviral vectors and systems include plasmids, episomal vectors, typically with an expression cassette for expressing a protein or RNA, and human artificial chromosomes (see, e.g., Harrington et al., Nat Genet 15:345, 1997). For example, nonviral vectors useful for expression of the FGF21-binding polynucleotides and polypeptides in mammalian (e g., human) cells include pThioHis A, B & C, pcDNA3.1/His, pEBVHis A, B & C, (Invitrogen, San Diego, Calif.), MPSV vectors, and numerous other vectors known in the art for expressing other proteins. Useful viral vectors include vectors based on retroviruses, adenoviruses, adeno-associated viruses, herpes viruses, vectors based on SV40, papilloma virus, HBP Epstein Barr virus, vaccinia virus vectors and Semliki Forest virus (SFV). See, Brent et al., supra; Smith, Annu. Rev. Microbiol. 49:807, 1995; and Rosenfeld et al., Cell 68:143, 1992.

The choice of expression vector depends on the intended host cells in which the vector is to be expressed. Typically, the expression vectors contain a promoter and other regulatory sequences (e.g., enhancers) that are operably linked to the polynucleotides encoding a β-klotho-binding antibody chain or fragment. In some embodiments, an inducible promoter is employed to prevent expression of inserted sequences except under inducing conditions. Inducible promoters include, e.g., arabinose, lacZ, metallothionein promoter or a heat shock promoter. Cultures of transformed organisms can be expanded under noninducing conditions without biasing the population for coding sequences whose expression products are better tolerated by the host cells. In addition to promoters, other regulatory elements may also be required or desired for efficient expression of a β-klotho-binding antibody chain or fragment. These elements typically include an ATG initiation codon and adjacent ribosome binding site or other sequences. In addition, the efficiency of expression may be enhanced by the inclusion of enhancers appropriate to the cell system in use (see, e.g., Scharf et al., Results Probl. Cell Differ. 20:125, 1994; and Bittner et al., Meth. Enzymol., 153:516, 1987). For example, the SV40 enhancer or CMV enhancer may be used to increase expression in mammalian host cells.

The expression vectors may also provide a secretion signal sequence position to form a fusion protein with polypeptides encoded by inserted FGF21-binding antibody sequences. More often, the inserted β-klotho-binding antibody sequences are linked to a signal sequences before inclusion in the vector. Vectors to be used to receive sequences encoding β-klotho-binding antibody light and heavy chain variable domains sometimes also encode constant regions or parts thereof. Such vectors allow expression of the variable regions as fusion proteins with the constant regions thereby leading to production of intact antibodies or fragments thereof. Typically, such constant regions are human.

The host cells for harboring and expressing the β-klotho-binding antibody chains can be either prokaryotic or eukaryotic. *E. coli* is one prokaryotic host useful for cloning and expressing the polynucleotides of the present invention. Other microbial hosts suitable for use include bacilli, such as *Bacillus subtilis*, and other enterobacteriaceae, such as *Salmonella, Serratia*, and various *Pseudomonas* species. In these prokaryotic hosts, one can also make expression vectors, which typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters typically control expression, optionally with an operator sequence, and have ribosome binding site sequences and the like, for initiating and completing transcription and translation. Other microbes, such as yeast, can also be employed to express FGF21-binding polypeptides of the invention. Insect cells in combination with baculovirus vectors can also be used.

In some preferred embodiments, mammalian host cells are used to express and produce the β-klotho-binding polypeptides of the present invention. For example, they can be either a hybridoma cell line expressing endogenous immunoglobulin genes (e.g., the 1D6.C9 myeloma hybridoma clone as described in the Examples) or a mammalian cell line harboring an exogenous expression vector (e.g., the SP2/0 myeloma cells exemplified below). These include any normal mortal or normal or abnormal immortal animal or human cell. For example, a number of suitable host cell lines capable of secreting intact immunoglobulins have been developed including the CHO cell lines, various Cos cell lines, HeLa cells, myeloma cell lines, transformed B-cells and hybridomas. The use of mammalian tissue cell culture to express polypeptides is discussed generally in, e.g., Winnacker, FROM GENES TO CLONES, VCH Publishers, N.Y., N.Y., 1987. Expression vectors for mammalian host cells can include expression control sequences, such as an origin of replication, a promoter, and an enhancer (see, e.g., Queen, et al., Immunol. Rev. 89:49-68, 1986), and necessary processing information sites, such as ribosome binding sites, RNA splice sites, polyadenylation sites, and transcriptional terminator sequences. These expression vectors usually contain promoters derived from mammalian genes or from mammalian viruses. Suitable promoters may be constitutive, cell type-specific, stage-specific, and/or modulatable or regulatable. Useful promoters include, but are not limited to, the metallothionein promoter, the constitutive adenovirus major late promoter, the dexamethasone-inducible MMTV promoter, the SV40 promoter, the MRP polIII promoter, the constitutive MPSV promoter, the tetracycline-inducible CMV promoter (such as the human immediate-early CMV promoter), the constitutive CMV promoter, and promoter-enhancer combinations known in the art.

Methods for introducing expression vectors containing the polynucleotide sequences of interest vary depending on the type of cellular host. For example, calcium chloride transfection is commonly utilized for prokaryotic cells, whereas calcium phosphate treatment or electroporation may be used for other cellular hosts. (See generally Sambrook, et al., supra). Other methods include, e.g., electroporation, calcium phosphate treatment, liposome-mediated transformation, injection and microinjection, ballistic methods, virosomes, immunoliposomes, polycation:nucleic acid conjugates, naked DNA, artificial virions, fusion to the herpes virus structural protein VP22 (Elliot and O'Hare, Cell 88:223, 1997), agent-enhanced uptake of DNA, and ex vivo transduction. For long-term, high-yield production of recombinant proteins, stable expression will often be desired. For example, cell lines which stably express β-klotho-binding antibody chains or binding fragments can be prepared using expression vectors of the invention which contain viral origins of replication or endogenous expression elements and a selectable marker gene. Following the introduction of the vector, cells may be allowed to grow for 1-2 days in an enriched media before they are switched to selective media. The purpose of the selectable marker is to confer resistance to selection, and its presence allows growth of cells which successfully express the introduced sequences in selective media. Resistant, stably transfected cells can be proliferated using tissue culture techniques appropriate to the cell type.

Generation of Monoclonal Antibodies

Monoclonal antibodies (mAbs) can be produced by a variety of techniques, including conventional monoclonal antibody methodology e.g., the standard somatic cell hybridization technique of Kohler and Milstein, 1975 Nature 256: 495. Many techniques for producing monoclonal antibody can be employed e.g., viral or oncogenic transformation of B lymphocytes.

Animal systems for preparing hybridomas include the murine, rat and rabbit systems. Hybridoma production in the mouse is a well established procedure Immunization protocols and techniques for isolation of immunized splenocytes for fusion are known in the art. Fusion partners (e.g., murine myeloma cells) and fusion procedures are also known.

Chimeric or humanized antibodies of the present invention can be prepared based on the sequence of a murine monoclonal antibody prepared as described above. DNA encoding the heavy and light chain immunoglobulins can be obtained from the murine hybridoma of interest and engineered to contain non-murine (e.g., human) immunoglobulin sequences using standard molecular biology techniques. For example, to create a chimeric antibody, the murine variable regions can be linked to human constant regions using methods known in the art (see e.g., U.S. Pat. No. 4,816,567 to Cabilly et al.). To create a humanized antibody, the murine CDR regions can be inserted into a human framework using methods known in the art. See e.g., U.S. Pat. No. 5,225,539 to Winter, and U.S. Pat. Nos. 5,530,101; 5,585,089; 5,693, 762 and 6,180,370 to Queen et al.

In a certain embodiment, the antibodies of the invention are human monoclonal antibodies. Such human monoclonal antibodies directed against β-klotho can be generated using transgenic or transchromosomic mice carrying parts of the human immune system rather than the mouse system. These transgenic and transchromosomic mice include mice referred to herein as HuMAb mice and KM mice, respectively, and are collectively referred to herein as "human Ig mice."

The HuMAb mouse (Medarex, Inc.) contains human immunoglobulin gene miniloci that encode un-rearranged human heavy (μ and γ) and x light chain immunoglobulin sequences, together with targeted mutations that inactivate the endogenousμ and x chain loci (see e.g., Lonberg, et al., 1994 Nature 368(6474): 856-859). Accordingly, the mice exhibit reduced expression of mouse IgM or κ, and in response to immunization, the introduced human heavy and light chain transgenes undergo class switching and somatic mutation to generate high affinity human IgGκ monoclonal (Lonberg, N. et al., 1994 supra; reviewed in Lonberg, N., 1994 Handbook of Experimental Pharmacology 113:49-101; Lonberg, N. and Huszar, D., 1995 Intern. Rev. Immunol. 13: 65-93, and Harding, F. and Lonberg, N., 1995 Ann. N. Y. Acad. Sci. 764:536-546). The preparation and use of HuMAb mice, and the genomic modifications carried by such mice, is further described in Taylor, L. et al., 1992 Nucleic Acids Research 20:6287-6295; Chen, J. et at., 1993 International Immunology 5: 647-656; Tuaillon et al., 1993 Proc. Natl. Acad. Sci. USA 94:3720-3724; Choi et al., 1993 Nature Genetics 4:117-123; Chen, J. et al., 1993 EMBO J. 12: 821-830; Tuaillon et al., 1994 J. Immunol. 152:2912-2920; Taylor, L. et al., 1994 International Immunology 579-591; and Fishwild, D. et al., 1996 Nature Biotechnology 14: 845-851, the contents of all of which are hereby specifically incorporated by reference in their entirety. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay; U.S. Pat. No. 5,545,807 to Surani et al.; PCT Publication Nos. WO 92103918, WO 93/12227, WO 94/25585, WO 97113852, WO 98/24884 and WO 99/45962, all to Lonberg and Kay; and PCT Publication No. WO 01/14424 to Korman et al.

In another embodiment, human antibodies of the invention can be raised using a mouse that carries human immunoglobulin sequences on transgenes and transchomosomes such as a mouse that carries a human heavy chain transgene and a human light chain transchromosome. Such mice, referred to herein as "KM mice", are described in detail in PCT Publication WO 02/43478 to Ishida et al.

Still further, alternative transgenic animal systems expressing human immunoglobulin genes are available in the art and can be used to raise β-klotho-binding antibodies of the invention. For example, an alternative transgenic system referred to as the Xenomouse (Abgenix, Inc.) can be used. Such mice are described in, e.g., U.S. Pat. Nos. 5,939,598; 6,075,181; 6,114,598; 6, 150,584 and 6,162,963 to Kucherlapati et al.

Moreover, alternative transchromosomic animal systems expressing human immunoglobulin genes are available in the art and can be used to raise β-klotho-binding antibodies of the invention. For example, mice carrying both a human heavy chain transchromosome and a human light chain tranchromosome, referred to as "TC mice" can be used; such mice are described in Tomizuka et al., 2000 Proc. Natl. Acad. Sci. USA 97:722-727. Furthermore, cows carrying human heavy and light chain transchromosomes have been described in the art (Kuroiwa et al., 2002 Nature Biotechnology 20:889-894) and can be used to raise FGF21-binding antibodies of the invention.

Human monoclonal antibodies of the invention can also be prepared using phage display methods for screening libraries of human immunoglobulin genes. Such phage display methods for isolating human antibodies are established in the art or described in the examples below. See for example: U.S. Pat. Nos. 5,223,409; 5,403,484; and U.S. Pat. No. 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885, 793; 6,521,404; 6,544,731; 6,555,313; 6,582,915 and 6,593, 081 to Griffiths et al.

Human monoclonal antibodies of the invention can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

Framework or Fc Engineering

Engineered antibodies of the invention include those in which modifications have been made to framework residues within VH and/or VL, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "backmutated" to the germline sequence by, for example, site-directed mutagenesis. Such "backmutated" antibodies are also intended to be encompassed by the invention.

Another type of framework modification involves mutating one or more residues within the framework region, or even within one or more CDR regions, to remove T cell-epitopes to thereby reduce the potential immunogenicity of the antibody. This approach is also referred to as "deimmunization" and is described in further detail in U.S. Patent Publication No. 20030153043 by Can et al.

In addition or alternative to modifications made within the framework or CDR regions, antibodies of the invention may be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the invention may be chemically modified (e.g., one or more chemical moieties can be attached to the antibody) or be modified to alter its glycosylation, again to alter one or more functional properties of the antibody. Each of these embodiments is described in further detail below. The numbering of residues in the Fc region is that of the EU index of Kabat.

In one embodiment, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In another embodiment, the Fc hinge region of an antibody is mutated to decrease the biological half-life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In another embodiment, the antibody is modified to increase its biological half-life. Various approaches are possible. For example, one or more of the following mutations can be introduced: T252L, T254S, T256F, as described in U.S. Pat. No. 6,277,375 to Ward. Alternatively, to increase the biological half life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al.

In yet other embodiments, the Fc region is altered by replacing at least one amino acid residue with a different amino acid residue to alter the effector functions of the antibody. For example, one or more amino acids can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter et al.

In another embodiment, one or more amino acids selected from amino acid residues can be replaced with a different amino acid residue such that the antibody has altered C1q binding and/or reduced or abolished complement dependent cytotoxicity (CDC). This approach is described in further detail in U.S. Pat. No. 6,194,551 by Idusogie et al.

In another embodiment, one or more amino acid residues are altered to thereby alter the ability of the antibody to fix complement. This approach is described further in PCT Publication WO 94/29351 by Bodmer et al.

In yet another embodiment, the Fc region is modified to increase the ability of the antibody to mediate antibody dependent cellular cytotoxicity (ADCC) and/or to increase the affinity of the antibody for an Fcγ receptor by modifying one or more amino acids. This approach is described further in PCT Publication WO 00/42072 by Presta. Moreover, the binding sites on human IgG1 for FcγR1, FcγRII, FcγRIII and FcRn have been mapped and variants with improved binding have been described (see Shields, R. L. et al., 2001 J. Biol. Chen. 276:6591-6604).

In still another embodiment, the glycosylation of an antibody is modified. For example, an aglycoslated antibody can be made (i.e., the antibody lacks glycosylation). Glycosylation can be altered to, for example, increase the affinity of the antibody for "antigen'. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. For example, EP 1,176,195 by Hang et al. describes a cell line with a functionally disrupted FUT8 gene, which encodes a fucosyl transferase, such that antibodies expressed in such a cell line exhibit hypofucosylation. PCT Publication WO 03/035835 by Presta describes a variant CHO cell line, Lec13 cells, with reduced ability to attach fucose to Asn(297)-linked carbohydrates, also resulting in hypofucosylation of antibodies expressed in that host cell (see also Shields, R. L. et al., 2002 J. Biol. Chem. 277:26733-26740). PCT Publication WO 99/54342 by Umana et al. describes cell lines engineered to express glycoprotein-modifying glycosyl transferases (e.g., beta(1, 4)-N acetylglucosaminyltransferase III (GnTIII)) such that antibodies expressed in the engineered cell lines exhibit increased bisecting GlcNac structures which results in increased ADCC activity of the antibodies (see also Umana et al., 1999 Nat. Biotech. 17:176-180).

Methods of Engineering Altered Antibodies

As discussed above, the β-klotho-binding antibodies having VH and VL sequences or full length heavy and light chain sequences shown herein can be used to create new β-klotho-binding antibodies by modifying full length heavy chain and/or light chain sequences, VH and/or VL sequences, or the constant region(s) attached thereto. Thus, in another aspect of the invention, the structural features of a β-klotho-binding antibody of the invention are used to create structurally related β-klotho-binding antibodies that retain at least one functional property of the antibodies of the invention, such as binding to human β-klotho and also activating one or more functional properties of the FGF21-receptor complex (e.g., activating FGF21-receptor signaling).

For example, one or more CDR regions of the antibodies of the present invention, or mutations thereof, can be combined recombinantly with known framework regions and/or other CDRs to create additional, recombinantly-engineered, β-klotho-binding antibodies of the invention, as discussed above. Other types of modifications include those described in the previous section. The starting material for the engineering method is one or more of the VH and/or VL sequences provided herein, or one or more CDR regions thereof. To create the engineered antibody, it is not necessary to actually prepare (i.e., express as a protein) an antibody having one or more of the VH and/or VL sequences provided herein, or one or more CDR regions thereof. Rather, the information contained in the sequence(s) is used as the starting material to create a "second generation" sequence(s) derived from the original sequence(s) and then the "second generation" sequence(s) is prepared and expressed as a protein.

Accordingly, in another embodiment, the invention provides a method for preparing a β-klotho-binding antibody consisting of a heavy chain variable region antibody sequence having a CDR1 sequence selected from the group consisting of SEQ ID NOs: 3, 23, 43, and 63, a CDR2 sequence selected from the group consisting of SEQ ID NOs: 4, 24, 44, and 64, and/or a CDR3 sequence selected from the group consisting of SEQ ID NOs: 5, 25, 45, and 65; and a light chain variable region antibody sequence having a CDR1 sequence selected from the group consisting of SEQ ID NOs: 13, 33, 53, and 73, a CDR2 sequence selected from the group consisting of SEQ ID NOs: 14, 34, 54, and 74, and/or a CDR3 sequence selected from the group consisting of SEQ ID NOs: 15, 35, 55, and 75; altering at least one amino acid residue within the heavy chain variable region antibody sequence and/or the light chain variable region antibody sequence to create at least one altered antibody sequence; and expressing the altered antibody sequence as a protein.

Accordingly, in another embodiment, the invention provides a method for preparing a β-klotho-binding antibody consisting of a heavy chain variable region antibody sequence having a CDR1 sequence selected from the group consisting of SEQ ID NOs: 6, 26, 46, and 66, a CDR2 sequence selected from the group consisting of SEQ ID NOs: 7, 27, 47, and 67, and/or a CDR3 sequence selected from the group consisting of SEQ ID NOs: 8, 28, 48, and 68; and a light chain variable region antibody sequence having a CDR1 sequence selected from the group consisting of SEQ ID NOs: 16, 36, 56, and 76, a CDR2 sequence selected from the group consisting of SEQ ID NOs: 17, 37, 57, and 77, and/or a CDR3 sequence selected from the group consisting of SEQ ID NOs: 18, 38, 58, and 78; altering at least one amino acid residue within the heavy chain variable region antibody sequence and/or the light chain variable region antibody sequence to create at least one altered antibody sequence; and expressing the altered antibody sequence as a protein.

Accordingly, in another embodiment, the invention provides a method for preparing a β-klotho-binding antibody optimized for expression in a mammalian cell consisting of: a full length heavy chain antibody sequence having a sequence selected from the group of SEQ ID NOs: 11, 31, 51, or 71; and a full length light chain antibody sequence having a sequence selected from the group of 21, 41, 61, or 81; altering at least one amino acid residue within the full length heavy chain antibody sequence and/or the full length light chain antibody sequence to create at least one altered antibody sequence; and expressing the altered antibody sequence as a protein. In one embodiment, the alteration of the heavy or light chain is in the framework region of the heavy or light chain.

The altered antibody sequence can also be prepared by screening antibody libraries having fixed CDR3 sequences or minimal essential binding determinants as described in US2005/0255552 and diversity on CDR1 and CDR2 sequences. The screening can be performed according to any screening technology appropriate for screening antibodies from antibody libraries, such as phage display technology.

Standard molecular biology techniques can be used to prepare and express the altered antibody sequence. The antibody encoded by the altered antibody sequence(s) is one that retains one, some or all of the functional properties of the β-klotho-binding antibodies described herein, which functional properties include, but are not limited to, specifically binding to human, cynomolgus, rat, and/or mouse β-klotho; and the antibody activates FGF21-mediated signaling, e.g., FGF21-receptor-dependent signaling, in a FGFR1c_β-klotho_HEK293 pERK cell assay.

In certain embodiments of the methods of engineering antibodies of the invention, mutations can be introduced randomly or selectively along all or part of a β-klotho-binding antibody coding sequence and the resulting modified β-klotho-binding antibodies can be screened for binding activity and/or other functional properties as described herein. Mutational methods have been described in the art. For example, PCT Publication WO 02/092780 by Short describes methods for creating and screening antibody mutations using saturation mutagenesis, synthetic ligation assembly, or a combination thereof. Alternatively, PCT Publication WO 03/074679 by Lazar et al. describes methods of using computational screening methods to optimize physiochemical properties of antibodies.

In certain embodiments of the invention antibodies have been engineered to remove sites of deamidation. Deamidation is known to cause structural and functional changes in a peptide or protein. Deamination can result in decreased bioactivity, as well as alterations in pharmacokinetics and antigenicity of the protein pharmaceutical. (*Anal Chem.* 2005 Mar. 1; 77(5):1432-9).

In certain embodiments of the invention the antibodies have been engineered to increase pI and improve their drug-like properties. The pI of a protein is a key determinant of the overall biophysical properties of a molecule. Antibodies that have low pIs have been known to be less soluble, less stable, and prone to aggregation. Further, the purification of antibodies with low pI is challenging and can be problematic especially during scale-up for clinical use. Increasing the pI of the anti-β-klotho antibodies, or Fabs, of the invention improved their solubility, enabling the antibodies to be formulated at higher concentrations (>100 mg/ml). Formulation of the antibodies at high concentrations (e.g. >100 mg/ml) offers the advantage of being able to administer higher doses of the antibodies into eyes of patients via intravitreal injections, which in turn may enable reduced dosing frequency, a significant advantage for treatment of chronic diseases including cardiovascular disorders. Higher pIs may also increase the FcRn-mediated recycling of the IgG version of the antibody thus enabling the drug to persist in the body for a longer duration, requiring fewer injections. Finally, the overall stability of the antibodies is significantly improved due to the higher pI resulting in longer shelf-life and bioactivity in vivo. Preferably, the pI is greater than or equal to 8.2.

The functional properties of the altered antibodies can be assessed using standard assays available in the art and/or described herein, such as those set forth in the Examples (e.g., ELISAs).

Prophylactic and Therapeutic Uses

Antibodies that bind β-klotho as described herein, can be used at a therapeutically useful concentration for the treatment of a disease or disorder associated with aberrant FGF21 signaling (e.g., aberrant activation of FGF21-mediated signaling and/or FGF21 receptor signaling), by administering to a subject in need thereof an effective amount of the antibodies or antigen-binding fragments of the invention. The present invention provides a method of treating FGF21-associated metabolic disorders by administering to a subject in need thereof an effective amount of the antibodies of the invention. The present invention provides a method of treating FGF21-associated cardiovascular disorders by administering to a subject in need thereof an effective amount of the antibodies of the invention.

The antibodies of the invention can be used, inter alia, to prevent treat, prevent, and improve FGF21 associated conditions or disorders, including but not limited to metabolic, endocrine, and cardiovascular disorders, such as obesity, type 1 and type 2 diabetes mellitus, pancreatitis, dyslipidemia, nonalcoholic fatty liver disease (NAFLD), nonalcoholic steatohepatitis (NASH), insulin resistance, hyperinsulinemia, glucose intolerance, hyperglycemia, metabolic syndrome, acute myocardial infarction, hypertension, cardiovascular disease, atherosclerosis, peripheral arterial disease, stroke, heart failure, coronary heart disease, kidney disease, diabetic complications, neuropathy, gastroparesis, disorders associated with severe inactivating mutations in the insulin receptor, and other metabolic disorders, and in reducing the mortality and morbidity of critically ill patients.

The antibodies of the invention can also be used in combination with other agents for the prevention, treatment, or improvement of FGF21 associated disorders. For example, statin therapies may be used in combination with the FGF21 mimetic antibodies and antigen-binding fragments of the invention for the treatment of patients with cardiovascular or metabolic disorders.

In particular aspects, provided herein is a method of reducing body weight (e.g., by at least 4%, at least 5%, at least 6%, at least 7%, at least 8%, at least 9%, at least 10%, at least 12%, at least 15%, or at least 20%) comprising administering to a subject in need thereof an effective amount of a pharmaceutical composition comprising an antibody or antigen-binding fragment described herein which binds β-klotho and is capable of increases the activity of β-klotho and FGFR1c.

In particular aspects, provided herein is a method of reducing appetite or food intake (e.g., by at least 4%, at least 5%, at least 6%, at least 7%, at least 8%, at least 9%, at least 10%, at least 12%, at least 15%, or at least 20%) comprising administering to a subject in need thereof an effective amount of a pharmaceutical composition comprising an antibody or antigen-binding fragment described herein which binds β-klotho and is capable of increases the activity of β-klotho and FGFR1c.

In particular aspects, provided herein is a method of reducing (e.g., by at least 4%, at least 5%, at least 6%, at least 7%, at least 8%, at least 9%, at least 10%, at least 12%, at least 15%, or at least 20%) plasma triglyceride (TG) concentrations or plasma total cholesterol (TC) concentrations in a subject, comprising administering to a subject in need thereof an effective amount of a pharmaceutical composition comprising an antibody or antigen-binding fragment described herein which binds β-klotho and is capable of increases the activity of β-klotho and FGFR1c.

In specific aspects, the subject is afflicted with a metabolic disorder, such as obesity, type 1 and type 2 diabetes mellitus, pancreatitis, dyslipidemia, nonalcoholic steatohepatitis (NASH), insulin resistance, hyperinsulinemia, glucose intolerance, hyperglycemia, and metabolic syndrome. In specific aspects, the subject is afflicted with a cardiovascular disorder.

Pharmaceutical Compositions

The invention provides pharmaceutical compositions comprising the β-klotho-binding antibodies (intact or binding fragments) formulated together with a pharmaceutically acceptable carrier. The compositions can additionally contain one or more other therapeutic agents that are suitable for treating or preventing, for example, cardiovascular disorders. Pharmaceutically acceptable carriers enhance or stabilize the composition, or can be used to facilitate preparation of the composition. Pharmaceutically acceptable carriers include solvents, dispersion media, coatings, antibacterial and antifungal agents, isotonic and absorption delaying agents, and the like that are physiologically compatible.

A pharmaceutical composition of the present invention can be administered by a variety of methods known in the art. The route and/or mode of administration vary depending upon the desired results. It is preferred that administration be intravitreal, intravenous, intramuscular, intraperitoneal, or subcutaneous, or administered proximal to the site of the target. The pharmaceutically acceptable carrier should be suitable for intravitreal, intravenous, intramuscular, subcutaneous, parenteral, spinal or epidermal administration (e.g., by injection or infusion). Depending on the route of administration, the active compound, i.e., antibody, bispecific and multispecific molecule, may be coated in a material to protect the compound from the action of acids and other natural conditions that may inactivate the compound.

The composition should be sterile and fluid. Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition. Long-term absorption of the injectable compositions can be brought about by including in the composition an agent which delays absorption, for example, aluminum monostearate or gelatin.

Pharmaceutical compositions of the invention can be prepared in accordance with methods well known and routinely practiced in the art. See, e.g., Remington: The Science and Practice of Pharmacy, Mack Publishing Co., 20th ed., 2000; and Sustained and Controlled Release Drug Delivery Systems, J. R. Robinson, ed., Marcel Dekker, Inc., New York, 1978. Pharmaceutical compositions are preferably manufactured under GMP conditions. Typically, a therapeutically effective dose or efficacious dose of the β-klotho-binding antibody is employed in the pharmaceutical compositions of the invention. The β-klotho-binding antibodies are formulated into pharmaceutically acceptable dosage forms by conventional methods known to those of skill in the art. Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

Actual dosage levels of the active ingredients in the pharmaceutical compositions of the present invention can be varied so as to obtain an amount of the active ingredient which is effective to achieve the desired therapeutic response for a particular patient, composition, and mode of administration, without being toxic to the patient. The selected dosage level depends upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors.

A physician or veterinarian can start doses of the antibodies of the invention employed in the pharmaceutical composition at levels lower than that required to achieve the desired therapeutic effect and gradually increase the dosage until the desired effect is achieved. In general, effective doses of the compositions of the present invention, for the treatment of a cardiovascular disorders described herein vary depending upon many different factors, including means of administration, target site, physiological state of the patient, whether the patient is human or an animal, other medications administered, and whether treatment is prophylactic or therapeutic. Treatment dosages need to be titrated to optimize safety and efficacy. In a particular embodiment, for systemic administration with an antibody, the dosage ranges from about 0.0001 to 100 mg/kg, or from 0.01 to 15 mg/kg, of the host body weight. In a specific embodiment, for intravitreal administration with an antibody, the dosage may range from 0.1 mg/eye to 5 mg/eye. For example, 0.1 mg/ml, 0.2 mg/ml, 0.3 mg/ml, 0.4 mg/ml, 0.5 mg/ml, 0.6 mg/ml, 0.7 mg/ml, 0.8 mg/ml, 0.9 mg/ml, 1.0 mg/ml, 1.1 mg/ml, 1.2 mg/ml, 1.3 mg/ml, 1.4 mg/ml, 1.5 mg/ml, 1.6 mg/ml, 1.7 mg/ml, 1.8 mg/ml, 1.9 mg/ml, 2.0 mg/ml, 2.1 mg/ml, 2.2 mg/ml, 2.3 mg/ml, 2.4 mg/ml, 2.5 mg/ml, 2.6 mg/ml, 2.7 mg/ml, 2.8 mg/ml, 2.9 mg/ml, 3.0 mg/ml, 3.1 mg/ml, 3.2 mg/ml, 3.3 mg/ml, 3.4 mg/ml, 3.5 mg/ml, 3.6 mg/ml, 3.7 mg/ml, 3.8 mg/ml, 3.9 mg/ml, 4.0 mg/ml, 4.1 mg/ml, 4.2 mg/ml, 4.3 mg/ml, 4.4 mg/ml, 4.5 mg/ml, 4.6 mg/ml, 4.7 mg/ml, 4.8 mg/ml, 4.9 mg/ml, or 5.0 mg/ml. An exemplary treatment regime entails systemic administration once per every two weeks or once a month or once every 3 to 6 months. An exemplary treatment regime entails systemic administration once per every two weeks or once a month or once every 3 to 6 months, or as needed (PRN).

Antibody is usually administered on multiple occasions. Intervals between single dosages can be weekly, monthly or yearly. Intervals can also be irregular as indicated by measuring blood levels of β-klotho-binding antibody in the patient. In addition alternative dosing intervals can be determined by a physician and administered monthly or as necessary to be efficacious. In some methods of systemic administration, dosage is adjusted to achieve a plasma antibody concentration of 1-1000 μg/ml and in some methods 25-500 μg/ml. Alternatively, antibody can be administered as a sustained release formulation, in which case less frequent administration is required. Dosage and frequency vary depending on the half-life of the antibody in the patient. In general, humanized antibodies show longer half life than that of chimeric antibodies and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

EXAMPLES

The following examples are provided to further illustrate the invention but not to limit its scope. Other variants of the

Example 1: Preparation of Human FGFR1c_β-Klotho 300.19 Cells for Use as an Antigen 300.19 cells which stably expressed the human FGFR1c (1-386 aa) and β-klotho were generated for use as a whole cell antigen. The full-length cDNA encoding human β-klotho (GenBank Accession number NM_175737) was cloned into the EcoRI and EcoRV sites of pEF1/Myc-His B (Invitrogen Cat. # V92120). The cDNA encoding amino acids 1-386 of human FGFR1c (GenBank Accession number NM_023106) was cloned into the BamHI and NoI sites of pEF6/Myc-His B (Invitrogen, Cat. number V96220). In both constructs a Kozak sequence (CACC) was included immediately before the start codon and a stop codon was added before the Myc-His tag in the vector. Murine pre-B 300-19 cells were co-transfected with β-klotho and FGFR1c plasmids by electroporation using the Amaxa Nucleofector device and Nucleofector kit (Lonza, Cat # VCA-1003). Stable clones were selected using 1 mg/ml Geneticin (Invitrogen, Cat #10131) and 8 ug/ml Blasticidin (Invitrogen, Cat #46-1120) for 3 weeks.

Example 2: Preparation of FGFR_β-Klotho HEK293 Cells for Use in Cell Assays

To test the binding specificity, functional activity, or ortholog cross-reactivity of β-klotho antibodies, HEK293 cells stably expressing human FGFR1c_β-klotho, human FGFR2c_β-klotho, human FGFR3c_β-klotho, human FGFR4_β-klotho, or cynomolgus monkey FGFR1c_β-klotho were generated using standard Lipofectamine 2000 transfection and cell clone selection methods.

The following mammalian expression plasmids encoding full-length human β-klotho (NM_175737), human FGFR1c (NM_023106), human FGFR2c (NP_001138387), human FGFR3c (NP_000133), or human FGFR4 (NP_998812) cDNAs were used: for cynomolgus monkey β-klotho, the full-length sequence was PCR amplified from cynomolgus monkey adipose tissue cDNA (BioChain, Cat. # C1534003-Cy) with primers based on the human and rhesus monkey β-klotho sequences, and cloned. The cynomolgus monkey FGFR1c cDNA was cloned from cynomolgus monkey adipose tissue cDNA (BioChain, Cat. # C1534003-Cy) using primers based on the human FGFR1c sequence (# NM_023106) and was shown to be 100% identical at the amino acid level to human FGFR1c. Hence, the human FGFR1c cDNA construct described above was used to make HEK293 cells which stably expressed cynomolgus monkey β-klotho and human FGFR1c (# NM_023106) since the human and cynomolgus monkey FGFR1c amino acid sequences are identical.

Example 3: Measuring FGFR_β-Klotho Receptor Activation Using a pERK Cell Assay Standard techniques were used for cell culture and to measure phospho-ERK 1/2 (pERK) levels. Briefly, HEK293 cells stably expressing human FGFR1c_β-klotho, human FGFR2c_β-klotho, human FGFR3c_β-klotho, human FGFR4_β-klotho, or cynomolgus monkey FGFR1c_β-klotho were maintained in DMEM medium (Invitrogen, 11995) containing 10% FBS (Hyclone, SH30071), blasticidin (Invitrogen, A1113902), and Geneticin (Invitrogen, 10131035) at 37° C. in 5% $CO_2$. Cells were plated into 384-well poly-D-lysine-coated plates (BD Biosciences, 354663) and incubated overnight at 37° C. in 5% $CO_2$, followed by serum-starvation.

Hybridoma supernatants or β-klotho antibodies were diluted in Freestyle 293 media and various concentrations of the antibodies were added to the plate. Following incubation, the cells were washed, then lysed with lysis buffer. Cell lysates were transferred to a 384-well assay plate (PerkinElmer, Cat. #6008280) and the AlphaScreen SureFire™ pERK 1/2 Kit (Perkin Elmer, TGRES10K) was used to measure phospho-ERK 1/2 levels. Plates were read on the EnVision 2104 multi-label reader (Perkin Elmer) using standard AlphaScreen settings. Dose-response data was graphed as pERK activity fold over basal versus protein concentration to determine $EC_{50}$ values using the equation Y=Bottom+(Top-Bottom)/(1+10^((Log $EC_{50}$–X)×HillSlope)) and GraphPad Prism 5 Software.

Example 4: Preparation of Monoclonal Antibodies

Anti-human-β-klotho antibodies were generated in Balb/c (Jackson Laboratory strain: BALB/cJ) or Bcl2 22 wehi (Jackson Laboratory strain: C.Cg-Tg(BCL2)22Wehi/J) mice by whole cell immunizations essentially as described in Dreyer et al (2010) (Dreyer A M et. al. (2010) BMC Biotechnology 10:87).

Briefly, $1\times10^7$ human FGFR1c_β-klotho_300.19 cells were injected into Balb/c mice six times at 10 to 30 day intervals. The first whole cell injections were done with Freund's Complete Adjuvant (Sigma-Aldrich F5881). Cells and adjuvant were not mixed, but injected separately in two close, but distinct subcutaneous sites. These were followed later by intraperitoneal injections of the same cells with either Sigma Adjuvant System (Sigma-Aldrich 56322) or without adjuvant.

Using Bcl2 22 wehi mice, $1\times10^7$ human FGFR1c_β-klotho_300.19 cells were injected into these animals four times at seven day intervals. The first injections were done with Freund's Complete Adjuvant (Sigma-Aldrich F5881). Cells and adjuvant were injected separately in two sets of two close, but distinct subcutaneous sites Subsequent injections of cells were done subcutaneously without adjuvant.

Immune responses in the immunized mice were measured by a fluorescence-activated cell sorting (FACS) assay. Serum from the immunized mice diluted 1,000- or 10,000-fold was used to stain human FGFR1c_β-klotho_HEK and human FGFR1c_β-klotho_300.19 cells, followed by an allophycocyanin (APC) secondary anti-murine IgG detection antibody (Jackson ImmunoResearch Cat #115-136-071). Fluorescence was read on a Becton Dickinson LSRII or Foressa flow cytometer. Four mice with the highest titer were chosen for electrofusions.

Example 5: Hybridoma Screening, Subcloning, and Selection $2\times10^8$ spleenoctyes and $5\times10^7$ fusion partner F0 cells (ATCC, CRL-1646) were washed in Cytofusion Medium (LCM-C, Cyto Pulse Sciences) and fused using a Hybrimune Waveform Generator (Cyto Pulse Sciences, model CEEF-50B) according to manufacturer's specification with a peak pulse of 600 volts. Cells were plated into 384 well plates at a calculated density of 3,000 F0 cells per well and cultured in HAT selection media (Sigma-Aldrich Cat. H0262).

The primary screen was performed using a high throughput FACS platform (Anderson, Paul. Automated Hybridoma Screening, Expansion, Archiving and Antibody Purification. In: 3rd Annual 2014 SLAS Conference. Jan. 18-22, 2014, San Diego, Calif.). Briefly, hybridoma supernatants were incubated with human FGFR1c_β-klotho stably expressing and non-expressing cell lines and antibody binding was determined with an anti-murine IgG-APC secondary antibody (Jackson ImmunoResearch Cat #115-136-071).

Antibodies from each hybridoma supernatant were tested for binding simultaneously against four barcoded cell lines: 300.19 parental cells, human_FGFR1c_β-klotho_300.19 cells, parental HEK 293 cells, and human FGFR1c-β-klotho_HEK 293 cells. 348 hits were chosen in the primary screen. Primary hits were expanded in 96-well plates and binding was confirmed again on human FGFR1c_β-klotho_HEK 293 cells by FACS, yielding 122 confirmed hits. HAT (hypoxanthine-aminopterin-thymidine) media-containing supernatants of 115 FACS binding reconfirmed hits were profiled for cell activation of the human FGFR1c_β-klotho receptor complex using the phospho-ERK 1/2 assay described in Example 2.

Hybridomas with the highest phospho-ERK 1/2 cell activity in there supernatants were expanded and IgGs were purified from their supernatants. Purified IgGs from 74 hybridomas were profiled for cell activation of the human FGFR1c_β-klotho receptor complex using the phospho-ERK 1/2 assay described in Example 2. IgGs from hybridomas with the best potency for phospho-ERK 1/2 activation of the human FGFR1c_β-klotho receptor complex were profiled for ortholog cross-reactivity to the cynomolgus monkey FGFR1c_β-klotho receptor complex and selectivity for the human FGFR2c_β-klotho and human FGFR3c_β-klotho receptor complexes using the phospho-ERK 1/2 assay described in Example 2. On the basis of these profiling results, the hybridoma clones, 99G09 and 127F19, were selected the for further profiling.

To evaluate 99G09 and 127F19 signalling in cells expressing α-klotho, HEK293 cells were transfected with α-klotho, Egr1-luciferase and *Renilla* luciferase. Briefly, HEK293 cells were cultured in DMEM, 10% FBS and plated at 30000 cells/well and transfected with Klotho, Egr-1-luc and TK-Rennila using Lipofectamine 2000. Next day, FGF23, FGF21, 99G09, and 127F19 were diluted to the indicated concentration in DMEM supplemented with 0.1% FBS and added to transfected cells overnight. Luciferase activities were detected by Dual-Glo luciferase assay kit (Promega, E2920) according to manufacturer's instruction. As expected, FGF23, which requires α-klotho expression for its signaling, showed strong luciferase expression. However, neither FGF21, 99G09, or 127F19 showed any significant luciferase expression, suggesting that α-klotho does not act as co-receptor for FGF21 or these FGF21 mimetic antibodies.

Example 6: Humanization and Affinity-Maturation of Monoclonal Antibodies

Humanization

The process of humanization is well described in the art (Jones P T et al. (1986) Nature 321: 522-525; Queen C et al. (1989) PNAS USA 86: 10029-10033; Riechmann L et al. (1988) Nature 33:323-327; Verhoeyen M et al. (1988) Science 239: 1534-1536). The term humanization describes the transfer of the antigen-binding site of a non-human antibody, e.g. a murine derived antibody, to a human acceptor framework, e.g. a human germline sequence (Retter I et al. (2005). Nucleic Acids Res. 33:D671-D674.).

The main rationale for humanizing an antibody is seen in minimizing the risk of developing an immunogenic response to the antibody in humans (Rebello P R et al. (1999) Transplantation 68: 1417-1420). The antigen-binding site comprises the complementary determining regions (CDRs) (Chothia C and Lesk A M (1987) Journal of Molecular Biology 196: 901-917; Kabat E et al. (1991) Anon. 5th Edition ed; NIH Publication No. 91: 3242) and positions outside the CDR, i.e. in the framework region of the variable domains (VL and VH) that directly or indirectly affect binding. Framework residues that may directly affect binding can, for example, be found in the so called "outer" loop region located between CDR2 and CDR3. Residues that indirectly affect binding are for example found at so called Vernier Zones (Foote J, Winter G. (1992) Journal of Molecular Biology 224:4 87-499). They are thought to support CDR conformation. Those positions outside the CDRs are taken into account when choosing a suitable acceptor framework to minimize the number of deviations of the final humanized antibody to the human germline acceptor sequence in the framework regions.

Sequence Optimization Affinity Maturation

Certain amino acid sequence motifs are known to undergo post-translational modification (PTM) such as glycosylation (i.e. N×S/T, x any but P), oxidation of free cysteines, deamidation (e.g. NG) or isomerization (e.g. DG). If present in the CDR regions, those motifs are ideally removed by site-directed mutagenesis in order to increase product homogeneity.

The process of affinity maturation is well described in the art. Among many display systems, phage display (Smith G P, 1985, Filamentous fusion phage: novel expression vectors that display cloned antigens on the virion surface. Science 228:1315-1317) and display on eukaryotic cells such as yeast (Boder E T and Wittrup K D, 1997, Yeast surface display for screening combinatorial polypeptide libraries. Nature Biotechnology 15: 553-557) seem to be the most commonly applied systems to select for antibody-antigen interaction. Advantages of those display systems are that they are suitable for a wide range of antigens and that the selection stringency can be easily adjusted. In phage display, scFv or Fab fragments can be displayed and in yeast display full-length IgG in addition. Those commonly applied methods allow selection of a desired antibody variants from larger libraries with diversities of more than 10E7. Libraries with smaller diversity, e.g. 10E3, may be screen by microexpression and ELISA. Non-targeted or random antibody variant libraries can be generated for example by error-prone PCR (Cadwell R C and Joyce G F, 1994, Mutagenic PCR. PCR Methods Appl. 3: S136-S140) and provide a very simple, but sometimes limited approach. Another strategy is the CDR directed diversification of an antibody candidate. One or more positions in one or more CDRs can be targeted specifically using for example degenerated oligos (Thompson J et al., 1996, Affinity maturation of a high-affinity human monoclonal antibody against the third hypervariable loop of human immunodeficiency virus: use of phage display to improve affinity and broaden strain reactivity. J. Mol. Biol. 256: 77-88) trinucleotide mutagenesis (TRIM) (Kayushin A L et al., 1996, A convenient approach to the synthesis of trinucleotide phosphoramidites—synthons for the generation of oligonucleotide/peptide libraries. Nucleic Acids Res. 24: 3748-3755) or any other approach known to the art.

Generation of Expression Plasmids

DNA sequences coding for humanized VL and VH domains were ordered at GeneArt (Life Technologies Inc. Regensburg, Germany) including codon optimization for homosapiens. Sequences coding for VL and VH domains were subcloned by cut and paste from the GeneArt derived vectors into expression vectors suitable for secretion in mammalian cells. The heavy and light chains were cloned into individual expression vectors to allow co-transfection. Elements of the expression vector include a promoter (Cytomegalovirus (CMV) enhancer-promoter), a signal sequence to facilitate secretion, a polyadenylation signal and transcription terminator (Bovine Growth Hormone (BGH) gene), an element allowing episomal replication and replication in prokaryotes (e.g. SV40 origin and ColE1 or others known in the art) and elements to allow selection (ampicillin resistance gene and zeocin marker).

Expression and Purification of Humanized Antibody Candidates

Human Embryonic Kidney cells constitutively expressing the SV40 large T antigen (HEK293-T ATCC11268) are one of the preferred host cell lines for transient expression of humanized and/or optimized IgG proteins. Transfection is performed using PEI (Polyethylenimine, MW 25.000 linear, Polysciences, USA Cat. No. 23966) as transfection reagent. The PEI stock solution is prepared by carefully dissolving 1 g of PEI in 900 ml cell culture grade water at room temperature (RT).

Purification was performed in two steps, from which humanized and affinity-matured mAbs were generated from mouse hybridomas. NOV001 is the humanized and affinity-matured mAb derived from the mouse hybridoma 99G09. NOV002 is the humanized and affinity-matured mAb derived from the mouse hybridoma 127F19. The IgG1 L234A/L235A (LALA) or IgG1κ D265A/P329A (DAPA) isotypes were selected as preventative measures to reduce the antibody's ability to promote antibody-dependent cell-mediated cytotoxicity (ADCC) and complement-dependent cytotoxicity (CDC) (Hezareh M et al. (2001) Journal of Virology 75: 12161-12168). NOV001 is the IgG1 (LALA) isotype and NOV003 is the IgG1 (DAPA) isotype of the same mAb. NOV002 is IgG1 (LALA) isotype and NOV004 is the IgG1 (DAPA) isotype of the same mAb.

Example 7: In Vitro Charactionization of Monoclonal Antibodies

Figure 1B:
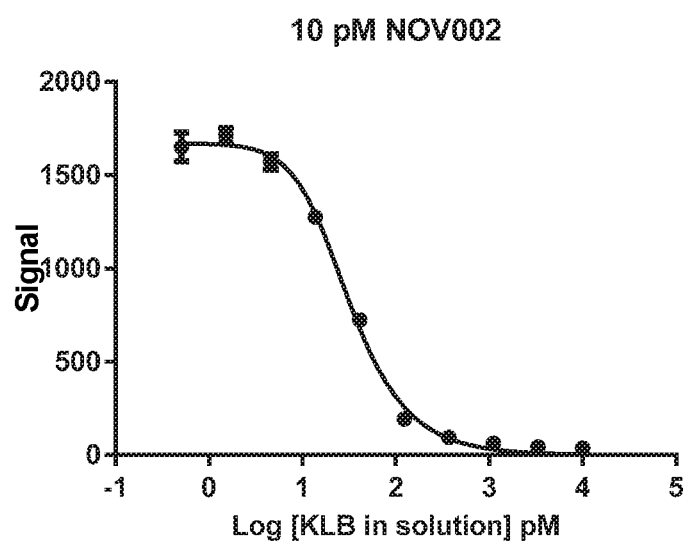
Figure 1C:
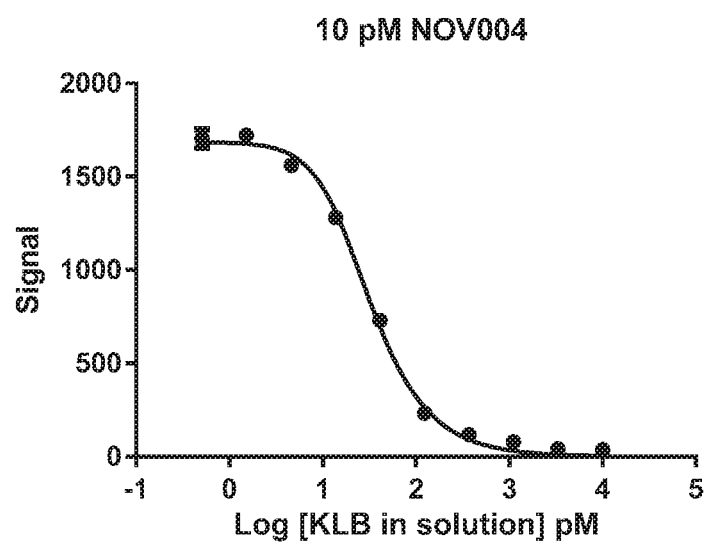
Figure 2A:
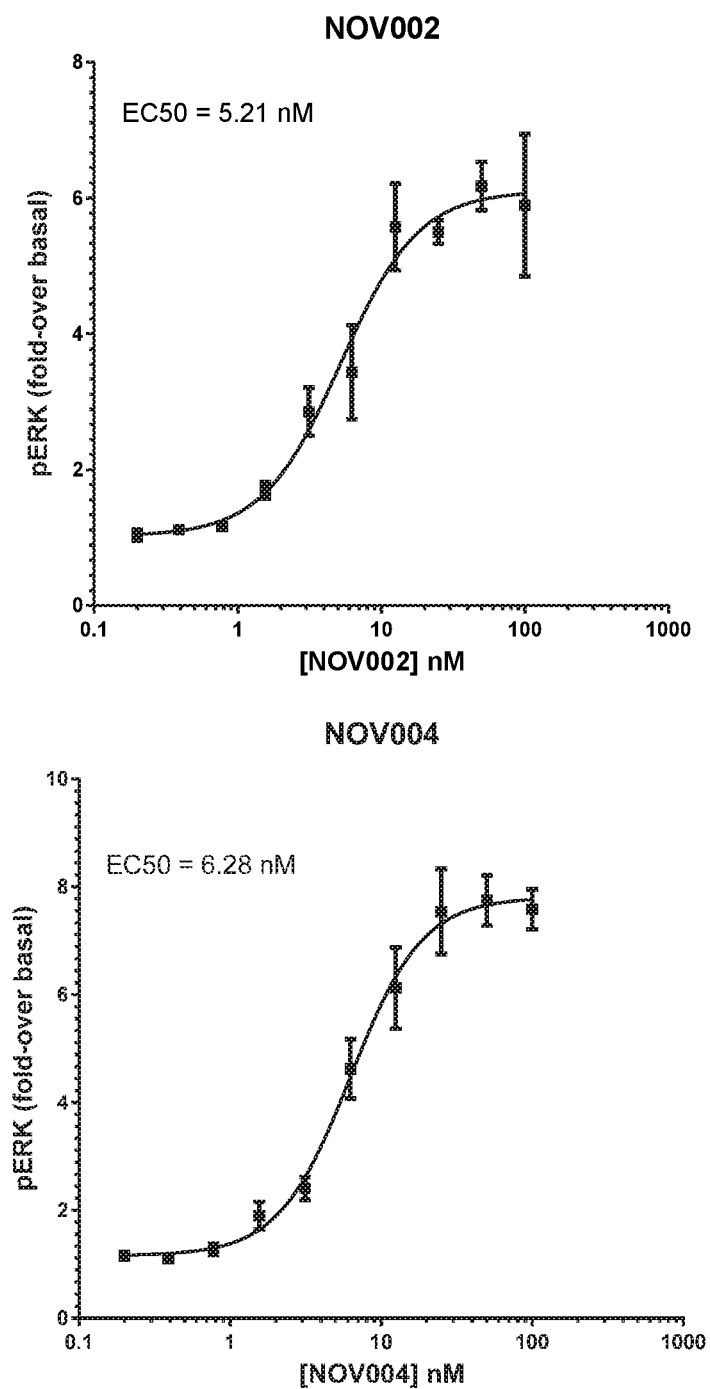
FIG. 2: pERK activation of A) human and B) cynomolgus monkey FGFR1c_β-klotho_HEK293 cells by NOV002 and NOV004.
Figure 2B:
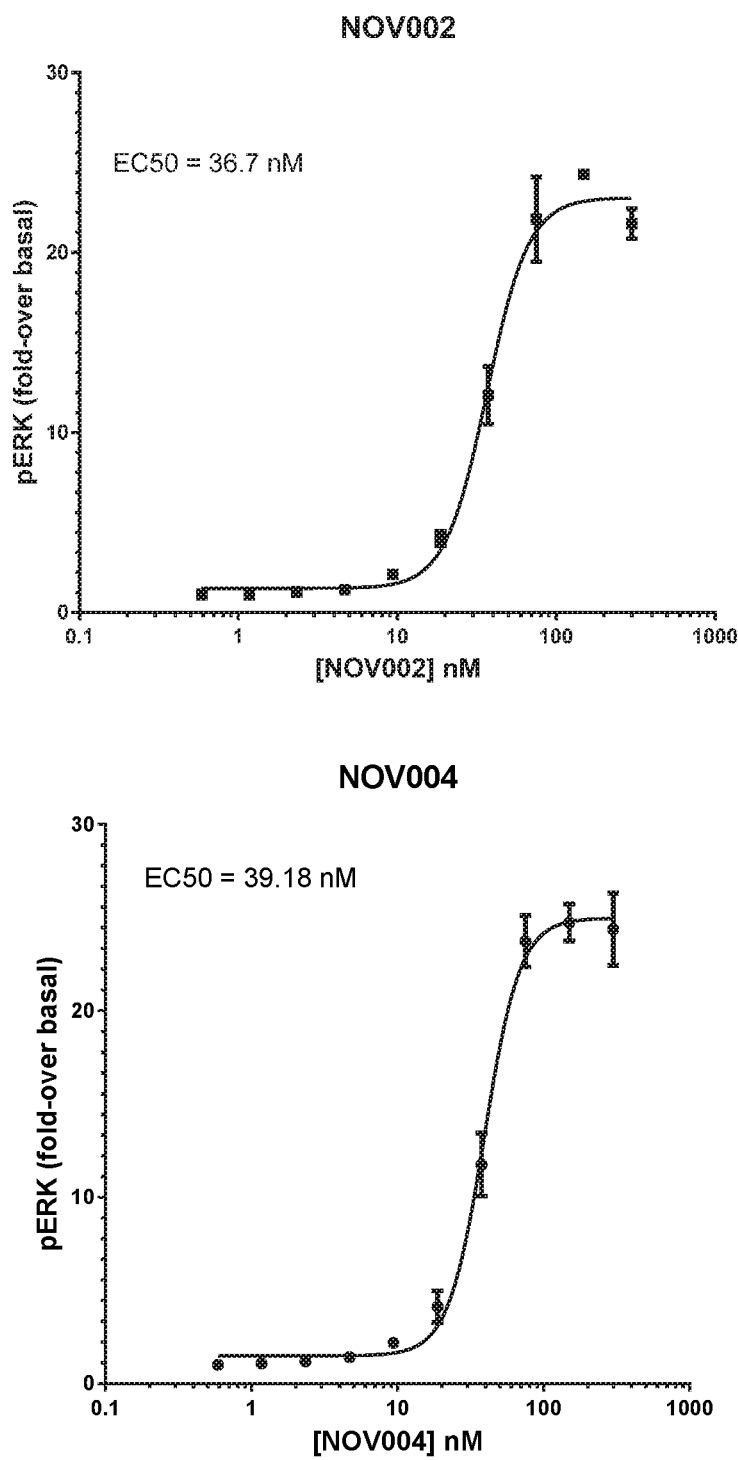
Figure 3A:
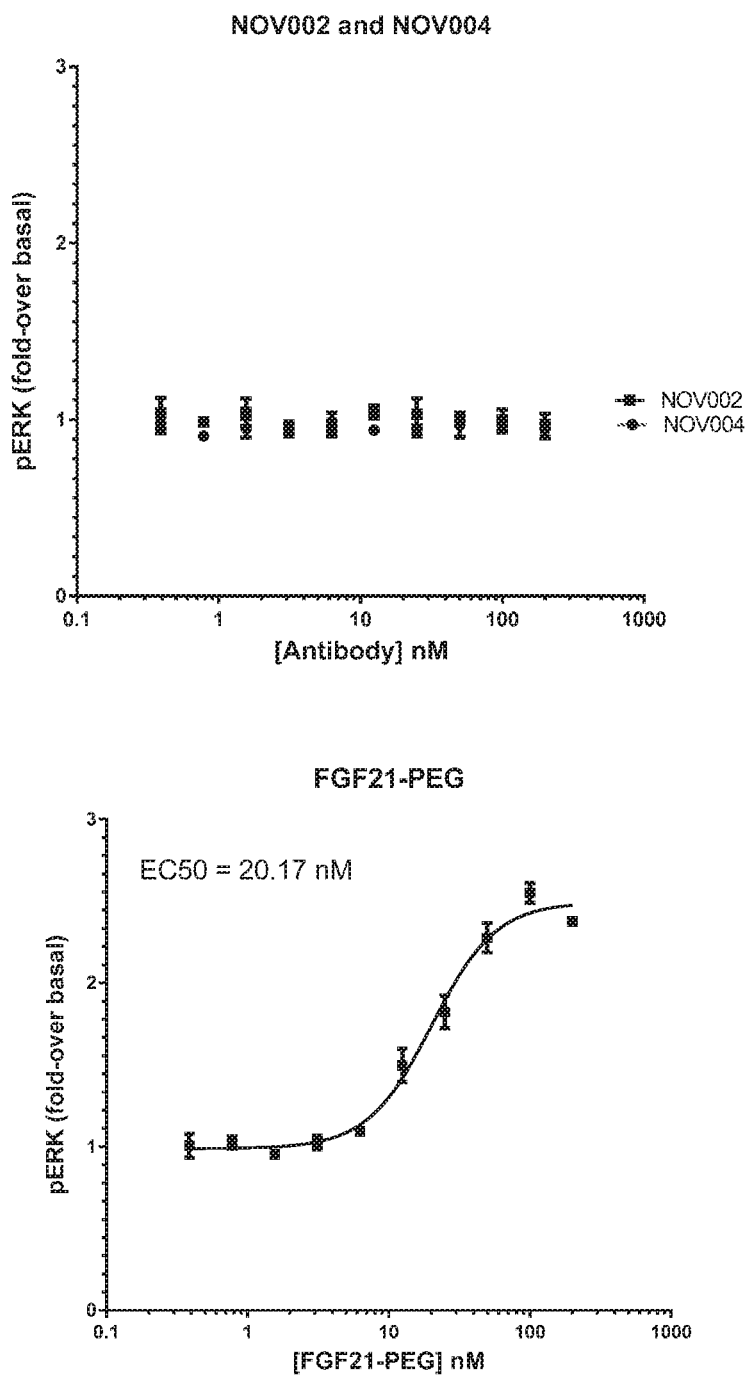
FIG. 3: Profiling of NOV002 and NOV004 for pERK activation of human A) FGFR2c_β-klotho, B) FGFR3c_β-klotho, and C) FGFR4_β-klotho HEK293 cells. FGF21 used as a positive control for activation of FGFR2c_β-klotho or FGFR3c_β-klotho. FGF19 used as positive control for activation of FGFR4_β-klotho.
Figure 3B:
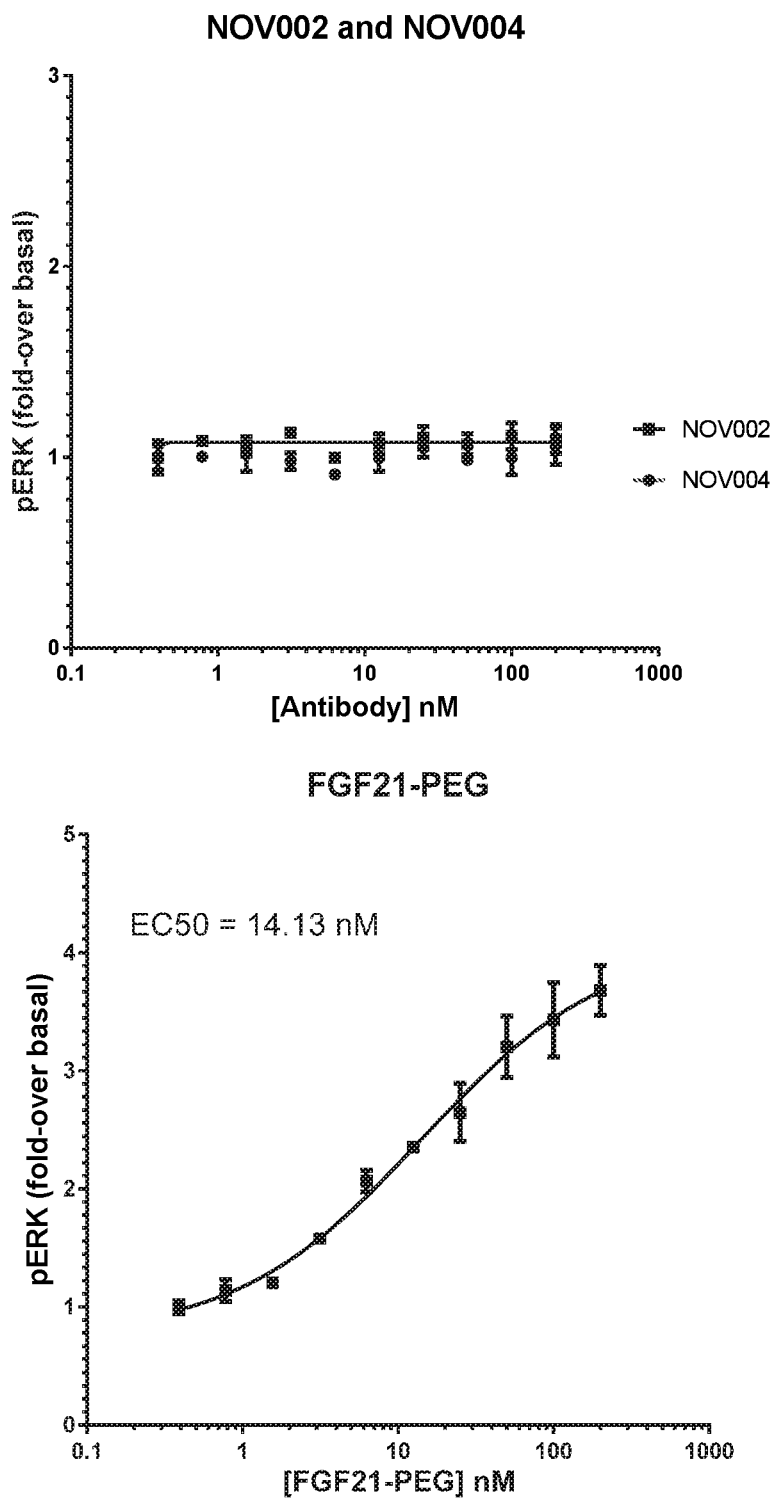
Figure 3C:
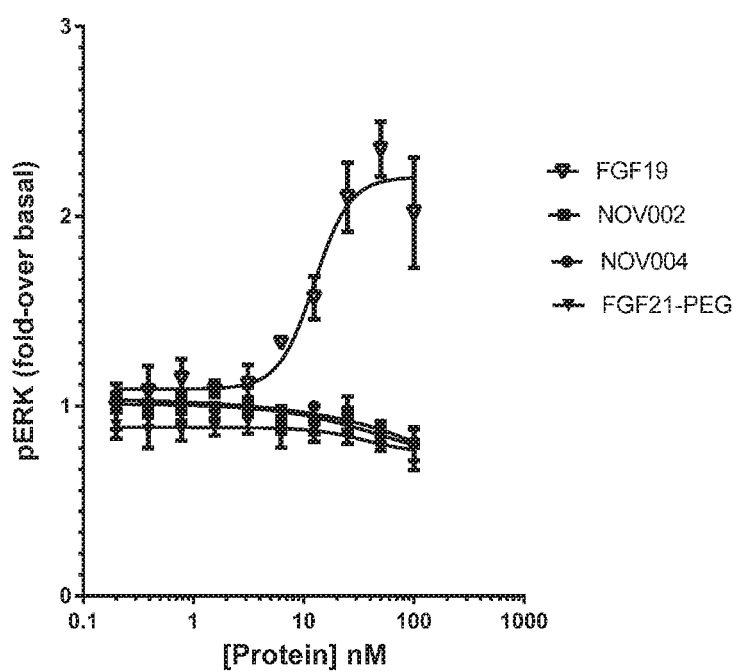
Figure 4:
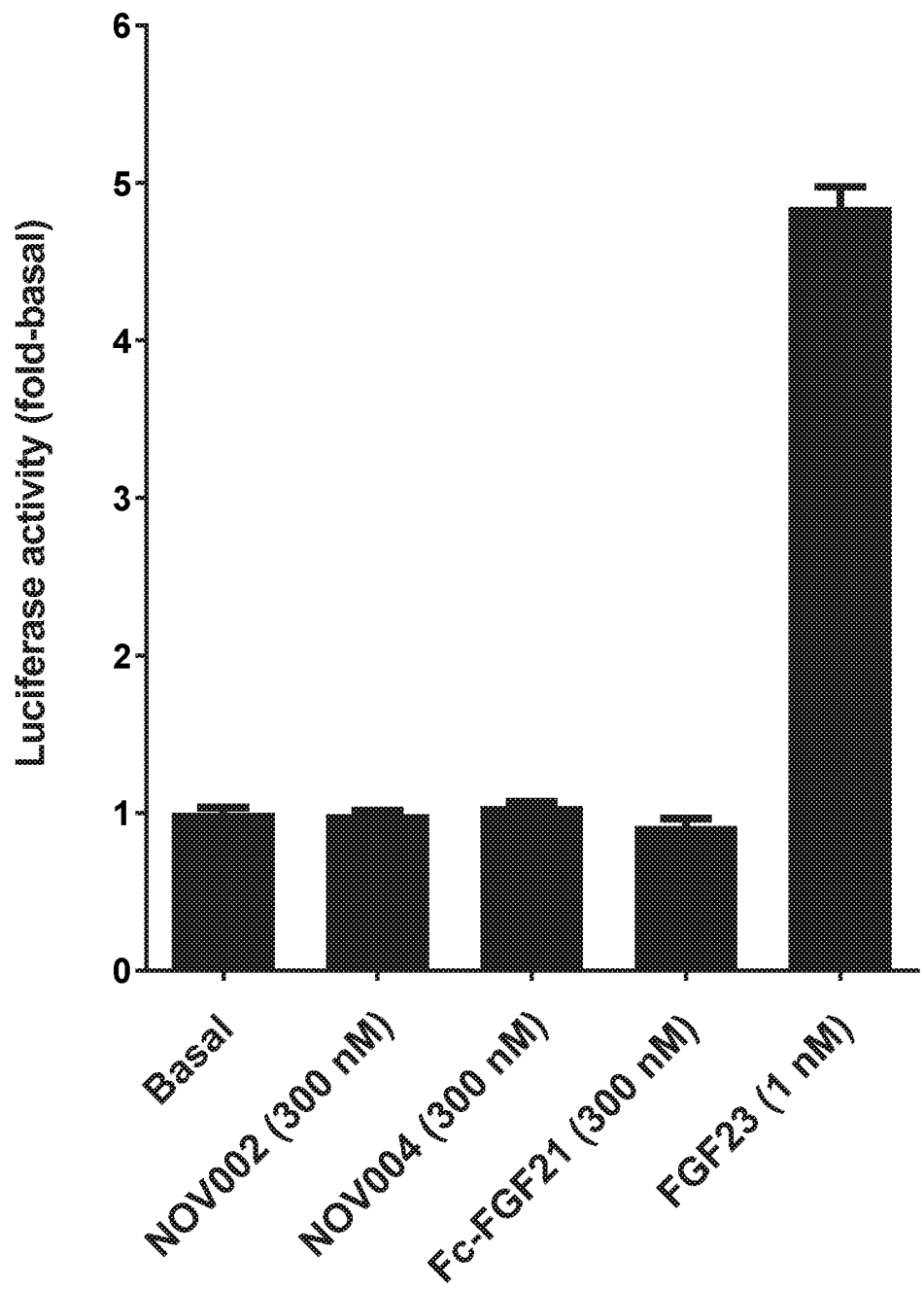
FIG. 4: Profiling of NOV002 and NOV004 for FGF23 activity using HEK293 cells transfected with α-klotho, Egr1-luciferase and Renilla luciferase. FGF23 was used as positive control.
Figure 5:
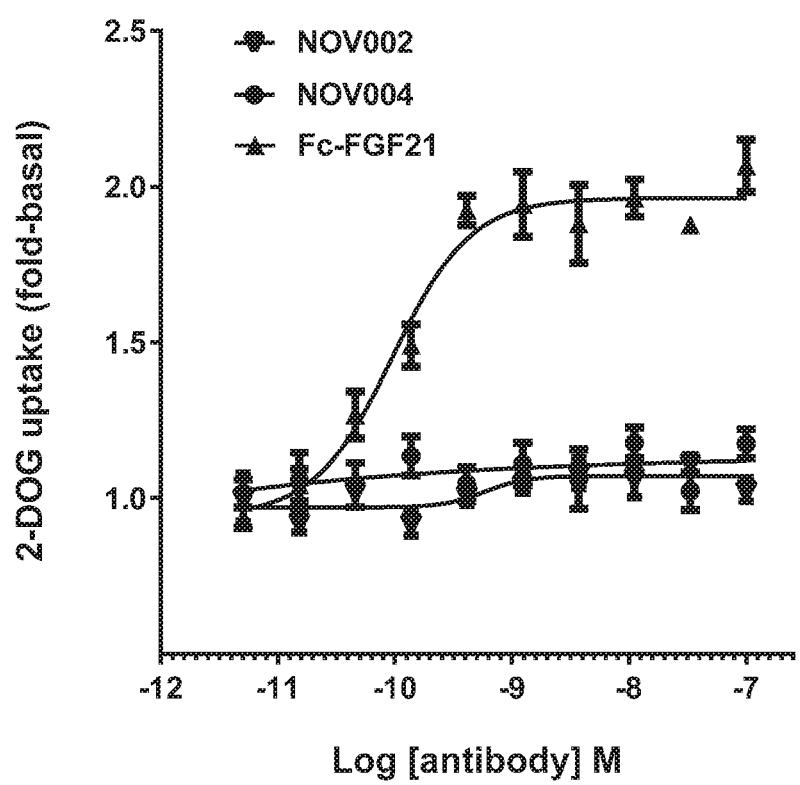
FIG. 5: Profiling of NOV002 and NOV004 for mouse cross-reactivity using 2-DOG uptake by 3T3-L1 adipocytes. FGF21 was used as positive control.

The SET assay as described in Example 5 was used to estimate the KDs of mAbs to human β-klotho. NOV001, NOV002, and NOV004 have KDs of about 42 pM, 8 pM, and 9 pM, respectively (FIG. 1). The pERK assay as described in Example 3 was used to profile mAbs for FGFR_β-klotho receptor activity. NOV002 activated the human and cynomolgus monkey FGFR1c_β-klotho receptor complex with EC50s of about 5 nM and 37 nM, respectively (FIG. 2). NOV004 activated the human and cynomolgus monkey FGFR1c_β-klotho receptor complex with an EC50s of about 6 nM and 40 nM, respectively (FIG. 2). NOV002 and NOV004 did not activate human FGFR2c_β-klotho, FGFR3c_β-klotho, or FGFR4_β-klotho receptor complexes (FIG. 3). The mAbs were profiled for FGF23 activity as described in Example 5. NOV002 and NOV004 did not exhibit FGF23 activity (FIG. 4). The mAbs were profiled for cross-reactivity to the mouse FGFR_β-klotho receptor complex as described in Example 5. The mAbs NOV002 and NOV004 did not lead to glucose-uptake by mouse 3T3L1 adipocyte cells (FIG. 5).

Example 8: Epitope Mapping by Hydrogen-Deuterium Exchange of Human β-Klotho Extracellular Domain with NOV001 and NOV002

Hydrogen-deuterium exchange (HDx) in combination with mass spectrometry (MS) (Woods V L et al. (2001) High Resolution, High-Throughput Amide Deuterium Exchange-Mass Spectrometry (DXMS) Determination of Protein Binding Site Structure and Dynamics: Utility in Pharmaceutical Design. J. Cell. Biochem. Supp.; 84(37): 89-98) was used to map the putative binding sites of NOV001 and NOV002 on human β-klotho extracellular domain (ECD) (52-997aa). In HDx backbone amide hydrogens of proteins are replaced by deuterium. This process is sensitive to protein structure/dynamics and solvent accessibility and, therefore, able to report on locations that undergo a decrease in deuterium uptake upon ligand binding. The goal of these experiments was to identify the potential epitopes and understand the dynamics of human β-klotho ECD when bound to NOV001 or NOV002. Changes in deuterium uptake are sensitive to both direct binding and allosteric events.

HDx-MS experiments were performed using methods similar to those described in the literature (Chalmers M J et al. (2006) Probing protein ligand interactions by automated hydrogen/deuterium exchange mass spectrometry. Anal. Chem.; 78(4): 1005-1014). The experiments were performed on a Waters HDx-MS platform that includes a LEAP autosampler, nanoACQUITY UPLC, and Synapt G2 mass spectrometer. The deuterium buffer used to label the protein backbone of human β-klotho ECD (52-997aa) was D-PBS, pH 7.2; the overall percentage of deuterium in the solution was 95%. The protein human β-klotho (52-997aa) was ordered from R&D System (5889-KB-050). The protein was dialyzed against PBS buffer pH 7.2 overnight prior to HDx-MS analysis. For human β-klotho ECD (52-997aa) deuterium labeling experiments in the absence of antibody, 300 pmol of human β-klotho ECD (52-997aa), volume of 13 was diluted using 100 μl of the deuterium buffer (95% deuterium) in a chilled tube and incubated for 15 minutes on a rotator at 4° C. The labeling reaction was then quenched with 100 μl of chilled quench buffer at 2° C. for five minutes followed by injected onto the LC-MS system for automated pepsin digestion and peptide analysis.

For human β-klotho ECD (52-997 aa) deuterium labeling experiments in the presence of NOV001 or NOV002, 350 pmol of NOV001 or NOV002 was first immobilized on Thermo Protein G Plus beads and cross-linked with DSS (disuccinimidyl suberate). To perform the labeling experiments, the antibody beads containing 350 pmol antibody were incubated with 300 pmol human β-klotho ECD (52-997aa) for 20 minutes at 4° C. After 20 minutes the beads were washed with 200 μl of PBS buffer. Then 200 μl of chilled deuterium buffer (84.1% deuterium) was added and the complex was incubated for 15 minutes at 4° C. After 15 minutes, the deuterium buffer was spun out and the labeling reaction was quenched with 200 μl of chilled quench buffer on ice for 4.5 minutes. After spinning the sample for 30 seconds in a centrifuge, the quenched solution was injected onto the LC-MS system for automated pepsin digestion and peptide analysis.

All deuterium exchange experiments were quenched using 0.5 M TCEP (tris(2-carboxyethyl)phosphine) and 3 M urea (pH=2.6). After quenching, the exchanged antigen was subjected to on-line pepsin digestion using a Poroszyme Immobilized Pepsin column (2.1×30 mm) at 12° C. followed by trapping on a Waters Vanguard HSS T3 trapping column. Peptides were eluted from the trapping column and separated on a Waters BEH C18 1×100 mm column (maintained at 1° C.) at a flow rate of 40 µl/min using a binary 8.4 minute gradient of 2 to 35% B (mobile phase A was 99.9% water and 0.1% formic acid; mobile phase B was 99.9% acetonitrile and 0.1% formic acid).

For human β-klotho ECD (52-997 aa) 82% of the sequence was monitored by the deuterium exchange experiments as described herein. For differential experiments between NOV001 or NOV002 bound and unbound β-klotho ECD, it is informative to examine the change in deuterium incorporation between the two states. In Table 2 a negative value indicates that the NOV001- or NOV002-β-klotho ECD complex undergoes less deuterium uptake relative to β-klotho ECD alone. A decrease in deuterium uptake can be due to protection of the antigen from exchangeable deuterium by the antibody or stabilization of the hydrogen bonding network. In contrast, a positive value indicates that the complex undergoes more deuterium uptake relative to β-klotho ECD alone. An increase in deuterium uptake can be due to destabilization of hydrogen bonding networks (i.e. localized unfolding of the protein). When examining the differential change in deuterium exchange between two different states, such as apo β-klotho ECD and NOV001- or NOV002-β-klotho ECD complex, an approach is typically used to determine if the changes are significant. Typically, as long as the difference is greater than 0.5 Da, the difference is considered significant (Houde D, et al. (2010) J. Pharma. Sci.; 100(6): 2071-2086).

Table 2 lists the change in deuterium incorporation for the NOV001- or NOV002-β-klotho ECD complex relative to the β-klotho ECD alone. Using a -0.5 Da significant cutoff (Houde D, et al. (2010) The Utility of Hydrogen/Deuterium Exchange Mass Spectrometry in Biopharmaceutical Comparability Studies. J. Pharma. Sci.; 100(6): 2071-2086). The following peptides are significantly protected in the NOV001-β-klotho ECD complex: 245-266, 344-349, 421-429, 488-498, 509-524, 536-550, 568-576, 646-670, 696-700, 773-804, 834-857, and 959-986 aa. The following peptides are significantly protected in the NOV002-β-klotho ECD complex: 246-265, 343-349, 421-429, 488-498, 509-524, 536-550, 568-576, 646-669, 773-804, 834-857, and 959-986 aa.

By comparing the protection values of overlapping peptides one can further improve the resolution of the deuterium exchange data. For example, the peptide 329-342aa is protected by only -0.51 Da in the NOV001-β-klotho ECD complex, while the larger peptide 330-348 aa is protected by -1.48 Da. Hence, one can deduce that the significantly protected region of the larger peptide must be the region 343-347aa. Performing this analysis across the data reveals that the regions, 246-265, 536-550, 834-857 and 959-986 aa are the most strongly protected upon either NOV002 or NOV001 binding to β-klotho ECD (e.g., to said regions within SEQ ID NO:262).

Moreover, overall many regions, besides the most strongly protected regions mentioned earlier, protected by NOV001 are also protected in NOV002. These regions of protection are spread across many regions in the linear sequence space although there are more regions of protection towards the C-terminal side of the ECD. In contrast, there are few regions that differentiate between the two antibodies. For NOV001 two regions are uniquely protected: 646-670 aa and 697-700 aa, and for NOV002 one region, 646-689 aa, is uniquely protected. Overall, differentiating the epitopes of NOV002 from NOV001 using HDx-MS alone on β-klotho ECD was challenging. HDx data suggest that the epitopes are quite similar.

Table 2 shows the effect of NOV001 and NOV002 binding on the deuterium incorporation human β-klotho (53-997aa). For each peptide detected by mass spectrometry, the change in deuterium incorporation (in Daltons) for the NOV001-β-klotho complex relative to β-klotho ECD alone and NOV002-β-klotho complex relative to β-klotho ECD alone is shown.

TABLE 2

HDx-MS peptide coverage of the human β-klotho extracellular domain (52-997 aa)

| Sequence | SEQ ID NO: | Start Position | End Position | Change in Deuterium Incorporation (NOV001) | Change in Deuterium Incorporation (NOV002) |
| --- | --- | --- | --- | --- | --- |
| FSGDGRAIW | 85 | 53 | 61 | -0.37 | -0.36 |
| FLYDTFPKNFF | 86 | 76 | 86 | -0.26 | -0.50 |
| FFWGIGT | 87 | 85 | 91 | 0.22 | 0.10 |
| FFWGIGTGAL | 88 | 85 | 94 | -0.10 | -0.12 |
| GIGTGALQ | 89 | 88 | 95 | -0.15 | -0.12 |
| QVEGSWKKDGKGPSIWDHF | 90 | 95 | 113 | -0.77 | -0.79 |
| LEKDLSA | 91 | 134 | 140 | -0.16 | -0.19 |
| LEKDLSAL | 92 | 134 | 141 | -0.12 | -0.20 |
| SALDFIGVSFYQFSISWPRLFPDGIVTVAN | 93 | 139 | 168 | -0.23 | -0.03 |
| SISWPRL | 94 | 152 | 158 | -0.07 | -0.07 |
| SISWPRLFPDGIVT | 95 | 152 | 165 | -0.28 | -0.34 |

TABLE 2-continued

HDx-MS peptide coverage of the human
β-klotho extracellular domain (52-997 aa)

| Sequence | SEQ ID NO: | Start Position | End Position | Change in Deuterium Incorporation (NOV001) | Change in Deuterium Incorporation (NOV002) |
|---|---|---|---|---|---|
| FPDGIVT | 96 | 159 | 165 | −0.19 | −0.24 |
| VANAKGLQ | 97 | 166 | 173 | −0.66 | −0.70 |
| VANAKGLQY | 98 | 166 | 174 | −0.67 | −0.67 |
| LVLRNIEPIVT | 99 | 182 | 192 | −0.02 | −0.07 |
| VLRNIEPIVT | 100 | 183 | 192 | −0.09 | −0.05 |
| RNIEPIVT | 101 | 185 | 192 | −0.11 | −0.12 |
| RNIEPIVTL | 102 | 185 | 193 | −0.07 | −0.08 |
| LYHWDLPLAL | 103 | 193 | 202 | −0.05 | −0.11 |
| IFNDYAT | 104 | 217 | 223 | −0.02 | −0.04 |
| FNDYATYC | 105 | 218 | 225 | −0.16 | −0.03 |
| CFQMFGDRVKY | 106 | 225 | 235 | −0.07 | −0.10 |
| FQMFGDRVK | 107 | 226 | 234 | −0.10 | −0.11 |
| FQMFGDRVKY | 108 | 226 | 235 | −0.03 | −0.05 |
| VAWHGYGTGMHAPGEKGNL | 109 | 245 | 263 | −0.84 | −0.82 |
| AWHGYGTGMHAPGEKGNL | 110 | 246 | 263 | −0.84 | −0.83 |
| WHGYGTGMHAPGEKGNL | 111 | 247 | 263 | −1.14 | −0.97 |
| WHGYGTGMHAPGEKGNLAA | 112 | 247 | 265 | −1.72 | −1.56 |
| HGYGTGMHAPGEKGNL | 113 | 248 | 263 | −0.71 | −0.72 |
| YTVGHNLIKA | 114 | 267 | 276 | −0.21 | −0.24 |
| YTVGHNLIKAHSKVWHNYNTHFRPHQKGW | 115 | 267 | 295 | 0.13 | 0.01 |
| YTVGHNLIKAHSKVWHNYNTHFRPHQKGWL | 116 | 267 | 296 | −0.23 | −0.26 |
| VGHNLIKAHSKVWHNYNTHFRPHQKGWL | 117 | 269 | 296 | −0.29 | −0.35 |
| GHNLIKAHSKVWHNYNTHFRPHQKGWL | 118 | 270 | 296 | −0.16 | −0.16 |
| LIKAHSKVWHNYNTHFRPHQKGWL | 119 | 273 | 296 | −0.24 | −0.27 |
| SITLGSH | 120 | 297 | 303 | −0.12 | −0.12 |
| SITLGSHWIEPNRSENTMD | 121 | 297 | 315 | −0.22 | −0.28 |
| IFKCQQSMV | 122 | 316 | 324 | 0.13 | 0.09 |
| FKCQQSM | 123 | 317 | 323 | −0.07 | −0.09 |
| KCQQSMV | 124 | 318 | 324 | −0.16 | −0.20 |
| FANPIHGDGDYPEG | 125 | 330 | 343 | −0.58 | −0.51 |
| FANPIHGDGDYPEGMRKKL | 126 | 330 | 348 | −1.12 | −1.18 |
| FANPIHGDGDYPEGMRKKLF | 127 | 330 | 349 | −0.92 | −1.00 |
| LPIFSEAEKHEMRGT | 128 | 352 | 366 | −0.99 | −1.03 |
| PIFSEAEKHEMRGTAD | 129 | 353 | 368 | −0.69 | −0.67 |
| PIFSEAEKHEMRGTADF | 130 | 353 | 369 | −0.48 | −0.47 |
| SEAEKHEMRGTADF | 131 | 356 | 369 | −0.54 | −0.54 |

TABLE 2-continued

HDx-MS peptide coverage of the human
β-klotho extracellular domain (52-997 aa)

| Sequence | SEQ ID NO: | Start Position | End Position | Change in Deuterium Incorporation (NOV001) | Change in Deuterium Incorporation (NOV002) |
|---|---|---|---|---|---|
| AEKHEMRGTADF | 132 | 358 | 369 | −0.29 | −0.32 |
| EKHEMRGTADF | 133 | 359 | 369 | −0.26 | −0.28 |
| FAFSFGPNNF | 134 | 370 | 379 | −0.05 | −0.10 |
| FAFSFGPNNFKPLNT | 135 | 370 | 384 | −0.51 | −0.62 |
| FGPNNFKPLNT | 136 | 374 | 384 | −0.50 | −0.48 |
| FGPNNFKPLNTM | 137 | 374 | 385 | −0.47 | −0.59 |
| NLREALN | 138 | 395 | 401 | −0.16 | −0.18 |
| IKLEYNNPRIL | 139 | 403 | 413 | −0.19 | −0.21 |
| EYNNPRIL | 140 | 406 | 413 | −0.02 | −0.05 |
| FTDSRVKTEDTTA | 141 | 420 | 432 | −1.06 | −1.02 |
| DSRVKTEDTTA | 142 | 422 | 432 | −0.94 | −0.91 |
| DTTAIYMMKNF | 143 | 429 | 439 | −0.58 | −0.48 |
| YMMKNFL | 144 | 434 | 440 | −0.05 | −0.01 |
| MMKNFLSQVLQA | 145 | 435 | 446 | −0.06 | −0.07 |
| MKNFLSQVLQA | 146 | 436 | 446 | −0.02 | −0.07 |
| QAIRLDE | 147 | 445 | 451 | −0.05 | −0.03 |
| DEIRVFGYTA | 148 | 450 | 459 | −0.30 | −0.26 |
| IRVFGYTA | 149 | 452 | 459 | −0.10 | −0.09 |
| IRVFGYTAWSL | 150 | 452 | 462 | −0.21 | −0.22 |
| YTAWSLL | 151 | 457 | 463 | −0.09 | −0.06 |
| DGFEWQDA | 152 | 464 | 471 | 0.00 | −0.12 |
| FEWQDAYT | 153 | 466 | 473 | −0.09 | −0.13 |
| YTIRRGLF | 154 | 472 | 479 | −0.09 | −0.11 |
| TIRRGLF | 155 | 473 | 479 | −0.12 | −0.13 |
| NSKQKERKPKSSAHY | 156 | 484 | 498 | −1.00 | −0.91 |
| NSKQKERKPKSSAHYYKQIIRE | 157 | 484 | 505 | −0.75 | −0.70 |
| NSKQKERKPKSSAHYYKQIIRENG | 158 | 484 | 507 | −0.80 | −0.76 |
| NSKQKERKPKSSAHYYKQIIRENGF | 159 | 484 | 508 | −0.65 | −0.66 |
| NSKQKERKPKSSAHYYKQIIRENGFS | 160 | 484 | 509 | −1.11 | −1.02 |
| SKQKERKPKSSAHYYKQIIRE | 161 | 485 | 505 | −0.72 | −0.69 |
| YKQIIRENG | 162 | 499 | 507 | −0.42 | −0.43 |
| FSLKESTPDVQGQFPCD | 163 | 508 | 524 | −0.79 | −0.89 |
| SLKESTPDVQGQFPCD | 164 | 509 | 524 | −1.02 | −1.22 |
| LKESTPDVQGQFPCD | 165 | 510 | 524 | −0.98 | −1.07 |
| FSWGVTE | 166 | 525 | 531 | −0.20 | −0.19 |
| SVLKPESVASSPQFSDPHL | 167 | 532 | 550 | −1.74 | −1.87 |

TABLE 2-continued

HDx-MS peptide coverage of the human
β-klotho extracellular domain (52-997 aa)

| Sequence | SEQ ID NO: | Start Position | End Position | Change in Deuterium Incorporation (NOV001) | Change in Deuterium Incorporation (NOV002) |
|---|---|---|---|---|---|
| KPESVASSPQFSDPHL | 168 | 535 | 550 | −1.74 | −1.74 |
| VRLKTRPAQC | 169 | 567 | 576 | −1.37 | −1.35 |
| FVNIKKQLEM | 170 | 579 | 588 | −0.91 | −0.90 |
| VNIKKQLEM | 171 | 580 | 588 | −0.68 | −0.68 |
| VNIKKQLEML | 172 | 580 | 589 | −0.72 | −0.74 |
| NIKKQLEM | 173 | 581 | 588 | −0.41 | −0.51 |
| LARMKVTHYR | 174 | 589 | 598 | −0.12 | −0.08 |
| LARMKVTHYRF | 175 | 589 | 599 | −0.16 | −0.16 |
| ARMKVTHYRF | 176 | 590 | 599 | −0.14 | −0.12 |
| ALDWASVL | 177 | 600 | 607 | −0.08 | −0.11 |
| YRCVVSEG | 178 | 623 | 630 | −0.23 | −0.22 |
| VVSEGLKLGISA | 179 | 626 | 637 | −0.13 | −0.10 |
| GLKLGISAM | 180 | 630 | 638 | −0.10 | −0.05 |
| LKLGISA | 181 | 631 | 637 | −0.06 | −0.06 |
| LKLGISAM | 182 | 631 | 638 | −0.04 | −0.06 |
| ISAMVTLYYPT | 183 | 635 | 645 | −0.22 | −0.18 |
| LYYPTHAHLGLPEPLL | 184 | 641 | 656 | −0.55 | −0.86 |
| YYPTHAHLGLPEPLL | 185 | 642 | 656 | −0.63 | −0.83 |
| YYPTHAHLGLPEPLLHADGWLNPSTAEA | 186 | 642 | 669 | −1.29 | −1.04 |
| HADGWLNPSTAEA | 187 | 657 | 669 | −0.83 | −0.61 |
| HADGWLNPSTAEAF | 188 | 657 | 670 | −0.62 | −0.48 |
| AFQAYAGL | 189 | 669 | 676 | −0.11 | −0.09 |
| FQAYAGLC | 190 | 670 | 677 | −0.08 | −0.09 |
| QAYAGLC | 191 | 671 | 677 | −0.13 | −0.15 |
| QAYAGLCF | 192 | 671 | 678 | −0.12 | −0.16 |
| CFQELGD | 193 | 677 | 683 | −0.18 | −0.20 |
| CFQELGDL | 194 | 677 | 684 | 0.01 | −0.07 |
| WITINEPNRL | 195 | 688 | 697 | −0.70 | −0.46 |
| WITINEPNRLSD | 196 | 688 | 699 | −0.80 | −0.54 |
| WITINEPNRLSDI | 197 | 688 | 700 | −1.24 | −0.68 |
| ITINEPNR | 198 | 689 | 696 | −0.68 | −0.40 |
| VAHALAWRL | 199 | 717 | 725 | −0.12 | −0.11 |
| AHALAWRL | 200 | 718 | 725 | −0.06 | −0.06 |
| HALAWRL | 201 | 719 | 725 | −0.14 | −0.13 |
| YDRQFRPSQRGAVS | 202 | 726 | 739 | −0.48 | −0.48 |
| YDRQFRPSQRGAVSL | 203 | 726 | 740 | −0.48 | −0.43 |

TABLE 2-continued

HDx-MS peptide coverage of the human
β-klotho extracellular domain (52-997 aa)

| Sequence | SEQ ID NO: | Start Position | End Position | Change in Deuterium Incorporation (NOV001) | Change in Deuterium Incorporation (NOV002) |
|---|---|---|---|---|---|
| DRQFRPSQRGAVS | 204 | 727 | 739 | −0.60 | −0.58 |
| SLHADWAEPANPYADSHWRAAERF | 205 | 741 | 764 | −0.45 | −0.68 |
| HADWAEPANPYADSHW | 206 | 743 | 758 | −0.34 | −0.43 |
| HADWAEPANPYADSHWRA | 207 | 743 | 760 | −0.69 | −0.78 |
| HADWAEPANPYADSHWRAAERF | 208 | 743 | 764 | −0.73 | −0.92 |
| WAEPANPYADSHWRAAERF | 209 | 746 | 764 | −0.74 | −0.92 |
| PANPYADSHWRAAERF | 210 | 749 | 764 | −0.33 | −0.51 |
| PYADSHWRAAERF | 211 | 752 | 764 | −0.51 | −0.68 |
| FAEPLFKTGDYPAA | 212 | 772 | 785 | −0.66 | −0.68 |
| FAEPLFKTGDYPAAM | 213 | 772 | 786 | −0.87 | −0.83 |
| KTGDYPAAM | 214 | 778 | 786 | −0.84 | −0.81 |
| REYIASKHRRGLSSSAL | 215 | 787 | 803 | −1.21 | −1.00 |
| REYIASKHRRGLSSSALPRL | 216 | 787 | 806 | −1.45 | −1.25 |
| YIASKHRRGLSSSAL | 217 | 789 | 803 | −1.22 | −0.98 |
| PRLTEAE | 218 | 804 | 810 | −0.53 | −0.58 |
| PRLTEAERRLLKGTVDF | 219 | 804 | 820 | −0.24 | −0.33 |
| AERRLLKGTVDF | 220 | 809 | 820 | −0.24 | −0.24 |
| ERRLLKGTVDF | 221 | 810 | 820 | −0.34 | −0.34 |
| RRLLKGTVDF | 222 | 811 | 820 | −0.21 | −0.23 |
| CALNHFTTRF | 223 | 821 | 830 | −0.28 | −0.29 |
| VMHEQLAGSRYDSDRD | 224 | 831 | 846 | −1.32 | −1.07 |
| VMHEQLAGSRYDSDRDIQF | 225 | 831 | 849 | −1.08 | −0.97 |
| HEQLAGSRYDSDRDIQF | 226 | 833 | 849 | −1.93 | −1.88 |
| AGSRYDSDRD | 227 | 837 | 846 | −0.99 | −0.85 |
| AGSRYDSDRDIQF | 228 | 837 | 849 | −0.64 | −0.55 |
| GSRYDSDRDIQF | 229 | 838 | 849 | −0.76 | −0.69 |
| LQDITRLSSPTR | 230 | 850 | 861 | −1.28 | −1.28 |
| LQDITRLSSPTRL | 231 | 850 | 862 | −1.69 | −1.70 |
| ITRLSSPTRL | 232 | 853 | 862 | −1.09 | −1.06 |
| TRLSSPTR | 233 | 854 | 861 | −1.00 | −0.91 |
| SPTRLAV | 234 | 858 | 864 | −0.19 | −0.20 |
| SPTRLAVIPWGVRKL | 235 | 858 | 872 | −0.13 | −0.18 |
| AVIPWGVRKL | 236 | 863 | 872 | −0.43 | −0.60 |
| AVIPWGVRKLLRWVRRNYGDM | 237 | 863 | 883 | −0.12 | −0.26 |
| AVIPWGVRKLLRWVRRNYGDMD | 238 | 863 | 884 | −0.23 | −0.42 |
| AVIPWGVRKLLRWVRRNYGDMDI | 239 | 863 | 885 | −0.01 | −0.20 |

TABLE 2-continued

HDx-MS peptide coverage of the human
β-klotho extracellular domain (52-997 aa)

| Sequence | SEQ ID NO: | Start Position | End Position | Change in Deuterium Incorporation (NOV001) | Change in Deuterium Incorporation (NOV002) |
|---|---|---|---|---|---|
| IPWGVRK | 240 | 865 | 871 | −0.51 | −0.35 |
| IPWGVRKLLRWVRRNYGDMD | 241 | 865 | 884 | −0.23 | −0.37 |
| LRWVRRNYGDMDI | 242 | 873 | 885 | −0.08 | −0.11 |
| IYITASGIDDQALED | 243 | 885 | 899 | −0.62 | −0.91 |
| YITASGIDDQAL | 244 | 886 | 897 | −0.30 | −0.21 |
| YITASGIDDQALEDDRLRKYYLGKY | 245 | 886 | 910 | −0.90 | −1.02 |
| EDDRLRKYYLGKY | 246 | 898 | 910 | −0.55 | −0.62 |
| DRLRKYYLGKY | 247 | 900 | 910 | −0.35 | −0.35 |
| DRLRKYYLGKYLQE | 248 | 900 | 913 | −0.44 | −0.50 |
| IDKVRIKG | 249 | 920 | 927 | −0.41 | −0.40 |
| IDKVRIKGY | 250 | 920 | 928 | −0.37 | −0.32 |
| IDKVRIKGYYA | 251 | 920 | 930 | −0.44 | −0.42 |
| IDKVRIKGYYAF | 252 | 920 | 931 | −0.28 | −0.30 |
| DKVRIKGYYA | 253 | 921 | 930 | −0.45 | −0.43 |
| KVRIKGYYA | 254 | 922 | 930 | −0.34 | −0.35 |
| KVRIKGYYAF | 255 | 922 | 931 | −0.40 | −0.40 |
| FKLAEEKSKPRFGF | 256 | 931 | 944 | −0.83 | −0.75 |
| FKLAEEKSKPRFGFF | 257 | 931 | 945 | −0.62 | −0.59 |
| KLAEEKSKPRFGFF | 258 | 932 | 945 | −0.75 | −0.74 |
| FKAKSSIQF | 259 | 949 | 957 | −0.89 | −0.88 |
| YNKVISSRGFPFENSSSRCSQTQE | 260 | 958 | 981 | −1.64 | −1.62 |
| SSRCSQTQENTECT | 261 | 973 | 986 | −1.95 | −2.01 |

Example 9: Pharmacokinetic Profiles of Monoclonal Antibodies in Rat

Animals and Maintenance Conditions

Animal care and husbandry were provided according to the Guide for the Care and Use of Laboratory Animals (Institute of Laboratory Animal Resources, National Research Council). All procedures were governed by the standards set forth by the US Department of Health and Human Services and performed according to protocol CV9054 approved by the Novartis East Hanover Animal Care and Use Committee. Male, Sprague-Dawley rats (n=3/group) were housed in solid-bottom cages on a rack equipped to automatically provide water ad libitum, maintained on a 12 hr light/dark cycle (6 am to 6 pm), and given free access to standard rodent chow (Harlan-Teklad; Frederick, Md.; cat #8604). The vivarium was maintained between 68 and 76° F. with 30 to 70% humidity.

NOV002 or NOV004 Preparation and Dosing

Stock solutions of NOV002 (12.00 mg/mL) and NOV004 (16.0 mg/mL) in 20 mM Histidine buffer (pH 6.0) were shipped frozen, stored at −80° C., and thawed under refrigeration prior to use. On the morning of dosing, both antibodies were diluted to 2 mg/mL in 20 mM Histidine buffer and appropriate volumes were drawn into dosing syringes (5 mL/kg) and kept at room temperature until administration Animals were placed in tube restrainers and administered either NOV002 or NOV004 via intravenous (IV) injection into the tail vein (10 mg/kg).

Blood Sample Collection

Blood samples were collected on day −3 (Baseline), day 0 (1 and 6 h post-dose), and days 1, 2, 4, 7, 14, 21, and 28 post-dose. All time points were timed from the end of administration of the dose given on day 0. At each timepoint, approximately 0.2 mL (200 µL) of blood was collected into BD Microtainer collection/separator tubes with EDTA (Becton, Dickinson, and Company; Franklin Lakes, N.J.; cat #365973). Pressure was applied with gauze to stop the bleeding. Samples were centrifuged for 10 min at 20, 817×g, and then ~100 µL plasma was transferred to 0.2 mL Thermostrip tube (Thermo-Scientific; Pittsburgh, Pa.; cat # AB-0451) and frozen at 80° C. Rats were returned to their home cage after each collection.

Measurement of Plasma Total NOV002 or NOV004 Concentrations

Human IgG (i.e. NOV002 or NOV004) in rat plasma was quantified using a custom sandwich immunoassay with a mouse anti-human-IgG monoclonal antibody (R10Z8E9) as capture antibody and a goat anti-human-IgG with an HRP label as detection antibody. The capture antibody (2 µg/mL in PBS, 30 µL/well) was coated on 384-well, white, microtiter plates (Greiner Bio-One; Monroe, N.C.; cat no. 781074). The plates were incubated overnight at room temperature (RT) without shaking. After aspirating the coating solution without washing, 90 µL of 1× Milk Diluent/Blocking solution (KPL; Gaithersburg, Md.; cat no. 50-82-01) was added to each well and the plates were incubated for 2 h at RT. At the end of the incubation, the solution was aspirated and the plates were stored in foil pouches with desiccant at −80° C.

On the day of the assay, sixteen NOV002 or NOV004 standard concentrations, ranging from 0.15-600 ng/mL, were prepared by serial dilution in Casein buffer, including a buffer negative control. All study samples were diluted 1:50 manually in Casein buffer and then serially diluted 5-fold using a Freedom EVO (Tecan; Mannedorf, Switzerland) for a total of five dilutions. The plates were incubated for 2 h at RT, with shaking at 300 rpm, and then washed 3 times with phosphate wash buffer (90 µL/well). HRP-labeled goat anti-human-IgG (400 ng/mL in Casein buffer, 30 µL/well) was added to each plate and the plates were incubated for 1 h at RT, with shaking at 300 rpm. The plates were washed 3 times with phosphate wash buffer (90 µL/well), and then KPL LumiGLO Chemiluminescent Substrate was added (30 µL/well; cat no. 54-61-00). Chemiluminescence was read immediately on a SpectraMax M5 plate reader (Molecular Devices) at all wavelengths with 50 ms integration time. Human Fc concentrations (ng/mL) in plasma samples were interpolated from the NOV002 or NOV004 standard curve, multiplied by dilution factors, and converted to nM concentrations.

Figure 6:
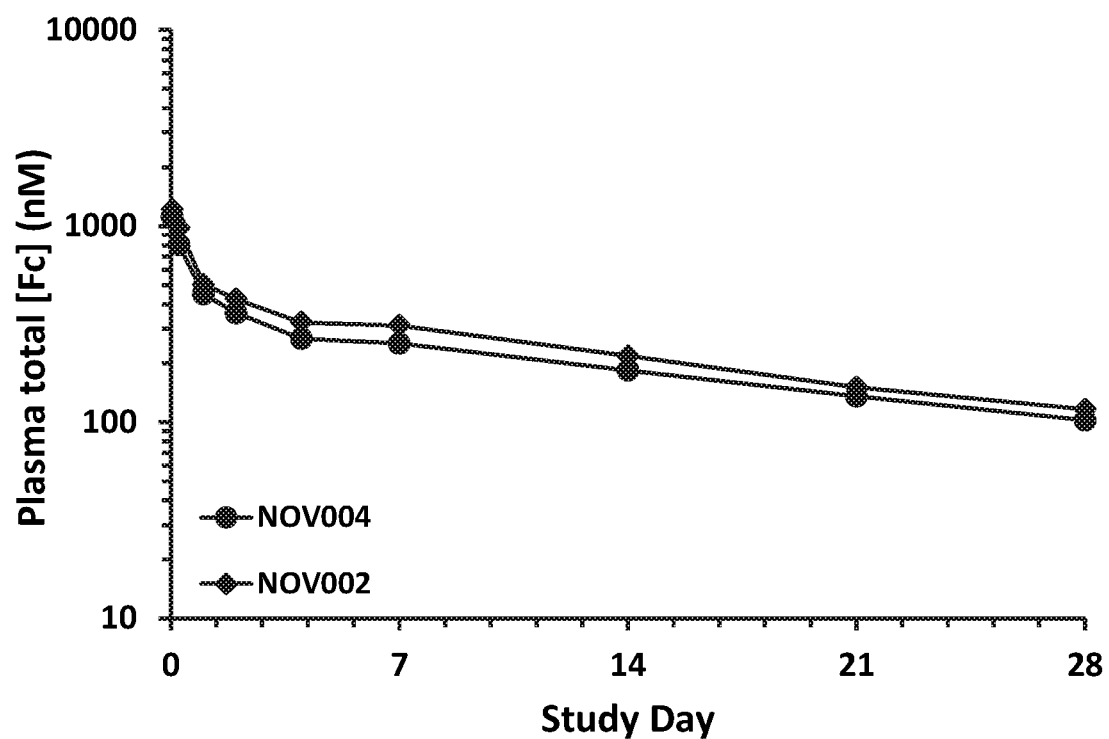
FIG. 6: NOV002 and NOV004 concentration-time profiles following IV injection in rats.

Animals exhibited mean $C_{max}$ of 1207 and 1115 nM at 1 h after IV administration of NOV002 or NOV004, respectively. NOV002 and NOV004 exhibit equivalent PK profiles in Sprague-Dawley rats (FIG. 6).

Example 10: Study in Obese, Cynomolgus Monkeys

The effects of NOV002 on food consumption, body weight, and plasma biomarkers in obese cynomolgus monkeys were studied.

Protocols:

Five male cynomolgus monkeys were treated with two subcutaneous (s.c.), 1 mg/kg doses of NOV002 administered one week apart (study days 0 and 7) and food consumption, body weights, and plasma biomarkers were assessed for more than 100 days post-dose. For each dose, animals were restrained in their home cage, blood samples were collected, and then each animal was given a subcutaneous dose of 1 mg/kg NOV002. Food consumption measurements started 1 week before the first dose and continued through the study. The study diet was weighed prior to feeding and divided into two equal portions for each day. The following morning, remaining diet was collected and weighed. The number of pellets (1 g each) dropped in the catch pan were counted and added to the weight of the remaining food. Daily food consumption was calculated as the weight of food provided minus food collected. Fruit and vegetable consumption were not measured. Non-fed body weights were measured in duplicate three mornings per week (prior to blood collection or dosing) using the dynamic feature on the scale.

Measurement of Plasma NOV002 Concentrations

Human Fc IgG in cynomologus monkey plasma was quantified using an ELISA based sandwich immunoassay. Anti-human-IgG mouse IgG1, a mouse monoclonal antibody against human IgG, was used as the capture antibody. White, Greiner, 384-well plates were coated with 2 µg/mL anti-human-IgG mouse IgG1 (30 µL/well) and incubated overnight at room temperature (RT). Coating antibody was aspirated and 1× milk blocker (KPL #50-82-01) was added at 90 µL/well for 2 h at RT. The blocking solution was aspirated and the plates were stored at −80° C. in plate bags with desiccant until assay. On the day of the assay, plates and reagents were brought to RT. Standards were made by diluting the purified IgG from 4000 to 16 pM in custom casein sample diluent and including a buffer control. Samples were diluted in duplicate 1:50, 1:250, 1:1250, and 1:6250 in the same diluent as standards, and then standards, diluted samples, and controls were added to the plate for 2 h at RT (working volume for all steps was 30 µL/well). Plates were then washed 3 times with a phosphate based wash buffer. Horseradish peroxidase (HRP)-labeled anti-human Fc-gamma antibody was added to the plate for 1 hour at RT, and then the plates were washed 3 times with a phosphate-based wash buffer. Chemiluminescent substrate was added to the plate and the plate was immediately read on a luminescence plate reader.

NOV002 standards were assayed in triplicate per plate. Diluted plasma samples were assayed in duplicate. Unknown samples were interpolated from the IgG standard curve. Curve fitting, back-calculation, % recovery, and interpolation of sample concentrations were performed using SoftMax Pro Software v5.4.1. Signal generated by the IgG standards was plotted and fit using a 4-parameter logistical curve-fitting option. Fc concentrations (pM) in plasma samples were interpolated from the NOV002 standard curve and multiplied by dilution factors. The assay lower limit of quantification (LLOQ) was 31.250 pM and the upper limit of quantification (ULOQ) was 4000 pM. LLOQ and ULOQ were defined as the lower and upper standard concentration with 100% recovery±20% and CV<20% and then multiplied by the dilution factors.

Detection of Anti-Drug Antibodies

Plasma samples were diluted 1:5 in LowCross Buffer (Boca Scientific; Boca Raton, Fla.; cat no. 100 500). Reaction Mixture was prepared containing 0.6 µg/mL of biotin-labeled NOV002 and 0.6 µg/mL of digoxigenin-labeled NOV002 in LowCross Buffer. Diluted plasma (80 µL) was combined with 160 µL of Reaction Mixture in 96-well U-bottom plates (BD Falcon; Billerica, Mass.; cat no. 351177). The edges of the plates were sealed with Parafilm and the plates were incubated on a shaking platform at 37° C. for 2 h (150 rpm, protected from light). An aliquot of each mixture (100 µL) was then transferred to duplicate wells of Streptavidin-coated 96-well plates (Roche; cat no. 11734776001), which were first washed 3 times with wash buffer consisting of 1×PBS containing 0.05% (v/v) Tween-20 (300 µL per well). The plates were sealed and then incubated at RT on a shaking platform for 1 h (300 rpm, protected from light). Plates were washed 3 times with wash buffer (300 µL per well), and then 100 µL of anti-digoxigenin peroxidase_POD Fab fragment (Roche; cat no. 11633716001) diluted 1:2500 in LowCross Buffer were added to each well. The plates were sealed, incubated at RT on a shaking platform for 45 minutes (300 rpm, protected from light), and then washed 3 times with wash buffer (300

μL per well). TMB One Component HRP Microwell Substrate (Bethyl Laboratories; Montgomery Tex.; cat no. E102; 100 μL/well) was added to each well and blue color was developed for 9-10 min., protected from light. The color reaction was stopped by adding 100 μL of 0.18 N H2SO4 to each well, the plates were shaken briefly, and yellow color was measured at OD450.

Measurement of Plasma Glucose Concentrations

Plasma glucose concentrations were measured using an Autokit Glucose assay (Wako Chemicals; Richmond, Va.; catalog no. 439-90901). A standard curve was prepared by diluting the calibrator to 500, 200, 100, 50, 20, and 0 mg/dL standards. Assay reagent (300 μL), pre-warmed to 37° C., was added to 2 μL of plasma, standards, and control samples in a clear, flat-bottom, 96-well plate (Thermo Scientific; cat no. 269620). The plate was mixed on a plate shaker for 30 s and then incubated at 37° C. for 5 min. Following a 20 s mix, the plate was read at 505/600 nm using a Molecular Devices SPECTRAmax PLUS 384 (Sunnyvale, Calif.). Sample glucose concentrations were calculated by comparing to the standard curve.

Measurement of Plasma Insulin Concentrations

Plasma insulin concentrations were determined using the Millipore Human Insulin Specific RIA Kit (Billerica, Mass.; cat no. HI-14K) according to the manufacturer instructions. Appropriate amounts of assay buffer, standards, or diluted plasma sample were mixed with $^{125}$I-insulin and anti-insulin antibody in 5 mL, 75×12 mm PP SARSTEDT tubes (catalog no. 55.526). The tubes were vortexed, covered, and incubated for 20 h at RT. After the incubation, 1 mL of 4° C. precipitating reagent was added and the tubes were vortexed and incubated for 30 min at 4° C. All tubes were centrifuged for 30 min (3000 rpm at 4° C.), the supernatants were decanted, and the pellets were counted on a PerkinElmer WIZARD2 Automatic Gamma Counter (model no. 2470; PerkinElmer; Waltham, Mass.). Insulin concentrations were calculated by comparing to a standard curve generated using known quantities of insulin.

Measurement of Plasma Triglyceride Concentrations

Plasma triglyceride (TG) concentrations were measured using the Triglyceride (GPO) Liquid Reagent set (Pointe Scientific; Canton, Mich.; cat no. T7532-500). Pre-warmed assay reagent (300 μL, 37° C.) was added to 5 μL of plasma in a clear, flat-bottom, 96-well plate (Thermo Fisher Scientific; Tewksbury, Mass.; cat no. 269620). The plate was mixed on a plate shaker for 30 s and then placed in an incubator at 37° C. for 5 min. Following a 20 s mix, absorbance was measured at 500 nm with a SPECTRAmax PLUS plate reader. TG concentrations were calculated by comparing to a calibration curve generated using known quantities of a TG standard (Pointe Scientific; cat no. T7531-STD).

Measurement of Plasma Cholesterol Concentrations:

Plasma total cholesterol (TC) was quantified using the Cholesterol (Liquid) Reagent Set, (Pointe Scientific; cat no. C7510-500). Pre-warmed assay reagent (200 μL, 37° C.) was added to 10 μL of plasma in a clear, flat-bottom, 96-well assay plate (Thermo Fisher Scientific; cat no. 269620). The plate was mixed on a plate shaker for 30 s and then incubated at 37° C. for 5 min Following a 20 s mix, absorbance was measured at 500 nm in a SPECTRAmax PLUS plate reader. Cholesterol concentrations were calculated by comparing to a calibration curve generated using known quantities of a cholesterol standard (Stanbio Laboratory; Boerne, Tex.; cat no. 1012-030).

Measurement of Plasma High-Density Lipoprotein Cholesterol Concentrations

For determination of high-density lipoprotein (HDL) cholesterol concentrations, 50 μL of plasma sample was combined with 50 μL of Cholesterol Precipitating Reagent (Wako Chemicals; Richmond, Va.; cat no. 431-52501) in a 0.5 mL microcentrifuge tube and vortexed briefly. The tube was placed at room temperature for 10 min and then centrifuged at 2000×g for 10 min at 4° C. Following centrifugation, approximately half of the supernatant (containing the HDL cholesterol portion of the original plasma sample) was removed and 10 μL was used for the cholesterol assay described above.

Measurement of Plasma β-Hydroxybutyrate Concentrations

Plasma β-hydroxybutyrate (β-HB) concentrations were measured using the β-Hydroxybutyrate LiquiColor Test kit (Stanbio Laboratory; cat no. 2440-058). Assay reagent R1 (215 μL pre-warmed to 37° C.) was added to 20 μL of quality control or plasma sample in a clear, flat-bottom, 96-well plate (Thermo Fisher Scientific; cat no. 269620). The plate was mixed on a plate shaker for 30 s and then placed in an incubator at 37° C. for 5 min. Pre-read absorbance was measured at 505 nm in a SPECTRAmax PLUS plate reader. Assay reagent R2 (35 μL pre-warmed to 37° C.) was added to each well, and the plate was again mixed on a plate shaker for 30 s and incubated at 37° C. for 5 min. Following a 20 s mix, final absorbance was measured at 505 nm from which the pre-read value was subtracted. β-HB concentrations were calculated by comparing to a calibration curve generated using known quantities of a β-HB calibrator (Wako Diagnostics; Richmond, Va.; cat no. 412-73791).

Statistical Analyses

Statistical analyses were performed using GraphPad Prism (Version 6.05; GraphPad Software; La Jolla, Calif.). Food intake data for each animal were normalized as a percent of baseline (calculated as the mean of days −6 to 0) and then group means±standard errors of the mean (SEM) were calculated; each day was compared to day 0 by nonparametric Friedman's test with Dunn's multiple comparisons post-test. Body weights are presented as group means±standard errors of the mean (SEM) calculated as percent of baseline (calculated as the mean of days −7, −5, −3, and 0). Raw body weight and plasma biomarker data were also analyzed by nonparametric Friedman's test with Dunn's multiple comparisons post-test. P<0.05 was considered significant.

Results

Before dosing NOV002, animals were screened for pre-existing anti-drug antibodies (ADA) and found that all monkeys were ADA negative. To determine whether NOV002 could reduce food intake and body weights of obese monkeys (mean baseline body weight=12.4±0.9 kg, which was calculated as the mean of days −6 to 0), each animal received two subcutaneous doses of 1 mg/kg NOV002 one week apart on study days 0 and 7. NOV002 significantly decreased food intake compared to baseline, with the mean peak reduction to ~44% of baseline occurring on day 32 post-dose. Food intake was significantly lower on days 18, 22, 24, 25, 26, 29, and 32 post-dose vs day 0 by Friedman test with Dunn's post-test). All five monkeys exhibited clear decreases in food consumption, but the magnitude and duration of the reduced food intake were variable across the group.

Body weights was also measured throughout the study and a peak mean body weight change of −8.9% on day 67 post-dose was observed. Body weight was significantly lower on days 37 through 70 post-dose vs day 0 by Friedman test with Dunn's post-test. Similar to the food intake effects, variable extent and duration of body weight changes were observed following treatment with 1 mg/kg NOV002 that were consistent with the food intake responses of the individual animals: the monkeys with the greatest reductions in food intake lost the most body weight during the study.

In addition to evaluating the effects of NOV002 on food intake and body weights, the effects on plasma biomarkers of lipid and carbohydrate metabolism were tested. NOV002 decreased both plasma TG and TC concentrations, with a significant difference on day 32 post-dose versus baseline (mean of days −7, −3, and 0; Friedman test with Dunn's post-test). Table 3 summarizes all plasma biomarker changes on day 32 versus baseline. Compared to baseline, NOV002 did not significantly change plasma high-density lipoprotein (HDL) cholesterol, β-hydroxybutyrate (β-HB), glucose, or insulin concentrations at any timepoint during the study, but NOV002 did significantly increase plasma adiponectin levels on day 35 post-dose.

TABLE 3

NOV002 improved plasma biomarker levels

| Biomarker | Baseline[1] | Day 32 | Mean %Δ[2] |
|---|---|---|---|
| TG (mg/dL) | 227 ± 89 | 93 ± 35* | −53 ± 6 |
| TC (mg/dL) | 126 ± 11 | 96 ± 6* | −22 ± 5 |
| HDL (mg/dL) | 53 ± 9 | 53 ± 5 | 6 ± 12 |
| β-HB (μM) | 53 ± 5 | 115 ± 31 | 137 ± 77 |
| Glucose (mg/dL) | 80 ± 3 | 76 ± 7 | −10 ± 9 |
| Insulin (μU/mL) | 271 ± 57 | 124 ± 12 | −40 ± 17 |
| Adiponectin (μg/mL)[3] | 2.9 ± 0.6 | 6.0 ± 1.8* | 94 ± 22 |

Values represent group means ± SEM.
[1]Baseline values reflect the mean of days −7, −3, and 0.
[2]Percent change was calculated for each individual and then averaged for group mean ± SEM.
[3]Adiponectin levels were measured only in a subset of samples, so data are from study days 0 and 35.
*$P < 0.05$ vs baseline by nonparametric Friedman test with Dunn's post-test.

ADA formation were also tested at various timepoints (e.g., days 1, 2, 3, 4, 7 (prior to dosing and 6 h post-dose), twice weekly from days 11 through 81, and then once weekly thereafter) throughout the study. None of the monkeys displayed NOV002 ADA in the pre-screen, but three animals developed ADA to NOV002 during the study. NOV002 PK profiles did not appear to be different between ADA positive and ADA negative animals.

NOV002 effectively lowered food intake and body weight in obese, cynomolgus monkeys. In animals treated with two subcutaneous doses of 1 mg/kg NOV002, the following were observed: 8.9% peak body weight reduction on day 67 post-dose, although the reductions in food intake and body weight varied between individual animals. The body weight loss was accompanied by reduced plasma TG and TC concentrations, showing beneficial effects of NOV002 on plasma lipid profiles. These data indicate that NOV002 is effective in reducing food intake, body weight, and plasma TG and TC concentrations; suggesting that NOV002, as well as its variants such as NOV004, other anti-β-klotho antibodies comprising CDRs of NOV002 or NOV004, and other anti-β-klotho antibodies which bind to the same epitope as NOV002 (e.g., antibodies binding to one or more of the protected peptides set forth in Table 2) or which competes with NOV002, would be an effective new therapy for metabolic disorders, such as obesity.

Incorporation by Reference

All references cited herein, including patents, patent applications, papers, text books, and the like, and the references cited therein, to the extent that they are not already, are hereby incorporated herein by reference in their entirety.

Equivalents

The foregoing written specification is considered to be sufficient to enable one skilled in the art to practice the invention. The foregoing description and examples detail certain preferred embodiments of the invention and describe the best mode contemplated by the inventors. It will be appreciated, however, that no matter how detailed the foregoing may appear in text, the invention may be practiced in many ways and the invention should be construed in accordance with the appended claims and any equivalents thereof.

The invention claimed is:

1. An isolated antibody or antigen-binding fragment thereof that specifically binds to the β-klotho sequence (SEQ ID NO: 262), and said antibody or antigen-binding fragment thereof comprises one of:
   (i) a heavy chain variable region comprising three heavy chain CDRs, wherein the three heavy chain CDRs comprise SEQ ID NOS: 23, 24, and 25, and a light chain variable region comprising three light chain CDRs, wherein the three light chain CDRs comprise SEQ ID NOS: 33, 34, and 35;
   (ii) a heavy chain variable region comprising three heavy chain CDRs, wherein the three heavy chain CDRs comprise SEQ ID NOS: 26, 27, and 28, and a light chain variable region comprising three light chain CDRs, wherein the three light chain CDRs comprise SEQ ID NOS: 36, 37, and 38;
   (iii) a heavy chain variable region comprising three heavy chain CDRs, wherein the three heavy chain CDRs comprise SEQ ID NOS: 268, 24, and 25, and a light chain variable region comprising three light chain CDRs, wherein the three light chain CDRs comprise SEQ ID NOS: 33, 34, and 35; and
   (iv) a heavy chain variable region comprising three heavy chain CDRs, wherein the three heavy chain CDRs comprise SEQ ID NOS: 269, 270, and 271, and a light chain variable region comprising three light chain CDRs, wherein the three light chain CDRs comprise SEQ ID NOS: 272, 273, and 35.

2. The isolated antibody or antigen-binding fragment thereof of claim 1, wherein the antibody or antigen-binding fragment thereof comprises a variable heavy chain sequence (VH) comprising the amino acid sequence of SEQ ID NO: 29 or an amino acid sequence with at least 80%, 90%, 95%, or 97% identity thereof; and a variable light chain sequence (VL) comprising the amino acid sequence of SEQ ID NO: 39 or an amino acid sequence with at least 80%, 90%, 95%, or 97% identity thereof.

3. The isolated antibody or antigen-binding fragment thereof of claim 1, wherein the antibody or antigen-binding fragment thereof comprises a variable heavy chain sequence (VH) comprising the amino acid sequence of SEQ ID NO: 29 and a variable light chain sequence (VL) comprising the amino acid sequence of SEQ ID NO: 39.

4. A method of reducing body weight comprising administering to a human subject in need thereof a pharmaceutical composition comprising an antibody or antigen-binding fragment according to claim 3 in an amount effective to reduce body weight of the human subject.

5. A method of reducing appetite or food intake comprising administering to a human subject in need thereof a pharmaceutical composition comprising an antibody or antigen-binding fragment according to claim 3 in an amount effective to reduce appetite or food intake in the human subject.

6. A method of reducing plasma triglyceride (TG) concentrations or plasma total cholesterol (TC) concentrations in a human subject, comprising administering to the human subject in need thereof a pharmaceutical composition comprising an antibody or antigen-binding fragment according to claim 3 in an amount effective to reduce the TG concentrations or the TC concentrations in the human subject.

7. The isolated antibody or antigen-binding fragment thereof of claim 1, wherein the antibody or antigen-binding fragment thereof comprises a heavy chain comprising the amino acid sequence of SEQ ID NO: 31 or SEQ ID NO: 71 and a light chain comprising the amino acid sequence of SEQ ID NO: 41.

8. A pharmaceutical composition comprising an antibody or antigen-binding fragment thereof of claim 1 and a pharmaceutically acceptable carrier.

* * * * *

UNITED STATES PATENT AND TRADEMARK OFFICE
CERTIFICATE OF CORRECTION

| | | |
|---|---|---|
| PATENT NO. | : 11,236,159 B2 | |
| APPLICATION NO. | : 15/749775 | |
| DATED | : February 1, 2022 | |
| INVENTOR(S) | : Boettcher et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 412 days.

Signed and Sealed this
Thirty-first Day of January, 2023

Katherine Kelly Vidal
*Director of the United States Patent and Trademark Office*

SEQUENCE LISTING

<160> NUMBER OF SEQ ID NOS: 274

<210> SEQ ID NO 1
<211> LENGTH: 209
<212> TYPE: PRT
<213> ORGANISM: Homo sapiens

<400> SEQUENCE: 1

```
Met Asp Ser Asp Glu Thr Gly Phe Glu His Ser Gly Leu Trp Val Ser
1               5                   10                  15

Val Leu Ala Gly Leu Leu Leu Gly Ala Cys Gln Ala His Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Gln Thr Glu Ala His Leu Glu Ile Arg
    50                  55                  60

Glu Asp Gly Thr Val Gly Gly Ala Ala Asp Gln Ser Pro Glu Ser Leu
65                  70                  75                  80

Leu Gln Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
            100                 105                 110
```

```
Ser Leu His Phe Asp Pro Glu Ala Cys Ser Phe Arg Glu Leu Leu Leu
        115                 120                 125

Glu Asp Gly Tyr Asn Val Tyr Gln Ser Glu Ala His Gly Leu Pro Leu
    130                 135                 140

His Leu Pro Gly Asn Lys Ser Pro His Arg Asp Pro Ala Pro Arg Gly
145                 150                 155                 160

Pro Ala Arg Phe Leu Pro Leu Pro Gly Leu Pro Pro Ala Leu Pro Glu
                165                 170                 175

Pro Pro Gly Ile Leu Ala Pro Gln Pro Pro Asp Val Gly Ser Ser Asp
            180                 185                 190

Pro Leu Ser Met Val Gly Pro Ser Gln Gly Arg Ser Pro Ser Tyr Ala
        195                 200                 205

Ser

<210> SEQ ID NO 2
<211> LENGTH: 938
<212> TYPE: DNA
<213> ORGANISM: Homo sapiens

<400> SEQUENCE: 2
ctgtcagctg aggatccagc cgaaagagga gccaggcact caggccacct gagtctactc      60
acctggacaa ctggaatctg gcaccaattc taaaccactc agcttctccg agctcacacc     120
ccggagatca cctgaggacc cgagccattg atggactcgg acgagaccgg gttcgagcac     180
tcaggactgt gggtttctgt gctggctggt cttctgctgg agcctgcca ggcacacccc      240 atccctgact ccagtcctct cctgcaattc ggggggcaag tccggcagcg gtacctctac     300
acagatgatg cccagcagac agaagcccac tggagatca gggaggatgg gacggtgggg      360
ggcgctgctg accagagccc cgaaagtctc ctgcagctga aagccttgaa gccgggagtt     420
attcaaatct tgggagtcaa gacatccagg ttcctgtgcc agcggccaga tggggccctg     480
tatggatcgc tccactttga ccctgaggcc tgcagcttcc gggagctgct tcttgaggac     540
ggatacaatg tttaccagtc gaagcccac ggcctcccgc tgcacctgcc agggaacaag      600
tccccacacc gggaccctgc accccgagga ccagctcgct tcctgccact accaggcctg     660 cccccgcac tcccggagcc acccggaatc ctggcccccc agccccccga tgtgggctcc      720
tcggaccctc tgagcatggt gggaccttcc cagggccgaa gccccagcta cgcttcctga     780
agccagaggc tgtttactat gacatctcct ctttatttat taggttattt atcttattta     840
tttttttatt tttcttactt gagataataa agagttccag aggagaaaaa aaaaaaaaa     900 aaaaaaaaa aaaaaaaaa aaaaaaaaa aaaaaaa                               938

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Asp Tyr Tyr Ile Asn
1               5

<210> SEQ ID NO 4
<211> LENGTH: 17
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 4

Arg Ile His Pro Gly Ser Gly Asn Thr Tyr Tyr Asn Glu Lys Phe Gln
1               5                   10                  15

Gly

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Leu Leu Leu Arg Ser Tyr Gly Met Asp Asp
1               5                   10

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Tyr Thr Phe Thr Asp Tyr
1               5

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

His Pro Gly Ser Gly Asn
1               5

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Leu Leu Leu Arg Ser Tyr Gly Met Asp Asp
1               5                   10

<210> SEQ ID NO 9
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Gln Val Gln Leu Val Gln Ser Gly Ala Glu Val Lys Lys Pro Gly Ser
```

```
  1               5                  10                 15
Ser Val Lys Val Ser Cys Lys Ala Ser Gly Tyr Thr Phe Thr Asp Tyr
            20                 25                 30

Tyr Ile Asn Trp Val Arg Gln Ala Pro Gly Gln Gly Leu Glu Trp Met
            35                 40                 45

Gly Arg Ile His Pro Gly Ser Gly Asn Thr Tyr Tyr Asn Glu Lys Phe
            50                 55                 60

Gln Gly Arg Val Thr Leu Thr Ala Asp Lys Ser Thr Ser Thr Ala Tyr
 65                 70                 75                 80

Met Glu Leu Ser Ser Leu Arg Ser Glu Asp Thr Ala Val Tyr Tyr Cys
            85                 90                 95

Ala Ile Leu Leu Leu Arg Ser Tyr Gly Met Asp Asp Trp Gly Gln Gly
            100                105                110

Thr Thr Val Thr Val Ser Ser
            115
```

<210> SEQ ID NO 10
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10

```
caggtgcagc tggtgcagtc tggcgccgaa gtgaagaaac ccggcagcag cgtgaaggtg     60
tcctgcaagg ccagcggcta cacctttacc gactactaca tcaactgggt gcgccaggcc    120
cctggacagg gcctggaatg gatgggcaga atccaccccg gctccggcaa cacctactac    180
aacgagaagt tccagggcag agtgaccctg accgccgaca agagcaccag caccgcctac    240
atggaactga gcagcctgcg gagcgaggac accgccgtgt actactgtgc catcctgctg    300
ctgcggagct acggcatgga tgattggggc cagggcacca ccgtgaccgt cagctca      357
```

<210> SEQ ID NO 11
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

```
Gln Val Gln Leu Val Gln Ser Gly Ala Glu Val Lys Lys Pro Gly Ser
 1               5                  10                 15

Ser Val Lys Val Ser Cys Lys Ala Ser Gly Tyr Thr Phe Thr Asp Tyr
            20                 25                 30

Tyr Ile Asn Trp Val Arg Gln Ala Pro Gly Gln Gly Leu Glu Trp Met
            35                 40                 45

Gly Arg Ile His Pro Gly Ser Gly Asn Thr Tyr Tyr Asn Glu Lys Phe
            50                 55                 60

Gln Gly Arg Val Thr Leu Thr Ala Asp Lys Ser Thr Ser Thr Ala Tyr
 65                 70                 75                 80

Met Glu Leu Ser Ser Leu Arg Ser Glu Asp Thr Ala Val Tyr Tyr Cys
            85                 90                 95

Ala Ile Leu Leu Leu Arg Ser Tyr Gly Met Asp Asp Trp Gly Gln Gly
            100                105                110

Thr Thr Val Thr Val Ser Ser Ala Ser Thr Lys Gly Pro Ser Val Phe
```

```
        115                 120                 125
Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 12
<211> LENGTH: 1347
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
caggtgcagc tggtgcagtc tggcgccgaa gtgaagaaac ccggcagcag cgtgaaggtg      60
tcctgcaagg ccagcggcta caccttaccc gactactaca tcaactgggt gcgccaggcc    120
```

```
cctggacagg gcctggaatg gatgggcaga atccaccccg gctccggcaa cacctactac    180
aacgagaagt tccagggcag agtgaccctg accgccgaca gagcaccag caccgcctac    240 atggaactga gcagcctgcg gagcgaggac accgccgtgt actactgtgc catcctgctg    300
ctgcggagct acggcatgga tgattggggc cagggcacca ccgtgaccgt cagctcagct    360
agcaccaagg gcccagcgt gttccccctg gccccagca gcaagagcac cagcggcggc      420
acagccgccc tgggctgcct ggtgaaggac tacttccccg agcccgtgac cgtgtcctgg    480
aacagcggag ccctgacctc cggcgtgcac accttccccg ccgtgctgca gagcagcggc    540
ctgtacagcc tgtccagcgt ggtgacagtg cccagcagca gcctgggcac ccagacctac    600
atctgcaacg tgaaccacaa gcccagcaac accaaggtgg acaagagagt ggagcccaag    660
agctgcgaca gaacccacac ctgcccccc tgcccagccc cagaggcagc gggcggaccc      720
tccgtgttcc tgttcccccc caagcccaag gacaccctga tgatcagcag gaccccgag    780 gtgacctgcg tggtggtgga cgtgagccac gaggacccag aggtgaagtt caactggtac    840
gtggacggcg tggaggtgca acgccaag accaagccca gagaggagca gtacaacagc      900
acctacaggg tggtgtccgt gctgaccgtg ctgcaccagg actggctgaa cggcaaggaa    960
tacaagtgca aggtctccaa caaggccctg ccagccccca tcgaaaagac catcagcaag    1020
gccaagggcc agccacggga gccccaggtg tacaccctgc cccctcccg ggaggagatg      1080 accaagaacc aggtgtccct gacctgtctg gtgaagggct tctacccag cgacatcgcc     1140 gtggagtggg agagcaacgg ccagcccgag aacaactaca agaccacccc cccagtgctg    1200
gacagcgacg gcagcttctt cctgtacagc aagctgaccg tggacaagtc caggtggcag    1260
cagggcaacg tgttcagctg cagcgtgatg cacgaggccc tgcacaacca ctacacccag    1320
aagagcctga gcctgtcccc cggcaag                                       1347
```

<210> SEQ ID NO 13
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Lys Ser Ser Gln Ser Ile Val His Ser Ser Gly Asn Thr Tyr Leu Glu
1               5                   10                  15

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Lys Val Ser Asn Arg Phe Ser
1               5

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 15

Phe Gln Gly Ser His Ile Pro Tyr Thr
1               5

<210> SEQ ID NO 16
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ser Gln Ser Ile Val His Ser Ser Gly Asn Thr Tyr
1               5                   10

<210> SEQ ID NO 17
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Lys Val Ser
1

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gly Ser His Ile Pro Tyr
1               5

<210> SEQ ID NO 19
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Asp Val Val Met Thr Gln Thr Pro Leu Ser Leu Ser Val Thr Pro Gly
1               5                   10                  15

Gln Pro Ala Ser Ile Ser Cys Lys Ser Ser Gln Ser Ile Val His Ser
            20                  25                  30

Ser Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Ile Pro Tyr Thr Phe Gly Gln Gly Thr Lys Leu Glu Ile Lys
            100                 105                 110
```

<210> SEQ ID NO 20
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20
gacgtggtga tgacccagac cccsctgagc ctgagcgtga cacctggaca gcctgccagc    60
atctcctgca agagcagcca gagcatcgtg cacagcagcg gcaacaccta cctggaatgg   120
tatctgcaga agcccggcca gagccccag ctgctgatct acaaggtgtc caaccggttc   180
agcggcgtgc ccgacagatt ttctggcagc ggctccggca ccgacttcac cctgaagatc   240
tcccgggtgg aagccgagga cgtgggcgtg tactactgtt ttcaaggctc ccacatcccc   300
tacaccttcg gccagggcac caagctggaa atcaag                              336

<210> SEQ ID NO 21
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Asp Val Val Met Thr Gln Thr Pro Leu Ser Leu Ser Val Thr Pro Gly
1               5                   10                  15

Gln Pro Ala Ser Ile Ser Cys Lys Ser Ser Gln Ser Ile Val His Ser
            20                  25                  30

Ser Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Ile Pro Tyr Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 22
<211> LENGTH: 657

<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22
gacgtggtga tgacccagac cccctgagc ctgagcgtga cacctggaca gcctgccagc    60
atctcctgca agagcagcca gagcatcgtg cacagcagcg gcaacaccta cctggaatgg   120
tatctgcaga agcccggcca gagcccccag ctgctgatct acaaggtgtc caaccggttc   180
agcggcgtgc ccgacagatt ttctggcagc ggctccggca ccgacttcac cctgaagatc   240
tcccgggtgg aagccgagga cgtgggcgtg tactactgtt ttcaaggctc ccacatcccc   300
tacaccttcg gccagggcac caagctggaa atcaagcgta cggtggccgc tcccagcgtg   360
ttcatcttcc ccccagcga cgagcagctg aagagcggca ccgccagcgt ggtgtgcctg   420
ctgaacaact tctaccccg ggaggccaag gtgcagtgga aggtggacaa cgccctgcag   480
agcggcaaca gccaggagag cgtcaccgag caggacagca aggactccac ctacagcctg   540
agcagcaccc tgaccctgag caaggccgac tacgagaagc ataaggtgta cgcctgcgag   600
gtgacccacc agggcctgtc cagccccgtg accaagagct tcaacagggg cgagtgc     657

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ser Gly Tyr Thr Trp His
1               5

<210> SEQ ID NO 24
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Tyr Ile His Tyr Ser Val Tyr Thr Asn Tyr Asn Pro Ser Val Lys Gly
1               5                   10                  15

<210> SEQ ID NO 25
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Arg Thr Thr Ser Leu Glu Arg Tyr Phe Asp Val
1               5                   10

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 26

Gly Tyr Ser Ile Thr Ser Gly Tyr
1               5

<210> SEQ ID NO 27
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

His Tyr Ser Val Tyr
1               5

<210> SEQ ID NO 28
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Arg Thr Thr Ser Leu Glu Arg Tyr Phe Asp Val
1               5                   10

<210> SEQ ID NO 29
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Glu Val Gln Leu Val Glu Ser Gly Gly Gly Leu Val Lys Pro Gly Gly
1               5                   10                  15

Ser Leu Arg Leu Ser Cys Ala Val Ser Gly Tyr Ser Ile Thr Ser Gly
            20                  25                  30

Tyr Thr Trp His Trp Val Arg Gln Ala Pro Gly Lys Gly Leu Glu Trp
        35                  40                  45

Leu Ser Tyr Ile His Tyr Ser Val Tyr Thr Asn Tyr Asn Pro Ser Val
    50                  55                  60

Lys Gly Arg Phe Thr Ile Ser Arg Asp Thr Ala Lys Asn Ser Phe Tyr
65                  70                  75                  80

Leu Gln Met Asn Ser Leu Arg Ala Glu Asp Thr Ala Val Tyr Tyr Cys
                85                  90                  95

Ala Arg Arg Thr Thr Ser Leu Glu Arg Tyr Phe Asp Val Trp Gly Gln
            100                 105                 110

Gly Thr Leu Val Thr Val Ser Ser
        115                 120

<210> SEQ ID NO 30
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

```
<400> SEQUENCE: 30
gaggtgcagc tggtggaatc tggcggcgga ctcgtgaagc ctggcggctc tctgagactg      60
agctgtgccg tgtccggcta cagcatcacc agcggctaca cctggcattg ggtgcgccag     120
gcccctggca aggactgga atggctgtcc tacatccact acagcgtgta caccaactac     180
aaccccagcg tgaagggccg gttcaccatc agcagagaca ccgccaagaa cagcttctac     240
ctgcaaatga acagcctgcg ggccgaggac accgccgtgt actactgtgc agacggacc      300 accagcctgg aacggtactt cgacgtgtgg ggccagggca cactcgtgac cgtcagctca     360

<210> SEQ ID NO 31
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31
```

Glu Val Gln Leu Val Glu Ser Gly Gly Gly Leu Val Lys Pro Gly Gly
1               5                   10                  15

Ser Leu Arg Leu Ser Cys Ala Val Ser Gly Tyr Ser Ile Thr Ser Gly
            20                  25                  30

Tyr Thr Trp His Trp Val Arg Gln Ala Pro Gly Lys Gly Leu Glu Trp
        35                  40                  45

Leu Ser Tyr Ile His Tyr Ser Val Tyr Thr Asn Tyr Asn Pro Ser Val
    50                  55                  60

Lys Gly Arg Phe Thr Ile Ser Arg Asp Thr Ala Lys Asn Ser Phe Tyr
65                  70                  75                  80

Leu Gln Met Asn Ser Leu Arg Ala Glu Asp Thr Ala Val Tyr Tyr Cys
                85                  90                  95

Ala Arg Arg Thr Thr Ser Leu Glu Arg Tyr Phe Asp Val Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

```
Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly Lys
    450

<210> SEQ ID NO 32
<211> LENGTH: 1350
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32
gaggtgcagc tggtggaatc tggcggcgga ctcgtgaagc ctggcggctc tctgagactg      60
agctgtgccg tgtccggcta cagcatcacc agcggctaca cctggcattg ggtgcgccag     120
gcccctggca aggactgga atggctgtcc tacatccact acagcgtgta caccaactac     180
aaccccagcg tgaagggccg gttcaccatc agcagagaca ccgccaagaa cagcttctac     240
ctgcaaatga acagcctgcg ggccgaggac accgccgtgt actactgtgc agacggacc      300 accagcctgg aacggtactt cgacgtgtgg ggccagggca cactcgtgac cgtcagctca     360
gctagcacca agggccccag cgtgttcccc ctggccccca gcagcaagag caccagcggc     420
ggcacagccg ccctgggctg cctggtgaag gactacttcc ccgagcccgt gaccgtgtcc     480
tggaacagcg gagccctgac ctccggcgtg cacaccttcc ccgccgtgct gcagagcagc     540
ggcctgtaca gcctgtccag cgtggtgaca gtgcccagca gcagcctggg cacccagacc     600
tacatctgca acgtgaacca caagcccagc aacaccaagg tggacaagag agtggagccc     660
aagagctgcg acaagaccca cacctgcccc cctgcccag cccagaggc agcgggcgga     720 ccctccgtgt tcctgttccc ccccaagccc aaggacaccc tgatgatcag caggaccccc     780
gaggtgacct gcgtggtggt ggacgtgagc cacgaggacc cagaggtgaa gttcaactgg     840
tacgtggacg gcgtggaggt gcacaacgcc aagaccaagc ccagagagga gcagtacaac     900
agcacctaca gggtggtgtc cgtgctgacc gtgctgcacc aggactggct gaacggcaag     960
gaatacaagt gcaaggtctc caacaaggcc ctgccagccc catcgaaaa gaccatcagc    1020 aaggccaagg gccagccacg ggagcccag gtgtacaccc tgcccccctc ccggaggag    1080
```

```
atgaccaaga accaggtgtc cctgacctgt ctggtgaagg gcttctaccc cagcgacatc   1140
gccgtggagt gggagagcaa cggccagccc gagaacaact acaagaccac ccccccagtg   1200
ctggacagcg acggcagctt cttcctgtac agcaagctga ccgtggacaa gtccaggtgg   1260
cagcagggca acgtgttcag ctgcagcgtg atgcacgagg ccctgcacaa ccactacacc   1320
cagaagagcc tgagcctgtc ccccggcaag                                    1350
```

<210> SEQ ID NO 33
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gln Ala Ser Gln Asp Ile Ser Asn Tyr Leu Asn
1               5                   10

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Tyr Thr Ser Arg Leu Gln Ser
1               5

<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gln Gln Gly Asn Thr Leu Pro Tyr Thr
1               5

<210> SEQ ID NO 36
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Ser Gln Asp Ile Ser Asn Tyr
1               5

<210> SEQ ID NO 37
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Tyr Thr Ser
1

<210> SEQ ID NO 38
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gly Asn Thr Leu Pro Tyr
1               5

<210> SEQ ID NO 39
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Gln Ser Gly Val Pro Ser Arg Phe Thr Gly
50                  55                  60

Ser Gly Ser Gly Ala Asp Tyr Thr Phe Thr Ile Ser Ser Leu Gln Pro
65                  70                  75                  80

Glu Asp Ile Ala Thr Tyr Phe Cys Gln Gln Gly Asn Thr Leu Pro Tyr
                85                  90                  95

Thr Phe Gly Gln Gly Thr Lys Leu Glu Ile Lys
            100                 105

<210> SEQ ID NO 40
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40
gacatccaga tgacccagag ccccagcagc ctgtctgcca gcgtgggcga cagagtgacc      60
atcacctgtc aggccagcca ggacatcagc aactacctga actggtatca gcagaagccc     120
ggcaaggccc ccaagctgct gatctactac accagcagac tgcagagcgg cgtgcccagc     180
agatttaccg gctctggaag cggagccgac tacaccttca ccatcagctc cctgcagccc     240
gaggatatcg ctacctactt ctgtcagcaa ggcaacaccc tgccttacac cttcggccag     300
ggcaccaagc tggaaatcaa g                                                321

<210> SEQ ID NO 41
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Gln Ser Gly Val Pro Ser Arg Phe Thr Gly
50                  55                  60

Ser Gly Ser Gly Ala Asp Tyr Thr Phe Thr Ile Ser Ser Leu Gln Pro
65                  70                  75                  80

Glu Asp Ile Ala Thr Tyr Phe Cys Gln Gln Gly Asn Thr Leu Pro Tyr
            85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 42
<211> LENGTH: 642
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 42
gacatccaga tgacccagag ccccagcagc ctgtctgcca gcgtgggcga cagagtgacc      60
atcacctgtc aggccagcca ggacatcagc aactacctga actggtatca gcagaagccc     120
ggcaaggccc ccaagctgct gatctactac accagcagac tgcagagcgg cgtgcccagc     180
agatttaccg gctctggaag cggagccgac tacaccttca ccatcagctc cctgcagccc     240
gaggatatcg ctacctactt ctgtcagcaa ggcaacaccc tgccttacac cttcggccag     300
ggcaccaagc tggaaatcaa gcgtacggtg gccgctccca gcgtgttcat cttcccccc      360
agcgacgagc agctgaagag cggcaccgcc agcgtggtgt gcctgctgaa caacttctac     420
ccccgggagg ccaaggtgca gtggaaggtg gacaacgccc tgcagagcgg caacagccag     480
gagagcgtca ccgagcagga cagcaaggac tccacctaca gcctgagcag caccctgacc     540
ctgagcaagg ccgactacga gaagcataag gtgtacgcct gcgaggtgac ccaccagggc     600
ctgtccagcc ccgtgaccaa gagcttcaac agggcgagt gc                         642

```
<210> SEQ ID NO 43
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Asp Tyr Tyr Ile Asn
1               5

<210> SEQ ID NO 44
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Arg Ile His Pro Gly Ser Gly Asn Thr Tyr Tyr Asn Glu Lys Phe Gln
1               5                   10                  15

Gly

<210> SEQ ID NO 45
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Leu Leu Leu Arg Ser Tyr Gly Met Asp Asp
1               5                   10

<210> SEQ ID NO 46
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gly Tyr Thr Phe Thr Asp Tyr
1               5

<210> SEQ ID NO 47
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

His Pro Gly Ser Gly Asn
1               5

<210> SEQ ID NO 48
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 48

Leu Leu Leu Arg Ser Tyr Gly Met Asp Asp
1               5                   10

<210> SEQ ID NO 49
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Tyr Ile Asn Trp Val Arg Gln Ala Pro Gly Gln Gly Leu Glu Trp Met
        35                  40                  45

Gly Arg Ile His Pro Gly Ser Gly Asn Thr Tyr Tyr Asn Glu Lys Phe
    50                  55                  60

Gln Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ile Leu Leu Leu Arg Ser Tyr Gly Met Asp Asp Trp Gly Gln Gly
            100                 105                 110

Thr Thr Val Thr Val Ser Ser
        115

<210> SEQ ID NO 50
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 50
caagtccaac tcgtccagtc cggagccgaa gtgaaaaagc cgggctcatc agtgaaggtg     60
tcctgcaagg cgtcgggcta caccttcacc gactactaca tcaactgggt gcgccaggcc    120
ccgggacagg gtctggaatg gatggggagg attcaccccg gatcgggaaa cacctactac    180
aacgagaagt tccagggcag agtgaccctg actgccgaca gtccacgtc cactgcctac     240 atggaactgt cgtccctgcg gtccgaggat accgccgtgt actattgtgc gatcctgctg    300
ttgcggagct acgggatgga tgactgggga cagggtacca ctgtgactgt gtccagc       357

<210> SEQ ID NO 51
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr

```
            20                  25                  30
Tyr Ile Asn Trp Val Arg Gln Ala Pro Gly Gln Gly Leu Glu Trp Met
            35                  40                  45
Gly Arg Ile His Pro Gly Ser Gly Asn Thr Tyr Tyr Asn Glu Lys Phe
        50                  55                  60
Gln Gly Arg Val Thr Leu Thr Ala Asp Lys Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Ile Leu Leu Leu Arg Ser Tyr Gly Met Asp Asp Trp Gly Gln Gly
            100                 105                 110
Thr Thr Val Thr Val Ser Ser Ala Ser Thr Lys Gly Pro Ser Val Phe
        115                 120                 125
Pro Leu Ala Pro Ser Ser Lys Ser Thr Ser Gly Gly Thr Ala Ala Leu
    130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
        195                 200                 205
Ser Asn Thr Lys Val Asp Lys Arg Val Glu Pro Lys Ser Cys Asp Lys
    210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Ala Val Ser His Glu Asp
            260                 265                 270
Pro Glu Val Lys Phe Asn Trp Tyr Val Asp Gly Val Glu Val His Asn
        275                 280                 285
Ala Lys Thr Lys Pro Arg Glu Glu Gln Tyr Asn Ser Thr Tyr Arg Val
    290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Ala Ala Pro Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Arg Glu Glu Met Thr Lys Asn Gln Val Ser Leu Thr
        355                 360                 365
Cys Leu Val Lys Gly Phe Tyr Pro Ser Asp Ile Ala Val Glu Trp Glu
    370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
        435                 440                 445
```

Lys

<210> SEQ ID NO 52
<211> LENGTH: 1347
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 52

```
caagtccaac tcgtccagtc cggagccgaa gtgaaaaagc cgggctcatc agtgaaggtg      60
tcctgcaagg cgtcgggcta caccttcacc gactactaca tcaactgggt gcgccaggcc     120
ccgggacagg gtctggaatg gatggggagg attcaccccg atcgggaaa cacctactac      180
aacgagaagt tccagggcag agtgaccctg actgccgaca gtccacgtc cactgcctac      240
atggaactgt cgtccctgcg gtccgaggat accgccgtgt actattgtgc gatcctgctg     300
ttgcggagct acgggatgga tgactgggga cagggtacca ctgtgactgt gtccagcgct     360
agcaccaagg gcccctccgt gttccctctg gccccttcca gcaagtctac ctccggcggc     420
acagctgctc tgggctgcct ggtcaaggac tacttccctg agcctgtgac agtgtcctgg     480
aactctggcg ccctgacctc tggcgtgcac accttccctg ccgtgctgca gtcctccggc     540
ctgtactccc tgtcctccgt ggtcacagtg ccttcaagca gcctgggcac ccagacctat     600
atctgcaacg tgaaccacaa gccttccaac accaaggtgg acaagcgggt ggagcctaag     660
tcctgcgaca gacccacac ctgtcctccc tgccctgctc ctgaactgct gggcggccct      720
tctgtgttcc tgttccctcc aaagcccaag gacaccctga tgatctcccg gacccctgaa     780
gtgacctgcg tggtggtggc cgtgtcccac gaggatcctg aagtgaagtt caattggtac     840
gtggacggcg tggaggtgca caacgccaag accaagcctc gggaggaaca gtacaactcc     900
acctaccggg tggtgtccgt gctgaccgtg ctgcaccagg actggctgaa cggcaaagag     960
tacaagtgca aagtctccaa caaggccctg ccgccccta tcgaaaagac aatctccaag    1020
gccaagggcc agcctaggga accccaggtg tacaccctgc cacccagccg ggaggaaatg    1080
accaagaacc aggtgtccct gacctgtctg gtcaagggct tctacccttc cgatatcgcc    1140
gtggagtggg agtctaacgg ccagcctgag aacaactaca agaccacccc tcctgtgctg    1200
gactccgacg gctccttctt cctgtactcc aaactgaccg tggacaagtc ccggtggcag    1260
cagggcaacg tgttctcctg ctccgtgatg cacgaggccc tgcacaacca ctacacccag    1320
aagtccctgt ccctgtctcc cggcaag                                         1347
```

<210> SEQ ID NO 53
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 53

Lys Ser Ser Gln Ser Ile Val His Ser Ser Gly Asn Thr Tyr Leu Glu
1               5                   10                  15

<210> SEQ ID NO 54
<211> LENGTH: 7
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 54

Lys Val Ser Asn Arg Phe Ser
1               5

<210> SEQ ID NO 55
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Phe Gln Gly Ser His Ile Pro Tyr Thr
1               5

<210> SEQ ID NO 56
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Ser Gln Ser Ile Val His Ser Ser Gly Asn Thr Tyr
1               5                   10

<210> SEQ ID NO 57
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Lys Val Ser
1

<210> SEQ ID NO 58
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Gly Ser His Ile Pro Tyr
1               5

<210> SEQ ID NO 59
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Asp Val Val Met Thr Gln Thr Pro Leu Ser Leu Ser Val Thr Pro Gly
1               5                   10                  15
```

Gln Pro Ala Ser Ile Ser Cys Lys Ser Ser Gln Ser Ile Val His Ser
                20                  25                  30

Ser Gly Asn Thr Tyr Leu Glu Trp Tyr Leu Gln Lys Pro Gly Gln Ser
            35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Ile Pro Tyr Thr Phe Gly Gln Gly Thr Lys Leu Glu Ile Lys
            100                 105                 110

<210> SEQ ID NO 60
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 60
gatgtcgtga tgacccagac tccgctgtcc ctgtccgtga cccctggaca gcccgcgtct    60
atctcgtgca agagctccca gtccattgtg cattcaagcg ggaacaccta tctggagtgg   120
tacctccaga agcctggcca gagcccacag ctgctgatct acaaagtgtc gaacagattc   180
tccggtgtcc cggaccggtt ctccggctcg ggaagcggca ctgactttac actgaagatc   240
tcacgggtgg aagccgagga cgtgggagtg tactactgtt tccaagggtc ccacattccc   300
tacaccttcg gccaaggaac taagctggaa atcaag                             336

<210> SEQ ID NO 61
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Asp Val Val Met Thr Gln Thr Pro Leu Ser Leu Ser Val Thr Pro Gly
1               5                   10                  15

Gln Pro Ala Ser Ile Ser Cys Lys Ser Ser Gln Ser Ile Val His Ser
                20                  25                  30

Ser Gly Asn Thr Tyr Leu Glu Trp Tyr Leu Gln Lys Pro Gly Gln Ser
            35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Ile Pro Tyr Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

```
Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 62
<211> LENGTH: 657
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 62

```
gatgtcgtga tgacccagac tccgctgtcc ctgtccgtga cccctggaca gcccgcgtct    60
atctcgtgca agagctccca gtccattgtg cattcaagcg ggaacaccta tctggagtgg   120
tacctccaga agcctggcca gagcccacag ctgctgatct acaaagtgtc gaacagattc   180
tccggtgtcc cggaccggtt ctccggctcg ggaagcggca ctgactttac actgaagatc   240
tcacgggtgg aagccgagga cgtgggagtg tactactgtt tccaagggtc ccacattccc   300
tacacccttcg gccaaggaac taagctggaa atcaagcgta cggtggccgc tcccagcgtg   360
ttcatcttcc cccccagcga cgagcagctg aagagcggca ccgccagcgt ggtgtgcctg   420
ctgaacaact tctaccccg ggaggccaag gtgcagtgga aggtggacaa cgccctgcag   480
agcggcaaca gccaggagag cgtcaccgag caggacagca aggactccac ctacagcctg   540
agcagcaccc tgaccctgag caaggccgac tacgagaagc ataaggtgta cgcctgcgag   600
gtgacccacc agggcctgtc cagccccgtg accaagagct caacaggggg cgagtgc     657
```

<210> SEQ ID NO 63
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

```
Ser Gly Tyr Thr Trp His
1               5
```

<210> SEQ ID NO 64
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

```
Tyr Ile His Tyr Ser Val Tyr Thr Asn Tyr Asn Pro Ser Val Lys Gly
1               5                   10                  15
```

<210> SEQ ID NO 65
<211> LENGTH: 11

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Arg Thr Thr Ser Leu Glu Arg Tyr Phe Asp Val
1               5                   10

<210> SEQ ID NO 66
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Gly Tyr Ser Ile Thr Ser Gly Tyr
1               5

<210> SEQ ID NO 67
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

His Tyr Ser Val Tyr
1               5

<210> SEQ ID NO 68
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Arg Thr Thr Ser Leu Glu Arg Tyr Phe Asp Val
1               5                   10

<210> SEQ ID NO 69
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Glu Val Gln Leu Val Glu Ser Gly Gly Gly Leu Val Lys Pro Gly Gly
1               5                   10                  15

Ser Leu Arg Leu Ser Cys Ala Val Ser Gly Tyr Ser Ile Thr Ser Gly
                20                  25                  30

Tyr Thr Trp His Trp Val Arg Gln Ala Pro Gly Lys Gly Leu Glu Trp
            35                  40                  45

Leu Ser Tyr Ile His Tyr Ser Val Tyr Thr Asn Tyr Asn Pro Ser Val
        50                  55                  60

Lys Gly Arg Phe Thr Ile Ser Arg Asp Thr Ala Lys Asn Ser Phe Tyr
65                  70                  75                  80
```

```
Leu Gln Met Asn Ser Leu Arg Ala Glu Asp Thr Ala Val Tyr Tyr Cys
                85                  90                  95

Ala Arg Arg Thr Thr Ser Leu Glu Arg Tyr Phe Asp Val Trp Gly Gln
            100                 105                 110

Gly Thr Leu Val Thr Val Ser Ser
        115                 120

<210> SEQ ID NO 70
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 70
gaagtccaac tcgtcgaatc cggcggcgga ctggtcaagc cgggaggatc gctgagactg      60
tcgtgcgcag tgtcagggta cagcatcacc tccggttaca cctggcactg ggtcagacag     120
gcgccgggaa aaggcctgga atggctgtcc tacattcatt actccgtgta cactaactac     180
aacccctcag tgaaggggcg gttcaccatc tcccgggaca ctgccaagaa tagcttctat     240
ctgcaaatga actccctgcg ggccgaggat accgccgtgt actactgcgc gaggcgcacc     300
acgtccctgg agcgctactt tgacgtgtgg ggccagggta ccctcgtgac tgtgtcctcg     360

<210> SEQ ID NO 71
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Glu Val Gln Leu Val Glu Ser Gly Gly Gly Leu Val Lys Pro Gly Gly
1               5                   10                  15

Ser Leu Arg Leu Ser Cys Ala Val Ser Gly Tyr Ser Ile Thr Ser Gly
            20                  25                  30

Tyr Thr Trp His Trp Val Arg Gln Ala Pro Gly Lys Gly Leu Glu Trp
        35                  40                  45

Leu Ser Tyr Ile His Tyr Ser Val Tyr Thr Asn Tyr Asn Pro Ser Val
    50                  55                  60

Lys Gly Arg Phe Thr Ile Ser Arg Asp Thr Ala Lys Asn Ser Phe Tyr
65                  70                  75                  80

Leu Gln Met Asn Ser Leu Arg Ala Glu Asp Thr Ala Val Tyr Tyr Cys
                85                  90                  95

Ala Arg Arg Thr Thr Ser Leu Glu Arg Tyr Phe Asp Val Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190
```

Ser Ser Ser Leu Gly Thr Gln Thr Tyr Ile Cys Asn Val Asn His Lys
            195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Ala Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Ala Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly Lys
    450

<210> SEQ ID NO 72
<211> LENGTH: 1350
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 72
gaagtccaac tcgtcgaatc cggcggcgga ctggtcaagc cgggaggatc gctgagactg      60
tcgtgcgcag tgtcagggta cagcatcacc tccggttaca cctggcactg ggtcagacag     120
gcgccgggaa aaggcctgga atggctgtcc tacattcatt actccgtgta cactaactac     180
aacccctcag tgaaggggcg gttcaccatc tcccgggaca ctgccaagaa tagcttctat     240
ctgcaaatga actccctgcg gccgaggat accgccgtgt actactgcgc gaggcgcacc     300
acgtccctgg agcgctactt tgacgtgtgg ggccagggta ccctcgtgac tgtgtcctcg     360
gctagcacca agggcccctc cgtgttccct ctggcccctt ccagcaagtc tacctccggc     420
ggcacagctg ctctgggctg cctggtcaag gactacttcc ctgagcctgt gacagtgtcc     480
tggaactctg gcgccctgac ctctggcgtg cacaccttcc ctgccgtgct gcagtcctcc     540

```
ggcctgtact ccctgtcctc cgtggtcaca gtgccttcaa gcagcctggg cacccagacc    600
tatatctgca acgtgaacca caagccttcc aacaccaagg tggacaagcg ggtggagcct    660
aagtcctgcg acaagaccca cacctgtcct ccctgccctg ctcctgaact gctgggcggc    720
ccttctgtgt tcctgttccc tccaaagccc aaggacaccc tgatgatctc ccggacccct    780
gaagtgacct gcgtggtggt ggccgtgtcc cacgaggatc ctgaagtgaa gttcaattgg    840
tacgtggacg gcgtggaggt gcacaacgcc aagaccaagc ctcgggagga acagtacaac    900
tccacctacc gggtggtgtc cgtgctgacc gtgctgcacc aggactggct gaacggcaaa    960
gagtacaagt gcaaagtctc caacaaggcc ctggccgccc ctatcgaaaa gacaatctcc   1020
aaggccaagg gccagcctag ggaaccccag gtgtacaccc tgccacccag ccgggaggaa   1080
atgaccaaga accaggtgtc cctgacctgt ctggtcaagg gcttctaccc ttccgatatc   1140
gccgtggagt gggagtctaa cggccagcct gagaacaact acaagaccac ccctcctgtg   1200
ctggactccg acggctcctt cttcctgtac tccaaactga ccgtggacaa gtcccggtgg   1260
cagcagggca acgtgttctc ctgctccgtg atgcacgagg ccctgcacaa ccactacacc   1320
cagaagtccc tgtccctgtc tcccggcaag                                    1350
```

<210> SEQ ID NO 73
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Gln Ala Ser Gln Asp Ile Ser Asn Tyr Leu Asn
1               5                   10

<210> SEQ ID NO 74
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Tyr Thr Ser Arg Leu Gln Ser
1               5

<210> SEQ ID NO 75
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Gln Gln Gly Asn Thr Leu Pro Tyr Thr
1               5

<210> SEQ ID NO 76
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Ser Gln Asp Ile Ser Asn Tyr
1               5

<210> SEQ ID NO 77
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Tyr Thr Ser
1

<210> SEQ ID NO 78
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Gly Asn Thr Leu Pro Tyr
1               5

<210> SEQ ID NO 79
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Gln Ser Gly Val Pro Ser Arg Phe Thr Gly
    50                  55                  60

Ser Gly Ser Gly Ala Asp Tyr Thr Phe Thr Ile Ser Ser Leu Gln Pro
65                  70                  75                  80

Glu Asp Ile Ala Thr Tyr Phe Cys Gln Gln Gly Asn Thr Leu Pro Tyr
                85                  90                  95

Thr Phe Gly Gln Gly Thr Lys Leu Glu Ile Lys
            100                 105

<210> SEQ ID NO 80
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 80
gatattcaga tgactcagag cccctcctcg ctctccgcct ccgtggggga tcgcgtgaca      60

```
atcacctgtc aagcgtccca ggacatctca aactacctga actggtatca gcagaagcca    120
gggaaggccc cgaagctgct gatctactac acttcgcggc tgcagtccgg cgtgccgtca    180
cggttcactg gctcgggctc cggagcagac tacaccttca ccattagcag cctgcagccc    240
gaggacatcg ctacctactt ttgccaacaa ggaaacaccc tgccttacac cttcggacag    300
ggtactaagc tggaaatcaa a                                              321
```

<210> SEQ ID NO 81
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Gln Ser Gly Val Pro Ser Arg Phe Thr Gly
    50                  55                  60

Ser Gly Ser Gly Ala Asp Tyr Thr Phe Thr Ile Ser Ser Leu Gln Pro
65                  70                  75                  80

Glu Asp Ile Ala Thr Tyr Phe Cys Gln Gln Gly Asn Thr Leu Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 82
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 82

```
gatattcaga tgactcagag cccctcctcg ctctccgcct ccgtggggga tcgcgtgaca    60
atcacctgtc aagcgtccca ggacatctca aactacctga actggtatca gcagaagcca    120
gggaaggccc cgaagctgct gatctactac acttcgcggc tgcagtccgg cgtgccgtca    180
```

```
cggttcactg gctcgggctc cggagcagac tacaccttca ccattagcag cctgcagccc    240
gaggacatcg ctacctactt ttgccaacaa ggaaacaccc tgccttacac cttcggacag    300
ggtactaagc tggaaatcaa acgtacggtg ccgctccca gcgtgttcat cttccccccc     360
agcgacgagc agctgaagag cggcaccgcc agcgtggtgt gcctgctgaa caacttctac    420
ccccgggagg ccaaggtgca gtggaaggtg gacaacgccc tgcagagcgg caacagccag    480
gagagcgtca ccgagcagga cagcaaggac tccacctaca gcctgagcag caccctgacc    540
ctgagcaagg ccgactacga gaagcataag gtgtacgcct gcgaggtgac ccaccagggc    600
ctgtccagcc ccgtgaccaa gagcttcaac aggggcgagt gc                      642
```

<210> SEQ ID NO 83
<211> LENGTH: 181
<212> TYPE: PRT
<213> ORGANISM: Homo sapiens
<400> SEQUENCE: 83

```
His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180
```

<210> SEQ ID NO 84
<211> LENGTH: 546
<212> TYPE: DNA
<213> ORGANISM: Homo sapiens
<400> SEQUENCE: 84

```
caccccatcc ctgactccag tcctctcctg caattcgggg gccaagtccg gcagcggtac    60
ctctacacag atgatgccca gcagacagaa gcccacctgg agatcaggga ggatgggacg    120 gtgggggggcg ctgctgacca gagccccgaa agtctcctgc agctgaaagc cttgaagccg    180
ggagttattc aaatcttggg agtcaagaca tccaggttcc tgtgccagcg gccagatggg    240
gccctgtatg gatcgctcca ctttgaccct gaggcctgca gcttccggga gctgcttctt    300
```

```
gaggacggat acaatgttta ccagtccgaa gcccacggcc tcccgctgca cctgccaggg    360
aacaagtccc cacaccggga ccctgcaccc cgaggaccag ctcgcttcct gccactacca    420
ggcctgcccc ccgcactccc ggagccaccc ggaatcctgg ccccccagcc ccccgatgtg    480
ggctcctcgg accctctgag catggtggga ccttcccagg gccgaagccc cagctacgct    540
tcctga                                                                546
```

```
<210> SEQ ID NO 85
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Phe Ser Gly Asp Gly Arg Ala Ile Trp
1               5

<210> SEQ ID NO 86
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Phe Leu Tyr Asp Thr Phe Pro Lys Asn Phe Phe
1               5                   10

<210> SEQ ID NO 87
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Phe Phe Trp Gly Ile Gly Thr
1               5

<210> SEQ ID NO 88
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Phe Phe Trp Gly Ile Gly Thr Gly Ala Leu
1               5                   10

<210> SEQ ID NO 89
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Gly Ile Gly Thr Gly Ala Leu Gln
1               5
```

<210> SEQ ID NO 90
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Gln Val Glu Gly Ser Trp Lys Lys Asp Gly Lys Gly Pro Ser Ile Trp
1               5                   10                  15

Asp His Phe

<210> SEQ ID NO 91
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Leu Glu Lys Asp Leu Ser Ala
1               5

<210> SEQ ID NO 92
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Leu Glu Lys Asp Leu Ser Ala Leu
1               5

<210> SEQ ID NO 93
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Ser Ala Leu Asp Phe Ile Gly Val Ser Phe Tyr Gln Phe Ser Ile Ser
1               5                   10                  15

Trp Pro Arg Leu Phe Pro Asp Gly Ile Val Thr Val Ala Asn
            20                  25                  30

<210> SEQ ID NO 94
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Ser Ile Ser Trp Pro Arg Leu
1               5

<210> SEQ ID NO 95
<211> LENGTH: 14

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Ser Ile Ser Trp Pro Arg Leu Phe Pro Asp Gly Ile Val Thr
1               5                   10

<210> SEQ ID NO 96
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Phe Pro Asp Gly Ile Val Thr
1               5

<210> SEQ ID NO 97
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Val Ala Asn Ala Lys Gly Leu Gln
1               5

<210> SEQ ID NO 98
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Val Ala Asn Ala Lys Gly Leu Gln Tyr
1               5

<210> SEQ ID NO 99
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Leu Val Leu Arg Asn Ile Glu Pro Ile Val Thr
1               5                   10

<210> SEQ ID NO 100
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Val Leu Arg Asn Ile Glu Pro Ile Val Thr
```

<210> SEQ ID NO 101
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Arg Asn Ile Glu Pro Ile Val Thr
1               5

<210> SEQ ID NO 102
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Arg Asn Ile Glu Pro Ile Val Thr Leu
1               5

<210> SEQ ID NO 103
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Leu Tyr His Trp Asp Leu Pro Leu Ala Leu
1               5                   10

<210> SEQ ID NO 104
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Ile Phe Asn Asp Tyr Ala Thr
1               5

<210> SEQ ID NO 105
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Phe Asn Asp Tyr Ala Thr Tyr Cys
1               5

<210> SEQ ID NO 106
<211> LENGTH: 11
<212> TYPE: PRT
<213> ORGANISM: Artificial Sequence
<220> FEATURE:
<223> OTHER INFORMATION: Description of Artificial Sequence: Synthetic

```
                               peptide

<400> SEQUENCE: 106

Cys Phe Gln Met Phe Gly Asp Arg Val Lys Tyr
1               5                   10

<210> SEQ ID NO 107
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Phe Gln Met Phe Gly Asp Arg Val Lys
1               5

<210> SEQ ID NO 108
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Phe Gln Met Phe Gly Asp Arg Val Lys Tyr
1               5                   10

<210> SEQ ID NO 109
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Val Ala Trp His Gly Tyr Gly Thr Gly Met His Ala Pro Gly Glu Lys
1               5                   10                  15

Gly Asn Leu

<210> SEQ ID NO 110
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Ala Trp His Gly Tyr Gly Thr Gly Met His Ala Pro Gly Glu Lys Gly
1               5                   10                  15

Asn Leu

<210> SEQ ID NO 111
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Trp His Gly Tyr Gly Thr Gly Met His Ala Pro Gly Glu Lys Gly Asn
```

-continued

```
1               5                   10                  15
Leu

<210> SEQ ID NO 112
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Trp His Gly Tyr Gly Thr Gly Met His Ala Pro Gly Glu Lys Gly Asn
1               5                   10                  15

Leu Ala Ala

<210> SEQ ID NO 113
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

His Gly Tyr Gly Thr Gly Met His Ala Pro Gly Glu Lys Gly Asn Leu
1               5                   10                  15

<210> SEQ ID NO 114
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Tyr Thr Val Gly His Asn Leu Ile Lys Ala
1               5                   10

<210> SEQ ID NO 115
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Tyr Thr Val Gly His Asn Leu Ile Lys Ala His Ser Lys Val Trp His
1               5                   10                  15

Asn Tyr Asn Thr His Phe Arg Pro His Gln Lys Gly Trp
            20                  25

<210> SEQ ID NO 116
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

Tyr Thr Val Gly His Asn Leu Ile Lys Ala His Ser Lys Val Trp His
1               5                   10                  15
```

```
Asn Tyr Asn Thr His Phe Arg Pro His Gln Lys Gly Trp Leu
            20                  25                  30
```

<210> SEQ ID NO 117
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

```
Val Gly His Asn Leu Ile Lys Ala His Ser Lys Val Trp His Asn Tyr
1               5                   10                  15

Asn Thr His Phe Arg Pro His Gln Lys Gly Trp Leu
            20                  25
```

<210> SEQ ID NO 118
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

```
Gly His Asn Leu Ile Lys Ala His Ser Lys Val Trp His Asn Tyr Asn
1               5                   10                  15

Thr His Phe Arg Pro His Gln Lys Gly Trp Leu
            20                  25
```

<210> SEQ ID NO 119
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

```
Leu Ile Lys Ala His Ser Lys Val Trp His Asn Tyr Asn Thr His Phe
1               5                   10                  15

Arg Pro His Gln Lys Gly Trp Leu
            20
```

<210> SEQ ID NO 120
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

```
Ser Ile Thr Leu Gly Ser His
1               5
```

<210> SEQ ID NO 121
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

```
Ser Ile Thr Leu Gly Ser His Trp Ile Glu Pro Asn Arg Ser Glu Asn
1               5                   10                  15

Thr Met Asp

<210> SEQ ID NO 122
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Ile Phe Lys Cys Gln Gln Ser Met Val
1               5

<210> SEQ ID NO 123
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Phe Lys Cys Gln Gln Ser Met
1               5

<210> SEQ ID NO 124
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Lys Cys Gln Gln Ser Met Val
1               5

<210> SEQ ID NO 125
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Phe Ala Asn Pro Ile His Gly Asp Gly Asp Tyr Pro Glu Gly
1               5                   10

<210> SEQ ID NO 126
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Phe Ala Asn Pro Ile His Gly Asp Gly Asp Tyr Pro Glu Gly Met Arg
1               5                   10                  15

Lys Lys Leu

<210> SEQ ID NO 127
```

```
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Phe Ala Asn Pro Ile His Gly Asp Gly Asp Tyr Pro Glu Gly Met Arg
1               5                   10                  15

Lys Lys Leu Phe
            20

<210> SEQ ID NO 128
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Leu Pro Ile Phe Ser Glu Ala Glu Lys His Glu Met Arg Gly Thr
1               5                   10                  15

<210> SEQ ID NO 129
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Pro Ile Phe Ser Glu Ala Glu Lys His Glu Met Arg Gly Thr Ala Asp
1               5                   10                  15

<210> SEQ ID NO 130
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Pro Ile Phe Ser Glu Ala Glu Lys His Glu Met Arg Gly Thr Ala Asp
1               5                   10                  15

Phe

<210> SEQ ID NO 131
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Ser Glu Ala Glu Lys His Glu Met Arg Gly Thr Ala Asp Phe
1               5                   10

<210> SEQ ID NO 132
<211> LENGTH: 12
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 132

Ala Glu Lys His Glu Met Arg Gly Thr Ala Asp Phe
1               5                   10

<210> SEQ ID NO 133
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Glu Lys His Glu Met Arg Gly Thr Ala Asp Phe
1               5                   10

<210> SEQ ID NO 134
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Phe Ala Phe Ser Phe Gly Pro Asn Asn Phe
1               5                   10

<210> SEQ ID NO 135
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Phe Ala Phe Ser Phe Gly Pro Asn Asn Phe Lys Pro Leu Asn Thr
1               5                   10                  15

<210> SEQ ID NO 136
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Phe Gly Pro Asn Asn Phe Lys Pro Leu Asn Thr
1               5                   10

<210> SEQ ID NO 137
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Phe Gly Pro Asn Asn Phe Lys Pro Leu Asn Thr Met
1               5                   10
```

```
<210> SEQ ID NO 138
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Asn Leu Arg Glu Ala Leu Asn
1               5

<210> SEQ ID NO 139
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Ile Lys Leu Glu Tyr Asn Asn Pro Arg Ile Leu
1               5                   10

<210> SEQ ID NO 140
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Glu Tyr Asn Asn Pro Arg Ile Leu
1               5

<210> SEQ ID NO 141
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Phe Thr Asp Ser Arg Val Lys Thr Glu Asp Thr Thr Ala
1               5                   10

<210> SEQ ID NO 142
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Asp Ser Arg Val Lys Thr Glu Asp Thr Thr Ala
1               5                   10

<210> SEQ ID NO 143
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143
```

```
Asp Thr Thr Ala Ile Tyr Met Met Lys Asn Phe
1               5                   10
```

<210> SEQ ID NO 144
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

```
Tyr Met Met Lys Asn Phe Leu
1               5
```

<210> SEQ ID NO 145
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

```
Met Met Lys Asn Phe Leu Ser Gln Val Leu Gln Ala
1               5                   10
```

<210> SEQ ID NO 146
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

```
Met Lys Asn Phe Leu Ser Gln Val Leu Gln Ala
1               5                   10
```

<210> SEQ ID NO 147
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

```
Gln Ala Ile Arg Leu Asp Glu
1               5
```

<210> SEQ ID NO 148
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

```
Asp Glu Ile Arg Val Phe Gly Tyr Thr Ala
1               5                   10
```

<210> SEQ ID NO 149
<211> LENGTH: 8
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 149

Ile Arg Val Phe Gly Tyr Thr Ala
1               5

<210> SEQ ID NO 150
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Ile Arg Val Phe Gly Tyr Thr Ala Trp Ser Leu
1               5                   10

<210> SEQ ID NO 151
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Tyr Thr Ala Trp Ser Leu Leu
1               5

<210> SEQ ID NO 152
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Asp Gly Phe Glu Trp Gln Asp Ala
1               5

<210> SEQ ID NO 153
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Phe Glu Trp Gln Asp Ala Tyr Thr
1               5

<210> SEQ ID NO 154
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Tyr Thr Ile Arg Arg Gly Leu Phe
1               5
```

<210> SEQ ID NO 155
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Thr Ile Arg Arg Gly Leu Phe
1               5

<210> SEQ ID NO 156
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Asn Ser Lys Gln Lys Glu Arg Lys Pro Lys Ser Ser Ala His Tyr
1               5                   10                  15

<210> SEQ ID NO 157
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Asn Ser Lys Gln Lys Glu Arg Lys Pro Lys Ser Ser Ala His Tyr Tyr
1               5                   10                  15

Lys Gln Ile Ile Arg Glu
            20

<210> SEQ ID NO 158
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Asn Ser Lys Gln Lys Glu Arg Lys Pro Lys Ser Ser Ala His Tyr Tyr
1               5                   10                  15

Lys Gln Ile Ile Arg Glu Asn Gly
            20

<210> SEQ ID NO 159
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Asn Ser Lys Gln Lys Glu Arg Lys Pro Lys Ser Ser Ala His Tyr Tyr
1               5                   10                  15

Lys Gln Ile Ile Arg Glu Asn Gly Phe
            20                  25

<210> SEQ ID NO 160
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Asn Ser Lys Gln Lys Glu Arg Lys Pro Lys Ser Ser Ala His Tyr Tyr
1               5                   10                  15

Lys Gln Ile Ile Arg Glu Asn Gly Phe Ser
            20                  25

<210> SEQ ID NO 161
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Ser Lys Gln Lys Glu Arg Lys Pro Lys Ser Ser Ala His Tyr Tyr Lys
1               5                   10                  15

Gln Ile Ile Arg Glu
            20

<210> SEQ ID NO 162
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Tyr Lys Gln Ile Ile Arg Glu Asn Gly
1               5

<210> SEQ ID NO 163
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Phe Ser Leu Lys Glu Ser Thr Pro Asp Val Gln Gly Gln Phe Pro Cys
1               5                   10                  15

Asp

<210> SEQ ID NO 164
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Ser Leu Lys Glu Ser Thr Pro Asp Val Gln Gly Gln Phe Pro Cys Asp
1               5                   10                  15

```
<210> SEQ ID NO 165
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Leu Lys Glu Ser Thr Pro Asp Val Gln Gly Gln Phe Pro Cys Asp
1               5                   10                  15

<210> SEQ ID NO 166
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Phe Ser Trp Gly Val Thr Glu
1               5

<210> SEQ ID NO 167
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Ser Val Leu Lys Pro Glu Ser Val Ala Ser Ser Pro Gln Phe Ser Asp
1               5                   10                  15

Pro His Leu

<210> SEQ ID NO 168
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Lys Pro Glu Ser Val Ala Ser Ser Pro Gln Phe Ser Asp Pro His Leu
1               5                   10                  15

<210> SEQ ID NO 169
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Val Arg Leu Lys Thr Arg Pro Ala Gln Cys
1               5                   10

<210> SEQ ID NO 170
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 170

Phe Val Asn Ile Lys Lys Gln Leu Glu Met
1               5                   10

<210> SEQ ID NO 171
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Val Asn Ile Lys Lys Gln Leu Glu Met
1               5

<210> SEQ ID NO 172
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Val Asn Ile Lys Lys Gln Leu Glu Met Leu
1               5                   10

<210> SEQ ID NO 173
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Asn Ile Lys Lys Gln Leu Glu Met
1               5

<210> SEQ ID NO 174
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Leu Ala Arg Met Lys Val Thr His Tyr Arg
1               5                   10

<210> SEQ ID NO 175
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Leu Ala Arg Met Lys Val Thr His Tyr Arg Phe
1               5                   10

<210> SEQ ID NO 176
<211> LENGTH: 10
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Ala Arg Met Lys Val Thr His Tyr Arg Phe
1               5                   10

<210> SEQ ID NO 177
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Ala Leu Asp Trp Ala Ser Val Leu
1               5

<210> SEQ ID NO 178
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Tyr Arg Cys Val Val Ser Glu Gly
1               5

<210> SEQ ID NO 179
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Val Val Ser Glu Gly Leu Lys Leu Gly Ile Ser Ala
1               5                   10

<210> SEQ ID NO 180
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Gly Leu Lys Leu Gly Ile Ser Ala Met
1               5

<210> SEQ ID NO 181
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Leu Lys Leu Gly Ile Ser Ala
```

```
<210> SEQ ID NO 182
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Leu Lys Leu Gly Ile Ser Ala Met
1               5

<210> SEQ ID NO 183
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Ile Ser Ala Met Val Thr Leu Tyr Tyr Pro Thr
1               5                   10

<210> SEQ ID NO 184
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Leu Tyr Tyr Pro Thr His Ala His Leu Gly Leu Pro Glu Pro Leu Leu
1               5                   10                  15

<210> SEQ ID NO 185
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Tyr Tyr Pro Thr His Ala His Leu Gly Leu Pro Glu Pro Leu Leu
1               5                   10                  15

<210> SEQ ID NO 186
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Tyr Tyr Pro Thr His Ala His Leu Gly Leu Pro Glu Pro Leu Leu His
1               5                   10                  15

Ala Asp Gly Trp Leu Asn Pro Ser Thr Ala Glu Ala
            20                  25

<210> SEQ ID NO 187
<211> LENGTH: 13
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 187

His Ala Asp Gly Trp Leu Asn Pro Ser Thr Ala Glu Ala
1               5                   10

<210> SEQ ID NO 188
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

His Ala Asp Gly Trp Leu Asn Pro Ser Thr Ala Glu Ala Phe
1               5                   10

<210> SEQ ID NO 189
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Ala Phe Gln Ala Tyr Ala Gly Leu
1               5

<210> SEQ ID NO 190
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Phe Gln Ala Tyr Ala Gly Leu Cys
1               5

<210> SEQ ID NO 191
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Gln Ala Tyr Ala Gly Leu Cys
1               5

<210> SEQ ID NO 192
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Gln Ala Tyr Ala Gly Leu Cys Phe
1               5

<210> SEQ ID NO 193
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Cys Phe Gln Glu Leu Gly Asp
1               5

<210> SEQ ID NO 194
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Cys Phe Gln Glu Leu Gly Asp Leu
1               5

<210> SEQ ID NO 195
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Trp Ile Thr Ile Asn Glu Pro Asn Arg Leu
1               5                   10

<210> SEQ ID NO 196
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Trp Ile Thr Ile Asn Glu Pro Asn Arg Leu Ser Asp
1               5                   10

<210> SEQ ID NO 197
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Trp Ile Thr Ile Asn Glu Pro Asn Arg Leu Ser Asp Ile
1               5                   10

<210> SEQ ID NO 198
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Ile Thr Ile Asn Glu Pro Asn Arg
1               5

<210> SEQ ID NO 199
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Val Ala His Ala Leu Ala Trp Arg Leu
1               5

<210> SEQ ID NO 200
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Ala His Ala Leu Ala Trp Arg Leu
1               5

<210> SEQ ID NO 201
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

His Ala Leu Ala Trp Arg Leu
1               5

<210> SEQ ID NO 202
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Tyr Asp Arg Gln Phe Arg Pro Ser Gln Arg Gly Ala Val Ser
1               5                   10

<210> SEQ ID NO 203
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Tyr Asp Arg Gln Phe Arg Pro Ser Gln Arg Gly Ala Val Ser Leu
1               5                   10                  15

<210> SEQ ID NO 204
<211> LENGTH: 13

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Asp Arg Gln Phe Arg Pro Ser Gln Arg Gly Ala Val Ser
1               5                   10

<210> SEQ ID NO 205
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Ser Leu His Ala Asp Trp Ala Glu Pro Ala Asn Pro Tyr Ala Asp Ser
1               5                   10                  15

His Trp Arg Ala Ala Glu Arg Phe
            20

<210> SEQ ID NO 206
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

His Ala Asp Trp Ala Glu Pro Ala Asn Pro Tyr Ala Asp Ser His Trp
1               5                   10                  15

<210> SEQ ID NO 207
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

His Ala Asp Trp Ala Glu Pro Ala Asn Pro Tyr Ala Asp Ser His Trp
1               5                   10                  15

Arg Ala

<210> SEQ ID NO 208
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

His Ala Asp Trp Ala Glu Pro Ala Asn Pro Tyr Ala Asp Ser His Trp
1               5                   10                  15

Arg Ala Ala Glu Arg Phe
            20

<210> SEQ ID NO 209
<211> LENGTH: 19
<212> TYPE: PRT

<213> ORGANISM: Artificial Sequence
<220> FEATURE:
<223> OTHER INFORMATION: Description of Artificial Sequence: Synthetic
      peptide

<400> SEQUENCE: 209

Trp Ala Glu Pro Ala Asn Pro Tyr Ala Asp Ser His Trp Arg Ala Ala
1               5                   10                  15

Glu Arg Phe

<210> SEQ ID NO 210
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Pro Ala Asn Pro Tyr Ala Asp Ser His Trp Arg Ala Ala Glu Arg Phe
1               5                   10                  15

<210> SEQ ID NO 211
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Pro Tyr Ala Asp Ser His Trp Arg Ala Ala Glu Arg Phe
1               5                   10

<210> SEQ ID NO 212
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Phe Ala Glu Pro Leu Phe Lys Thr Gly Asp Tyr Pro Ala Ala
1               5                   10

<210> SEQ ID NO 213
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Phe Ala Glu Pro Leu Phe Lys Thr Gly Asp Tyr Pro Ala Ala Met
1               5                   10                  15

<210> SEQ ID NO 214
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

```
Lys Thr Gly Asp Tyr Pro Ala Ala Met
1               5
```

<210> SEQ ID NO 215
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

```
Arg Glu Tyr Ile Ala Ser Lys His Arg Arg Gly Leu Ser Ser Ser Ala
1               5                   10                  15

Leu
```

<210> SEQ ID NO 216
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

```
Arg Glu Tyr Ile Ala Ser Lys His Arg Arg Gly Leu Ser Ser Ser Ala
1               5                   10                  15

Leu Pro Arg Leu
            20
```

<210> SEQ ID NO 217
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

```
Tyr Ile Ala Ser Lys His Arg Arg Gly Leu Ser Ser Ser Ala Leu
1               5                   10                  15
```

<210> SEQ ID NO 218
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

```
Pro Arg Leu Thr Glu Ala Glu
1               5
```

<210> SEQ ID NO 219
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

```
Pro Arg Leu Thr Glu Ala Glu Arg Arg Leu Leu Lys Gly Thr Val Asp
1               5                   10                  15

Phe
```

<210> SEQ ID NO 220
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Ala Glu Arg Arg Leu Leu Lys Gly Thr Val Asp Phe
1               5                   10

<210> SEQ ID NO 221
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Glu Arg Arg Leu Leu Lys Gly Thr Val Asp Phe
1               5                   10

<210> SEQ ID NO 222
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Arg Arg Leu Leu Lys Gly Thr Val Asp Phe
1               5                   10

<210> SEQ ID NO 223
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Cys Ala Leu Asn His Phe Thr Thr Arg Phe
1               5                   10

<210> SEQ ID NO 224
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Val Met His Glu Gln Leu Ala Gly Ser Arg Tyr Asp Ser Asp Arg Asp
1               5                   10                  15

<210> SEQ ID NO 225
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

Val Met His Glu Gln Leu Ala Gly Ser Arg Tyr Asp Ser Asp Arg Asp
1               5                   10                  15

Ile Gln Phe

<210> SEQ ID NO 226
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

His Glu Gln Leu Ala Gly Ser Arg Tyr Asp Ser Asp Arg Asp Ile Gln
1               5                   10                  15

Phe

<210> SEQ ID NO 227
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

Ala Gly Ser Arg Tyr Asp Ser Asp Arg Asp
1               5                   10

<210> SEQ ID NO 228
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Ala Gly Ser Arg Tyr Asp Ser Asp Arg Asp Ile Gln Phe
1               5                   10

<210> SEQ ID NO 229
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

Gly Ser Arg Tyr Asp Ser Asp Arg Asp Ile Gln Phe
1               5                   10

<210> SEQ ID NO 230
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

Leu Gln Asp Ile Thr Arg Leu Ser Ser Pro Thr Arg
1               5                   10

<210> SEQ ID NO 231
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 231

Leu Gln Asp Ile Thr Arg Leu Ser Ser Pro Thr Arg Leu
1               5                   10

<210> SEQ ID NO 232
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

Ile Thr Arg Leu Ser Ser Pro Thr Arg Leu
1               5                   10

<210> SEQ ID NO 233
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233

Thr Arg Leu Ser Ser Pro Thr Arg
1               5

<210> SEQ ID NO 234
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Ser Pro Thr Arg Leu Ala Val
1               5

<210> SEQ ID NO 235
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Ser Pro Thr Arg Leu Ala Val Ile Pro Trp Gly Val Arg Lys Leu
1               5                   10                  15

<210> SEQ ID NO 236
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 236

Ala Val Ile Pro Trp Gly Val Arg Lys Leu
1               5                   10

<210> SEQ ID NO 237
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

Ala Val Ile Pro Trp Gly Val Arg Lys Leu Leu Arg Trp Val Arg Arg
1               5                   10                  15

Asn Tyr Gly Asp Met
            20

<210> SEQ ID NO 238
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Ala Val Ile Pro Trp Gly Val Arg Lys Leu Leu Arg Trp Val Arg Arg
1               5                   10                  15

Asn Tyr Gly Asp Met Asp
            20

<210> SEQ ID NO 239
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Ala Val Ile Pro Trp Gly Val Arg Lys Leu Leu Arg Trp Val Arg Arg
1               5                   10                  15

Asn Tyr Gly Asp Met Asp Ile
            20

<210> SEQ ID NO 240
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

Ile Pro Trp Gly Val Arg Lys
1               5

<210> SEQ ID NO 241
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 241

Ile Pro Trp Gly Val Arg Lys Leu Leu Arg Trp Val Arg Arg Asn Tyr
1               5                   10                  15

Gly Asp Met Asp
            20

<210> SEQ ID NO 242
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

Leu Arg Trp Val Arg Arg Asn Tyr Gly Asp Met Asp Ile
1               5                   10

<210> SEQ ID NO 243
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

Ile Tyr Ile Thr Ala Ser Gly Ile Asp Asp Gln Ala Leu Glu Asp
1               5                   10                  15

<210> SEQ ID NO 244
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

Tyr Ile Thr Ala Ser Gly Ile Asp Asp Gln Ala Leu
1               5                   10

<210> SEQ ID NO 245
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

Tyr Ile Thr Ala Ser Gly Ile Asp Asp Gln Ala Leu Glu Asp Asp Arg
1               5                   10                  15

Leu Arg Lys Tyr Tyr Leu Gly Lys Tyr
            20                  25

<210> SEQ ID NO 246
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246
```

```
Glu Asp Asp Arg Leu Arg Lys Tyr Tyr Leu Gly Lys Tyr
1               5                   10

<210> SEQ ID NO 247
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 247

Asp Arg Leu Arg Lys Tyr Tyr Leu Gly Lys Tyr
1               5                   10

<210> SEQ ID NO 248
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

Asp Arg Leu Arg Lys Tyr Tyr Leu Gly Lys Tyr Leu Gln Glu
1               5                   10

<210> SEQ ID NO 249
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

Ile Asp Lys Val Arg Ile Lys Gly
1               5

<210> SEQ ID NO 250
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 250

Ile Asp Lys Val Arg Ile Lys Gly Tyr
1               5

<210> SEQ ID NO 251
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 251

Ile Asp Lys Val Arg Ile Lys Gly Tyr Tyr Ala
1               5                   10

<210> SEQ ID NO 252
<211> LENGTH: 12
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 252

Ile Asp Lys Val Arg Ile Lys Gly Tyr Tyr Ala Phe
1               5                   10

<210> SEQ ID NO 253
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 253

Asp Lys Val Arg Ile Lys Gly Tyr Tyr Ala
1               5                   10

<210> SEQ ID NO 254
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

Lys Val Arg Ile Lys Gly Tyr Tyr Ala
1               5

<210> SEQ ID NO 255
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 255

Lys Val Arg Ile Lys Gly Tyr Tyr Ala Phe
1               5                   10

<210> SEQ ID NO 256
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 256

Phe Lys Leu Ala Glu Glu Lys Ser Lys Pro Arg Phe Gly Phe
1               5                   10

<210> SEQ ID NO 257
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 257

Phe Lys Leu Ala Glu Glu Lys Ser Lys Pro Arg Phe Gly Phe Phe
1               5                   10                  15

```
<210> SEQ ID NO 258
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 258

Lys Leu Ala Glu Glu Lys Ser Lys Pro Arg Phe Gly Phe Phe
1               5                   10

<210> SEQ ID NO 259
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 259

Phe Lys Ala Lys Ser Ser Ile Gln Phe
1               5

<210> SEQ ID NO 260
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 260

Tyr Asn Lys Val Ile Ser Ser Arg Gly Phe Pro Phe Glu Asn Ser Ser
1               5                   10                  15

Ser Arg Cys Ser Gln Thr Gln Glu
            20

<210> SEQ ID NO 261
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 261

Ser Ser Arg Cys Ser Gln Thr Gln Glu Asn Thr Glu Cys Thr
1               5                   10

<210> SEQ ID NO 262
<211> LENGTH: 1044
<212> TYPE: PRT
<213> ORGANISM: Homo sapiens

<400> SEQUENCE: 262

Met Lys Pro Gly Cys Ala Ala Gly Ser Pro Gly Asn Glu Trp Ile Phe
1               5                   10                  15

Phe Ser Thr Asp Glu Ile Thr Thr Arg Tyr Arg Asn Thr Met Ser Asn
            20                  25                  30

Gly Gly Leu Gln Arg Ser Val Ile Leu Ser Ala Leu Ile Leu Leu Arg
        35                  40                  45

Ala Val Thr Gly Phe Ser Gly Asp Gly Arg Ala Ile Trp Ser Lys Asn
    50                  55                  60

Pro Asn Phe Thr Pro Val Asn Glu Ser Gln Leu Phe Leu Tyr Asp Thr
```

```
            65                  70                  75                  80
        Phe Pro Lys Asn Phe Phe Trp Gly Ile Gly Thr Gly Ala Leu Gln Val
                            85                  90                  95
        Glu Gly Ser Trp Lys Lys Asp Gly Lys Gly Pro Ser Ile Trp Asp His
                        100                 105                 110
        Phe Ile His Thr His Leu Lys Asn Val Ser Ser Thr Asn Gly Ser Ser
                        115                 120                 125
        Asp Ser Tyr Ile Phe Leu Glu Lys Asp Leu Ser Ala Leu Asp Phe Ile
                    130                 135                 140
        Gly Val Ser Phe Tyr Gln Phe Ser Ile Ser Trp Pro Arg Leu Phe Pro
        145                 150                 155                 160
        Asp Gly Ile Val Thr Val Ala Asn Ala Lys Gly Leu Gln Tyr Tyr Ser
                            165                 170                 175
        Thr Leu Leu Asp Ala Leu Val Leu Arg Asn Ile Glu Pro Ile Val Thr
                        180                 185                 190
        Leu Tyr His Trp Asp Leu Pro Leu Ala Leu Gln Glu Lys Tyr Gly Gly
                        195                 200                 205
        Trp Lys Asn Asp Thr Ile Ile Asp Ile Phe Asn Asp Tyr Ala Thr Tyr
                    210                 215                 220
        Cys Phe Gln Met Phe Gly Asp Arg Val Lys Tyr Trp Ile Thr Ile His
        225                 230                 235                 240
        Asn Pro Tyr Leu Val Ala Trp His Gly Tyr Gly Thr Gly Met His Ala
                            245                 250                 255
        Pro Gly Glu Lys Gly Asn Leu Ala Ala Val Tyr Thr Val Gly His Asn
                        260                 265                 270
        Leu Ile Lys Ala His Ser Lys Val Trp His Asn Tyr Asn Thr His Phe
                        275                 280                 285
        Arg Pro His Gln Lys Gly Trp Leu Ser Ile Thr Leu Gly Ser His Trp
                    290                 295                 300
        Ile Glu Pro Asn Arg Ser Glu Asn Thr Met Asp Ile Phe Lys Cys Gln
        305                 310                 315                 320
        Gln Ser Met Val Ser Val Leu Gly Trp Phe Ala Asn Pro Ile His Gly
                            325                 330                 335
        Asp Gly Asp Tyr Pro Glu Gly Met Arg Lys Lys Leu Phe Ser Val Leu
                        340                 345                 350
        Pro Ile Phe Ser Glu Ala Glu Lys His Glu Met Arg Gly Thr Ala Asp
                        355                 360                 365
        Phe Phe Ala Phe Ser Phe Gly Pro Asn Asn Phe Lys Pro Leu Asn Thr
                    370                 375                 380
        Met Ala Lys Met Gly Gln Asn Val Ser Leu Asn Leu Arg Glu Ala Leu
        385                 390                 395                 400
        Asn Trp Ile Lys Leu Glu Tyr Asn Asn Pro Arg Ile Leu Ile Ala Glu
                            405                 410                 415
        Asn Gly Trp Phe Thr Asp Ser Arg Val Lys Thr Glu Asp Thr Thr Ala
                        420                 425                 430
        Ile Tyr Met Met Lys Asn Phe Leu Ser Gln Val Leu Gln Ala Ile Arg
                        435                 440                 445
        Leu Asp Glu Ile Arg Val Phe Gly Tyr Thr Ala Trp Ser Leu Leu Asp
                    450                 455                 460
        Gly Phe Glu Trp Gln Asp Ala Tyr Thr Ile Arg Arg Gly Leu Phe Tyr
        465                 470                 475                 480
        Val Asp Phe Asn Ser Lys Gln Lys Glu Arg Lys Pro Lys Ser Ser Ala
                            485                 490                 495
```

```
His Tyr Tyr Lys Gln Ile Ile Arg Glu Asn Gly Phe Ser Leu Lys Glu
            500                 505                 510

Ser Thr Pro Asp Val Gln Gly Gln Phe Pro Cys Asp Phe Ser Trp Gly
            515                 520                 525

Val Thr Glu Ser Val Leu Lys Pro Glu Ser Val Ala Ser Ser Pro Gln
530                 535                 540

Phe Ser Asp Pro His Leu Tyr Val Trp Asn Ala Thr Gly Asn Arg Leu
545                 550                 555                 560

Leu His Arg Val Glu Gly Val Arg Leu Lys Thr Arg Pro Ala Gln Cys
            565                 570                 575

Thr Asp Phe Val Asn Ile Lys Lys Gln Leu Glu Met Leu Ala Arg Met
            580                 585                 590

Lys Val Thr His Tyr Arg Phe Ala Leu Asp Trp Ala Ser Val Leu Pro
            595                 600                 605

Thr Gly Asn Leu Ser Ala Val Asn Arg Gln Ala Leu Arg Tyr Tyr Arg
            610                 615                 620

Cys Val Val Ser Glu Gly Leu Lys Leu Gly Ile Ser Ala Met Val Thr
625                 630                 635                 640

Leu Tyr Tyr Pro Thr His Ala His Leu Gly Leu Pro Glu Pro Leu Leu
            645                 650                 655

His Ala Asp Gly Trp Leu Asn Pro Ser Thr Ala Glu Ala Phe Gln Ala
            660                 665                 670

Tyr Ala Gly Leu Cys Phe Gln Glu Leu Gly Asp Leu Val Lys Leu Trp
            675                 680                 685

Ile Thr Ile Asn Glu Pro Asn Arg Leu Ser Asp Ile Tyr Asn Arg Ser
            690                 695                 700

Gly Asn Asp Thr Tyr Gly Ala Ala His Asn Leu Leu Val Ala His Ala
705                 710                 715                 720

Leu Ala Trp Arg Leu Tyr Asp Arg Gln Phe Arg Pro Ser Gln Arg Gly
            725                 730                 735

Ala Val Ser Leu Ser Leu His Ala Asp Trp Ala Glu Pro Ala Asn Pro
            740                 745                 750

Tyr Ala Asp Ser His Trp Arg Ala Ala Glu Arg Phe Leu Gln Phe Glu
            755                 760                 765

Ile Ala Trp Phe Ala Glu Pro Leu Phe Lys Thr Gly Asp Tyr Pro Ala
            770                 775                 780

Ala Met Arg Glu Tyr Ile Ala Ser Lys His Arg Arg Gly Leu Ser Ser
785                 790                 795                 800

Ser Ala Leu Pro Arg Leu Thr Glu Ala Glu Arg Arg Leu Leu Lys Gly
            805                 810                 815

Thr Val Asp Phe Cys Ala Leu Asn His Phe Thr Thr Arg Phe Val Met
            820                 825                 830

His Glu Gln Leu Ala Gly Ser Arg Tyr Asp Ser Asp Arg Asp Ile Gln
            835                 840                 845

Phe Leu Gln Asp Ile Thr Arg Leu Ser Ser Pro Thr Arg Leu Ala Val
            850                 855                 860

Ile Pro Trp Gly Val Arg Lys Leu Leu Arg Trp Val Arg Arg Asn Tyr
865                 870                 875                 880

Gly Asp Met Asp Ile Tyr Ile Thr Ala Ser Gly Ile Asp Asp Gln Ala
            885                 890                 895

Leu Glu Asp Asp Arg Leu Arg Lys Tyr Tyr Leu Gly Lys Tyr Leu Gln
            900                 905                 910
```

```
Glu Val Leu Lys Ala Tyr Leu Ile Asp Lys Val Arg Ile Lys Gly Tyr
            915                 920                 925

Tyr Ala Phe Lys Leu Ala Glu Glu Lys Ser Lys Pro Arg Phe Gly Phe
        930                 935                 940

Phe Thr Ser Asp Phe Lys Ala Lys Ser Ser Ile Gln Phe Tyr Asn Lys
945                 950                 955                 960

Val Ile Ser Ser Arg Gly Phe Pro Glu Asn Ser Ser Arg Cys
                965                 970                 975

Ser Gln Thr Gln Glu Asn Thr Glu Cys Thr Val Cys Leu Phe Leu Val
            980                 985                 990

Gln Lys Lys Pro Leu Ile Phe Leu  Gly Cys Cys Phe Phe  Ser Thr Leu
            995             1000                 1005

Val Leu  Leu Leu Ser Ile Ala  Ile Phe Gln Arg Gln  Lys Arg Arg
    1010                1015                 1020

Lys Phe  Trp Lys Ala Lys Asn  Leu Gln His Ile Pro  Leu Lys Lys
    1025                1030                 1035

Gly Lys  Arg Val Val Ser
    1040
```

<210> SEQ ID NO 263
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 263

```
Gly Tyr Thr Phe Thr Asp Tyr Tyr Ile Asn
1               5                   10
```

<210> SEQ ID NO 264
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 264

```
Gly Tyr Thr Phe Thr Asp Tyr Tyr
1               5
```

<210> SEQ ID NO 265
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 265

```
Ile His Pro Gly Ser Gly Asn Thr
1               5
```

<210> SEQ ID NO 266
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 266

```
Ala Ile Leu Leu Leu Arg Ser Tyr Gly Met Asp Asp
1               5                   10
```

<210> SEQ ID NO 267
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 267

```
Gln Ser Ile Val His Ser Ser Gly Asn Thr Tyr
1               5                   10
```

<210> SEQ ID NO 268
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 268

```
Gly Tyr Ser Ile Thr Ser Gly Tyr Thr Trp His
1               5                   10
```

<210> SEQ ID NO 269
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 269

```
Gly Tyr Ser Ile Thr Ser Gly Tyr Thr
1               5
```

<210> SEQ ID NO 270
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 270

```
Ile His Tyr Ser Val Tyr Thr
1               5
```

<210> SEQ ID NO 271
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 271

```
Ala Arg Arg Thr Thr Ser Leu Glu Arg Tyr Phe Asp Val
1               5                   10
```

<210> SEQ ID NO 272
<211> LENGTH: 6
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 272

Gln Asp Ile Ser Asn Tyr
1               5

<210> SEQ ID NO 273
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 273

Tyr Thr Ser
1

<210> SEQ ID NO 274
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 274

His His His His His His
1               5
```